US011248045B2

(12) United States Patent
Sonoda et al.

(10) Patent No.: US 11,248,045 B2
(45) Date of Patent: Feb. 15, 2022

(54) ANTI-HUMAN TRANSFERRIN RECEPTOR ANTIBODY PERMEATING BLOOD-BRAIN BARRIER

(71) Applicant: JCR Pharmaceuticals Co., Ltd., Hyogo (JP)

(72) Inventors: Hiroyuki Sonoda, Hyogo (JP); Kenichi Takahashi, Hyogo (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 0 days.

(21) Appl. No.: 15/739,200

(22) PCT Filed: Jun. 24, 2016

(86) PCT No.: PCT/JP2016/068738
§ 371 (c)(1),
(2) Date: Dec. 22, 2017

(87) PCT Pub. No.: WO2016/208695
PCT Pub. Date: Dec. 29, 2016

(65) Prior Publication Data

US 2018/0171012 A1 Jun. 21, 2018

(30) Foreign Application Priority Data

Jun. 24, 2015 (JP) ............................ JP2015-144379

(51) Int. Cl.

| | |
|---|---|
| ***C07K 16/28*** | (2006.01) |
| ***C12N 9/16*** | (2006.01) |
| ***A61K 39/395*** | (2006.01) |
| ***C12N 9/10*** | (2006.01) |
| ***C07K 19/00*** | (2006.01) |
| ***C07K 14/475*** | (2006.01) |
| ***C12N 5/10*** | (2006.01) |
| ***A61K 45/00*** | (2006.01) |
| ***C07K 16/46*** | (2006.01) |
| ***C07K 16/18*** | (2006.01) |
| ***C12N 15/09*** | (2006.01) |
| ***C12N 9/64*** | (2006.01) |
| ***C12N 9/24*** | (2006.01) |
| ***C12N 15/113*** | (2010.01) |
| ***A61P 25/00*** | (2006.01) |
| ***C07K 14/505*** | (2006.01) |
| ***C07K 14/715*** | (2006.01) |
| ***C12N 9/14*** | (2006.01) |
| ***C12N 9/48*** | (2006.01) |
| ***A61K 39/00*** | (2006.01) |

(52) U.S. Cl.
CPC ............ *C07K 16/28* (2013.01); *A61K 39/395* (2013.01); *A61K 45/00* (2013.01); *A61P 25/00* (2018.01); *C07K 14/475* (2013.01); *C07K 14/505* (2013.01); *C07K 14/7151* (2013.01); *C07K 16/18* (2013.01); *C07K 16/46* (2013.01); *C07K 19/00* (2013.01); *C12N 5/10* (2013.01); *C12N 9/10* (2013.01); *C12N 9/14* (2013.01); *C12N 9/16* (2013.01); *C12N 9/24* (2013.01); *C12N 9/2402* (2013.01); *C12N 9/48* (2013.01); *C12N 9/64* (2013.01); *C12N 15/09* (2013.01); *C12N 15/113* (2013.01); *C12Y 301/02* (2013.01); *C12Y 302/01076* (2013.01); *C12Y 304/14009* (2013.01); *C12Y 310/01001* (2013.01); *A61K 2039/505* (2013.01); *C07K 2317/24* (2013.01); *C07K 2317/92* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,154,924 | A | 10/1992 | Friden |
| 5,442,043 | A | 8/1995 | Fukuta et al. |
| 5,527,527 | A | 6/1996 | Friden |
| 5,977,307 | A | 11/1999 | Friden et al. |
| 6,472,147 | B1 | 10/2002 | Janda et al. |
| 7,560,431 | B2 | 7/2009 | Zankel et al. |
| 8,663,598 | B2 | 3/2014 | Yang et al. |
| 2004/0101904 | A1 | 5/2004 | Pardridge et al. |
| 2010/0077498 | A1 | 3/2010 | Pardridge et al. |

(Continued)

FOREIGN PATENT DOCUMENTS

| | | | |
|---|---|---|---|
| CA | 2607771 | A1 | 5/2009 |
| CA | 3034589 | A1 | 3/2018 |

(Continued)

OTHER PUBLICATIONS

Kussie "A Single Engineered Amino Acid Substitution Changes Antibody Fine Specificity" J immunol 152(1):146-52 (Year: 1994).*

(Continued)

*Primary Examiner* — Adam Weidner
(74) *Attorney, Agent, or Firm* — Morgan, Lewis & Bockius LLP

(57) ABSTRACT

Disclosed are a means to convert compounds having physiological or pharmacological activity and unable to pass through the blood-brain barrier into a form that allows them to pass through the blood-brain barrier, and compounds converted thereby. The means is an anti-human transferrin receptor antibody and the converted compounds are molecular conjugates between physiologically active protein or pharmacologically active low-molecular-weight compounds and an anti-human transferrin receptor antibody.

6 Claims, 10 Drawing Sheets

Specification includes a Sequence Listing.

(56) References Cited

U.S. PATENT DOCUMENTS

| | | | | |
|---|---|---|---|---|
| 2010/0266613 | A1 | 10/2010 | Harding et al. | |
| 2011/0110935 | A1* | 5/2011 | Pardridge | C07K 16/18 424/133.1 |
| 2012/0171120 | A1 | 7/2012 | Dennis et al. | |
| 2012/0231023 | A1* | 9/2012 | Zurawski | C07K 16/2851 424/178.1 |
| 2013/0171061 | A1 | 7/2013 | Yang et al. | |
| 2014/0114054 | A1 | 4/2014 | Kurosawa et al. | |
| 2015/0110791 | A1 | 4/2015 | Zhang et al. | |
| 2016/0369001 | A1 | 12/2016 | Sonoda et al. | |
| 2017/0044259 | A1 | 2/2017 | Tipton et al. | |
| 2017/0252458 | A1 | 9/2017 | Albone et al. | |
| 2017/0355756 | A1* | 12/2017 | Julien | C07K 16/18 |
| 2018/0171012 | A1 | 6/2018 | Sonoda et al. | |
| 2018/0179291 | A1 | 6/2018 | Sonoda et al. | |
| 2019/0338043 | A1 | 11/2019 | Sonoda et al. | |

FOREIGN PATENT DOCUMENTS

| | | | |
|---|---|---|---|
| CN | 101245107 | A | 8/2008 |
| CN | 103502273 | A | 1/2014 |
| EP | 3563863 | A1 | 11/2019 |
| EP | 3679945 | A1 | 7/2020 |
| JP | H05-500944 | A | 2/1993 |
| JP | H06-228199 | A | 8/1994 |
| JP | 2006-511516 | A | 4/2006 |
| JP | 2007-504166 | A | 3/2007 |
| JP | 2009-515819 | A | 4/2009 |
| JP | 2009-525963 | A | 7/2009 |
| JP | 2011-144178 | A | 7/2011 |
| JP | 2012-062312 | A | 3/2012 |
| JP | 2014-514313 | A | 6/2014 |
| JP | 2018-033454 | A | 3/2018 |
| WO | 91/003259 | A1 | 3/1991 |
| WO | 93/10819 | A1 | 6/1993 |
| WO | 95/02421 | A1 | 1/1995 |
| WO | 02/031510 | A1 | 4/2002 |
| WO | 02/034771 | A2 | 5/2002 |
| WO | 03/083069 | A2 | 10/2003 |
| WO | 2004/050016 | A2 | 6/2004 |
| WO | 2005/021064 | A2 | 3/2005 |
| WO | 2007/044323 | A2 | 4/2007 |
| WO | 2007/084737 | A2 | 7/2007 |
| WO | WO2008068048 | * | 6/2008 |
| WO | 2010/037395 | A2 | 4/2010 |
| WO | 2012/075037 | A1 | 6/2012 |
| WO | 2012/143379 | A1 | 10/2012 |
| WO | 2013/177062 | A2 | 11/2013 |
| WO | 2014/105810 | A1 | 7/2014 |
| WO | 2014/189973 | A2 | 11/2014 |
| WO | 2014/190305 | A2 | 11/2014 |
| WO | 2014/194282 | A2 | 12/2014 |
| WO | 2015/098989 | A1 | 12/2014 |
| WO | 2015/009961 | A1 | 1/2015 |
| WO | 2015/014884 | A1 | 2/2015 |
| WO | 2015/101588 | A1 | 7/2015 |
| WO | 2016/208695 | A1 | 12/2016 |
| WO | 2016/208696 | A1 | 12/2016 |
| WO | 2017/011580 | A2 | 1/2017 |
| WO | 2019/049967 | A1 | 3/2019 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*

Formica "5-Fluorouracil can cross brain-blood barrier and cause encephalopathy: should we expect the same from capecitabine? A case report on capecitabine-induced central neurotoxicity progressing to coma" Cancer Chem Pharma 58:276-278 (Year: 2006).*

Pardridge "Blood-brain barrier drug delivery of IgG fusion proteins with a transferrin receptor monoclonal antibody" Expert Opinion on Drug Delivery, 12:2, 207-222 (Year: 2014).*

Xie et al., "Transport of nerve growth factor encapsulated into liposomes across the blood-brain barrier: In vitro and in vivo studies," Journal of Controlled Release, 105: 106-119 (2005).

Ou et al., "High-Dose Enzyme Replacement Therapy in Murine Hurler Syndrome," Molecular Genetics and Metabolism (author manuscript), 111: 116-122 (2014).

Li et al., "Gentically engineered brain drug delivery vectors: cloning, expression and in vivo application of an anti-transferrin receptor single chain antibody-streptavidin fusion gene and protein," Protein Engineering, 12: 787-796 (1999).

Bien-Ly et al., "Transferrin receptor (TfR) trafficking determines brain uptake of TfR antibody affinity variants," Journal of Experimental Medicine, 211: 233-244 (2014).

Sade et al., "A Human Blood-Brain Barrier Transcytosis Assay Reveals Antibody Transcytosis Influenced by pH-Dependent Receptor Binding," PLOS One, 9: e96340 (2014).

Friden et al., "Characterization, Receptor Mapping and Blood-Brain Barrier Transcytosis of Antibodies to the Human Transferrin Receptor," Journal of Pharmacology and Experimental Therapeutics, 278: 1491-1498 (1996).

Pardridge, "Blood-brain barrier drug delivery of IgG fusion proteins with a transferrin receptor monoclonal antibody," Expert Opinion Drug Drug Delivery, 12:207-222 (2015).

International Search Report issued in corresponding International Patent Application No. PCT/JP2016/068738 dated Sep. 6, 2016.

International Preliminary Report on Patentability and Written Opinion issued in corresponding International Patent Application No. PCT/JP2016/068738 dated Dec. 26, 2017.

Partial Supplemental European Search Report issued in counterpart European Patent Application No. 16814464.0 dated Dec. 17, 2018.

Li et al., "The role of the transferrin-transferrin-receptor system in drug delivery and targeting," Trends in Pharmacological Sciences, 23: 206-209 (2002).

Helguera et al., "An Antibody Recognizing the Apical Domain of Human Transferrin Receptor 1 Efficiently Inhibits the Entry of All New World Hemorrhagic Fever Arenaviruses," Journal of Virology, 86: 4024-4028 (2012).

Qing et al., "The in vitro antitumor effect and in vivo tumor-specificity distribution of human-mouse chimeric antibody against transferrin receptor", Cancer Immunology Immunotherapy, 55: 1111-1121 (2006).

Tucker et al., "Drug delivery to the brain via the blood-brain barrier: a review of the literature and some recent patent disclosures," Therapeutic Delivery, 2: 311-327 (2011).

Extended European Search Report issued in counterpart European Patent Application No. 16814464.0 dated Mar. 25, 2019.

Niewoehner et al., "Increased Brain Penetration and Potency of a Therapeutic Antibody Using a Monovalent Molecular Shuttle," Neuron 81: 49-60 (2014).

Office Action issued in counterpart Singapore Patent Application No. 11201710734U dated Jan. 3, 2019.

Gosk et al, "Targeting Anti-Transferrin Receptor Antibody (OX26) and OX26-Conjugated Liposomes to Brain Capillary Endothelial Cells Using In Situ Perfusion," Journal of Cerebral Blood Flow & Metabolism, 24: 1193-1196 (2004).

Chao, "Neurotrophins and their receptors: a convergence point for many signalling pathways," Nature Reviews Neurosicence, 4: 299-309 (2003).

Tabakman et al., "Interactions between the cells of the immune and nervous system: neurotrophins as neuroprotection mediators in CNS injury," Progress in Brain Research, 146: 387-401 (2004).

Bollen et al., "7,8-Dihydroxyflavone improves memory consolidation processes in rats and mice," Behavioural Brain Research, 257: 8-12 (2013).

Altar et al., "Efficacy of brain-derived neurotrophic factor and neurotrophin-3 on neurochemical and behavioral deficits associated with partial nigrostriatal dopamine lesions," Journal of Neurochemistry, 63: 1021-1032 (1994).

Zuccato et al., "Role of brain-derived neurotrophic factor in Huntington's disease," Progress in Neurobiology, 81: 294-330 (2007).

Wu, "Neuroprotection in experimental stroke with targeted neurotrophins," The Journal of the American Society for Experimental Neurotherapeutics, 2: 120-128 (2005).

(56) References Cited

OTHER PUBLICATIONS

Katz, Brain-derived neurotrophic factor and Rett syndrome, The Handbook of Experimental Pharmacology, 220: 481-495 (2014).
Castren, "Neurotrophins and psychiatric disorders," The Handbook of Experimental Pharmacology, 220: 461-479 (2014).
Boado et al., "Genetic engineering, expression, and activity of a fusion protein of a human neurotrophin and a molecular Trojan horse for delivery across the human blood-brain barrier," Biotechnology and Bioengineering, 97: 1376-1386 (2007).
Zhou et al., "Monoclonal Antibody-Glial-Derived Neurotrophic Factor Fusion Protein Penetrates the Blood-Brain Barrier in the Mouse," Drug Metabolism and Disposition, 38: 566-572 (2010).
Wu et al., "Neuroprotection with noninvasive neurotrophin delivery to the brain," Proceedings of the National Academy of Sciences, 96: 254-259 (1999).
Pardridge et al., "Reengineering Biopharmaceuticals for Targeted Delivery Across the Blood-Brain Barrier," Methods in Enzymology, 503: 269-292 (2012).
Torres et al., "The immunoglobulin constant region contributes to affinity and specificity," Trends in Immunology 29: 91-97 (2007).
Yan et al., "Studies of the Expression and Biologic Activity of an Anti-transferrin Receptor ScFv-BDNF Fusion Protein," China Biotechnology, 26: 1-5 (2006) (see English abstract).
Extended European Search Report issued in counterpart European Patent Application No. 16814465.7 dated May 8, 2019.
Bowie et al., "Deciphering the Message in Protein Sequences: Tolerance to Amino Acid Substitutions," Science, 247: 1306-1310 (1990).
Pawson et al., "Assembly of Cell Regulatory Systems Through Protein Interaction Domains," Science, 300: 445-452 (2003).
Burgess et al., "Possible Dissociation of the Heparin-binding and Mitogenic Activities of the Heparin-binding (Acidic Fibroblast) Growth Factor-1 form its Receptor-binding Activities by Site-directed Mutagenesis of a Single Lysine Residue," Journal of Cell Biology, 111: 2129-2138 (1990).
Alaoui-Ismaili et al., "Design of second generation therapeutic recombinant bone morphogenetic proteins," Cytokine & Growth Factor Reviews, 20: 501-507 (2009).
Guo et al., "Protein tolerance to random amino acid change," PNAS, 101: 9205-9210 (2004).
Rudikoff et al., "Single amino acid substitution altering antigen-binding specificity," PNAS, 79: 1979-1983 (1982).
Holm et al., "Functional mapping and single chain construction of the anti-cytokeratin 8 monoclonal antibody TS1," Molecular Immunology, 44: 1075-1084 (2007).
Holmes et al., "Structural Consequences of Humanizing an Antibody," Journal of Immunology, 2192-2201 (1997).
MacCallum et al., "Antibody-antigen Interactions: Contact Analysis and Binding Site Topography," Journal of Molecular Biology, 262: 732-745 (1996).
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," Journal of Immunology, 169: 3076-3084 (2002).
Casset et al., "A peptide mimetic of an anti-CD4 monoclonal antibody by rational design," Biochemical and Biophysical Research Communications, 307: 198-205 (2003).
Vajdos et al., "Comprehensive Functional Maps of the Antigen-binding Site of an Anti-ErbB2 Antibody Obtained with Shotgun Scanning Mutagenesis," Journal of Molecular Biology, 320: 415-428 (2002).
Chen et al., "Selection and Analysis of an Optimized Anti-VEGF Antibody: Crystal Structure of an Affinity-matured Fab in Complex with Antigen," Journal of Molecular Biology, 293: 865-881 (1999).
Wu et al., "Humanization of a Murine Monoclonal Antibody by Simultaneous Optimization of Framework and CDR Residues," Journal of Molecular Biology, 294: 151-162 (1999).
Walus et al., "Enhanced Uptake of rsCD4 across the Rodent and Primate Blood-Brain Barrier after Conjugation to Anti-Transferrin Receptor Antibodies," Journal of Pharmacology and Experimental Therapeutics, 277: 1067-1075 (1996).
Zhou et al., "Delivery of a Peptide Radiopharmaceutical to Brain with an IgG-Avidin Fusion Protein," Bioconjugate Chemistry, 22: 1611-1618 (2011).
Boado et al., "Engineering and Expression of a Chimeric Transferrin Receptor Monoclonal Antibody for Blood-Brain Barrier Delivery in the Mouse," Biotechnology and Bioengineering, 102: 1251-1258 (2009).
International Search Report issued in corresponding International Patent Application No. PCT/JP2017/046735 dated Apr. 3, 2018.
International Preliminary Report on Patentability and Written Opinion issued in corresponding International Patent Application No. PCT/JP2017/046735 dated Jul. 11, 2019.
International Search Report issued in corresponding International Patent Application No. PCT/JP2016/068739 dated Sep. 6, 2016.
International Preliminary Report on Patentability and Written Opinion issued in corresponding International Patent Application No. PCT/JP2016/068739 dated Jan. 4, 2018.
International Search Report issued in corresponding International Patent Application No. PCT/JP2017/046762 dated Mar. 27, 2018.
International Preliminary Report on Patentability and Written Opinion issued in corresponding International Patent Application No. PCT/JP2017/046762 dated Jul. 11, 2019.
Extended European Search Report issued in European Patent Application No. 17889016.6 dated Jul. 15, 2020.
"Overview of the Immune System," Immunology: A Short Course, 7th ed., Richard Coico and Geoffrey Sunshine, 61-62 (2015).
Altshuler et al., "Generation of Recombinant Antibodies and Means for Increasing Their Affinity," Biochemistry (Moscow), 75 (13): 1584-1605 (2010). (Original Russian text: Uspekhi Biologicheskoi Khimii, 50: 203-258 (2010)).
Brown, et al., "Tolerance to Single, but Not Multiple, Amino Acid Replacements in Antibody VH CDR2," Journal of Immunology, 3286-3291 (1996).
Office Action issued in related Eurasian Patent Application No. 201991577 dated Feb. 26, 2021.
Zhou et al., "Brain-Penetrating IgG-Iduronate 2-Sulfatase Fusion Protein for the Mouse," Drug Metabolism and Disposition, 40 (2): 329-335 (2012).

* cited by examiner

SEQUENCE LISTING

<160> NUMBER OF SEQ ID NOS: 279

<210> SEQ ID NO 1
<211> LENGTH: 760
<212> TYPE: PRT
<213> ORGANISM: Homo sapiens

<400> SEQUENCE: 1

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Glu Asn Ala
        35                  40                  45

Asp Asn Asn Thr Lys Ala Asn Val Thr Lys Pro Lys Arg Cys Ser Gly
    50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Gly Thr Ile
    130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

```
Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
        355                 360                 365

Glu Ser Lys Asn Val Lys Leu Thr Val Ser Asn Val Leu Lys Glu Ile
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
```

```
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760


<210> SEQ ID NO 2
<211> LENGTH: 760
<212> TYPE: PRT
<213> ORGANISM: Macaca fascicularis

<400> SEQUENCE: 2

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Asp Glu Glu Asn Ala
        35                  40                  45

Asp Asn Asn Thr Lys Ala Asn Gly Thr Lys Pro Lys Arg Cys Gly Gly
    50                  55                  60

Asn Ile Cys Tyr Gly Thr Ile Ala Val Ile Ile Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Ala Arg Glu Glu Pro
            100                 105                 110

Glu Glu Asp Phe Pro Ala Ala Pro Arg Leu Tyr Trp Asp Asp Leu Lys
        115                 120                 125

Arg Lys Leu Ser Glu Lys Leu Asp Thr Thr Asp Phe Thr Ser Thr Ile
    130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Lys Ala Asp Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320

Phe Pro Pro Ser Gln Ser Ser Gly Leu Pro Asn Ile Pro Val Gln Thr
                325                 330                 335
```

-continued

```
Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Lys Met Val Thr Ser
        355                 360                 365

Glu Asn Lys Ser Val Lys Leu Thr Val Ser Asn Val Leu Lys Glu Thr
    370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Ser Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asp
            500                 505                 510

Val Lys His Pro Val Thr Gly Arg Ser Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Val Glu Arg Ile Pro Glu Leu Asn Lys Val Ala Arg Ala Ala Ala Glu
            580                 585                 590

Val Ala Gly Gln Phe Val Ile Lys Leu Thr His Asp Thr Glu Leu Asn
        595                 600                 605

Leu Asp Tyr Glu Arg Tyr Asn Ser Gln Leu Leu Leu Phe Leu Arg Asp
    610                 615                 620

Leu Asn Gln Tyr Arg Ala Asp Val Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Arg Asn Ala Glu Lys Arg Asp Lys Phe Val Met Lys
            660                 665                 670

Lys Leu Asn Asp Arg Val Met Arg Val Glu Tyr Tyr Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Ser Ala Leu Leu Glu Ser Leu Lys Leu Arg Arg
705                 710                 715                 720

Gln Asn Asn Ser Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
```

755 760

<210> SEQ ID NO 3
<211> LENGTH: 5
<212> TYPE: PRT
<213> ORGANISM: Artificial Sequence
<220> FEATURE:
<223> OTHER INFORMATION: Amino acid sequence of exemplified linker 1

<400> SEQUENCE: 3

Gly Gly Gly Gly Ser
1 5

<210> SEQ ID NO 4
<211> LENGTH: 6
<212> TYPE: PRT
<213> ORGANISM: Artificial Sequence
<220> FEATURE:
<223> OTHER INFORMATION: Amino acid sequence of exemplified linker 2

<400> SEQUENCE: 4

Gly Gly Gly Gly Gly Ser
1 5

<210> SEQ ID NO 5
<211> LENGTH: 5
<212> TYPE: PRT
<213> ORGANISM: Artificial Sequence
<220> FEATURE:
<223> OTHER INFORMATION: Amino acid sequence of exemplified linker 3

<400> SEQUENCE: 5

Ser Gly Gly Gly Gly
1 5

<210> SEQ ID NO 6
<211> LENGTH: 6
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.1

<400> SEQUENCE: 6

Gln Asp Val Asn Ser Ala
1 5

<210> SEQ ID NO 7
<211> LENGTH: 11
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.1

<400> SEQUENCE: 7

Lys Ala Ser Gln Asp Val Asn Ser Ala Val Ala
1 5 10

<210> SEQ ID NO 8
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.1

<400> SEQUENCE: 8

Trp Thr Ser Thr Arg His
1 5

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.1

<400> SEQUENCE: 9

Trp Thr Ser Thr Arg His Thr
1 5

<210> SEQ ID NO 10
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.1

<400> SEQUENCE: 10

Gln Gln His Tyr Ser Thr Pro Arg Thr
1 5

<210> SEQ ID NO 11
<211> LENGTH: 6
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.2

<400> SEQUENCE: 11

Gln Ser Ile Ser Asn Asn
1 5

<210> SEQ ID NO 12
<211> LENGTH: 11
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.2

<400> SEQUENCE: 12

Arg Ala Ser Gln Ser Ile Ser Asn Asn Leu Gln
1 5 10

<210> SEQ ID NO 13
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.2

<400> SEQUENCE: 13

Tyr Ala Ser Gln Ser Ile
1 5

<210> SEQ ID NO 14
<211> LENGTH: 7
<212> TYPE: PRT
<213> ORGANISM: Artificial Sequence

```
<220> FEATURE:
<223> OTHER INFORMATION: Amino acid sequence 2 of CDR 2 in the light
      chain of mouse anti-hTfR antibody No.2

<400> SEQUENCE: 14

Tyr Ala Ser Gln Ser Ile Ser
1               5


<210> SEQ ID NO 15
<211> LENGTH: 9
<212> TYPE: PRT
<213> ORGANISM: Artificial Sequence
<220> FEATURE:
<223> OTHER INFORMATION: Amino acid sequence of CDR 3 in the light
      chain of mouse anti-hTfR antibody No.2

<400> SEQUENCE: 15

Gln Gln Ser Asn Ser Trp Pro Arg Thr
1               5


<210> SEQ ID NO 16
<211> LENGTH: 11
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.3

<400> SEQUENCE: 16

Gln Ser Leu Val His Ser Asn Gly Asn Thr Tyr
1               5                   10


<210> SEQ ID NO 17
<211> LENGTH: 16
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.3

<400> SEQUENCE: 17

Arg Ser Ser Gln Ser Leu Val His Ser Asn Gly Asn Thr Tyr Leu His
1               5                   10                  15


<210> SEQ ID NO 18
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.3

<400> SEQUENCE: 18

Lys Val Ser Asn Arg Phe
1               5


<210> SEQ ID NO 19
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.3

<400> SEQUENCE: 19

Lys Val Ser Asn Arg Phe Ser
1               5
```

<210> SEQ ID NO 20
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.3

<400> SEQUENCE: 20

Ser Gln Ser Thr His Val Pro Trp Thr
1 5

<210> SEQ ID NO 21
<211> LENGTH: 5
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.4

<400> SEQUENCE: 21

Ser Asn Val Asn Tyr
1 5

<210> SEQ ID NO 22
<211> LENGTH: 10
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.4

<400> SEQUENCE: 22

Ser Ala Ser Ser Asn Val Asn Tyr Met His
1 5 10

<210> SEQ ID NO 23
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.4

<400> SEQUENCE: 23

Asp Thr Ser Lys Leu Ala
1 5

<210> SEQ ID NO 24
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.4

<400> SEQUENCE: 24

Asp Thr Ser Lys Leu Ala Ser
1 5

<210> SEQ ID NO 25
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.4

<400> SEQUENCE: 25

Phe Gln Gly Asn Gly Asn Pro Tyr Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.5

<400> SEQUENCE: 26

Ser Ser Ile Ser Ser
1               5

<210> SEQ ID NO 27
<211> LENGTH: 10
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.5

<400> SEQUENCE: 27

Ser Ala Ser Ser Ser Ile Ser Ser Ile His
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.5

<400> SEQUENCE: 28

Asp Thr Ser Thr Leu Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.5

<400> SEQUENCE: 29

Asp Thr Ser Thr Leu Ala Ser
1               5

<210> SEQ ID NO 30
<211> LENGTH: 8
<212> TYPE: PRT
<213> ORGANISM: Artificial Sequence
<220> FEATURE:
<223> OTHER INFORMATION: Amino acid sequence of CDR 3 in the light
      chain of mouse anti-hTfR antibody No.5

<400> SEQUENCE: 30

His Gln Arg Ser Ser Tyr Pro Thr
1               5

<210> SEQ ID NO 31
<211> LENGTH: 6
<212> TYPE: PRT

```
<213> ORGANISM: Artificial Sequence
<220> FEATURE:
<223> OTHER INFORMATION: Amino acid sequence 1 of CDR 1 in the light
      chain of mouse anti-hTfR antibody No.6

<400> SEQUENCE: 31

Gln Glu Ile Ser Gly Tyr
1               5


<210> SEQ ID NO 32
<211> LENGTH: 11
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.6

<400> SEQUENCE: 32

Arg Ala Ser Gln Glu Ile Ser Gly Tyr Leu Ser
1               5                   10


<210> SEQ ID NO 33
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.6

<400> SEQUENCE: 33

Ala Ala Ser Thr Leu Asp
1               5


<210> SEQ ID NO 34
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.6

<400> SEQUENCE: 34

Ala Ala Ser Thr Leu Asp Ser
1               5


<210> SEQ ID NO 35
<211> LENGTH: 9
<212> TYPE: PRT
<213> ORGANISM: Artificial Sequence
<220> FEATURE:
<223> OTHER INFORMATION: Amino acid sequence of CDR 3 in the light
      chain of mouse anti-hTfR antibody No.6

<400> SEQUENCE: 35

Leu Gln Tyr Ser Ser Tyr Pro Arg Thr
1               5


<210> SEQ ID NO 36
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.7

<400> SEQUENCE: 36

Ser Ser Val Asn Tyr
1               5
```

<210> SEQ ID NO 37
<211> LENGTH: 10
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.7

<400> SEQUENCE: 37

Ser Ala Ser Ser Ser Val Asn Tyr Ile His
1 5 10

<210> SEQ ID NO 38
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.7

<400> SEQUENCE: 38

Gln Thr Ser Asn Leu Ala
1 5

<210> SEQ ID NO 39
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.7

<400> SEQUENCE: 39

Gln Thr Ser Asn Leu Ala Ser
1 5

<210> SEQ ID NO 40
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.7

<400> SEQUENCE: 40

His Gln Trp Ser Ser Tyr Pro Trp Thr
1 5

<210> SEQ ID NO 41
<211> LENGTH: 5
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.8

<400> SEQUENCE: 41

Ser Ser Val Ser Tyr
1 5

<210> SEQ ID NO 42
<211> LENGTH: 10
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.8

<400> SEQUENCE: 42

Ser Ala Ser Ser Ser Val Ser Tyr Met His
1 5 10

<210> SEQ ID NO 43
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.8

<400> SEQUENCE: 43

Gly Thr Ser Asn Leu Ala
1 5

<210> SEQ ID NO 44
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.8

<400> SEQUENCE: 44

Gly Thr Ser Asn Leu Ala Ser
1 5

<210> SEQ ID NO 45
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.8

<400> SEQUENCE: 45

His Gln Trp Ser Ser Tyr Pro Trp Thr
1 5

<210> SEQ ID NO 46
<211> LENGTH: 5
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.9

<400> SEQUENCE: 46

Ser Ser Val Ser Leu
1 5

<210> SEQ ID NO 47
<211> LENGTH: 10
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.9

<400> SEQUENCE: 47

Ser Ala Ser Ser Ser Val Ser Leu Met Phe
1 5 10

<210> SEQ ID NO 48
<211> LENGTH: 6

<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.9

<400> SEQUENCE: 48

Phe Thr Ser Tyr Arg Ala
1               5

<210> SEQ ID NO 49
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.9

<400> SEQUENCE: 49

Phe Thr Ser Tyr Arg Ala Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.9

<400> SEQUENCE: 50

Gln Gln Trp Thr Ser Asp Pro Pro Thr
1               5

<210> SEQ ID NO 51
<211> LENGTH: 6
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.10

<400> SEQUENCE: 51

Gln Glu Ile Ser Gly Tyr
1               5

<210> SEQ ID NO 52
<211> LENGTH: 11
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.10

<400> SEQUENCE: 52

Arg Pro Ser Gln Glu Ile Ser Gly Tyr Leu Ser
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.10

<400> SEQUENCE: 53

Ala Ala Ser Thr Leu Asp 1 5

<210> SEQ ID NO 54
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.10

<400> SEQUENCE: 54

Ala Ala Ser Thr Leu Asp Ser
1 5

<210> SEQ ID NO 55
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.10

<400> SEQUENCE: 55

Leu Gln Tyr Ala Ser Tyr Pro Arg Thr
1 5

<210> SEQ ID NO 56
<211> LENGTH: 6
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.11

<400> SEQUENCE: 56

Gln Ser Ile Arg Asn Tyr
1 5

<210> SEQ ID NO 57
<211> LENGTH: 11
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.11

<400> SEQUENCE: 57

Arg Ala Ser Gln Ser Ile Arg Asn Tyr Leu His
1 5 10

<210> SEQ ID NO 58
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.11

<400> SEQUENCE: 58

Tyr Ala Ser Gln Ser Ile
1 5

<210> SEQ ID NO 59
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.11

<400> SEQUENCE: 59

Tyr Ala Ser Gln Ser Ile Ser
1 5

<210> SEQ ID NO 60
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.11

<400> SEQUENCE: 60

Gln Gln Thr Asn Ser Trp Pro Tyr Thr
1 5

<210> SEQ ID NO 61
<211> LENGTH: 6
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.12

<400> SEQUENCE: 61

His Asp Val Lys Thr Ala
1 5

<210> SEQ ID NO 62
<211> LENGTH: 11
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.12

<400> SEQUENCE: 62

Lys Ala Ser His Asp Val Lys Thr Ala Val Ala
1 5 10

<210> SEQ ID NO 63
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.12

<400> SEQUENCE: 63

Trp Ser Ser Thr Arg His
1 5

<210> SEQ ID NO 64
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.12

<400> SEQUENCE: 64

Trp Ser Ser Thr Arg His Thr
1 5

<210> SEQ ID NO 65

<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.12

<400> SEQUENCE: 65

Gln Gln His Phe Ser Thr Pro Leu Thr
1 5

<210> SEQ ID NO 66
<211> LENGTH: 6
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.13

<400> SEQUENCE: 66

Gln Ser Ile Arg Asn Tyr
1 5

<210> SEQ ID NO 67
<211> LENGTH: 11
<212> TYPE: PRT
<213> ORGANISM: Artificial Sequence
<220> FEATURE:
<223> OTHER INFORMATION: Amino acid sequence 2 of CDR 1 in the light chain of mouse anti-hTfR antibody No.13

<400> SEQUENCE: 67

Arg Ala Ser Gln Ser Ile Arg Asn Tyr Leu His
1 5 10

<210> SEQ ID NO 68
<211> LENGTH: 6
<212> TYPE: PRT
<213> ORGANISM: Artificial Sequence
<220> FEATURE:
<223> OTHER INFORMATION: Amino acid sequence 1 of CDR 2 in the light chain of mouse anti-hTfR antibody No.13

<400> SEQUENCE: 68

Tyr Ala Ser Gln Ser Ile
1 5

<210> SEQ ID NO 69
<211> LENGTH: 7
<212> TYPE: PRT
<213> ORGANISM: Artificial Sequence
<220> FEATURE:
<223> OTHER INFORMATION: Amino acid sequence 2 of CDR 2 in the light chain of mouse anti-hTfR antibody No.13

<400> SEQUENCE: 69

Tyr Ala Ser Gln Ser Ile Ser
1 5

<210> SEQ ID NO 70
<211> LENGTH: 9
<212> TYPE: PRT
<213> ORGANISM: Artificial Sequence
<220> FEATURE:
<223> OTHER INFORMATION: Amino acid sequence of CDR 3 in the light chain of mouse anti-hTfR antibody No.13

<400> SEQUENCE: 70

```
Gln Gln Thr Asn Ser Trp Pro Tyr Thr
1               5


<210> SEQ ID NO 71
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.14

<400> SEQUENCE: 71

Ser Asn Ile Asn Ser
1               5


<210> SEQ ID NO 72
<211> LENGTH: 10
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.14

<400> SEQUENCE: 72

Ser Ala Ser Ser Asn Ile Asn Ser Ile His
1               5                   10


<210> SEQ ID NO 73
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.14

<400> SEQUENCE: 73

Asp Thr Ser Asn Leu Ala
1               5


<210> SEQ ID NO 74
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.14

<400> SEQUENCE: 74

Asp Thr Ser Asn Leu Ala Ser
1               5


<210> SEQ ID NO 75
<211> LENGTH: 9
<212> TYPE: PRT
<213> ORGANISM: Artificial Sequence
<220> FEATURE:
<223> OTHER INFORMATION: Amino acid sequence of CDR 3 in the light
      chain of mouse anti-hTfR antibody No.14

<400> SEQUENCE: 75

His Gln Arg Ser Gly Tyr Pro Phe Thr
1               5


<210> SEQ ID NO 76
<211> LENGTH: 5
<212> TYPE: PRT
<213> ORGANISM: Artificial Sequence
<220> FEATURE:
```

<223> OTHER INFORMATION: Amino acid sequence 1 of CDR 1 in the heavy chain of mouse anti-hTfR antibody No.1

<400> SEQUENCE: 76

Asn Tyr Gly Met Ser
1               5

<210> SEQ ID NO 77
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.1

<400> SEQUENCE: 77

Gly Leu Thr Phe Ser Asn Tyr Gly
1               5

<210> SEQ ID NO 78
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.1

<400> SEQUENCE: 78

Ile Asn Thr Asn Gly Gly Ser Thr
1               5

<210> SEQ ID NO 79
<211> LENGTH: 17
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.1

<400> SEQUENCE: 79

Asn Ile Asn Thr Asn Gly Gly Ser Thr Tyr Tyr Pro Asp Ser Val Lys
1               5                   10                  15

Gly

<210> SEQ ID NO 80
<211> LENGTH: 7
<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.1

<400> SEQUENCE: 80

Asn Arg Tyr Asp Glu Asp Tyr
1               5

<210> SEQ ID NO 81
<211> LENGTH: 9
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.1

<400> SEQUENCE: 81

Thr Asn Asn Arg Tyr Asp Glu Asp Tyr
1               5

-continued

```
<210> SEQ ID NO 82
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.2

<400> SEQUENCE: 82

Asp Tyr Val Met His
1               5


<210> SEQ ID NO 83
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.2

<400> SEQUENCE: 83

Gly Tyr Thr Phe Thr Asp Tyr Val
1               5


<210> SEQ ID NO 84
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.2

<400> SEQUENCE: 84

Ile Ser Thr Tyr Tyr Gly His Gly
1               5


<210> SEQ ID NO 85
<211> LENGTH: 17
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.2

<400> SEQUENCE: 85

Val Ile Ser Thr Tyr Tyr Gly His Gly Ser Tyr Asn Gln Arg Phe Lys
1               5                   10                  15

Gly


<210> SEQ ID NO 86
<211> LENGTH: 14
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.2

<400> SEQUENCE: 86

Gly Gly Tyr Gly Ser Ser Ser Leu Ala Gly Asn Phe Asp Val
1               5                   10


<210> SEQ ID NO 87
<211> LENGTH: 16
<212> TYPE: PRT
<213> ORGANISM: Artificial Sequence
<220> FEATURE:
```

<223> OTHER INFORMATION: Amino acid sequence 2 of CDR 3 in the heavy
      chain of mouse anti-hTfR antibody No.2

<400> SEQUENCE: 87

Val Arg Gly Gly Tyr Gly Ser Ser Ser Leu Ala Gly Asn Phe Asp Val
1               5                   10                  15

<210> SEQ ID NO 88
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.3

<400> SEQUENCE: 88

Asn Tyr Trp Leu Gly
1               5

<210> SEQ ID NO 89
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.3

<400> SEQUENCE: 89

Gly Tyr Ser Phe Thr Asn Tyr Trp
1               5

<210> SEQ ID NO 90
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.3

<400> SEQUENCE: 90

Ile Tyr Pro Gly Gly Asp Tyr Pro
1               5

<210> SEQ ID NO 91
<211> LENGTH: 17
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.3

<400> SEQUENCE: 91

Asp Ile Tyr Pro Gly Gly Asp Tyr Pro Thr Tyr Ser Glu Lys Phe Lys
1               5                   10                  15

Val

<210> SEQ ID NO 92
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.3

<400> SEQUENCE: 92

Ser Gly Asn Tyr Asp Glu Val Ala Tyr
1               5

<210> SEQ ID NO 93
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.3

<400> SEQUENCE: 93

Ala Arg Ser Gly Asn Tyr Asp Glu Val Ala Tyr
1 5 10

<210> SEQ ID NO 94
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.4

<400> SEQUENCE: 94

Asn Tyr Leu Ile Glu
1 5

<210> SEQ ID NO 95
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.4

<400> SEQUENCE: 95

Gly Tyr Ala Phe Thr Asn Tyr Leu
1 5

<210> SEQ ID NO 96
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.4

<400> SEQUENCE: 96

Ile Asn Pro Gly Ser Gly Gly Ile
1 5

<210> SEQ ID NO 97
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.4

<400> SEQUENCE: 97

Ile Asn Pro Gly Ser Gly Gly Ile Ile Tyr Asn Glu Lys Phe Thr Asp
1 5 10 15

<210> SEQ ID NO 98
<211> LENGTH: 13
<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.4

<400> SEQUENCE: 98

Ser Asn Tyr Tyr Gly Thr Thr Tyr Trp His Phe Asp Val
1 5 10

<210> SEQ ID NO 99
<211> LENGTH: 15
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.4

<400> SEQUENCE: 99

Ala Arg Ser Asn Tyr Tyr Gly Thr Thr Tyr Trp His Phe Asp Val
1 5 10 15

<210> SEQ ID NO 100
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.5

<400> SEQUENCE: 100

Asn Phe Val Ile His
1 5

<210> SEQ ID NO 101
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.5

<400> SEQUENCE: 101

Gly Tyr Thr Phe Thr Asn Phe Val
1 5

<210> SEQ ID NO 102
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.5

<400> SEQUENCE: 102

Phe Asn Pro His Lys Asn Gly Ala
1 5

<210> SEQ ID NO 103
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.5

<400> SEQUENCE: 103

Phe Asn Pro His Lys Asn Gly Ala Glu Tyr Asn Glu Lys Phe Gln Val
1 5 10 15

<210> SEQ ID NO 104
<211> LENGTH: 9

<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.5

<400> SEQUENCE: 104

Ser Phe Tyr Tyr Tyr Ser Met Asp Tyr
1 5

<210> SEQ ID NO 105
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.5

<400> SEQUENCE: 105

Ala Arg Ser Phe Tyr Tyr Tyr Ser Met Asp Tyr
1 5 10

<210> SEQ ID NO 106
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.6

<400> SEQUENCE: 106

Thr Tyr Gly Val Tyr
1 5

<210> SEQ ID NO 107
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.6

<400> SEQUENCE: 107

Gly Phe Ser Leu Ser Thr Tyr Gly
1 5

<210> SEQ ID NO 108
<211> LENGTH: 7
<212> TYPE: PRT
<213> ORGANISM: Artificial Sequence
<220> FEATURE:
<223> OTHER INFORMATION: Amino acid sequence of CDR 2 in the heavy chain of mouse anti-hTfR antibody No.6

<400> SEQUENCE: 108

Ile Trp Gly Asp Gly Ser Thr
1 5

<210> SEQ ID NO 109
<211> LENGTH: 4
<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.6

<400> SEQUENCE: 109

Pro Asp Asp Val

1

<210> SEQ ID NO 110
<211> LENGTH: 6
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.6

<400> SEQUENCE: 110

Ala Lys Pro Asp Asp Val
1 5

<210> SEQ ID NO 111
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.7

<400> SEQUENCE: 111

Asn Tyr Phe Met Ser
1 5

<210> SEQ ID NO 112
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.7

<400> SEQUENCE: 112

Gly Ile Thr Phe Arg Asn Tyr Phe
1 5

<210> SEQ ID NO 113
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.7

<400> SEQUENCE: 113

Ile Ser Ser Ala Gly Gly Tyr Thr
1 5

<210> SEQ ID NO 114
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.7

<400> SEQUENCE: 114

Ile Ser Ser Ala Gly Gly Tyr Thr Tyr Tyr Ala Asp Ser Val Lys Gly
1 5 10 15

<210> SEQ ID NO 115
<211> LENGTH: 11
<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.7

<400> SEQUENCE: 115

Gln Glu Val Pro Tyr Pro Tyr Ala Met Asp Tyr
1 5 10

<210> SEQ ID NO 116
<211> LENGTH: 13
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.7

<400> SEQUENCE: 116

Ala Arg Gln Glu Val Pro Tyr Pro Tyr Ala Met Asp Tyr
1 5 10

<210> SEQ ID NO 117
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.8

<400> SEQUENCE: 117

Thr Tyr Gly Val Ser
1 5

<210> SEQ ID NO 118
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.8

<400> SEQUENCE: 118

Gly Phe Ser Leu Thr Thr Tyr Gly
1 5

<210> SEQ ID NO 119
<211> LENGTH: 7
<212> TYPE: PRT
<213> ORGANISM: Artificial Sequence
<220> FEATURE:
<223> OTHER INFORMATION: Amino acid sequence of CDR 2 in the heavy chain of mouse anti-hTfR antibody No.8

<400> SEQUENCE: 119

Ile Trp Gly Asp Gly Ser Thr
1 5

<210> SEQ ID NO 120
<211> LENGTH: 4
<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.8

<400> SEQUENCE: 120

Pro Asp Asp Tyr
1

<210> SEQ ID NO 121

<211> LENGTH: 6
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.8

<400> SEQUENCE: 121

Ala Lys Pro Asp Asp Tyr
1 5

<210> SEQ ID NO 122
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.9

<400> SEQUENCE: 122

Asn Tyr Gly Val Ser
1 5

<210> SEQ ID NO 123
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.9

<400> SEQUENCE: 123

Gly Tyr Thr Phe Thr Asn Tyr Gly
1 5

<210> SEQ ID NO 124
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.9

<400> SEQUENCE: 124

Ile Tyr Thr Phe Thr Gly Glu Ala
1 5

<210> SEQ ID NO 125
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.9

<400> SEQUENCE: 125

Ile Tyr Thr Phe Thr Gly Glu Ala Thr Tyr Ile Asp Asp Phe Arg Gly
1 5 10 15

<210> SEQ ID NO 126
<211> LENGTH: 8
<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.9

<400> SEQUENCE: 126

Arg Asn Gly Ala Trp Phe Glu Asp
1 5

<210> SEQ ID NO 127
<211> LENGTH: 10
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.9

<400> SEQUENCE: 127

Ser Arg Arg Asn Gly Ala Trp Phe Glu Asp
1 5 10

<210> SEQ ID NO 128
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.10

<400> SEQUENCE: 128

Asn Tyr Ala Met Ser
1 5

<210> SEQ ID NO 129
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.10

<400> SEQUENCE: 129

Gly Ile Thr Phe Arg Asn Tyr Ala
1 5

<210> SEQ ID NO 130
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.10

<400> SEQUENCE: 130

Ile Ser Ser Tyr Gly Gly Tyr Thr
1 5

<210> SEQ ID NO 131
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.10

<400> SEQUENCE: 131

Ile Ser Ser Tyr Gly Gly Tyr Thr Tyr Tyr Ala Asp Ser Val Lys Gly
1 5 10 15

<210> SEQ ID NO 132
<211> LENGTH: 11
<212> TYPE: PRT
<213> ORGANISM: Artificial Sequence
<220> FEATURE:

<223> OTHER INFORMATION: Amino acid sequence 1 of CDR 3 in the heavy chain of mouse anti-hTfR antibody No.10

<400> SEQUENCE: 132

Gln Glu Val Pro Tyr Pro Tyr Pro Met Asp Asn
1 5 10

<210> SEQ ID NO 133
<211> LENGTH: 13
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.10

<400> SEQUENCE: 133

Ala Arg Gln Glu Val Pro Tyr Pro Tyr Pro Met Asp Asn
1 5 10

<210> SEQ ID NO 134
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.11

<400> SEQUENCE: 134

Ile Tyr Trp Ile Asn
1 5

<210> SEQ ID NO 135
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.11

<400> SEQUENCE: 135

Gly Tyr Ala Phe Ser Ile Tyr Trp
1 5

<210> SEQ ID NO 136
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.11

<400> SEQUENCE: 136

Ile Tyr Pro Gly Asn Gly Asp Thr
1 5

<210> SEQ ID NO 137
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.11

<400> SEQUENCE: 137

Ile Tyr Pro Gly Asn Gly Asp Thr Asn Tyr Asn Gly Lys Phe Lys Gly
1 5 10 15

<210> SEQ ID NO 138
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy
chain of mouse anti-hTfR antibody No.11

<400> SEQUENCE: 138

Trp Gly Asp Asp Tyr Ala Met Asp Phe
1               5

<210> SEQ ID NO 139
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy
chain of mouse anti-hTfR antibody No.11

<400> SEQUENCE: 139

Gly Arg Trp Gly Asp Asp Tyr Ala Met Asp Phe
1               5                   10

<210> SEQ ID NO 140
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
chain of mouse anti-hTfR antibody No.12

<400> SEQUENCE: 140

Asn Tyr Leu Ile Glu
1               5

<210> SEQ ID NO 141
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
chain of mouse anti-hTfR antibody No.12

<400> SEQUENCE: 141

Gly Tyr Val Phe Ile Asn Tyr Leu
1               5

<210> SEQ ID NO 142
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
chain of mouse anti-hTfR antibody No.12

<400> SEQUENCE: 142

Ile His Ser Gly Ser Gly Gly Thr
1               5

<210> SEQ ID NO 143
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
chain of mouse anti-hTfR antibody No.12

<400> SEQUENCE: 143

Ile His Ser Gly Ser Gly Gly Thr Asn Tyr Asn Asp Asn Phe Lys Asp
1               5                   10                  15

<210> SEQ ID NO 144
<211> LENGTH: 10
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.12

<400> SEQUENCE: 144

Arg Asn Phe Gly Asn Tyr Tyr Phe Asp Tyr
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.12

<400> SEQUENCE: 145

Ala Arg Arg Asn Phe Gly Asn Tyr Tyr Phe Asp Tyr
1               5                   10

<210> SEQ ID NO 146
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.13

<400> SEQUENCE: 146

Ile Tyr Trp Ile Asn
1               5

<210> SEQ ID NO 147
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.13

<400> SEQUENCE: 147

Gly Tyr Ala Phe Ser Ile Tyr Trp
1               5

<210> SEQ ID NO 148
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.13

<400> SEQUENCE: 148

Ile Tyr Pro Gly Asn Gly Asp Thr
1               5

<210> SEQ ID NO 149
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy chain of mouse anti-hTfR antibody No.13

<400> SEQUENCE: 149

Ile Tyr Pro Gly Asn Gly Asp Thr Asn Tyr Asn Gly Lys Phe Lys Gly
1 5 10 15

<210> SEQ ID NO 150
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy chain of mouse anti-hTfR antibody No.13

<400> SEQUENCE: 150

Trp Gly Asp Asp Tyr Ala Met Asp Phe
1 5

<210> SEQ ID NO 151
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy chain of mouse anti-hTfR antibody No.13

<400> SEQUENCE: 151

Gly Arg Trp Gly Asp Asp Tyr Ala Met Asp Phe
1 5 10

<210> SEQ ID NO 152
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy chain of mouse anti-hTfR antibody No.14

<400> SEQUENCE: 152

Gly Tyr Val Ile His
1 5

<210> SEQ ID NO 153
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy chain of mouse anti-hTfR antibody No.14

<400> SEQUENCE: 153

Gly Tyr Ala Phe Thr Gly Tyr Val
1 5

<210> SEQ ID NO 154
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy chain of mouse anti-hTfR antibody No.14

<400> SEQUENCE: 154

Leu Asn Pro His Lys Asp Asp Ser
1 5

```
<210> SEQ ID NO 155
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.14

<400> SEQUENCE: 155

Leu Asn Pro His Lys Asp Asp Ser Glu Tyr Asn Glu Lys Phe Arg Gly
1               5                   10                  15


<210> SEQ ID NO 156
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.14

<400> SEQUENCE: 156

Gly Tyr Tyr Tyr Tyr Ser Met Asp Tyr
1               5


<210> SEQ ID NO 157
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.14

<400> SEQUENCE: 157

Ala Arg Gly Tyr Tyr Tyr Tyr Ser Met Asp Tyr
1               5                   10


<210> SEQ ID NO 158
<211> LENGTH: 107
<212> TYPE: PRT
<213> ORGANISM: Artificial Sequence
<220> FEATURE:
<223> OTHER INFORMATION: Amino acid sequence 1 of the variable region of
      light chain of humanized anti-hTfR antibody No.1

<400> SEQUENCE: 158

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Asn Ser Ala
            20                  25                  30

Val Ala Trp Tyr Gln Gln Lys Pro Gly Gln Pro Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ser Thr Pro Arg
                85                  90                  95

Thr Phe Gly Gly Gly Thr Lys Leu Glu Ile Lys
            100                 105


<210> SEQ ID NO 159
<211> LENGTH: 107
<212> TYPE: PRT
<213> ORGANISM: Artificial Sequence
```

<220> FEATURE:
<223> OTHER INFORMATION: Amino acid sequence 2 of the variable region of light chain of humanized anti-hTfR antibody No.1

<400> SEQUENCE: 159

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Leu
        35                  40                  45

Tyr Trp Thr Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys
            100                 105
```

<210> SEQ ID NO 160
<211> LENGTH: 107
<212> TYPE: PRT
<213> ORGANISM: Artificial Sequence
<220> FEATURE:
<223> OTHER INFORMATION: Amino acid sequence 3 of the variable region of light chain of humanized anti-hTfR antibody No.1

<400> SEQUENCE: 160

```
Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys
            100                 105
```

<210> SEQ ID NO 161
<211> LENGTH: 107
<212> TYPE: PRT
<213> ORGANISM: Artificial Sequence
<220> FEATURE:
<223> OTHER INFORMATION: Amino acid sequence 4 of the variable region of light chain of humanized anti-hTfR antibody No.1

<400> SEQUENCE: 161

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Ile
        35                  40                  45
```

```
Tyr Trp Thr Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys
            100                 105


<210> SEQ ID NO 162
<211> LENGTH: 107
<212> TYPE: PRT
<213> ORGANISM: Artificial Sequence
<220> FEATURE:
<223> OTHER INFORMATION: Amino acid sequence 5 of the variable region of
      light chain of humanized anti-hTfR antibody No.1

<400> SEQUENCE: 162

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gln Gly Thr Lys Val Glu Ile Lys
            100                 105


<210> SEQ ID NO 163
<211> LENGTH: 107
<212> TYPE: PRT
<213> ORGANISM: Artificial Sequence
<220> FEATURE:
<223> OTHER INFORMATION: Amino acid sequence 6 of the variable region of
      light chain of humanized anti-hTfR antibody No.1

<400> SEQUENCE: 163

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gln Gly Thr Lys Val Glu Ile Lys
            100                 105


<210> SEQ ID NO 164
<211> LENGTH: 214
```

<212> TYPE: PRT
<213> ORGANISM: Artificial Sequence
<220> FEATURE:
<223> OTHER INFORMATION: Amino acid sequence of the light chain of humanized anti-hTfR antibody No.1 containing amino acid sequence 6 as the variable region

<400> SEQUENCE: 164

```
Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Phe Gln Gln Lys Pro Gly Lys Ala Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Val Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 165
<211> LENGTH: 725
<212> TYPE: DNA
<213> ORGANISM: Artificial Sequence
<220> FEATURE:
<223> OTHER INFORMATION: Nucleotide sequence encoding the amino acid sequence of the light chain of humanized anti-hTfR antibody No.1 containing amino acid sequence 6 as the variable region, synthetic sequence

<400> SEQUENCE: 165

```
acgcgtgccg ccaccatggg ctggagctgg attctgctgt tcctcctgag cgtgacagca     60

ggagtgcaca gcgacatcca ggtcacacag tcaccaagtt ttctgagcgc aagcgtgggc    120

gacagggtca ctatcacatg caaggcaagc caggacgtga actccgcagt ggcctggttc    180

cagcagaagc cagggaaagc acccaagctg ctgatctatt ggacctctac aaggcacacc    240

ggtgtcccag atcggttctc aggttccggc agcggaacag tgtatactct gaccatttcc    300

agcctgcagc ctgaagactt cgctacttac tattgccagc agcattactc caccccaaga    360

acatttggcg gagggactaa agtggagatc aagaggaccg tggccgctcc ctccgtcttc    420

atttttcccc ctagcgacga acagctgaag agtggcacag cctcagtggt ctgtctgctg    480
```

```
aacaatttct accctaggga ggctaaagtg cagtggaagg tcgataacgc actgcagtct    540

ggaaatagtc aggagtcagt gacagaacag gactccaaag atagcactta ttctctgtct    600

agtacactga ctctgagcaa ggccgattac gaaaagcaca aagtgtatgc ttgcgaagtc    660

acccatcagg ggctgtcatc accagtcacc aagtcattca atagaggcga gtgctaagcg    720

gccgc                                                                725
```

<210> SEQ ID NO 166
<211> LENGTH: 116
<212> TYPE: PRT
<213> ORGANISM: Artificial Sequence
<220> FEATURE:
<223> OTHER INFORMATION: Amino acid sequence 1 of the variable region of the heavy chain of humanized anti-hTfR antibody No.1

<400> SEQUENCE: 166

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Asn Ile Asn Thr Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Tyr Asp Glu Asp Tyr Trp Gly Gln Gly Thr Leu Val
            100                 105                 110

Thr Val Ser Ser
        115
```

<210> SEQ ID NO 167
<211> LENGTH: 116
<212> TYPE: PRT
<213> ORGANISM: Artificial Sequence
<220> FEATURE:
<223> OTHER INFORMATION: Amino acid sequence 2 of the variable region of the heavy chain of humanized anti-hTfR antibody No.1

<400> SEQUENCE: 167

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Asn Ile Asn Thr Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Tyr Asp Glu Asp Tyr Trp Gly Gln Gly Thr Leu Val
            100                 105                 110

Thr Val Ser Ser
```

115

<210> SEQ ID NO 168
<211> LENGTH: 116
<212> TYPE: PRT
<213> ORGANISM: Artificial Sequence
<220> FEATURE:
<223> OTHER INFORMATION: Amino acid sequence 3 of the variable region of the heavy chain of humanized anti-hTfR antibody No.1

<400> SEQUENCE: 168

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Gly Met Ser Trp Val Arg Gln Ala Pro Gly Lys Gly Leu Glu Tyr Val
        35                  40                  45

Ser Asn Ile Asn Thr Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Lys Asn Arg Tyr Asp Glu Asp Tyr Trp Gly Gln Gly Thr Leu Val
            100                 105                 110

Thr Val Ser Ser
        115
```

<210> SEQ ID NO 169
<211> LENGTH: 116
<212> TYPE: PRT
<213> ORGANISM: Artificial Sequence
<220> FEATURE:
<223> OTHER INFORMATION: Amino acid sequence 4 of the variable region of the heavy chain of humanized anti-hTfR antibody No.1

<400> SEQUENCE: 169

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Arg Tyr Asp Glu Asp Tyr Trp Gly Gln Gly Thr Leu Val
            100                 105                 110

Thr Val Ser Ser
        115
```

<210> SEQ ID NO 170
<211> LENGTH: 116
<212> TYPE: PRT
<213> ORGANISM: Artificial Sequence
<220> FEATURE:
<223> OTHER INFORMATION: Amino acid sequence 5 of the variable region of the heavy chain of humanized anti-hTfR antibody No.1

<400> SEQUENCE: 170

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gly Met Ser Trp Val Arg Gln Ala Pro Gly Lys Gly Leu Val Trp Val
35 40 45

Ser Asn Ile Asn Thr Asn Gly Gly Ser Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Arg Tyr Asp Glu Asp Tyr Trp Gly Gln Gly Thr Leu Val
100 105 110

Thr Val Ser Ser
115

<210> SEQ ID NO 171
<211> LENGTH: 116
<212> TYPE: PRT
<213> ORGANISM: Artificial Sequence
<220> FEATURE:
<223> OTHER INFORMATION: Amino acid sequence 6 of the variable region of
the heavy chain of humanized anti-hTfR antibody No.1

<400> SEQUENCE: 171

Glu Val Gln Leu Val Glu Ser Gly Gly Gly Leu Val Gln Pro Gly Gly
1 5 10 15

Ser Leu Arg Leu Ser Cys Ala Ala Ser Gly Leu Thr Phe Ser Asn Tyr
20 25 30

Gly Met Ser Trp Val Arg Gln Ala Pro Gly Lys Gly Leu Glu Leu Val
35 40 45

Ala Asn Ile Asn Thr Asn Gly Gly Ser Thr Tyr Tyr Pro Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Thr Asn Asn Arg Tyr Asp Glu Asp Tyr Trp Gly Gln Gly Thr Leu Val
100 105 110

Thr Val Ser Ser
115

<210> SEQ ID NO 172
<211> LENGTH: 446
<212> TYPE: PRT
<213> ORGANISM: Artificial Sequence
<220> FEATURE:
<223> OTHER INFORMATION: Amino acid sequence of the heavy chain of
humanized anti-hTfR antibody No.1 containing amino acid sequence 6
as the variable region

<400> SEQUENCE: 172

Glu Val Gln Leu Val Glu Ser Gly Gly Gly Leu Val Gln Pro Gly Gly
1 5 10 15

Ser Leu Arg Leu Ser Cys Ala Ala Ser Gly Leu Thr Phe Ser Asn Tyr

```
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445
```

<210> SEQ ID NO 173
<211> LENGTH: 1421
<212> TYPE: DNA
<213> ORGANISM: Artificial Sequence
<220> FEATURE:
<223> OTHER INFORMATION: Nucleotide sequence encoding the amino acid sequence of the heavy chain of humanized anti-hTfR antibody No.1 containing amino acid sequence 6 as the variable region, synthetic sequence

<400> SEQUENCE: 173
acgcgtgccg ccaccatggg ctggagctgg attctgctgt tcctcctgag cgtgacagca 60
ggagtgcaca gcgaagtgca gctggtcgaa tcaggggggg ggctggtgca gcctggaggc 120
agcctgagac tgtcctgcgc cgcttctggc ttgaccttta gcaactacgg gatgtcctgg 180
gtgcggcagg ctcctggcaa gggactggag ttggtggcca acatcaatac caacggcgga 240
agtacatact atcccgattc agtgaagggc cggttcacca tcagcaggga caacgccaag 300
aacagcctgt atctgcagat gaactctctg agggccgagg atacagccgt gtactattgc 360
actaacaacc ggtacgacga ggactattgg ggccagggca ccctggtgac agtgtctagc 420
gcctctacca agggcccaag cgtgtttcct ctggctccat cctctaaatc cacctctggc 480
ggcacagccg ctctgggctg tctggtgaag gattacttcc cagagcccgt gacagtgtct 540
tggaacagcg gcgccctgac ctccggcgtg cacacatttc ctgctgtgct gcagagctcc 600
ggcctgtaca gcctgtctag cgtggtgacc gtgccatcct ctagcctggg cacccagaca 660
tatatctgca acgtgaatca caagcccagc aatacaaagg tggataagaa ggtggagcca 720
aagtcctgtg acaagaccca cacatgcccc ccttgtcctg ctccagagct gctgggagga 780
ccaagcgtgt tcctgtttcc acccaagccc aaggataccc tgatgatctc tcggacccca 840
gaggtgacat gcgtggtggt ggatgtgagc cacgaggacc ccgaggtgaa gttcaactgg 900
tatgtggacg gcgtggaggt gcacaatgct aagaccaagc ccagggagga gcagtacaac 960
tccacctata gagtggtgtc tgtgctgaca gtgctgcacc aggattggct gaacggcaag 1020
gagtataagt gcaaggtgtc caataaggcc ctgcccgctc ctatcgagaa gaccatctct 1080
aaggccaagg gccagcccag agagcctcag gtgtacacac tgcctccatc ccgggatgag 1140
ctgaccaaga accaggtgtc tctgacatgt ctggtcaagg gcttctatcc ctctgacatc 1200
gccgtggagt gggagagcaa tggccagcct gagaacaatt acaagaccac accccctgtg 1260
ctggattccg acggctcttt ctttctgtat agcaagctga ccgtggacaa gtcccggtgg 1320
cagcagggca acgtgttcag ctgttccgtg atgcacgaag ctctgcataa tcactatact 1380
cagaaatccc tgtcactgtc acctggtaaa taagcggccg c 1421

<210> SEQ ID NO 174
<211> LENGTH: 107
<212> TYPE: PRT
<213> ORGANISM: Artificial Sequence
<220> FEATURE:
<223> OTHER INFORMATION: Amino acid sequence 1 of the variable region of the light chain of humanized anti-hTfR antibody No.2

<400> SEQUENCE: 174

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Ile Ser Asn Asn
20 25 30

-continued

```
Leu Gln Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Trp Pro Arg
                85                  90                  95

Thr Phe Gly Gln Gly Thr Lys Val Asp Ile Lys
            100                 105


<210> SEQ ID NO 175
<211> LENGTH: 107
<212> TYPE: PRT
<213> ORGANISM: Artificial Sequence
<220> FEATURE:
<223> OTHER INFORMATION: Amino acid sequence 2 of the variable region of
      the light chain of humanized anti-hTfR antibody No.2

<400> SEQUENCE: 175

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu Gln Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Arg
                85                  90                  95

Thr Phe Gly Gly Gly Thr Lys Val Glu Ile Lys
            100                 105


<210> SEQ ID NO 176
<211> LENGTH: 107
<212> TYPE: PRT
<213> ORGANISM: Artificial Sequence
<220> FEATURE:
<223> OTHER INFORMATION: Amino acid sequence 3 of the variable region of
      the light chain of humanized anti-hTfR antibody No.2

<400> SEQUENCE: 176

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
            20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Ser Trp Pro Arg
                85                  90                  95

Thr Phe Gly Gln Gly Thr Lys Val Glu Ile Lys
            100                 105
```

<210> SEQ ID NO 177
<211> LENGTH: 107
<212> TYPE: PRT
<213> ORGANISM: Artificial Sequence
<220> FEATURE:
<223> OTHER INFORMATION: Amino acid sequence 4 of the variable region of the light chain of humanized anti-hTfR antibody No.2

<400> SEQUENCE: 177

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
            20                  25                  30

Leu Gln Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Arg
                85                  90                  95

Thr Phe Gly Gln Gly Thr Lys Val Glu Ile Lys
            100                 105
```

<210> SEQ ID NO 178
<211> LENGTH: 107
<212> TYPE: PRT
<213> ORGANISM: Artificial Sequence
<220> FEATURE:
<223> OTHER INFORMATION: Amino acid sequence 5 of the variable region of the light chain of humanized anti-hTfR antibody No.2

<400> SEQUENCE: 178

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Gln Trp Tyr Gln Gln Lys Pro Gly Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Arg
                85                  90                  95

Thr Phe Gly Gly Gly Thr Lys Val Glu Ile Lys
            100                 105
```

<210> SEQ ID NO 179
<211> LENGTH: 107
<212> TYPE: PRT
<213> ORGANISM: Artificial Sequence
<220> FEATURE:
<223> OTHER INFORMATION: Amino acid sequence 6 of the variable region of the light chain of humanized anti-hTfR antibody No.2

<400> SEQUENCE: 179

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
```

```
            20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys
            100                 105


<210> SEQ ID NO 180
<211> LENGTH: 214
<212> TYPE: PRT
<213> ORGANISM: Artificial Sequence
<220> FEATURE:
<223> OTHER INFORMATION: Amino acid sequence of the light chain of
      humanized anti-hTfR antibody No.2 containing amino acid sequence 6
      as the variable region

<400> SEQUENCE: 180

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
            20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 181
<211> LENGTH: 725
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.2
```

containing amino acid sequence 6 as the variable region, synthetic sequence

<400> SEQUENCE: 181
acgcgtgccg ccaccatggg ctggagctgg attctgctgt tcctcctgag cgtgacagca 60
ggagtgcaca gcgaaattgt gctgacccag tctcccgatt tccagtccgt gacccccaag 120
gagaaagtca ccatcacatg cagagcatca cagtccatta gcaacaatct gcagtggtac 180
cagcagaagc cagaccagag ccccaagctg ctgatcaaat atgcctctca gagtatttca 240
ggcatacctt ctaggttctc cggtagcggc tctggaaccg actttactct gaccatcaac 300
agtctggagg ctgaagatgc cgctacatac ttgtgccagc agagtaattc atggcctagg 360
acctttggcc aggggacaaa ggtggagatc aaaaggactg tggcagcccc aagtgtcttc 420
atttttcccc cttcagacga acagctgaag agcggcacag catctgtggt ctgtctgctg 480
aacaatttct acccacggga ggctaaggtg cagtggaaag tcgataacgc actgcagtcc 540
ggaaatagcc aggagtctgt gactgaacag gacagtaagg attcaaccta ttccctgtcc 600
agcacactga ctctgagcaa agccgattac gagaagcaca aagtgtatgc ttgcgaagtc 660
acacatcagg ggctgtctag tcccgtgact aagtctttta ataggggtga atgttaagcg 720
gccgc 725

<210> SEQ ID NO 182
<211> LENGTH: 120
<212> TYPE: PRT
<213> ORGANISM: Artificial Sequence
<220> FEATURE:
<223> OTHER INFORMATION: Amino acid sequence 1 of the variable region of the heavy chain of humanized anti-hTfR antibody No.2

<400> SEQUENCE: 182

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Val Met His Trp Val Arg Gln Ala Pro Gly Gln Gly Leu Glu Trp Met
35 40 45

Gly Val Ile Ser Thr Tyr Tyr Gly His Gly Ser Tyr Asn Gln Arg Phe
50 55 60

Lys Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Gly Tyr Gly Ser Ser Ser Leu Ala Gly Asn Phe Asp Val
100 105 110

Trp Gly Gln Gly Thr Leu Val Thr
115 120

<210> SEQ ID NO 183
<211> LENGTH: 120
<212> TYPE: PRT
<213> ORGANISM: Artificial Sequence
<220> FEATURE:
<223> OTHER INFORMATION: Amino acid sequence 2 of the variable region of the heavy chain of humanized anti-hTfR antibody No.2

<400> SEQUENCE: 183

Gln Val Gln Leu Val Gln Ser Gly Ala Glu Val Lys Lys Pro Gly Ala
1 5 10 15

```
Ser Val Lys Val Ser Cys Lys Ala Ser Gly Tyr Thr Phe Thr Asp Tyr
            20                  25                  30

Val Met His Trp Val Arg Gln Ala Pro Gly Gln Arg Leu Glu Trp Met
        35                  40                  45

Gly Val Ile Ser Thr Tyr Tyr Gly His Gly Ser Tyr Asn Gln Arg Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Ser Ser Ser Leu Ala Gly Asn Phe Asp Val
            100                 105                 110

Trp Gly Gln Gly Thr Leu Val Thr
        115                 120


<210> SEQ ID NO 184
<211> LENGTH: 120
<212> TYPE: PRT
<213> ORGANISM: Artificial Sequence
<220> FEATURE:
<223> OTHER INFORMATION: Amino acid sequence 3 of the variable region of
      the heavy chain of humanized anti-hTfR antibody No.2

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Met
        35                  40                  45

Gly Val Ile Ser Thr Tyr Tyr Gly His Gly Ser Tyr Asn Gln Arg Phe
    50                  55                  60

Lys Gly Arg Val Thr Met Thr Thr Asp Thr Ser Thr Ser Ala Ala Tyr
65                  70                  75                  80

Met Glu Leu Arg Ser Leu Arg Ser Asp Asp Thr Ala Val Tyr Tyr Cys
                85                  90                  95

Ala Ser Gly Gly Tyr Gly Ser Ser Ser Leu Ala Gly Asn Phe Asp Val
            100                 105                 110

Trp Gly Gln Gly Thr Leu Val Thr
        115                 120


<210> SEQ ID NO 185
<211> LENGTH: 120
<212> TYPE: PRT
<213> ORGANISM: Artificial Sequence
<220> FEATURE:
<223> OTHER INFORMATION: Amino acid sequence 4 of the variable region of
      the heavy chain of humanized anti-hTfR antibody No.2

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Met
        35                  40                  45

Gly Val Ile Ser Thr Tyr Tyr Gly His Gly Ser Tyr Asn Gln Arg Phe
    50                  55                  60
```

Lys Gly Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Gly Gly Tyr Gly Ser Ser Ser Leu Ala Gly Asn Phe Asp Val
100 105 110

Trp Gly Gln Gly Thr Thr Val Thr
115 120

<210> SEQ ID NO 186
<211> LENGTH: 120
<212> TYPE: PRT
<213> ORGANISM: Artificial Sequence
<220> FEATURE:
<223> OTHER INFORMATION: Amino acid sequence 5 of the variable region of the heavy chain of humanized anti-hTfR antibody No.2

<400> SEQUENCE: 186

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Asp Tyr
20 25 30

Val Met His Trp Val Arg Gln Ala Pro Gly Gln Gly Leu Glu Trp Met
35 40 45

Gly Val Ile Ser Thr Tyr Tyr Gly His Gly Ser Tyr Asn Gln Arg Phe
50 55 60

Lys Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Tyr Gly Ser Ser Ser Leu Ala Gly Asn Phe Asp Val
100 105 110

Trp Gly Gln Gly Thr Val Val Thr
115 120

<210> SEQ ID NO 187
<211> LENGTH: 120
<212> TYPE: PRT
<213> ORGANISM: Artificial Sequence
<220> FEATURE:
<223> OTHER INFORMATION: Amino acid sequence 6 of the variable region of the heavy chain of humanized anti-hTfR antibody No.2

<400> SEQUENCE: 187

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Val Met His Trp Val Arg Gln Ala Pro Gly Gln Gly Leu Glu Trp Ile
35 40 45

Gly Val Ile Ser Thr Tyr Tyr Gly His Gly Ser Tyr Asn Gln Arg Phe
50 55 60

Lys Gly Arg Ala Thr Met Thr Val Asp Lys Ser Ile Ser Thr Ala Tyr
65 70 75 80

Met Glu Leu Val Arg Leu Arg Ser Asp Asp Thr Ala Val Tyr Tyr Cys
85 90 95

Val Arg Gly Gly Tyr Gly Ser Ser Ser Leu Ala Gly Asn Phe Asp Val
100 105 110

Trp Gly Gln Gly Thr Thr Val Thr
115 120

<210> SEQ ID NO 188
<211> LENGTH: 453
<212> TYPE: PRT
<213> ORGANISM: Artificial Sequence
<220> FEATURE:
<223> OTHER INFORMATION: Amino acid sequence of the heavy chain of humanized anti-hTfR antibody No.2 containing amino acid sequence 6 as the variable region

<400> SEQUENCE: 188

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Val Met His Trp Val Arg Gln Ala Pro Gly Gln Gly Leu Glu Trp Ile
35 40 45

Gly Val Ile Ser Thr Tyr Tyr Gly His Gly Ser Tyr Asn Gln Arg Phe
50 55 60

Lys Gly Arg Ala Thr Met Thr Val Asp Lys Ser Ile Ser Thr Ala Tyr
65 70 75 80

Met Glu Leu Val Arg Leu Arg Ser Asp Asp Thr Ala Val Tyr Tyr Cys
85 90 95

Val Arg Gly Gly Tyr Gly Ser Ser Ser Leu Ala Gly Asn Phe Asp Val
100 105 110

Trp Gly Gln Gly Thr Thr Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Leu
225 230 235 240

Leu Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 189
<211> LENGTH: 1442
<212> TYPE: DNA
<213> ORGANISM: Artificial Sequence
<220> FEATURE:
<223> OTHER INFORMATION: Nucleotide sequence encoding the amino acid
      sequence of the heavy chain of humanized anti-hTfR antibody No.2
      containing amino acid sequence 6 as the variable region, synthetic
      sequence

<400> SEQUENCE: 189

acgcgtgccg ccaccatggg ctggagctgg attctgctgt tcctcctgag cgtgacagca     60

ggagtgcaca gccaggtgca gctggtccag tcaggagccg aagtgaaaaa gcccggagcc    120

tcagtcaaag tgtcttgtaa agcatcaggt tatacattta cagactacgt catgcactgg    180

gtgaggcagg cacctggaca gggtctggaa tggatcggcg tgatctccac ttactatggc    240

catggaagct acaaccagag attcaagggc agggcgacaa tgactgtaga caaatcaatt    300

tccactgctt atatggagct ggtaaggctg cggtccgacg ataccgctgt gtactattgc    360

gtacgaggag gatacggctc cagctctctg gctggtaatt tcgatgtgtg ggggcagggt    420

accacagtca ccgtgagttc agcaagcaca aagggcccat ctgtgtttcc actggccccc    480

tccagcaaaa gcacctctgg gggtacagcc gctctgggat gtctggtgaa ggattatttc    540

ccagagccag tcaccgtgtc ctggaacagc ggagccctga catctggagt ccacactttt    600

ccagctgtgc tgcagtctag tgggctgtac tccctgtcat ccgtggtcac tgtccccagc    660

tctagtctgg gtacccagac atatatctgc aacgtgaatc acaagccatc taataccaaa    720

gtcgacaaga aagtggaacc caagtcctgt gataaaactc atacctgccc cccttgtcct    780

gcaccagagc tgctgggagg accatccgtg ttcctgtttc cacccaagcc taaagacacc    840

ctgatgatta gccgaactcc cgaagtcacc tgcgtggtcg tggacgtgtc tcacgaggac    900

cctgaagtca agtttaactg gtacgtggat ggcgtcgagg tgcataatgc taagacaaaa    960

ccccgagagg aacagtacaa cagtacatat cgtgtcgtgt cagtgctgac cgtcctgcat   1020

caggactggc tgaacgggaa ggaatataag tgcaaagtgt ccaataaggc actgcccgcc   1080

cctatcgaga aaaccattag caaggccaaa ggacagccta gggaaccaca ggtgtacaca   1140

ctgcctccat cccgggacga gctgactaag aaccaggtca gcctgacctg tctggtgaaa   1200

ggcttctatc cttcagatat cgctgtggag tgggaaagta atggacagcc agagaacaat   1260
```

tacaagacta cccccccctgt gctggactct gatgggagtt tctttctgta ttctaagctg 1320
accgtggata aaagtcggtg gcagcagggt aatgtcttta gttgttcagt gatgcacgaa 1380
gcactgcaca accactacac ccagaaatca ctgtcactgt caccagggaa ataagcggcc 1440
gc 1442

<210> SEQ ID NO 190
<211> LENGTH: 112
<212> TYPE: PRT
<213> ORGANISM: Artificial Sequence
<220> FEATURE:
<223> OTHER INFORMATION: Amino acid sequence 1 of the variable region of the light chain of humanized anti-hTfR antibody No.3

<400> SEQUENCE: 190

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val His Ser
20 25 30

Asn Gly Asn Thr Tyr Leu His Trp Phe Gln Gln Arg Pro Gly Gln Ser
35 40 45

Pro Arg Arg Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Trp Thr Phe Gly Gly Gly Thr Lys Val Glu Ile Lys
100 105 110

<210> SEQ ID NO 191
<211> LENGTH: 112
<212> TYPE: PRT
<213> ORGANISM: Artificial Sequence
<220> FEATURE:
<223> OTHER INFORMATION: Amino acid sequence 2 of the variable region of the light chain of humanized anti-hTfR antibody No.3

<400> SEQUENCE: 191

Asp Ile Val Met Thr Gln Thr Pro Leu Ser Leu Ser Val Thr Pro Gly
1 5 10 15

Gln Pro Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Trp Thr Phe Gly Gln Gly Thr Lys Val Glu Ile Lys
100 105 110

<210> SEQ ID NO 192
<211> LENGTH: 112
<212> TYPE: PRT
<213> ORGANISM: Artificial Sequence
<220> FEATURE:
<223> OTHER INFORMATION: Amino acid sequence 3 of the variable region of the light chain of humanized anti-hTfR antibody No.3

<400> SEQUENCE: 192

Asp Ile Val Met Thr Gln Thr Pro Leu Ser Ser Pro Val Thr Leu Gly
1 5 10 15

Gln Pro Ala Ser Ile Ser Cys Arg Ser Ser Gln Ser Leu Val His Ser
20 25 30

Asn Gly Asn Thr Tyr Leu His Trp Leu Gln Gln Arg Pro Gly Gln Pro
35 40 45

Pro Arg Leu Leu Ile Tyr Lys Val Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Trp Thr Phe Gly Gln Gly Thr Lys Leu Glu Ile Lys
100 105 110

<210> SEQ ID NO 193
<211> LENGTH: 112
<212> TYPE: PRT
<213> ORGANISM: Artificial Sequence
<220> FEATURE:
<223> OTHER INFORMATION: Amino acid sequence 4 of the variable region of the light chain of humanized anti-hTfR antibody No.3

<400> SEQUENCE: 193

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Ser Gln Ser
85 90 95

Thr His Val Pro Trp Thr Phe Gly Gln Gly Thr Lys Val Glu Ile Lys
100 105 110

<210> SEQ ID NO 194
<211> LENGTH: 112
<212> TYPE: PRT
<213> ORGANISM: Artificial Sequence
<220> FEATURE:
<223> OTHER INFORMATION: Amino acid sequence 5 of the variable region of the light chain of humanized anti-hTfR antibody No.3

<400> SEQUENCE: 194

Asp Ile Val Met Thr Gln Thr Pro Leu Ser Leu Pro Val Thr Pro Gly
1 5 10 15

Glu Pro Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Arg Leu Glu Ile Lys
            100                 105                 110


<210> SEQ ID NO 195
<211> LENGTH: 112
<212> TYPE: PRT
<213> ORGANISM: Artificial Sequence
<220> FEATURE:
<223> OTHER INFORMATION: Amino acid sequence 6 of the variable region of
      the light chain of humanized anti-hTfR antibody No.3

<400> SEQUENCE: 195

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Phe Cys Ser Gln Ser
                85                  90                  95

Thr His Val Pro Trp Thr Phe Gly Gln Gly Thr Lys Val Glu Ile Lys
            100                 105                 110


<210> SEQ ID NO 196
<211> LENGTH: 219
<212> TYPE: PRT
<213> ORGANISM: Artificial Sequence
<220> FEATURE:
<223> OTHER INFORMATION: Amino acid sequence of the light chain of
      humanized anti-hTfR antibody No.3 containing amino acid sequence 2
      as the variable region

<400> SEQUENCE: 196

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
```

```
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 197
<211> LENGTH: 740
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.3
      containing amino acid sequence 2 as the variable region, synthetic
      sequence

<400> SEQUENCE: 197

acgcgtgccg ccaccatggg ctggagctgg attctgctgt tcctcctgag cgtgacagca     60

ggagtgcaca gcgacatcgt gatgacccag actcccctga gcctgagcgt gacacctggc    120

cagcctgcca gcatcagctg cagaagctct cagagcctgg tgcacagcaa cggcaacacc    180

tacctgcact ggtatctgca gaagcccggc cagagccctc agctgctgat ctacaaggtg    240

tccaacagat tcagcggcgt gcccgacaga ttctccggca gcggctctgg caccgacttc    300

accctgaaga tttccagagt ggaagccgag gacgtgggcg tgtactactg cagccagagc    360

acccacgtgc cctggacatt cggccagggc accaaggtgg aaatcaagag aaccgtggcc    420

gctcccagcg tgttcatctt cccacctagc gacgagcagc tgaagtccgg cacagcctct    480

gtcgtgtgcc tgctgaacaa cttctacccc cgcgaggcca aggtgcagtg gaaggtggac    540

aacgccctgc agagcggcaa cagccaggaa agcgtgaccg agcaggactc caaggacagc    600

acctacagcc tgagcagcac cctgaccctg agcaaggccg actacgagaa gcacaaggtg    660

tacgcctgcg aagtgaccca ccagggcctg tctagccccg tgaccaagag cttcaacaga    720

ggcgagtgct aagcggccgc                                                740


<210> SEQ ID NO 198
<211> LENGTH: 219
<212> TYPE: PRT
<213> ORGANISM: Artificial Sequence
<220> FEATURE:
<223> OTHER INFORMATION: Amino acid sequence of the light chain of
      humanized anti-hTfR antibody No.3 containing amino acid sequence 4
      as the variable region

<400> SEQUENCE: 198

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
            85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 199
<211> LENGTH: 740
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.3
      containing amino acid sequence 4 as the variable region, synthetic
      sequence

<400> SEQUENCE: 199
acgcgtgccg ccaccatggg ctggagctgg attctgctgt tcctcctgag cgtgacagca    60
ggagtgcaca gcgacatcgt gatgacccag agccccctga gcctgcctgt gacacctggc   120
gagcctgcca gcatcagctg cagatctagc cagagcctgg tgcacagcaa cggcaacacc   180
tacctgcact ggtatctgca gaagcccggc cagagccctc agctgctgat ctacaaggtg   240
tccaacagat tcagcggcgt gcccgacaga ttctccggca gcggctctgg caccgacttc   300
accctgaaga tctccagagt ggaagccgag gacgtgggcg tgtactactg cagccagagc   360
acccacgtgc cctggacatt cggccagggc accaaggtgg aaatcaagag aaccgtggcc   420
gctcccagcg tgttcatctt cccacctagc gacgagcagc tgaagtccgg cacagcctct   480
gtcgtgtgcc tgctgaacaa cttctacccc cgcgaggcca aggtgcagtg gaaggtggac   540
aacgccctgc agagcggcaa cagccaggaa agcgtgaccg agcaggactc caaggacagc   600
acctacagcc tgagcagcac cctgaccctg agcaaggccg actacgagaa gcacaaggtg   660
tacgcctgcg aagtgaccca ccagggcctg tctagccccg tgaccaagag cttcaacaga   720
ggcgagtgct aagcggccgc                                               740

<210> SEQ ID NO 200
<211> LENGTH: 219
<212> TYPE: PRT
<213> ORGANISM: Artificial Sequence
<220> FEATURE:
<223> OTHER INFORMATION: Amino acid sequence of the light chain of
      humanized anti-hTfR antibody No.3 containing amino acid sequence 5
      as the variable region

<400> SEQUENCE: 200

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 201
<211> LENGTH: 740
<212> TYPE: DNA
<213> ORGANISM: Artificial Sequence
<220> FEATURE:
<223> OTHER INFORMATION: Nucleotide sequence encoding the amino acid sequence of the light chain of humanized anti-hTfR antibody No.3 containing amino acid sequence 5 as the variable region, synthetic sequence

<400> SEQUENCE: 201
acgcgtgccg ccaccatggg ctggagctgg attctgctgt tcctcctgag cgtgacagca 60
ggagtgcaca gcgacatcgt gatgacccag acacccctga gcctgcctgt gacacctggc 120
gagcctgcca gcatcagctg cagatctagc cagagcctgg tgcacagcaa cggcaacacc 180
tacctgcact ggtatctgca gaagcccggc cagagccctc agctgctgat ctacaaggtg 240
tccaacagat tcagcggcgt gcccgacaga ttctccggca gcggctctgg caccgacttc 300
accctgaaga tctccagagt ggaagccgag gacgtgggcg tgtactactg cagccagagc 360
acccacgtgc cctggacatt cggccagggc accaggctgg aaatcaagag aaccgtggcc 420
gctcccagcg tgttcatctt cccacctagc gacgagcagc tgaagtccgg cacagcctct 480
gtcgtgtgcc tgctgaacaa cttctacccc cgcgaggcca aggtgcagtg gaaggtggac 540
aacgccctgc agagcggcaa cagccaggaa agcgtgaccg agcaggactc caaggacagc 600
acctacagcc tgagcagcac cctgaccctg agcaaggccg actacgagaa gcacaaggtg 660
tacgcctgcg aagtgaccca ccagggcctg tctagccccg tgaccaagag cttcaacaga 720
ggcgagtgct aagcggccgc 740

<210> SEQ ID NO 202
<211> LENGTH: 219
<212> TYPE: PRT
<213> ORGANISM: Artificial Sequence
<220> FEATURE:
<223> OTHER INFORMATION: Amino acid sequence of the light chain of humanized anti-hTfR antibody No.3 containing amino acid sequence 6 as the variable region

<400> SEQUENCE: 202

Asp Ile Val Met Thr Gln Thr Pro Leu Ser Leu Ser Val Thr Pro Gly
1 5 10 15

Gln Pro Ala Ser Ile Ser Cys Arg Ser Ser Gln Ser Leu Val His Ser
20 25 30

Asn Gly Asn Thr Tyr Leu His Trp Tyr Leu Gln Lys Pro Gly Gln Ser
35 40 45

Pro Gln Leu Leu Ile Tyr Lys Val Ser Asn Arg Phe Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Phe Phe Cys Ser Gln Ser
85 90 95

Thr His Val Pro Trp Thr Phe Gly Gln Gly Thr Lys Val Glu Ile Lys
100 105 110

Arg Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys
210 215

<210> SEQ ID NO 203
<211> LENGTH: 740
<212> TYPE: DNA
<213> ORGANISM: Artificial Sequence
<220> FEATURE:
<223> OTHER INFORMATION: Nucleotide sequence encoding the amino acid sequence of the light chain of humanized anti-hTfR antibody No.3 containing amino acid sequence 6 as the variable region, synthetic sequence

<400> SEQUENCE: 203
acgcgtgccg ccaccatggg ctggagctgg attctgctgt tcctcctgag cgtgacagca 60
ggagtgcaca gcgacatcgt gatgacccag actcccctga gcctgagcgt gacacctggc 120
cagcctgcca gcatcagctg cagatccagc cagagcctgg tgcacagcaa cggcaacacc 180
tacctgcact ggtatctgca gaagcccggc cagagccctc agctgctgat ctacaaggtg 240

```
tccaacagat tcagcggcgt gcccgacaga ttctccggca gcggctctgg caccgacttc    300

accctgaaga tttccagagt ggaagccgag gacgtgggcg tgttcttctg cagccagagc    360

acccacgtgc cctggacatt cggccagggc accaaggtgg aaatcaagag aaccgtggcc    420

gctcccagcg tgttcatctt cccacctagc gacgagcagc tgaagtccgg cacagcctct    480

gtcgtgtgcc tgctgaacaa cttctacccc cgcgaggcca aggtgcagtg gaaggtggac    540

aacgccctgc agagcggcaa cagccaggaa agcgtgaccg agcaggactc caaggacagc    600

acctacagcc tgagcagcac cctgaccctg agcaaggccg actacgagaa gcacaaggtg    660

tacgcctgcg aagtgaccca ccagggcctg tctagccccg tgaccaagag cttcaacaga    720

ggcgagtgct aagcggccgc                                                740
```

<210> SEQ ID NO 204
<211> LENGTH: 118
<212> TYPE: PRT
<213> ORGANISM: Artificial Sequence
<220> FEATURE:
<223> OTHER INFORMATION: Amino acid sequence 1 of the variable region of the heavy chain of humanized anti-hTfR antibody No.3

<400> SEQUENCE: 204

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115
```

<210> SEQ ID NO 205
<211> LENGTH: 118
<212> TYPE: PRT
<213> ORGANISM: Artificial Sequence
<220> FEATURE:
<223> OTHER INFORMATION: Amino acid sequence 2 of the variable region of the heavy chain of humanized anti-hTfR antibody No.3

<400> SEQUENCE: 205

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80
```

Leu Gln Trp Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser
115

<210> SEQ ID NO 206
<211> LENGTH: 118
<212> TYPE: PRT
<213> ORGANISM: Artificial Sequence
<220> FEATURE:
<223> OTHER INFORMATION: Amino acid sequence 3 of the variable region of the heavy chain of humanized anti-hTfR antibody No.3

<400> SEQUENCE: 206

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Trp Leu Gly Trp Val Arg Gln Ala Pro Gly Gln Gly Leu Glu Trp Met
35 40 45

Gly Asp Ile Tyr Pro Gly Gly Asp Tyr Pro Thr Tyr Ser Glu Lys Phe
50 55 60

Lys Val Arg Val Thr Met Thr Arg Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ala Arg Ser Gly Asn Tyr Asp Glu Val Ala Tyr Trp Gly Gln Gly Thr
100 105 110

Thr Val Thr Val Ser Ser
115

<210> SEQ ID NO 207
<211> LENGTH: 118
<212> TYPE: PRT
<213> ORGANISM: Artificial Sequence
<220> FEATURE:
<223> OTHER INFORMATION: Amino acid sequence 4 of the variable region of the heavy chain of humanized anti-hTfR antibody No.3

<400> SEQUENCE: 207

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Trp Leu Gly Trp Val Arg Gln Ala Pro Gly Gln Arg Leu Glu Trp Met
35 40 45

Gly Asp Ile Tyr Pro Gly Gly Asp Tyr Pro Thr Tyr Ser Glu Lys Phe
50 55 60

Lys Val Arg Val Thr Ile Thr Arg Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser
115

<210> SEQ ID NO 208
<211> LENGTH: 118
<212> TYPE: PRT
<213> ORGANISM: Artificial Sequence
<220> FEATURE:
<223> OTHER INFORMATION: Amino acid sequence 5 of the variable region of the heavy chain of humanized anti-hTfR antibody No.3

<400> SEQUENCE: 208

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Asn Tyr Asp Glu Val Ala Tyr Trp Gly Gln Gly Thr
            100                 105                 110

Val Val Thr Val Ser Ser
        115
```

<210> SEQ ID NO 209
<211> LENGTH: 118
<212> TYPE: PRT
<213> ORGANISM: Artificial Sequence
<220> FEATURE:
<223> OTHER INFORMATION: Amino acid sequence 6 of the variable region of the heavy chain of humanized anti-hTfR antibody No.3

<400> SEQUENCE: 209

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Met Asn Tyr
            20                  25                  30

Trp Leu Gly Trp Val Arg Gln Met Pro Gly Lys Gly Leu Glu Trp Ile
        35                  40                  45

Gly Asp Ile Tyr Pro Gly Gly Asp Tyr Pro Thr Tyr Ser Glu Lys Phe
    50                  55                  60

Lys Val Lys Ala Ile Ile Ser Ala Asp Thr Ser Ile Ser Thr Val Tyr
65                  70                  75                  80

Leu Gln Leu Ser Ser Leu Lys Ala Ser Asp Thr Ala Met Tyr Phe Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115
```

<210> SEQ ID NO 210
<211> LENGTH: 448
<212> TYPE: PRT
<213> ORGANISM: Artificial Sequence
<220> FEATURE:
<223> OTHER INFORMATION: Amino acid sequence of the heavy chain of humanized anti-hTfR antibody No.3 containing amino acid sequence 2 as the variable region

<400> SEQUENCE: 210

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

-continued

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 211
<211> LENGTH: 1427
<212> TYPE: DNA
<213> ORGANISM: Artificial Sequence
<220> FEATURE:
<223> OTHER INFORMATION: Nucleotide sequence encoding the amino acid sequence of the heavy chain of humanized anti-hTfR antibody No.3 containing amino acid sequence 2 as the variable region, synthetic sequence

<400> SEQUENCE: 211
acgcgtgccg ccaccatggg ctggagctgg attctgctgt tcctcctgag cgtgacagca 60
ggagtgcaca gcgaggtgca actagtgcag tctggagcag aggtgaaaaa gcccggggag 120
tctctgaaga tttcctgtaa gggttctgga tacagcttta ccaactactg gctgggatgg 180
gtgcgccaga tgcccgggaa aggcctggag tggatggggg acatctaccc cggcggagac 240
taccctacat acagcgagaa gttcaaggtc caggtcacca tctcagccga caagtccatc 300
agcaccgcct acctgcagtg gagcagcctg aaggcctcgg acaccgccat gtattactgt 360
gcgagatcag gcaattacga cgaagtggcc tactggggcc aaggaaccct ggtcaccgtc 420
tcctcagcta gcaccaaggg cccatcggtc ttccccctgg caccctcctc caagagcacc 480
tctgggggca cagcggccct gggctgcctg gtcaaggact acttccccga accggtgacg 540
gtgtcgtgga actcaggcgc cctgaccagc ggcgtgcaca ccttcccggc tgtcctacag 600
tcctcaggac tctactccct cagcagcgtg gtgaccgtgc cctccagcag cttgggcacc 660
cagacctaca tctgcaacgt gaatcacaag cccagcaaca ccaaggtgga caagaaagtt 720
gagcccaaat cttgtgacaa aactcacacg tgcccaccgt gcccagcacc tgaactcctg 780
ggaggtccgt cagtcttcct cttcccccca aaacccaagg acaccctcat gatctcccgg 840
acccctgagg tcacatgcgt ggtggtggac gtgagccacg aagaccctga ggtcaagttc 900
aactggtacg tggacggcgt ggaggtgcat aatgccaaga caaagccgcg ggaggagcag 960
tacaacagca cgtaccgggt ggtcagcgtc ctcaccgtcc tgcaccagga ctggctgaat 1020
ggcaaggagt acaagtgcaa ggtctccaac aaagccctcc cagcccccat cgagaaaacc 1080
atctccaaag ccaaagggca gccccgagaa ccacaggtgt acaccctgcc cccatcccgg 1140
gatgagctga ccaagaacca ggtcagcctg acctgcctgg tcaaaggctt ctatcccagc 1200
gacatcgccg tggagtggga gagcaatggg cagccggaga acaactacaa gaccacgcct 1260
cccgtgctgg actccgacgg ctccttcttc ctctacagca agctcaccgt ggacaagagc 1320
aggtggcagc aggggaacgt cttctcatgc tccgtgatgc atgaggctct gcacaaccac 1380
tacacgcaga agagcctctc cctgtctccg ggtaaataag cggccgc 1427

<210> SEQ ID NO 212
<211> LENGTH: 445
<212> TYPE: PRT
<213> ORGANISM: Artificial Sequence
<220> FEATURE:
<223> OTHER INFORMATION: Amino acid sequence of the heavy chain (IgG4) of humanized anti-hTfR antibody No.3 containing amino acid sequence 2 as the variable region

<400> SEQUENCE: 212

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asn Tyr
20 25 30

Trp Leu Gly Trp Val Arg Gln Met Pro Gly Lys Gly Leu Glu Trp Met
35 40 45

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Lys Thr Tyr Thr Cys Asn Val Asp His Lys Pro Ser
195 200 205

Asn Thr Lys Val Asp Lys Arg Val Glu Ser Lys Tyr Gly Pro Pro Cys
210 215 220

Pro Pro Cys Pro Ala Pro Glu Phe Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser Gln Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Gly Leu Pro Ser Ser Ile Glu Lys Thr Ile Ser Lys
325 330 335

Ala Lys Gly Gln Pro Arg Glu Pro Gln Val Tyr Thr Leu Pro Pro Ser
340 345 350

Gln Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Arg Leu Thr Val Asp Lys Ser Arg Trp Gln 405 410 415

Glu Gly Asn Val Phe Ser Cys Ser Val Met His Glu Ala Leu His Asn
420 425 430

His Tyr Thr Gln Lys Ser Leu Ser Leu Ser Pro Gly Lys
435 440 445

<210> SEQ ID NO 213
<211> LENGTH: 1418
<212> TYPE: DNA
<213> ORGANISM: Artificial Sequence
<220> FEATURE:
<223> OTHER INFORMATION: Nucleotide sequence encoding the amino acid sequence of the heavy chain (IgG4) of humanized anti-hTfR antibody No.3 containing amino acid sequence 2 as the variable region, synthetic sequence

<400> SEQUENCE: 213
acgcgtgccg ccaccatggg ctggagctgg attctgctgt tcctcctgag cgtgacagca 60
ggagtgcaca gcgaggtgca actagtgcag tctggagcag aggtgaaaaa gcccggggag 120
tctctgaaga tttcctgtaa gggttctgga tacagcttta ccaactactg gctgggatgg 180
gtgcgccaga tgcccgggaa aggcctggag tggatggggg acatctaccc cggcggagac 240
taccctacat acagcgagaa gttcaaggtc caggtcacca tctcagccga caagtccatc 300
agcaccgcct acctgcagtg gagcagcctg aaggcctcgg acaccgccat gtattactgt 360
gcgagatcag gcaattacga cgaagtggcc tactggggcc aaggaaccct ggtcaccgtc 420
tcctcagcta gcaccaaggg cccatcggtc ttccccctgg cgccctgctc caggagcacc 480
tccgagagca cagccgccct gggctgcctg gtcaaggact acttccccga accggtgacg 540
gtgtcgtgga actcaggcgc cctgaccagc ggcgtgcaca ccttcccggc tgtcctacag 600
tcctcaggac tctactccct cagcagcgtg gtgaccgtgc cctccagcag cttgggcacg 660
aagacctaca cctgcaacgt agatcacaag cccagcaaca ccaaggtgga caagagagtt 720
gagtccaaat atggtccccc atgcccacca tgcccagcac ctgagttcct ggggggtcca 780
tcagtcttcc tgttcccccc aaaacccaag gacactctca tgatctcccg gacccctgag 840
gtcacgtgcg tggtggtgga cgtgagccag gaagaccccg aggtccagtt caactggtac 900
gtggatggcg tggaggtgca taatgccaag acaaagccgc gggaggagca gttcaacagc 960
acgtaccgtg tggtcagcgt cctcaccgtc ctgcaccagg actggctgaa cggcaaggag 1020
tacaagtgca aggtctccaa caaaggcctc ccgtcctcca tcgagaaaac catctccaaa 1080
gccaaagggc agccccgaga gccacaggtg tacaccctgc ccccatccca ggaggagatg 1140
accaagaacc aggtcagcct gacctgcctg gtcaaaggct tctaccccag cgacatcgcc 1200
gtggagtggg agagcaatgg gcagccggag aacaactaca agaccacgcc tcccgtgctg 1260
gactccgacg gctccttctt cctctacagc aggctcaccg tggacaagag caggtggcag 1320
gaggggaatg tcttctcatg ctccgtgatg catgaggctc tgcacaacca ctacacacag 1380
aagagcctct ccctgtctcc gggtaaataa gcggccgc 1418

<210> SEQ ID NO 214
<211> LENGTH: 43
<212> TYPE: DNA
<213> ORGANISM: Artificial Sequence
<220> FEATURE:
<223> OTHER INFORMATION: Primer hTfR5', synthetic sequence

<400> SEQUENCE: 214
ccgacgcgtc gccaccatga tggatcaagc tagatcagca ttc 43

<210> SEQ ID NO 215
<211> LENGTH: 59
<212> TYPE: DNA
<213> ORGANISM: Artificial Sequence
<220> FEATURE:
<223> OTHER INFORMATION: Primer hTfR3', synthetic sequence

<400> SEQUENCE: 215
ataatgcggc cgcttaatga tgatgatgat gatgaaactc attgtcaatg tcccaaacg 59

<210> SEQ ID NO 216
<211> LENGTH: 20
<212> TYPE: DNA
<213> ORGANISM: Artificial Sequence
<220> FEATURE:
<223> OTHER INFORMATION: Primer Hyg-Sfi5', synthetic sequence

<400> SEQUENCE: 216
gaggccgcct cggcctctga 20

<210> SEQ ID NO 217
<211> LENGTH: 29
<212> TYPE: DNA
<213> ORGANISM: Artificial Sequence
<220> FEATURE:
<223> OTHER INFORMATION: Primer Hyg-BstX3', synthetic sequence

<400> SEQUENCE: 217
aaccatcgtg atgggtgcta ttcctttgc 29

<210> SEQ ID NO 218
<211> LENGTH: 108
<212> TYPE: PRT
<213> ORGANISM: Artificial Sequence
<220> FEATURE:
<223> OTHER INFORMATION: Amino acid sequence of the variable region of the light chain of anti-hTfR antibody No.1

<400> SEQUENCE: 218

Asp Ile Val Leu Thr Gln Ser Ser Lys Phe Met Ser Thr Ser Val Gly
1 5 10 15

Asp Arg Val Ser Ile Thr Cys Lys Ala Ser Gln Asp Val Asn Ser Ala
20 25 30

Val Ala Trp Phe Gln Gln Lys Pro Gly Gln Ser Pro Lys Leu Leu Ile
35 40 45

Tyr Trp Thr Ser Thr Arg His Thr Gly Val Pro Asp Arg Phe Thr Gly
50 55 60

Ser Gly Ser Gly Thr Val Tyr Thr Leu Thr Ile Ser Ser Val Gln Ala
65 70 75 80

Glu Asp Leu Ala Leu Tyr Tyr Cys Gln Gln His Tyr Ser Thr Pro Arg
85 90 95

Thr Phe Gly Gly Gly Thr Lys Leu Glu Ile Lys Arg
100 105

<210> SEQ ID NO 219
<211> LENGTH: 116
<212> TYPE: PRT
<213> ORGANISM: Artificial Sequence
<220> FEATURE:
<223> OTHER INFORMATION: Amino acid sequence of the variable region of the heavy chain of anti-hTfR antibody No.1

<400> SEQUENCE: 219

Glu Val Gln Leu Gln Glu Ser Gly Gly Gly Leu Val Gln Pro Gly Gly
1 5 10 15

Ser Leu Lys Leu Ser Cys Ala Ala Ser Gly Leu Thr Phe Ser Asn Tyr
20 25 30

Gly Met Ser Trp Ile Arg Gln Thr Pro Asp Lys Arg Leu Glu Leu Val
35 40 45

Ala Asn Ile Asn Thr Asn Gly Gly Ser Thr Tyr Tyr Pro Asp Ser Val
50 55 60

Lys Gly Arg Phe Thr Ile Ser Arg Asp Asn Ala Lys Asn Thr Leu Tyr
65 70 75 80

Leu Gln Met Asn Ser Leu Lys Ser Glu Asp Thr Ala Ile Tyr Tyr Cys
85 90 95

Thr Asn Asn Arg Tyr Asp Glu Asp Tyr Trp Gly Gln Gly Thr Ser Val
100 105 110

Thr Val Ser Ser
115

<210> SEQ ID NO 220
<211> LENGTH: 108
<212> TYPE: PRT
<213> ORGANISM: Artificial Sequence
<220> FEATURE:
<223> OTHER INFORMATION: Amino acid sequence of the variable region of the light chain of anti-hTfR antibody No.2

<400> SEQUENCE: 220

Asp Ile Val Leu Thr Gln Ser Pro Ala Thr Leu Ser Val Thr Pro Gly
1 5 10 15

Asp Ser Val Ser Leu Ser Cys Arg Ala Ser Gln Ser Ile Ser Asn Asn
20 25 30

Leu Gln Trp Tyr Gln Gln Lys Ser His Glu Ser Pro Arg Leu Leu Ile
35 40 45

Lys Tyr Ala Ser Gln Ser Ile Ser Gly Ile Pro Ser Arg Phe Ser Gly
50 55 60

Ser Gly Ser Gly Thr Asp Phe Thr Leu Ser Ile Asn Ser Val Glu Thr
65 70 75 80

Glu Asp Phe Gly Met Tyr Phe Cys Gln Gln Ser Asn Ser Trp Pro Arg
85 90 95

Thr Phe Gly Ala Gly Thr Lys Leu Glu Leu Lys Arg
100 105

<210> SEQ ID NO 221
<211> LENGTH: 123
<212> TYPE: PRT
<213> ORGANISM: Artificial Sequence
<220> FEATURE:
<223> OTHER INFORMATION: Amino acid sequence of the variable region of the heavy chain of anti-hTfR antibody No.2

<400> SEQUENCE: 221

Glu Val Gln Leu Gln Glu Ser Gly Ala Glu Leu Val Arg Pro Gly Val
1 5 10 15

Ser Val Lys Ile Ser Cys Lys Gly Ser Gly Tyr Thr Phe Thr Asp Tyr
20 25 30

Val Met His Trp Val Arg Gln Ser His Ala Lys Ser Leu Glu Trp Ile
35 40 45

Gly Val Ile Ser Thr Tyr Tyr Gly His Gly Ser Tyr Asn Gln Arg Phe

```
    50                  55                  60

Lys Gly Lys Ala Thr Met Thr Val Asp Lys Ser Ser Ser Thr Ala Tyr
65                  70                  75                  80

Leu Glu Leu Val Arg Leu Thr Ser Glu Asp Ser Ala Ile Tyr Tyr Cys
                85                  90                  95

Val Arg Gly Gly Tyr Gly Ser Ser Ser Leu Ala Gly Asn Phe Asp Val
            100                 105                 110

Trp Gly Ala Gly Thr Thr Val Thr Val Ser Ser
        115                 120


<210> SEQ ID NO 222
<211> LENGTH: 113
<212> TYPE: PRT
<213> ORGANISM: Artificial Sequence
<220> FEATURE:
<223> OTHER INFORMATION: Amino acid sequence of the variable region of
      the light chain of anti-hTfR antibody No.3

<400> SEQUENCE: 222

Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Phe Cys Ser Gln Ser
                85                  90                  95

Thr His Val Pro Trp Thr Phe Gly Gly Gly Thr Lys Leu Glu Ile Lys
            100                 105                 110

Arg


<210> SEQ ID NO 223
<211> LENGTH: 118
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.3

<400> SEQUENCE: 223

Glu Val Gln Leu Gln Glu Ser Gly Ala Glu Leu Val Arg Pro Gly Thr
1               5                   10                  15

Ser Val Lys Ile Ser Cys Lys Ala Ser Gly Tyr Thr Phe Met Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Asp Tyr Pro Thr Tyr Ser Glu Lys Phe
    50                  55                  60

Lys Val Lys Ala Ile Leu Thr Ala Asp Thr Ser Ser Ser Ser Val Tyr
65                  70                  75                  80

Leu His Leu Ser Ser Leu Thr Ser Glu Asp Ser Ala Val Tyr Phe Cys
                85                  90                  95

Ala Arg Ser Gly Asn Tyr Asp Glu Val Ala Tyr Trp Gly Gln Gly Thr
            100                 105                 110
```

Leu Val Thr Val Ser Thr
115

<210> SEQ ID NO 224
<211> LENGTH: 106
<212> TYPE: PRT
<213> ORGANISM: Artificial Sequence
<220> FEATURE:
<223> OTHER INFORMATION: Amino acid sequence of the variable region of the light chain of anti-hTfR antibody No.4

<400> SEQUENCE: 224

Asp Ile Val Leu Thr Gln Thr Pro Ala Ile Met Ser Ala Ser Pro Gly
1 5 10 15

Glu Lys Val Thr Met Thr Cys Ser Ala Ser Ser Asn Val Asn Tyr Met
20 25 30

His Trp Tyr Gln Gln Lys Ser Ser Thr Ser Pro Lys Leu Trp Ile Tyr
35 40 45

Asp Thr Ser Lys Leu Ala Ser Gly Val Pro Gly Arg Phe Ser Gly Ser
50 55 60

Gly Ser Gly Asn Ser Tyr Ser Leu Thr Ile Ser Ser Met Glu Ala Glu
65 70 75 80

Asp Val Ala Thr Tyr Tyr Cys Phe Gln Gly Asn Gly Asn Pro Tyr Thr
85 90 95

Phe Gly Gly Gly Thr Lys Leu Glu Ile Lys
100 105

<210> SEQ ID NO 225
<211> LENGTH: 122
<212> TYPE: PRT
<213> ORGANISM: Artificial Sequence
<220> FEATURE:
<223> OTHER INFORMATION: Amino acid sequence of the variable region of the heavy chain of anti-hTfR antibody No.4

<400> SEQUENCE: 225

Glu Val Gln Leu Gln Glu Ser Gly Ala Glu Leu Val Arg Pro Gly Thr
1 5 10 15

Ser Val Arg Val Phe Cys Lys Ala Ser Gly Tyr Ala Phe Thr Asn Tyr
20 25 30

Leu Ile Glu Trp Val Lys Gln Arg Pro Gly Gln Gly Leu Glu Trp Ile
35 40 45

Gly Leu Ile Asn Pro Gly Ser Gly Gly Ile Ile Tyr Asn Glu Lys Phe
50 55 60

Thr Asp Arg Ala Thr Leu Thr Ala Asp Lys Ser Ser Ser Thr Ala Tyr
65 70 75 80

Met Gln Leu Ser Ser Leu Thr Ser Asp Asp Ser Ala Val Tyr Phe Cys
85 90 95

Ala Arg Ser Asn Tyr Tyr Gly Thr Thr Tyr Trp His Phe Asp Val Trp
100 105 110

Gly Ala Gly Thr Thr Val Thr Val Ser Ser
115 120

<210> SEQ ID NO 226
<211> LENGTH: 105
<212> TYPE: PRT
<213> ORGANISM: Artificial Sequence
<220> FEATURE:
<223> OTHER INFORMATION: Amino acid sequence of the variable region of the light chain of anti-hTfR antibody No.5

<400> SEQUENCE: 226

Asp Ile Val Met Thr Gln Thr Pro Ala Ile Met Ser Ala Ser Pro Gly
1 5 10 15

Glu Lys Val Thr Met Thr Cys Ser Ala Ser Ser Ser Ile Ser Ser Ile
20 25 30

His Trp Tyr Gln Gln Lys Pro Gly Thr Ser Pro Lys Arg Trp Ile Tyr
35 40 45

Asp Thr Ser Thr Leu Ala Ser Gly Val Pro Val Arg Phe Ser Gly Ser
50 55 60

Gly Ser Gly Thr Ser Tyr Ser Leu Thr Ile Ser Ser Met Glu Ala Glu
65 70 75 80

Asp Ala Ala Thr Tyr Tyr Cys His Gln Arg Ser Ser Tyr Pro Thr Phe
85 90 95

Gly Gly Gly Thr Lys Leu Glu Ile Lys
100 105

<210> SEQ ID NO 227
<211> LENGTH: 118
<212> TYPE: PRT
<213> ORGANISM: Artificial Sequence
<220> FEATURE:
<223> OTHER INFORMATION: Amino acid sequence of the variable region of the heavy chain of anti-hTfR antibody No.5

<400> SEQUENCE: 227

Glu Val Gln Leu Gln Glu Ser Gly Pro Glu Leu Val Lys Pro Gly Ala
1 5 10 15

Ser Val Lys Met Ser Cys Lys Ala Ser Gly Tyr Thr Phe Thr Asn Phe
20 25 30

Val Ile His Trp Val Lys Gln Arg Pro Gly Gln Gly Leu Glu Trp Ile
35 40 45

Gly Phe Phe Asn Pro His Lys Asn Gly Ala Glu Tyr Asn Glu Lys Phe
50 55 60

Gln Val Lys Ala Thr Leu Thr Ser Asp Lys Ser Ser Thr Thr Ala Tyr
65 70 75 80

Met Glu Leu Asn Ser Leu Thr Ser Glu Asp Ser Ala Val Tyr Tyr Cys
85 90 95

Ala Arg Ser Phe Tyr Tyr Tyr Ser Met Asp Tyr Trp Gly Gln Gly Thr
100 105 110

Ser Val Thr Val Ser Ser
115

<210> SEQ ID NO 228
<211> LENGTH: 107
<212> TYPE: PRT
<213> ORGANISM: Artificial Sequence
<220> FEATURE:
<223> OTHER INFORMATION: Amino acid sequence of the variable region of the light chain of anti-hTfR antibody No.6

<400> SEQUENCE: 228

Asp Ile Val Leu Thr Gln Thr Pro Ser Ser Leu Ser Ala Ser Leu Gly
1 5 10 15

Glu Arg Val Ser Leu Thr Cys Arg Ala Ser Gln Glu Ile Ser Gly Tyr
20 25 30

Leu Ser Trp Leu Gln Gln Lys Pro Asp Gly Thr Ile Lys Arg Leu Ile
35 40 45

```
Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ser Ser Tyr Pro Arg
                85                  90                  95

Thr Phe Gly Gly Gly Thr Lys Leu Glu Ile Lys
            100                 105


<210> SEQ ID NO 229
<211> LENGTH: 112
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.6

<400> SEQUENCE: 229

Glu Val Gln Leu Gln Glu Ser Gly Pro Gly Leu Val Ala Pro Ser Gln
1               5                   10                  15

Ser Leu Ser Ile Thr Cys Ser Val Ser Gly Phe Ser Leu Ser Thr Tyr
            20                  25                  30

Gly Val Tyr Trp Val Arg Gln Pro Pro Gly Lys Gly Leu Glu Trp Leu
        35                  40                  45

Gly Ile Ile Trp Gly Asp Gly Ser Thr Asn Tyr His Ser Ala Leu Ile
    50                  55                  60

Ser Arg Leu Thr Ile Ser Lys Asp Asn Ser Lys Ser Gln Val Phe Leu
65                  70                  75                  80

Lys Leu Asn Ser Leu Gln Thr Ala Asp Thr Ala Thr Tyr Tyr Cys Ala
                85                  90                  95

Lys Pro Asp Asp Val Trp Gly Ala Gly Thr Thr Val Thr Val Ser Ser
            100                 105                 110


<210> SEQ ID NO 230
<211> LENGTH: 106
<212> TYPE: PRT
<213> ORGANISM: Artificial Sequence
<220> FEATURE:
<223> OTHER INFORMATION: Amino acid sequence of the variable region of
      the light chain of anti-hTfR antibody No.7

<400> SEQUENCE: 230

Asp Ile Val Leu Thr Gln Ser Pro Val Ile Met Ser Ala Ser Leu Gly
1               5                   10                  15

Glu Glu Ile Thr Leu Thr Cys Ser Ala Ser Ser Ser Val Asn Tyr Ile
            20                  25                  30

His Trp Tyr Gln Gln Lys Ser Gly Thr Ser Pro Lys Val Leu Ile Tyr
        35                  40                  45

Gln Thr Ser Asn Leu Ala Ser Gly Val Pro Ser Arg Phe Ser Gly Ser
    50                  55                  60

Arg Ser Gly Thr Phe Tyr Ser Leu Lys Ile Ser Ser Val Glu Ala Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys
            100                 105


<210> SEQ ID NO 231
<211> LENGTH: 120
```

<212> TYPE: PRT
<213> ORGANISM: Artificial Sequence
<220> FEATURE:
<223> OTHER INFORMATION: Amino acid sequence of the variable region of the heavy chain of anti-hTfR antibody No.7

<400> SEQUENCE: 231

```
Glu Val Gln Leu Gln Glu Ser Gly Gly Ala Leu Val Lys Pro Gly Gly
1               5                   10                  15

Ser Leu Lys Val Ser Cys Glu Ala Ser Gly Ile Thr Phe Arg Asn Tyr
            20                  25                  30

Phe Met Ser Trp Val Arg Gln Thr Pro Glu Lys Arg Leu Glu Trp Val
        35                  40                  45

Ala Thr Ile Ser Ser Ala Gly Gly Tyr Thr Tyr Tyr Ala Asp Ser Val
    50                  55                  60

Lys Gly Arg Phe Thr Ile Ser Arg Asp Asn Ala Gly Asn Thr Leu Tyr
65                  70                  75                  80

Leu Gln Met Ser Ser Leu Arg Ser Glu Asp Thr Ala Met Tyr Phe Cys
                85                  90                  95

Ala Arg Gln Glu Val Pro Tyr Pro Tyr Ala Met Asp Tyr Trp Gly Gln
            100                 105                 110

Gly Thr Ser Val Ile Val Ser Ser
        115                 120
```

<210> SEQ ID NO 232
<211> LENGTH: 106
<212> TYPE: PRT
<213> ORGANISM: Artificial Sequence
<220> FEATURE:
<223> OTHER INFORMATION: Amino acid sequence of the variable region of the light chain of anti-hTfR antibody No.8

<400> SEQUENCE: 232

```
Asp Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
            20                  25                  30

His Trp Tyr Gln Gln Lys Ser Gly Thr Ser Pro Lys Val Leu Ile Tyr
        35                  40                  45

Gly Thr Ser Asn Leu Ala Ser Glu Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys
            100                 105
```

<210> SEQ ID NO 233
<211> LENGTH: 112
<212> TYPE: PRT
<213> ORGANISM: Artificial Sequence
<220> FEATURE:
<223> OTHER INFORMATION: Amino acid sequence of the variable region of the heavy chain of anti-hTfR antibody No.8

<400> SEQUENCE: 233

```
Glu Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
```

```
            20                  25                  30

Gly Val Ser Trp Ile Arg Gln Pro Pro Gly Lys Gly Leu Glu Trp Leu
        35                  40                  45

Gly Ile Ile Trp Gly Asp Gly Ser Thr Asn Tyr Arg Ser Ala Leu Ile
    50                  55                  60

Ser Arg Leu Ser Ile Ser Lys Asp Asn Ser Lys Asn Gln Val Phe Leu
65                  70                  75                  80

Lys Leu Asn Ser Leu Gln Thr Asp Asp Thr Ala Thr Tyr Tyr Cys Ala
                85                  90                  95

Lys Pro Asp Asp Tyr Trp Gly Gln Gly Thr Ser Val Thr Val Ser Ser
            100                 105                 110


<210> SEQ ID NO 234
<211> LENGTH: 106
<212> TYPE: PRT
<213> ORGANISM: Artificial Sequence
<220> FEATURE:
<223> OTHER INFORMATION: Amino acid sequence of the variable region of
      the light chain of anti-hTfR antibody No.9

<400> SEQUENCE: 234

Asp Ile Val Leu Thr Gln Ser Pro Ala Leu Met Ser Ala Ser Pro Gly
1               5                   10                  15

Glu Thr Val Thr Met Thr Cys Ser Ala Ser Ser Ser Val Ser Leu Met
            20                  25                  30

Phe Trp Tyr Gln Gln Lys Pro Arg Ser Ser Pro Lys Pro Trp Ile Tyr
        35                  40                  45

Phe Thr Ser Tyr Arg Ala Ser Gly Val Pro Ile Arg Phe Ser Gly Ser
    50                  55                  60

Gly Ser Gly Thr Ser Phe Ser Leu Thr Ile Ser Asn Leu Glu Ala Glu
65                  70                  75                  80

Asp Ala Ala Thr Tyr Tyr Cys Gln Gln Trp Thr Ser Asp Pro Pro Thr
                85                  90                  95

Phe Gly Ser Gly Thr Lys Leu Glu Ile Glu
            100                 105


<210> SEQ ID NO 235
<211> LENGTH: 117
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.9

<400> SEQUENCE: 235

Glu Val Gln Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Val Ser Trp Val Lys Gln Ala Pro Gly Lys Asp Leu Lys Trp Met
        35                  40                  45

Gly Trp Ile Tyr Thr Phe Thr Gly Glu Ala Thr Tyr Ile Asp Asp Phe
    50                  55                  60

Arg Gly Arg Phe Ala Phe Ser Leu Glu Thr Ser Ala Asn Thr Ala Tyr
65                  70                  75                  80

Leu Gln Ile Asn Asn Leu Lys Asn Glu Asp Thr Ala Thr Tyr Phe Cys
                85                  90                  95

Ser Arg Arg Asn Gly Ala Trp Phe Glu Asp Trp Gly Gln Gly Thr Leu
```

```
            100                 105                 110

Val Thr Val Ser Ala
        115


<210> SEQ ID NO 236
<211> LENGTH: 107
<212> TYPE: PRT
<213> ORGANISM: Artificial Sequence
<220> FEATURE:
<223> OTHER INFORMATION: Amino acid sequence of the variable region of
      the light chain of anti-hTfR antibody No.10

<400> SEQUENCE: 236

Asp Ile Val Met Thr Gln Thr Pro Ser Ser Leu Ser Ala Ser Leu Gly
1               5                   10                  15

Glu Arg Val Ser Leu Thr Cys Arg Pro Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Arg
                85                  90                  95

Thr Phe Gly Gly Gly Thr Lys Leu Glu Ile Lys
            100                 105


<210> SEQ ID NO 237
<211> LENGTH: 120
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.10

<400> SEQUENCE: 237

Glu Val Gln Leu Gln Glu Ser Gly Gly Gly Leu Val Lys Pro Gly Gly
1               5                   10                  15

Ser Leu Lys Leu Ser Cys Glu Ala Ser Gly Ile Thr Phe Arg Asn Tyr
            20                  25                  30

Ala Met Ser Trp Val Arg Gln Thr Pro Glu Lys Arg Leu Glu Trp Val
        35                  40                  45

Ala Thr Ile Ser Ser Tyr Gly Gly Tyr Thr Tyr Tyr Ala Asp Ser Val
    50                  55                  60

Lys Gly Arg Phe Thr Val Ser Arg Asp Asn Ala Gly Asn Thr Leu Tyr
65                  70                  75                  80

Leu Gln Met Ser Ser Leu Arg Ser Glu Asp Thr Ala Met Tyr His Cys
                85                  90                  95

Ala Arg Gln Glu Val Pro Tyr Pro Tyr Pro Met Asp Asn Trp Gly Gln
            100                 105                 110

Gly Thr Ser Val Ile Val Ser Ser
        115                 120


<210> SEQ ID NO 238
<211> LENGTH: 107
<212> TYPE: PRT
<213> ORGANISM: Artificial Sequence
<220> FEATURE:
<223> OTHER INFORMATION: Amino acid sequence of the variable region of
```

the light chain of anti-hTfR antibody No.11

<400> SEQUENCE: 238

Asp Ile Val Leu Thr Gln Ser Pro Ala Thr Leu Ser Val Thr Pro Gly
1 5 10 15

Asp Arg Val Ser Leu Ser Cys Arg Ala Ser Gln Ser Ile Arg Asn Tyr
20 25 30

Leu His Trp Tyr Gln Gln Lys Ser His Glu Ser Pro Arg Leu Leu Ile
35 40 45

Lys Tyr Ala Ser Gln Ser Ile Ser Gly Ile Pro Ser Arg Phe Ser Gly
50 55 60

Ser Gly Ser Gly Thr Asp Phe Thr Leu Ser Ile Asn Ser Val Glu Thr
65 70 75 80

Glu Asp Phe Gly Met Tyr Phe Cys Gln Gln Thr Asn Ser Trp Pro Tyr
85 90 95

Thr Phe Gly Gly Gly Thr Lys Leu Glu Ile Lys
100 105

<210> SEQ ID NO 239
<211> LENGTH: 118
<212> TYPE: PRT
<213> ORGANISM: Artificial Sequence
<220> FEATURE:
<223> OTHER INFORMATION: Amino acid sequence of the variable region of the heavy chain of anti-hTfR antibody No.11

<400> SEQUENCE: 239

Glu Val Gln Leu Gln Glu Ser Gly Ala Glu Leu Val Arg Pro Gly Ser
1 5 10 15

Ser Val Lys Ile Ser Cys Lys Ala Ser Gly Tyr Ala Phe Ser Ile Tyr
20 25 30

Trp Ile Asn Trp Leu Lys Gln Arg Pro Gly Gln Gly Leu Glu Trp Ile
35 40 45

Gly Gln Ile Tyr Pro Gly Asn Gly Asp Thr Asn Tyr Asn Gly Lys Phe
50 55 60

Lys Gly Lys Ala Thr Leu Thr Ala Asp Lys Ser Ser Asn Thr Val Tyr
65 70 75 80

Met Arg Leu Ser Ser Leu Thr Ser Glu Asp Ser Ala Val Tyr Phe Cys
85 90 95

Gly Arg Trp Gly Asp Asp Tyr Ala Met Asp Phe Trp Gly Gln Gly Thr
100 105 110

Ser Val Thr Val Ser Ser
115

<210> SEQ ID NO 240
<211> LENGTH: 107
<212> TYPE: PRT
<213> ORGANISM: Artificial Sequence
<220> FEATURE:
<223> OTHER INFORMATION: Amino acid sequence of the variable region of the light chain of anti-hTfR antibody No.12

<400> SEQUENCE: 240

Asp Ile Val Leu Thr Gln Ser His Lys Phe Met Ser Thr Val Ile Gly
1 5 10 15

Asp Arg Val Ser Ile Thr Cys Lys Ala Ser His Asp Val Lys Thr Ala
20 25 30

Val Ala Trp Tyr Gln Gln Thr Pro Gly Gln Ser Pro Lys Leu Leu Thr
35 40 45

```
Tyr Trp Ser Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Phe Ser Thr Pro Leu
                85                  90                  95

Thr Phe Gly Ala Gly Thr Lys Leu Glu Leu Lys
            100                 105


<210> SEQ ID NO 241
<211> LENGTH: 119
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.12

<400> SEQUENCE: 241

Glu Val Gln Leu Gln Glu Ser Gly Ala Glu Leu Ala Arg Pro Gly Thr
1               5                   10                  15

Ser Val Lys Val Ser Cys Lys Ala Ala Gly Tyr Val Phe Ile Asn Tyr
            20                  25                  30

Leu Ile Glu Trp Val Lys Gln Arg Pro Gly Gln Gly Leu Glu Trp Ile
        35                  40                  45

Gly Val Ile His Ser Gly Ser Gly Gly Thr Asn Tyr Asn Asp Asn Phe
    50                  55                  60

Lys Asp Lys Ala Thr Leu Thr Arg Asp Val Ser Ser Ser Thr Ala Tyr
65                  70                  75                  80

Met Gln Leu Ser Ser Leu Thr Ser Asp Asp Ser Ala Val Tyr Phe Cys
                85                  90                  95

Ala Arg Arg Asn Phe Gly Asn Tyr Tyr Phe Asp Tyr Trp Gly Gln Gly
            100                 105                 110

Thr Thr Leu Thr Val Ser Ser
        115


<210> SEQ ID NO 242
<211> LENGTH: 107
<212> TYPE: PRT
<213> ORGANISM: Artificial Sequence
<220> FEATURE:
<223> OTHER INFORMATION: Amino acid sequence of the variable region of
      the light chain of anti-hTfR antibody No.13

<400> SEQUENCE: 242

Asp Ile Val Ile Thr Gln Thr Pro Ala Thr Leu Ser Val Thr Pro Gly
1               5                   10                  15

Asp Arg Val Ser Leu Ser Cys Arg Ala Ser Gln Ser Ile Arg Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Val Glu Thr
65                  70                  75                  80

Glu Asp Phe Gly Met Tyr Phe Cys Gln Gln Thr Asn Ser Trp Pro Tyr
                85                  90                  95

Thr Phe Gly Gly Gly Thr Lys Leu Glu Ile Lys
            100                 105
```

<210> SEQ ID NO 243
<211> LENGTH: 118
<212> TYPE: PRT
<213> ORGANISM: Artificial Sequence
<220> FEATURE:
<223> OTHER INFORMATION: Amino acid sequence of the variable region of the heavy chain of anti-hTfR antibody No.13

<400> SEQUENCE: 243

```
Glu Val Gln Leu Gln Glu Ser Gly Ala Glu Leu Val Arg Pro Gly Ser
1               5                   10                  15

Ser Val Lys Ile Ser Cys Lys Ala Ser Gly Tyr Ala Phe Ser Ile Tyr
            20                  25                  30

Trp Ile Asn Trp Leu Lys Gln Arg Pro Gly Gln Gly Leu Glu Trp Ile
        35                  40                  45

Gly Gln Ile Tyr Pro Gly Asn Gly Asp Thr Asn Tyr Asn Gly Lys Phe
    50                  55                  60

Lys Gly Lys Ala Thr Leu Thr Ala Asp Lys Ser Ser Asn Thr Val Tyr
65                  70                  75                  80

Met Arg Leu Ser Ser Leu Thr Ser Glu Asp Ser Ala Val Tyr Phe Cys
                85                  90                  95

Gly Arg Trp Gly Asp Asp Tyr Ala Met Asp Phe Trp Gly Gln Gly Thr
            100                 105                 110

Ser Val Thr Val Ser Ser
        115
```

<210> SEQ ID NO 244
<211> LENGTH: 106
<212> TYPE: PRT
<213> ORGANISM: Artificial Sequence
<220> FEATURE:
<223> OTHER INFORMATION: Amino acid sequence of the variable region of the light chain of anti-hTfR antibody No.14

<400> SEQUENCE: 244

```
Asp Ile Val Leu Thr Gln Thr Pro Val Ile Met Ser Ala Tyr Pro Gly
1               5                   10                  15

Glu Lys Val Thr Leu Thr Cys Ser Ala Ser Ser Asn Ile Asn Ser Ile
            20                  25                  30

His Trp Tyr Gln Gln Lys Pro Gly Thr Ser Pro Lys Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ser Tyr Tyr Cys His Gln Arg Ser Gly Tyr Pro Phe Thr
                85                  90                  95

Phe Gly Ser Gly Thr Lys Leu Glu Ile Lys
            100                 105
```

<210> SEQ ID NO 245
<211> LENGTH: 118
<212> TYPE: PRT
<213> ORGANISM: Artificial Sequence
<220> FEATURE:
<223> OTHER INFORMATION: Amino acid sequence of the variable region of the heavy chain of anti-hTfR antibody No.14

<400> SEQUENCE: 245

```
Glu Val Gln Leu Gln Glu Ser Gly Pro Glu Leu Leu Lys Pro Gly Ala
1               5                   10                  15

Ser Val Lys Met Ser Cys Lys Ala Ser Gly Tyr Ala Phe Thr Gly Tyr
            20                  25                  30

Val Ile His Trp Val Lys Gln Lys Pro Gly Gln Gly Leu Glu Trp Ile
        35                  40                  45

Gly Phe Leu Asn Pro His Lys Asp Asp Ser Glu Tyr Asn Glu Lys Phe
    50                  55                  60

Arg Gly Lys Ala Thr Leu Thr Ser Asp Lys Ser Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Arg Gly Tyr Tyr Tyr Tyr Ser Met Asp Tyr Trp Gly Gln Gly Thr
            100                 105                 110

Ser Val Thr Val Ser Ser
        115


<210> SEQ ID NO 246
<211> LENGTH: 525
<212> TYPE: PRT
<213> ORGANISM: Homo sapiens

<400> SEQUENCE: 246

Ser Glu Thr Gln Ala Asn Ser Thr Thr Asp Ala Leu Asn Val Leu Leu
1               5                   10                  15

Ile Ile Val Asp Asp Leu Arg Pro Ser Leu Gly Cys Tyr Gly Asp Lys
            20                  25                  30

Leu Val Arg Ser Pro Asn Ile Asp Gln Leu Ala Ser His Ser Leu Leu
        35                  40                  45

Phe Gln Asn Ala Phe Ala Gln Gln Ala Val Cys Ala Pro Ser Arg Val
    50                  55                  60

Ser Phe Leu Thr Gly Arg Arg Pro Asp Thr Thr Arg Leu Tyr Asp Phe
65                  70                  75                  80

Asn Ser Tyr Trp Arg Val His Ala Gly Asn Phe Ser Thr Ile Pro Gln
                85                  90                  95

Tyr Phe Lys Glu Asn Gly Tyr Val Thr Met Ser Val Gly Lys Val Phe
            100                 105                 110

His Pro Gly Ile Ser Ser Asn His Thr Asp Asp Ser Pro Tyr Ser Trp
        115                 120                 125

Ser Phe Pro Pro Tyr His Pro Ser Ser Glu Lys Tyr Glu Asn Thr Lys
    130                 135                 140

Thr Cys Arg Gly Pro Asp Gly Glu Leu His Ala Asn Leu Leu Cys Pro
145                 150                 155                 160

Val Asp Val Leu Asp Val Pro Glu Gly Thr Leu Pro Asp Lys Gln Ser
                165                 170                 175

Thr Glu Gln Ala Ile Gln Leu Leu Glu Lys Met Lys Thr Ser Ala Ser
            180                 185                 190

Pro Phe Phe Leu Ala Val Gly Tyr His Lys Pro His Ile Pro Phe Arg
        195                 200                 205

Tyr Pro Lys Glu Phe Gln Lys Leu Tyr Pro Leu Glu Asn Ile Thr Leu
    210                 215                 220

Ala Pro Asp Pro Glu Val Pro Asp Gly Leu Pro Pro Val Ala Tyr Asn
225                 230                 235                 240

Pro Trp Met Asp Ile Arg Gln Arg Glu Asp Val Gln Ala Leu Asn Ile
                245                 250                 255
```

```
Ser Val Pro Tyr Gly Pro Ile Pro Val Asp Phe Gln Arg Lys Ile Arg
            260                 265                 270

Gln Ser Tyr Phe Ala Ser Val Ser Tyr Leu Asp Thr Gln Val Gly Arg
        275                 280                 285

Leu Leu Ser Ala Leu Asp Asp Leu Gln Leu Ala Asn Ser Thr Ile Ile
    290                 295                 300

Ala Phe Thr Ser Asp His Gly Trp Ala Leu Gly Glu His Gly Glu Trp
305                 310                 315                 320

Ala Lys Tyr Ser Asn Phe Asp Val Ala Thr His Val Pro Leu Ile Phe
                325                 330                 335

Tyr Val Pro Gly Arg Thr Ala Ser Leu Pro Glu Ala Gly Glu Lys Leu
            340                 345                 350

Phe Pro Tyr Leu Asp Pro Phe Asp Ser Ala Ser Gln Leu Met Glu Pro
        355                 360                 365

Gly Arg Gln Ser Met Asp Leu Val Glu Leu Val Ser Leu Phe Pro Thr
    370                 375                 380

Leu Ala Gly Leu Ala Gly Leu Gln Val Pro Pro Arg Cys Pro Val Pro
385                 390                 395                 400

Ser Phe His Val Glu Leu Cys Arg Glu Gly Lys Asn Leu Leu Lys His
                405                 410                 415

Phe Arg Phe Arg Asp Leu Glu Glu Asp Pro Tyr Leu Pro Gly Asn Pro
            420                 425                 430

Arg Glu Leu Ile Ala Tyr Ser Gln Tyr Pro Arg Pro Ser Asp Ile Pro
        435                 440                 445

Gln Trp Asn Ser Asp Lys Pro Ser Leu Lys Asp Ile Lys Ile Met Gly
    450                 455                 460

Tyr Ser Ile Arg Thr Ile Asp Tyr Arg Tyr Thr Val Trp Val Gly Phe
465                 470                 475                 480

Asn Pro Asp Glu Phe Leu Ala Asn Phe Ser Asp Ile His Ala Gly Glu
                485                 490                 495

Leu Tyr Phe Val Asp Ser Asp Pro Leu Gln Asp His Asn Met Tyr Asn
            500                 505                 510

Asp Ser Gln Gly Gly Asp Leu Phe Gln Leu Leu Met Pro
        515                 520                 525


<210> SEQ ID NO 247
<211> LENGTH: 973
<212> TYPE: PRT
<213> ORGANISM: Artificial Sequence
<220> FEATURE:
<223> OTHER INFORMATION: Amino acid sequence of the fusion protein of
      heavy chain of anti-hTfR antibody No.1 (humanized 6) and hI2S

<400> SEQUENCE: 247

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                85                  90                  95

Thr Asn Asn Arg Tyr Asp Glu Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Gly Ser
        435                 440                 445

Ser Glu Thr Gln Ala Asn Ser Thr Thr Asp Ala Leu Asn Val Leu Leu
    450                 455                 460

Ile Ile Val Asp Asp Leu Arg Pro Ser Leu Gly Cys Tyr Gly Asp Lys
465                 470                 475                 480

Leu Val Arg Ser Pro Asn Ile Asp Gln Leu Ala Ser His Ser Leu Leu
                485                 490                 495

Phe Gln Asn Ala Phe Ala Gln Gln Ala Val Cys Ala Pro Ser Arg Val
            500                 505                 510
```

```
Ser Phe Leu Thr Gly Arg Arg Pro Asp Thr Thr Arg Leu Tyr Asp Phe
        515                 520                 525

Asn Ser Tyr Trp Arg Val His Ala Gly Asn Phe Ser Thr Ile Pro Gln
    530                 535                 540

Tyr Phe Lys Glu Asn Gly Tyr Val Thr Met Ser Val Gly Lys Val Phe
545                 550                 555                 560

His Pro Gly Ile Ser Ser Asn His Thr Asp Asp Ser Pro Tyr Ser Trp
                565                 570                 575

Ser Phe Pro Pro Tyr His Pro Ser Ser Glu Lys Tyr Glu Asn Thr Lys
            580                 585                 590

Thr Cys Arg Gly Pro Asp Gly Glu Leu His Ala Asn Leu Leu Cys Pro
        595                 600                 605

Val Asp Val Leu Asp Val Pro Glu Gly Thr Leu Pro Asp Lys Gln Ser
    610                 615                 620

Thr Glu Gln Ala Ile Gln Leu Leu Glu Lys Met Lys Thr Ser Ala Ser
625                 630                 635                 640

Pro Phe Phe Leu Ala Val Gly Tyr His Lys Pro His Ile Pro Phe Arg
                645                 650                 655

Tyr Pro Lys Glu Phe Gln Lys Leu Tyr Pro Leu Glu Asn Ile Thr Leu
            660                 665                 670

Ala Pro Asp Pro Glu Val Pro Asp Gly Leu Pro Pro Val Ala Tyr Asn
        675                 680                 685

Pro Trp Met Asp Ile Arg Gln Arg Glu Asp Val Gln Ala Leu Asn Ile
    690                 695                 700

Ser Val Pro Tyr Gly Pro Ile Pro Val Asp Phe Gln Arg Lys Ile Arg
705                 710                 715                 720

Gln Ser Tyr Phe Ala Ser Val Ser Tyr Leu Asp Thr Gln Val Gly Arg
                725                 730                 735

Leu Leu Ser Ala Leu Asp Asp Leu Gln Leu Ala Asn Ser Thr Ile Ile
            740                 745                 750

Ala Phe Thr Ser Asp His Gly Trp Ala Leu Gly Glu His Gly Glu Trp
        755                 760                 765

Ala Lys Tyr Ser Asn Phe Asp Val Ala Thr His Val Pro Leu Ile Phe
    770                 775                 780

Tyr Val Pro Gly Arg Thr Ala Ser Leu Pro Glu Ala Gly Glu Lys Leu
785                 790                 795                 800

Phe Pro Tyr Leu Asp Pro Phe Asp Ser Ala Ser Gln Leu Met Glu Pro
                805                 810                 815

Gly Arg Gln Ser Met Asp Leu Val Glu Leu Val Ser Leu Phe Pro Thr
            820                 825                 830

Leu Ala Gly Leu Ala Gly Leu Gln Val Pro Pro Arg Cys Pro Val Pro
        835                 840                 845

Ser Phe His Val Glu Leu Cys Arg Glu Gly Lys Asn Leu Leu Lys His
    850                 855                 860

Phe Arg Phe Arg Asp Leu Glu Glu Asp Pro Tyr Leu Pro Gly Asn Pro
865                 870                 875                 880

Arg Glu Leu Ile Ala Tyr Ser Gln Tyr Pro Arg Pro Ser Asp Ile Pro
                885                 890                 895

Gln Trp Asn Ser Asp Lys Pro Ser Leu Lys Asp Ile Lys Ile Met Gly
            900                 905                 910

Tyr Ser Ile Arg Thr Ile Asp Tyr Arg Tyr Thr Val Trp Val Gly Phe
        915                 920                 925
```

```
Asn Pro Asp Glu Phe Leu Ala Asn Phe Ser Asp Ile His Ala Gly Glu
    930                 935                 940

Leu Tyr Phe Val Asp Ser Asp Pro Leu Gln Asp His Asn Met Tyr Asn
945                 950                 955                 960

Asp Ser Gln Gly Gly Asp Leu Phe Gln Leu Leu Met Pro
                965                 970


<210> SEQ ID NO 248
<211> LENGTH: 3002
<212> TYPE: DNA
<213> ORGANISM: Artificial Sequence
<220> FEATURE:
<223> OTHER INFORMATION: Nucleotide sequence encoding the amino acid
      sequence of fusion protein of heavy chain of anti-hTfR antibody
      No.1 (humanized 6) and hI2S, synthetic sequence

<400> SEQUENCE: 248

acgcgtgccg ccaccatggg ctggagctgg attctgctgt tcctcctgag cgtgacagca      60

ggagtgcaca gcgaagtgca gctggtcgaa tcaggggggg ggctggtgca gcctggaggc     120

agcctgagac tgtcctgcgc cgcttctggc ttgaccttta gcaactacgg gatgtcctgg     180

gtgcggcagg ctcctggcaa gggactggag ttggtggcca acatcaatac caacggcgga     240

agtacatact atcccgattc agtgaagggc cggttcacca tcagcaggga caacgccaag     300

aacagcctgt atctgcagat gaactctctg agggccgagg atacagccgt gtactattgc     360

actaacaacc ggtacgacga ggactattgg ggccagggca ccctggtgac agtgtctagc     420

gcctctacca agggcccaag cgtgtttcct ctggctccat cctctaaatc cacctctggc     480

ggcacagccg ctctgggctg tctggtgaag gattacttcc cagagcccgt gacagtgtct     540

tggaacagcg gcgccctgac ctccggcgtg cacacatttc ctgctgtgct gcagagctcc     600

ggcctgtaca gcctgtctag cgtggtgacc gtgccatcct ctagcctggg cacccagaca     660

tatatctgca acgtgaatca caagcccagc aatacaaagg tggataagaa ggtggagcca     720

aagtcctgtg acaagaccca cacatgcccc ccttgtcctg ctccagagct gctgggagga     780

ccaagcgtgt tcctgtttcc acccaagccc aaggataccc tgatgatctc tcggacccca     840

gaggtgacat gcgtggtggt ggatgtgagc cacgaggacc ccgaggtgaa gttcaactgg     900

tatgtggacg gcgtggaggt gcacaatgct aagaccaagc ccagggagga gcagtacaac     960

tccacctata gagtggtgtc tgtgctgaca gtgctgcacc aggattggct gaacggcaag    1020

gagtataagt gcaaggtgtc caataaggcc ctgcccgctc ctatcgagaa gaccatctct    1080

aaggccaagg gccagcccag agagcctcag gtgtacacac tgcctccatc ccgggatgag    1140

ctgaccaaga accaggtgtc tctgacatgt ctggtcaagg gcttctatcc ctctgacatc    1200

gccgtggagt gggagagcaa tggccagcct gagaacaatt acaagaccac accccctgtg    1260

ctggattccg acggctcttt ctttctgtat agcaagctga ccgtggacaa gtcccggtgg    1320

cagcagggca acgtgttcag ctgttccgtg atgcacgaag ctctgcataa tcactatact    1380

cagaaatccc tgtcactgtc acctggtaaa ggatcttccg aaacgcaggc caactcgacc    1440

acagatgctc tgaacgttct tctcatcatc gtggatgacc tgcgcccctc cctgggctgt    1500

tatggggata agctggtgag gtccccaaat attgaccaac tggcatccca cagcctcctc    1560

ttccagaatg cctttgcgca gcaagcagtg tgcgccccga gccgcgtttc tttcctcact    1620

ggcaggagac ctgacaccac ccgcctgtac gacttcaact cctactggag ggtgcacgct    1680

ggaaacttct ccaccatccc ccagtacttc aaggagaatg gctatgtgac catgtcggtg    1740
```

ggaaaagtct ttcaccctgg gatatcttct aaccataccg atgattctcc gtatagctgg 1800
tcttttccac cttatcatcc ttcctctgag aagtatgaaa acactaagac atgtcgaggg 1860
ccagatggag aactccatgc caacctgctt tgccctgtgg atgtgctgga tgttcccgag 1920
ggcaccttgc ctgacaaaca gagcactgag caagccatac agttgttgga aaagatgaaa 1980
acgtcagcca gtcctttctt cctggccgtt gggtatcata agccacacat ccccttcaga 2040
taccccaagg aatttcagaa gttgtatccc ttggagaaca tcaccctggc ccccgatccc 2100
gaggtccctg atggcctacc ccctgtggcc tacaacccct ggatggacat caggcaacgg 2160
gaagacgtcc aagccttaaa catcagtgtg ccgtatggtc caattcctgt ggactttcag 2220
cggaaaatcc gccagagcta ctttgcctct gtgtcatatt tggatacaca ggtcggccgc 2280
ctcttgagtg ctttggacga tcttcagctg gccaacagca ccatcattgc atttacctcg 2340
gatcatgggt gggctctagg tgaacatgga gaatgggcca aatacagcaa ttttgatgtt 2400
gctacccatg ttcccctgat attctatgtt cctggaagga cggcttcact tccggaggca 2460
ggcgagaagc ttttccctta cctcgaccct tttgattccg cctcacagtt gatggagcca 2520
ggcaggcaat ccatggacct tgtggaactt gtgtctcttt ttcccacgct ggctggactt 2580
gcaggactgc aggttccacc tcgctgcccc gttccttcat ttcacgttga gctgtgcaga 2640
gaaggcaaga accttctgaa gcattttcga ttccgtgact tggaagaaga tccgtacctc 2700
cctggtaatc cccgtgaact gattgcctat agccagtatc ccggccttc agacatccct 2760 cagtggaatt ctgacaagcc gagtttaaaa gatataaaga tcatgggcta ttccatacgc 2820
accatagact ataggtatac tgtgtgggtt ggcttcaatc ctgatgaatt tctagctaac 2880
ttttctgaca tccatgcagg ggaactgtat tttgtggatt ctgacccatt gcaggatcac 2940
aatatgtata atgattccca aggtggagac cttttccagt tgttgatgcc ttaagcggcc 3000
gc 3002

<210> SEQ ID NO 249
<211> LENGTH: 980
<212> TYPE: PRT
<213> ORGANISM: Artificial Sequence
<220> FEATURE:
<223> OTHER INFORMATION: Amino acid sequence of the fusion protein of heavy chain of anti-hTfR antibody No.2 (humanized 6) and hI2S

<400> SEQUENCE: 249

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Val Met His Trp Val Arg Gln Ala Pro Gly Gln Gly Leu Glu Trp Ile
35 40 45

Gly Val Ile Ser Thr Tyr Tyr Gly His Gly Ser Tyr Asn Gln Arg Phe
50 55 60

Lys Gly Arg Ala Thr Met Thr Val Asp Lys Ser Ile Ser Thr Ala Tyr
65 70 75 80

Met Glu Leu Val Arg Leu Arg Ser Asp Asp Thr Ala Val Tyr Tyr Cys
85 90 95

Val Arg Gly Gly Tyr Gly Ser Ser Ser Leu Ala Gly Asn Phe Asp Val
100 105 110

Trp Gly Gln Gly Thr Thr Val Thr Val Ser Ser Ala Ser Thr Lys Gly
115 120 125

```
Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Ser Ser Glu Thr Gln Ala Asn Ser Thr Thr
    450                 455                 460

Asp Ala Leu Asn Val Leu Leu Ile Ile Val Asp Asp Leu Arg Pro Ser
465                 470                 475                 480

Leu Gly Cys Tyr Gly Asp Lys Leu Val Arg Ser Pro Asn Ile Asp Gln
                485                 490                 495

Leu Ala Ser His Ser Leu Leu Phe Gln Asn Ala Phe Ala Gln Gln Ala
            500                 505                 510

Val Cys Ala Pro Ser Arg Val Ser Phe Leu Thr Gly Arg Arg Pro Asp
        515                 520                 525

Thr Thr Arg Leu Tyr Asp Phe Asn Ser Tyr Trp Arg Val His Ala Gly
    530                 535                 540

Asn Phe Ser Thr Ile Pro Gln Tyr Phe Lys Glu Asn Gly Tyr Val Thr
```

545 550 555 560

Met Ser Val Gly Lys Val Phe His Pro Gly Ile Ser Ser Asn His Thr
565 570 575

Asp Asp Ser Pro Tyr Ser Trp Ser Phe Pro Pro Tyr His Pro Ser Ser
580 585 590

Glu Lys Tyr Glu Asn Thr Lys Thr Cys Arg Gly Pro Asp Gly Glu Leu
595 600 605

His Ala Asn Leu Leu Cys Pro Val Asp Val Leu Asp Val Pro Glu Gly
610 615 620

Thr Leu Pro Asp Lys Gln Ser Thr Glu Gln Ala Ile Gln Leu Leu Glu
625 630 635 640

Lys Met Lys Thr Ser Ala Ser Pro Phe Phe Leu Ala Val Gly Tyr His
645 650 655

Lys Pro His Ile Pro Phe Arg Tyr Pro Lys Glu Phe Gln Lys Leu Tyr
660 665 670

Pro Leu Glu Asn Ile Thr Leu Ala Pro Asp Pro Glu Val Pro Asp Gly
675 680 685

Leu Pro Pro Val Ala Tyr Asn Pro Trp Met Asp Ile Arg Gln Arg Glu
690 695 700

Asp Val Gln Ala Leu Asn Ile Ser Val Pro Tyr Gly Pro Ile Pro Val
705 710 715 720

Asp Phe Gln Arg Lys Ile Arg Gln Ser Tyr Phe Ala Ser Val Ser Tyr
725 730 735

Leu Asp Thr Gln Val Gly Arg Leu Leu Ser Ala Leu Asp Asp Leu Gln
740 745 750

Leu Ala Asn Ser Thr Ile Ile Ala Phe Thr Ser Asp His Gly Trp Ala
755 760 765

Leu Gly Glu His Gly Glu Trp Ala Lys Tyr Ser Asn Phe Asp Val Ala
770 775 780

Thr His Val Pro Leu Ile Phe Tyr Val Pro Gly Arg Thr Ala Ser Leu
785 790 795 800

Pro Glu Ala Gly Glu Lys Leu Phe Pro Tyr Leu Asp Pro Phe Asp Ser
805 810 815

Ala Ser Gln Leu Met Glu Pro Gly Arg Gln Ser Met Asp Leu Val Glu
820 825 830

Leu Val Ser Leu Phe Pro Thr Leu Ala Gly Leu Ala Gly Leu Gln Val
835 840 845

Pro Pro Arg Cys Pro Val Pro Ser Phe His Val Glu Leu Cys Arg Glu
850 855 860

Gly Lys Asn Leu Leu Lys His Phe Arg Phe Arg Asp Leu Glu Glu Asp
865 870 875 880

Pro Tyr Leu Pro Gly Asn Pro Arg Glu Leu Ile Ala Tyr Ser Gln Tyr
885 890 895

Pro Arg Pro Ser Asp Ile Pro Gln Trp Asn Ser Asp Lys Pro Ser Leu
900 905 910

Lys Asp Ile Lys Ile Met Gly Tyr Ser Ile Arg Thr Ile Asp Tyr Arg
915 920 925

Tyr Thr Val Trp Val Gly Phe Asn Pro Asp Glu Phe Leu Ala Asn Phe
930 935 940

Ser Asp Ile His Ala Gly Glu Leu Tyr Phe Val Asp Ser Asp Pro Leu
945 950 955 960

Gln Asp His Asn Met Tyr Asn Asp Ser Gln Gly Gly Asp Leu Phe Gln
965 970 975

Leu Leu Met Pro
980

<210> SEQ ID NO 250
<211> LENGTH: 3023
<212> TYPE: DNA
<213> ORGANISM: Artificial Sequence
<220> FEATURE:
<223> OTHER INFORMATION: Nucleotide sequence encoding the amino acid sequence of fusion protein of heavy chain of anti-hTfR antibody No.2 (humanized 6) and hI2S, synthetic sequence

<400> SEQUENCE: 250
acgcgtgccg ccaccatggg ctggagctgg attctgctgt tcctcctgag cgtgacagca 60
ggagtgcaca gccaggtgca gctggtccag tcaggagccg aagtgaaaaa gcccggagcc 120
tcagtcaaag tgtcttgtaa agcatcaggt tatacattta cagactacgt catgcactgg 180
gtgaggcagg cacctggaca gggtctggaa tggatcggcg tgatctccac ttactatggc 240
catggaagct acaaccagag attcaagggc agggcgacaa tgactgtaga caaatcaatt 300
tccactgctt atatggagct ggtaaggctg cggtccgacg ataccgctgt gtactattgc 360
gtacgaggag gatacggctc cagctctctg gctggtaatt tcgatgtgtg ggggcagggt 420
accacagtca ccgtgagttc agcaagcaca aagggcccat ctgtgtttcc actggccccc 480
tccagcaaaa gcacctctgg gggtacagcc gctctgggat gtctggtgaa ggattatttc 540
ccagagccag tcaccgtgtc ctggaacagc ggagccctga catctggagt ccacactttt 600
ccagctgtgc tgcagtctag tggcctgtac tccctgtcat ccgtggtcac tgtccccagc 660
tctagtctgg gtacccagac atatatctgc aacgtgaatc acaagccatc taataccaaa 720
gtcgacaaga aagtggaacc caagtcctgt gataaaactc atacctgccc cccttgtcct 780
gcaccagagc tgctgggagg accatccgtg ttcctgtttc cacccaagcc taaagacacc 840
ctgatgatta gccgaactcc cgaagtcacc tgcgtggtcg tggacgtgtc tcacgaggac 900
cctgaagtca agtttaactg gtacgtggat ggcgtcgagg tgcataatgc taagacaaaa 960
ccccgagagg aacagtacaa cagtacatat cgtgtcgtgt cagtgctgac cgtcctgcat 1020
caggactggc tgaacgggaa ggaatataag tgcaaagtgt ccaataaggc actgcccgcc 1080
cctatcgaga aaaccattag caaggccaaa ggacagccta gggaaccaca ggtgtacaca 1140
ctgcctccat cccgggacga gctgactaag aaccaggtca gcctgacctg tctggtgaaa 1200
ggcttctatc cttcagatat cgctgtggag tgggaaagta atggacagcc agagaacaat 1260
tacaagacta ccccccctgt gctggactct gatgggagtt tctttctgta ttctaagctg 1320
accgtggata aaagtcggtg gcagcagggt aatgtcttta gttgttcagt gatgcacgaa 1380
gcactgcaca accactacac ccagaaatca ctgtcactgt caccagggaa aggatcttcc 1440
gaaacgcagg ccaactcgac cacagatgct ctgaacgttc ttctcatcat cgtggatgac 1500
ctgcgcccct ccctgggctg ttatggggat aagctggtga ggtccccaaa tattgaccaa 1560
ctggcatccc acagcctcct cttccagaat gcctttgcgc agcaagcagt gtgcgccccg 1620
agccgcgttt ctttcctcac tggcaggaga cctgacacca cccgcctgta cgacttcaac 1680
tcctactgga gggtgcacgc tggaaacttc tccaccatcc cccagtactt caaggagaat 1740
ggctatgtga ccatgtcggt gggaaaagtc tttcaccctg ggatatcttc taaccatacc 1800
gatgattctc cgtatagctg gtcttttcca ccttatcatc cttcctctga gaagtatgaa 1860
aacactaaga catgtcgagg gccagatgga gaactccatg ccaacctgct ttgccctgtg 1920

```
gatgtgctgg atgttcccga gggcaccttg cctgacaaac agagcactga gcaagccata   1980

cagttgttgg aaaagatgaa aacgtcagcc agtcctttct tcctggccgt tgggtatcat   2040

aagccacaca tccccttcag ataccccaag gaatttcaga agttgtatcc cttggagaac   2100

atcaccctgg cccccgatcc cgaggtccct gatggcctac cccctgtggc ctacaacccc   2160

tggatggaca tcaggcaacg ggaagacgtc caagccttaa acatcagtgt gccgtatggt   2220

ccaattcctg tggactttca gcggaaaatc cgccagagct actttgcctc tgtgtcatat   2280

ttggatacac aggtcggccg cctcttgagt gctttggacg atcttcagct ggccaacagc   2340

accatcattg catttacctc ggatcatggg tgggctctag gtgaacatgg agaatgggcc   2400

aaatacagca attttgatgt tgctacccat gttcccctga tattctatgt tcctggaagg   2460

acggcttcac ttccggaggc aggcgagaag cttttccctt acctcgaccc ttttgattcc   2520

gcctcacagt tgatggagcc aggcaggcaa tccatggacc ttgtggaact tgtgtctctt   2580

tttcccacgc tggctggact tgcaggactg caggttccac ctcgctgccc cgttccttca   2640

tttcacgttg agctgtgcag agaaggcaag aaccttctga agcattttcg attccgtgac   2700

ttggaagaag atccgtacct ccctggtaat ccccgtgaac tgattgccta tagccagtat   2760

ccccggcctt cagacatccc tcagtggaat tctgacaagc cgagtttaaa agatataaag   2820

atcatgggct attccatacg caccatagac tataggtata ctgtgtgggt tggcttcaat   2880

cctgatgaat ttctagctaa cttttctgac atccatgcag ggaactgtta ttttgtggat   2940

tctgacccat tgcaggatca caatatgtat aatgattccc aaggtggaga cctttttccag   3000

ttgttgatgc cttaagcggc cgc                                           3023
```

```
<210> SEQ ID NO 251
<211> LENGTH: 975
<212> TYPE: PRT
<213> ORGANISM: Artificial Sequence
<220> FEATURE:
<223> OTHER INFORMATION: Amino acid sequence of fusion protein of heavy
      chain of anti-hTfR antibody No.3 (humanized 2) and hI2S, synthetic
      sequence

<400> SEQUENCE: 251

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
```

```
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser Ser Glu Thr Gln Ala Asn Ser Thr Thr Asp Ala Leu Asn Val
    450                 455                 460

Leu Leu Ile Ile Val Asp Asp Leu Arg Pro Ser Leu Gly Cys Tyr Gly
465                 470                 475                 480

Asp Lys Leu Val Arg Ser Pro Asn Ile Asp Gln Leu Ala Ser His Ser
                485                 490                 495

Leu Leu Phe Gln Asn Ala Phe Ala Gln Gln Ala Val Cys Ala Pro Ser
            500                 505                 510

Arg Val Ser Phe Leu Thr Gly Arg Arg Pro Asp Thr Thr Arg Leu Tyr
        515                 520                 525

Asp Phe Asn Ser Tyr Trp Arg Val His Ala Gly Asn Phe Ser Thr Ile
    530                 535                 540

Pro Gln Tyr Phe Lys Glu Asn Gly Tyr Val Thr Met Ser Val Gly Lys
545                 550                 555                 560

Val Phe His Pro Gly Ile Ser Ser Asn His Thr Asp Asp Ser Pro Tyr
                565                 570                 575
```

Ser Trp Ser Phe Pro Pro Tyr His Pro Ser Ser Glu Lys Tyr Glu Asn
580 585 590

Thr Lys Thr Cys Arg Gly Pro Asp Gly Glu Leu His Ala Asn Leu Leu
595 600 605

Cys Pro Val Asp Val Leu Asp Val Pro Glu Gly Thr Leu Pro Asp Lys
610 615 620

Gln Ser Thr Glu Gln Ala Ile Gln Leu Leu Glu Lys Met Lys Thr Ser
625 630 635 640

Ala Ser Pro Phe Phe Leu Ala Val Gly Tyr His Lys Pro His Ile Pro
645 650 655

Phe Arg Tyr Pro Lys Glu Phe Gln Lys Leu Tyr Pro Leu Glu Asn Ile
660 665 670

Thr Leu Ala Pro Asp Pro Glu Val Pro Asp Gly Leu Pro Pro Val Ala
675 680 685

Tyr Asn Pro Trp Met Asp Ile Arg Gln Arg Glu Asp Val Gln Ala Leu
690 695 700

Asn Ile Ser Val Pro Tyr Gly Pro Ile Pro Val Asp Phe Gln Arg Lys
705 710 715 720

Ile Arg Gln Ser Tyr Phe Ala Ser Val Ser Tyr Leu Asp Thr Gln Val
725 730 735

Gly Arg Leu Leu Ser Ala Leu Asp Asp Leu Gln Leu Ala Asn Ser Thr
740 745 750

Ile Ile Ala Phe Thr Ser Asp His Gly Trp Ala Leu Gly Glu His Gly
755 760 765

Glu Trp Ala Lys Tyr Ser Asn Phe Asp Val Ala Thr His Val Pro Leu
770 775 780

Ile Phe Tyr Val Pro Gly Arg Thr Ala Ser Leu Pro Glu Ala Gly Glu
785 790 795 800

Lys Leu Phe Pro Tyr Leu Asp Pro Phe Asp Ser Ala Ser Gln Leu Met
805 810 815

Glu Pro Gly Arg Gln Ser Met Asp Leu Val Glu Leu Val Ser Leu Phe
820 825 830

Pro Thr Leu Ala Gly Leu Ala Gly Leu Gln Val Pro Pro Arg Cys Pro
835 840 845

Val Pro Ser Phe His Val Glu Leu Cys Arg Glu Gly Lys Asn Leu Leu
850 855 860

Lys His Phe Arg Phe Arg Asp Leu Glu Glu Asp Pro Tyr Leu Pro Gly
865 870 875 880

Asn Pro Arg Glu Leu Ile Ala Tyr Ser Gln Tyr Pro Arg Pro Ser Asp
885 890 895

Ile Pro Gln Trp Asn Ser Asp Lys Pro Ser Leu Lys Asp Ile Lys Ile
900 905 910

Met Gly Tyr Ser Ile Arg Thr Ile Asp Tyr Arg Tyr Thr Val Trp Val
915 920 925

Gly Phe Asn Pro Asp Glu Phe Leu Ala Asn Phe Ser Asp Ile His Ala
930 935 940

Gly Glu Leu Tyr Phe Val Asp Ser Asp Pro Leu Gln Asp His Asn Met
945 950 955 960

Tyr Asn Asp Ser Gln Gly Gly Asp Leu Phe Gln Leu Leu Met Pro
965 970 975

<210> SEQ ID NO 252
<211> LENGTH: 3011

```
<212> TYPE: DNA
<213> ORGANISM: Artificial Sequence
<220> FEATURE:
<223> OTHER INFORMATION: Nucleotide sequence encoding the amino acid
      sequence of fusion protein of heavy chain of anti-hTfR antibody
      No.3 (humanized 2) and hI2S, synthetic sequence

<400> SEQUENCE: 252

acgcgtgccg ccaccatggg ctggagctgg attctgctgt tcctcctgag cgtgacagca     60

ggagtgcaca gcgaggtgca actagtgcag tctggagcag aggtgaaaaa gcccggggag    120

tctctgaaga tttcctgtaa gggttctgga tacagcttta ccaactactg gctgggatgg    180

gtgcgccaga tgcccgggaa aggcctggag tggatggggg acatctaccc cggcggagac    240

taccctacat acagcgagaa gttcaaggtc caggtcacca tctcagccga caagtccatc    300

agcaccgcct acctgcagtg gagcagcctg aaggcctcgg acaccgccat gtattactgt    360

gcgagatcag gcaattacga cgaagtggcc tactggggcc aaggaaccct ggtcaccgtc    420

tcctcagcta gcaccaaggg cccatcggtc ttccccctgg caccctcctc caagagcacc    480

tctgggggca cagcggccct gggctgcctg gtcaaggact acttccccga accggtgacg    540

gtgtcgtgga actcaggcgc cctgaccagc ggcgtgcaca ccttcccggc tgtcctacag    600

tcctcaggac tctactccct cagcagcgtg gtgaccgtgc cctccagcag cttgggcacc    660

cagacctaca tctgcaacgt gaatcacaag cccagcaaca ccaaggtgga caagaaagtt    720

gagcccaaat cttgtgacaa aactcacacg tgcccaccgt gcccagcacc tgaactcctg    780

ggaggtccgt cagtcttcct cttcccccca aaacccaagg acaccctcat gatctcccgg    840

acccctgagg tcacatgcgt ggtggtggac gtgagccacg aagaccctga ggtcaagttc    900

aactggtacg tggacggcgt ggaggtgcat aatgccaaga caaagccgcg ggaggagcag    960

tacaacagca cgtaccgggt ggtcagcgtc ctcaccgtcc tgcaccagga ctggctgaat   1020

ggcaaggagt acaagtgcaa ggtctccaac aaagccctcc cagcccccat cgagaaaacc   1080

atctccaaag ccaaagggca gccccgagaa ccacaggtgt acaccctgcc cccatcccgg   1140

gatgagctga ccaagaacca ggtcagcctg acctgcctgg tcaaaggctt ctatcccagc   1200

gacatcgccg tggagtggga gagcaatggg cagccggaga acaactacaa gaccacgcct   1260

cccgtgctgg actccgacgg ctccttcttc ctctacagca agctcaccgt ggacaagagc   1320

aggtggcagc aggggaacgt cttctcatgc tccgtgatgc atgaggctct gcacaaccac   1380

tacacgcaga agagcctctc cctgtctccg ggtaaaggat cttccgaaac gcaggccaac   1440

tcgaccacag atgctctgaa cgttcttctc atcatcgtgg atgacctgcg cccctccctg   1500

ggctgttatg ggataagct ggtgaggtcc ccaaatattg accaactggc atcccacagc   1560

ctcctcttcc agaatgcctt tgcgcagcaa gcagtgtgcg ccccgagccg cgtttctttc   1620

ctcactggca ggagacctga caccacccgc ctgtacgact tcaactccta ctggagggtg   1680

cacgctggaa acttctccac catcccccag tacttcaagg agaatggcta tgtgaccatg   1740

tcggtgggaa aagtctttca ccctgggata tcttctaacc ataccgatga ttctccgtat   1800

agctggtctt ttccacctta tcatccttcc tctgagaagt atgaaaacac taagacatgt   1860

cgagggccag atggagaact ccatgccaac ctgctttgcc ctgtggatgt gctggatgtt   1920

cccgagggca ccttgcctga caaacagagc actgagcaag ccatacagtt gttggaaaag   1980

atgaaaacgt cagccagtcc tttcttcctg gccgttgggt atcataagcc acacatcccc   2040

ttcagatacc ccaaggaatt tcagaagttg tatcccttgg agaacatcac cctggccccc   2100
```

```
gatcccgagg tccctgatgg cctaccccct gtggcctaca acccctggat ggacatcagg   2160

caacgggaag acgtccaagc cttaaacatc agtgtgccgt atggtccaat tcctgtggac   2220

tttcagcgga aaatccgcca gagctacttt gcctctgtgt catatttgga tacacaggtc   2280

ggccgcctct tgagtgcttt ggacgatctt cagctggcca acagcaccat cattgcattt   2340

acctcggatc atgggtgggc tctaggtgaa catggagaat gggccaaata cagcaatttt   2400

gatgttgcta cccatgttcc cctgatattc tatgttcctg gaaggacggc ttcacttccg   2460

gaggcaggcg agaagctttt cccttacctc gaccctttg attccgcctc acagttgatg   2520

gagccaggca ggcaatccat ggaccttgtg gaacttgtgt ctctttttcc cacgctggct   2580

ggacttgcag gactgcaggt tccacctcgc tgccccgttc cttcatttca cgttgagctg   2640

tgcagagaag gcaagaacct tctgaagcat tttcgattcc gtgacttgga agaagatccg   2700

tacctccctg gtaatccccg tgaactgatt gcctatagcc agtatccccg gccttcagac   2760

atccctcagt ggaattctga caagccgagt ttaaaagata taaagatcat gggctattcc   2820

atacgcacca tagactatag gtatactgtg tgggttggct tcaatcctga tgaatttcta   2880

gctaactttt ctgacatcca tgcaggggaa ctgtattttg tggattctga cccattgcag   2940

gatcacaata tgtataatga ttcccaaggt ggagaccttt tccagttgtt gatgccttaa   3000

taagcggccg c                                                         3011
```

<210> SEQ ID NO 253
<211> LENGTH: 4460
<212> TYPE: DNA
<213> ORGANISM: Artificial Sequence
<220> FEATURE:
<223> OTHER INFORMATION: Nucleotide sequence of the DNA formed of a cDNA encoding chimeric hTfR and a loxP-flanked neomycin resistance gene placed on the cDNA's 3' side, synthetic sequence

<400> SEQUENCE: 253

```
gtttatcctc ccttgtagca gctgagaatg atggatcaag ccagatcagc attctctaac     60

ttgtttggtg gggaaccatt gtcatacacc cggtttagcc ttgctcggca agtagatgga    120

gataacagtc atgtggagat gaaactggct gcagatgaag aagaaaatgc cgacaataac    180

atgaaggcta gtgtcagaaa acccaagagg tttaatggaa gactctgctt tgcagctatt    240

gcactagtca ttttcttctt gattggattc atgagtggct acctgggcta ttgtaaaggg    300

gtagaaccaa aaactgagtg tgagagactg gcaggaaccg agtctccagt gagggaggag    360

ccaggagagg acttccctgc agcacgtcgc ttatattggg atgacctgaa gagaaagttg    420

tcggagaaac tggacagcac agacttcacc ggcaccatca agctgctgaa tgaaaattca    480

tatgtccctc gtgaggctgg atctcaaaaa gatgaaaatc ttgcgttgta tgttgaaaat    540

caatttcgtg aatttaaact cagcaaagtc tggcgtgatc aacattttgt taagattcag    600

gtcaaagaca gcgctcaaaa ctcggtgatc atagttgata agaacggtag acttgtttac    660

ctggtggaga atcctggggg ttatgtggcg tatagtaagg ctgcaacagt tactggtaaa    720

ctggtccatg ctaattttgg tactaaaaaa gattttgagg atttatacac tcctgtgaat    780

ggatctatag tgattgtcag agcagggaaa atcacctttg cagaaaaggt tgcaaatgct    840

gaaagcttaa atgcaattgg tgtgttgata tacatggacc agactaaatt tcccattgtt    900

aacgcagaac tttcattctt tggacatgct catctgggga caggtgaccc ttacacacct    960

ggattccctt ccttcaatca cactcagttt ccaccatctc ggtcatcagg attgcctaat   1020

atacctgtcc agacaatctc cagagctgct gcagaaaagc tgtttgggaa tatggaagga   1080
```

gactgtccct ctgactggaa aacagactct acatgtagga tggtaacctc agaaagcaag 1140
aatgtgaagc tcactgtgag caatgtgctg aaagagataa aaattcttaa catctttgga 1200
gttattaaag gctttgtaga accagatcac tatgttgtag ttggggccca gagagatgca 1260
tggggccctg gagctgcaaa atccggtgta ggcacagctc tcctattgaa acttgcccag 1320
atgttctcag atatggtctt aaaagatggg tttcagccca gcagaagcat tatctttgcc 1380
agttggagtg ctggagactt tggatcggtt ggtgccactg aatggctaga gggatacctt 1440
tcgtccctgc atttaaaggc tttcacttat attaatctgg ataaagcggt tcttggtacc 1500
agcaacttca aggtttctgc cagcccactg ttgtatacgc ttattgagaa aacaatgcaa 1560
aatgtgaagc atccggttac tgggcaattt ctatatcagg acagcaactg ggccagcaaa 1620
gttgagaaac tcactttaga caatgctgct ttccctttcc ttgcatattc tggaatccca 1680
gcagtttctt tctgtttttg cgaggacaca gattatcctt atttgggtac caccatggac 1740
acctataagg aactgattga gaggattcct gagttgaaca aagtggcacg agcagctgca 1800
gaggtcgctg gtcagttcgt gattaaacta acccatgatg ttgaattgaa cctggactat 1860
gagaggtaca acagccaact gctttcattt gtgagggatc tgaaccaata cagagcagac 1920
ataaaggaaa tgggcctgag tttacagtgg ctgtattctg ctcgtggaga cttcttccgt 1980
gctacttcca gactaacaac agatttcggg aatgctgaga aaacagacag atttgtcatg 2040
aagaaactca atgatcgtgt catgagagtg gagtatcact tcctctctcc ctacgtatct 2100
ccaaaagagt ctcctttccg acatgtcttc tggggctccg gctctcacac gctgccagct 2160
ttactggaga acttgaaact gcgtaaacaa aataacggtg cttttaatga aacgctgttc 2220
agaaaccagt tggctctagc tacttggact attcagggag ctgcaaatgc cctctctggt 2280
gacgtttggg acattgacaa tgagttttaa cgtggctcgc tgatcagcct cgactgtgcc 2340
ttctagttgc cagccatctg ttgtttgccc ctcccccgtg ccttccttga ccctggaagg 2400
tgccactccc actgtccttt cctaataaaa tgaggaaatt gcatcgcatt gtctgagtag 2460
gtgtcattct attctggggg gtggggtggg gcaggacagc aagggggagg attgggaaga 2520
caatagcagg catgctgggg atgcggtggg ctctatggct tctgaggcgg aaagaaccag 2580
ctggggctcg atcctctagt taagcttccc agcggccgct atcgaattcc gatcatattc 2640
aataaccctt aatataactt cgtataatgt atgctatacg aagttattag gtctgaagag 2700
gagtttacgt ccagccaagc taattctacc gggtagggga ggcgcttttc ccaaggcagt 2760
ctggagcatg cgctttagca gccccgctgg gcacttggcg ctacacaagt ggcctctggc 2820
ctcgcacaca ttccacatcc accggtaggc gccaaccggc tccgttcttt ggtggcccct 2880
tcgcgccacc ttctactcct cccctagtca ggaagttccc ccccgccccg cagctcgcgt 2940
cgtgcaggac gtgacaaatg gaagtagcac gtctcactag tctcgtgcag atggacagca 3000
ccgctgagca atggaagcgg gtaggccttt ggggcagcgg ccaatagcag ctttgctcct 3060
tcgctttctg ggctcagagg ctgggaaggg gtgggtccgg gggcgggctc aggggcgggc 3120
tcaggggcgg ggcgggcgcc cgaaggtcct ccggaggccc ggcattctgc acgcttcaaa 3180
agcgcacgtc tgccgcgctg ttctcctctt cctcatctcc gggcctttcg acctgcagcc 3240
aatatgggat cggccattga acaagatgga ttgcacgcag gttctccggc cgcttgggtg 3300
gagaggctat tcggctatga ctgggcacaa cagacaatcg gctgctctga tgccgccgtg 3360
ttccggctgt cagcgcaggg gcgcccggtt ctttttgtca agaccgacct gtccggtgcc 3420

-continued ctgaatgaac tgcaggacga ggcagcgcgg ctatcgtggc tggccacgac gggcgttcct 3480
tgcgcagctg tgctcgacgt tgtcactgaa gcgggaaggg actggctgct attgggcgaa 3540
gtgccggggc aggatctcct gtcatctcac cttgctcctg ccgagaaagt atccatcatg 3600
gctgatgcaa tgcggcggct gcatacgctt gatccggcta cctgcccatt cgaccaccaa 3660
gcgaaacatc gcatcgagcg agcacgtact cggatggaag ccggtcttgt cgatcaggat 3720
gatctggacg aagagcatca ggggctcgcg ccagccgaac tgttcgccag gctcaaggcg 3780
cgcatgcccg acggcgagga tctcgtcgtg acccatggcg atgcctgctt gccgaatatc 3840
atggtggaaa atggccgctt ttctggattc atcgactgtg gccggctggg tgtggcggac 3900
cgctatcagg acatagcgtt ggctacccgt gatattgctg aagagcttgg cggcgaatgg 3960
gctgaccgct tcctcgtgct ttacggtatc gccgctcccg attcgcagcg catcgccttc 4020
tatcgccttc ttgacgagtt cttctgaggg gatccgctgt aagtctgcag aaattgatga 4080
tctattaaac aataaagatg tccactaaaa tggaagtttt tcctgtcata ctttgttaag 4140
aagggtgaga acagagtacc tacattttga atggaaggat tggagctacg gggtggggg 4200 tggggtggga ttagataaat gcctgctctt tactgaaggc tctttactat tgctttatga 4260
taatgtttca tagttggata tcataattta aacaagcaaa accaaattaa gggccagctc 4320
attcctccca ctcatgatct atagatccct cgatcgagat ccggaaccct taatataact 4380
tcgtataatg tatgctatac gaagttatta ggtccctcga agaggttcac tagttctaga 4440
gcatttaaat acgtgctagc 4460

<210> SEQ ID NO 254
<211> LENGTH: 5003
<212> TYPE: DNA
<213> ORGANISM: Artificial Sequence
<220> FEATURE:
<223> OTHER INFORMATION: Nucleotide sequence of the 5'-arm of targeting vector

<400> SEQUENCE: 254
aaagacattc ccagggtccc taagggctcc atctgggagc gcgctatctg tagtcctgtt 60
gtggtttaag ataccactct ctttgttatt tgtaaattta ccacaggctg ggcagtaaag 120
tacagatagg aagaaaagag tgtgaacgtt tgcagtttta acagaactcc ttttatttgc 180
tatgcattgc aacaaccctc taaaagcaat aatggcgata aacatgcaag ttaatctaca 240
actttatcac cctagtaaat cattggttcc tatttccctt ccataggctg aacatagtga 300
gcactggtag ctctttgctt ggcttaagcg ctgcttgtta aaatctaaaa aaaaaaaaaa 360
aaaagatttg cagttttgct ttaaagtttt tcctttaaag catctctgag ctgcaaaaac 420
tcgtctttag gatatggttt tggcggagac ctaagcctgc aagtaggaat attttaaaga 480
gtaaaggctg atactttcga acttgcaccg cagggttggg tgtcggtcaa ggttaggcgg 540
agggcgacag gccaactcca aagacacggc gggggagggg tgcggtggag aaagcgagcc 600
gcagccaatc gcacgcgctc tcccgacacc tgccgccttg gcgccttttc taggctactc 660
cgcgcacgca ctggctgcgc gcgcagttcg cctccagcgg tcttggggga gcacctcggt 720
aggtgtacgt gcggaaggaa gtgacgtaga tccagagggc cggccggggg gtggggccga 780
gctataagct ttgggtggga ggcagcgctg ccttcagaag gcgtgcggag cgcgggctgc 840
tgcattgcgg actgtagagg cgcttcctag tgagtgactc ccttgtcagc ggcacggccc 900
atcgtggtcc tcgcgtggcg ggcggaccag agcgagacgc cagggcctgg gtggtgcggg 960

-continued

```
cggggaggcg gaggggtgtc gcggagtccg gggctgagga gcgcgggttg caggtgcagc   1020
gcggtgggtg tggggagccg ctgtaccctg cgcccctcgg gtcctccggg ccttcgcagg   1080
ccagtgctag gccgcgggtt cgagagtcac cacgctgagg cgcaggcttg ttccgccggg   1140
agcacgtggt ggcggctgga ggaagtcgcc ccagggaacg gctgtcgggg tacgtgggtg   1200
accttggggc ccctcgcagg agggcgtcac agctgaaaag gacaaagctg ttttctattc   1260
ggttactagt gtcacggaca tttagagggg cggggggagc ttccaataac tgcacgttgg   1320
aacttcggca ccacctggtc ggtttttttg ccagtctctc cctcttggcc cagcgtgtgg   1380
aatctcattt ttctagggca gaataggtct gaacgctgca ggtaatacta agaacgtctc   1440
tagcatctcc taagatggga gaacgtagaa atacgacctc tttgtacgag ctcttttaga   1500
actagctgta gagaaccagc gtgcaccctg gtgttggaca gctctctaaa atggtgtttg   1560
agggtaagaa aactgcattt gcaaattttt cagttagcac actttgtccc gagcgtaaaa   1620
tgaaatgatc tccttatact taggcagaag actggactgg attgctgttc agtttctgtg   1680
ctattttttt aaaataggat ttaagtggga aatagttgtg ttacagaaat tctcggctat   1740
tctgtgctat ttttttttaa ataggattta agtgggaaat agttgtgtta cagaaattct   1800
cggctacctg atacttttat tctaagatta gatgagttgg ctctgagctg tgaaatatga   1860
cctctttgac aaagacattt aagctgattc aggatgttat ctacaaagaa aacgggattt   1920
agcttgtgtg ggtccacttg catttatttt ctgttaagga ttataataaa ctgctttata   1980
caggaatcca atatcagctg ttttttatat agagagcata atacttttta ctttgagaga   2040
ggatgttgtc aaggaatggt ggctgtgaac ctggcctgtg ttgactggtt agatctgtct   2100
gcctaacccc accctaaggc taagtagtta tatgcttgtg gcaatgtgct tatttataat   2160
agggcaagat tatgggctaa atttgggtta gacaacaatg aaagttaatt aaacgaccct   2220
caggccttgg gtctactatg tgtaagtgat ttccttctct cccagatgag tgctatacaa   2280
aataaacttc agtgacctca agtggttttg accttttggt tgctattcag aaaactatgg   2340
aaatgaaaac ctgctaccta tttcctattg ccttttcaat ttcccaaaga aggtctcccc   2400
tatgaatcca tgggtagcct tgaactcaga tccacctgct tctgtttgga gagtgataag   2460
attaaaggca agtgccacca cacccagcaa agtaggctct taaaactaaa acctttgcag   2520
tcgggcatgg tgccacacac ctttggtccc agcactgggg ggtaaggcag aggcaggtgg   2580
atcactgagt ttgaggtcag ctagtgctga agagtaagag cctgtcttta aaacatctca   2640
acagctgggc agtcgtggtc cattccttta atcccagcac ttgggaggca gaggcaagtg   2700
gatttttgag ttcgaggcca gcctggtcta cagagtgagt tccaggacag ccagggatac   2760
acagagaaac cctgtctcaa aaaaccaaaa tataaataaa taaataaaga ttgggagaga   2820
agtcaaggat ctcataggtg gtcagggagc tacaactgca gtagtaaaga agtaggactt   2880
aaaagaacag ggccggcact aattttgagg atctagatcg ggccctcaat taaggaactt   2940
ccttttgtgt gaactcagaa tttgaaatga aatgtgcttg tcagaaccat tgcatggctt   3000
attttttaat gaaaagtctg gctagtatct gcttatcttc cagcttccag ctcaaagtta   3060
aggtcataga tcaaaagaac tatgtcttta tcttagttgt atcttaattt ttattagaat   3120
tgaatggttt tcctaatgtt tggtaacatc aaaggtgtgt aagtaaaagt gagaaatcaa   3180
gattaacttt ctcttggcaa agattgttga cattggtgac atcttggacc aaatgagaat   3240
tgttttactt ttaaatgtcc catcaacagc tctcagttag gctgttctat ctggtttgtc   3300
ttgccatgct tgcagagtat agatttgaca atttgaaaat tcaaaaagct atataaatag   3360
```

gtatgttgct atatgtaaga ttttaaatga gtcagttaag acttaaagaa taactgggtt 3420
tattttatct tgtcaggtta tcactgtgta gaccaggttg accttgaaaa caaattctct 3480
gcttcccaag tgctgggatt aaaggcgtgt gtcactagct ctgacactgg ctactttgga 3540
actactatgg tgttcacaaa tgcagagttg agtgttggga ttaaatggaa atttcatgtc 3600
ttttttttta actttccctt ctacacaggg cttctctgtg tagtcctggc tgtccttgta 3660
gctctagact aggctgaatt caaactcaga tccacccacc taagtgctga gattaaaggc 3720
atgtgccacc actgcccagt tctgaattgt tggggttttt tttttgttgt tattcttaat 3780
tttagttcga tgaattaaaa tcgaaataac ttgtttctta gaaaaataag gtgtaattgg 3840
gttataaagc caaatttaga cattaatacc aacagcctgt ttaggctcaa aattgttcaa 3900
tcattttatt agtattatta ttaatcatat caacttgaga cctgtttggg aaagcagaat 3960
attttaggga tagctatttc agacaagcat taatgtgtta gctgtttttt tccccctaga 4020
atatgattaa aattggctca gggtggggcc ttctagttct ggctctagcg attgggtctg 4080
tttctggtga ggtggtagtg ataaactgta acagaaggga caagagattg ggcttctgag 4140
aacatgtatg atctggtatg tgactttaat cattaaagca tggggattca aaaatactaa 4200
tgaataggcc ttagaactag tcctgagtgt tttgtaaaat aacagtctta attctcctag 4260
tttctggatt tttttctttg tctttggata ctaagtttaa gcatttattt ggacagagtg 4320
gtgcccacta gctgttctat tctagtactt gggaggcaag aggcagaacg aacatggcca 4380
gcttggacaa cttaagaaaa ctgaaaggct tgccatccta gtttttcttt tgattaaaca 4440
cacttatatt ctaactagtt ttctctatcc tttgggtttt gttttgtttt ttatttgttt 4500
tgtagctcta gctggctggc ttcggaattg cctgcctccc aagtgctagg attaaaggca 4560
tcacagtcac tacccaattg atatcatgat tcttaattca acttctaaga acaaattatc 4620
acactctgaa tctaacatgg aatagcatta tccatgttca gatatctttg tctcaaggct 4680
caggtttatc ctttgtagct ttctttttgc tatcccacct ctattcagca tccagtcaag 4740
gatcactgag ttggttatca gtaaattaaa cattttaatt aatgtctagg agacaggtta 4800
tggtatagtt ctcagtgctg ggaagttgac atggtaggat ctcagttcat ggccagccag 4860
aactttctgg tgagatcctg gttcaagcac tacagagctt ttctagaaaa gtaactatat 4920
ttaggagtaa gtttgatata atgacaatcc catcgtaagc cttcagtaac ctgatgcatt 4980
ggtctctgtt ttaatatcag gta 5003

<210> SEQ ID NO 255
<211> LENGTH: 2604
<212> TYPE: DNA
<213> ORGANISM: Artificial Sequence
<220> FEATURE:
<223> OTHER INFORMATION: Nucleotide sequence of the 3'-arm of targeting vector

<400> SEQUENCE: 255
gcattctcta acttggtaag gtactttcat ctatctgaaa aaatgttcag taaaaaacaa 60
aacaaaaaca tgacttcacc cagtgagtac aagatgatac ccccaatttt tttttttttt 120
attatatgta tgtacactgt agctgtcttc agacacacca gaagagggcg tcagatctca 180
tcagatggtt gtgagccacc atgtggttgc tgggacttga acactggacc tttggaaaag 240
cagttgggta ctcttaccca ctgagctatc acaccagccc caatacccca aattttgacc 300
agcctttttt tttttttttt tttttttttt aaatctgaac taatggtatt aaggtgaaac 360

```
agattgcaca aaagaggtac taggtttttc tttgaggcaa ggtctttcta tattgcctca    420
ggttgacctt aaactccaac ttcctttttt tccccaagtg ctggagattg tagacagata    480
tatacaacac cccaaaacaa atatgtttag tttcgattaa gattcattat gtggggctag    540
agggatgact tagaggttaa gaacactgcc tgctcttcca gaggtcctga gttcaattcc    600
cagcaaccac gtggtggctc acaaccatct gtaatgggat ccgatgccct ctttctggtg    660
tgtttgaaga cagctacagt gtcctcatac ataaaaaaaa taaacaaaca gatcttttaa    720
aaaaaaaggt acagtgtact tatacattat ataaatgaat gattctttaa aaaattaatt    780
atgggaaata cttatgaaga atagggtagc tttggctgtt ttggaaacgt tatataacaa    840
ggtagaacta aaatgtatgc cagtaatccc agaggaatca ttagccagtc agggctagtc    900
tgagcaatgt ggcaagataa acccatctct ttaaaaaaaa aaaaaagtat tataaataga    960
aatgttatag gaaacaggaa atagaaaccc tcgaaaggct gaatgaaaga gtattagtgg   1020
gctggagaga tggttcagcg gttaagagca ctatctcctg agttcagttc ccagtgacca   1080
catggtggct cacagccatc tgtaatgaga tctgacgccc tcttctgggg tgtctgaaga   1140
cagcgacagt gtactcacat aaaataaata cataaagact gttagttagc cttcatctac   1200
catttacaga actgggcaca gaaaggagtt catcagttat aaagggtaac tttccatatg   1260
aatgtttgtc atattattat gcatatagta taatgaccaa actactgtaa tgtcttaata   1320
tttgtatctc ttttctcttt tttaaaaata tcagtttggt ggggaaccat tgtcatacac   1380
ccggtttagc cttgctcggc aagtagatgg agataacagt catgtggaga tgaaactggc   1440
tgcagatgaa gaagaaaatg ccgacaataa catgaaggct agtgtcagaa aacccaagag   1500
gtttaatgga agactctgct ttgcagctat tgcactagtc attttcttct tgattggtaa   1560
gaatgagtgg ccattcagaa ggatttctta tgactaacta gttcttagac tagctagttc   1620
ttagactagc tagttcttgt ttcttttgga tgaggagatg ctttgtactt taaatggcac   1680
tggggctccc tacctgccgg cagattaggt cctgcaagat gggaaacgtt tacattatgg   1740
atgttttatt agagatatgc aggacatttg gaatagtact aagaaaggct tccagtaaga   1800
caaggtgtgc acccatgtct taaacaggtc actgtaaaat atgacttagt tgtggtaatt   1860
taaattccat taaactcagg ttcataattt tctattagat tctcatagtt taattaaaag   1920
ttttcaggga taagttaaaa atgagttctg tgagtttagc tctaaaactt cctgttttta   1980
ggattcatga gtggctacct gggctattgt aagcgtgtag aacaaaaaga ggagtgtgtg   2040
aaactggctg aaacggagga gacagacaag tcagaaacca tggaaacaga ggatgttcct   2100
acatcatctc gcttatattg ggcagacctc aaaacactgt tgtcagagaa gttgaactcc   2160
atagagtttg ctgacaccat caagtaagct caacttccca agttcagtcc tgatggaaac   2220
gtttttgttg ggggggtagg gagacttgaa aggctttcag agggtcctcc tgacaatgtg   2280
gaactatgct gacaggaaat taggacttac ctggagagcc tcatagcctc ctttttcttc   2340
agaatcgttt tatcagttgt agtttagtgt gggatgtcag attttcttct gttctaatat   2400
tcctttttaaa aattttttaa aattaaaatt actttttatg tattatgagt atagcctgca   2460
tatatgaatg aatgtgcatt actaattaca cttatctcct agtgcctaca taagccttat   2520
agatggttgt gagccagcat gtgggtgctg gaatccaaaa tggttcttgc aagaccaaat   2580
atgttacatc ccagagccat taca                                          2604
```

<210> SEQ ID NO 256

<211> LENGTH: 166
<212> TYPE: PRT
<213> ORGANISM: Homo sapiens

<400> SEQUENCE: 256

```
Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 257
<211> LENGTH: 616
<212> TYPE: PRT
<213> ORGANISM: Artificial Sequence
<220> FEATURE:
<223> OTHER INFORMATION: Amino acid sequence of the fusion protein of heavy chain of anti-hTfR antibody No.3 (humanized 2) and hEPO

<400> SEQUENCE: 257

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

-continued

```
Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser Ala Pro Pro Arg Leu Ile Cys Asp Ser Arg Val Leu Glu Arg
    450                 455                 460

Tyr Leu Leu Glu Ala Lys Glu Ala Glu Asn Ile Thr Thr Gly Cys Ala
465                 470                 475                 480

Glu His Cys Ser Leu Asn Glu Asn Ile Thr Val Pro Asp Thr Lys Val
                485                 490                 495

Asn Phe Tyr Ala Trp Lys Arg Met Glu Val Gly Gln Gln Ala Val Glu
            500                 505                 510

Val Trp Gln Gly Leu Ala Leu Leu Ser Glu Ala Val Leu Arg Gly Gln
        515                 520                 525

Ala Leu Leu Val Asn Ser Ser Gln Pro Trp Glu Pro Leu Gln Leu His
    530                 535                 540

Val Asp Lys Ala Val Ser Gly Leu Arg Ser Leu Thr Thr Leu Leu Arg
545                 550                 555                 560

Ala Leu Gly Ala Gln Lys Glu Ala Ile Ser Pro Pro Asp Ala Ala Ser
                565                 570                 575
```

Ala Ala Pro Leu Arg Thr Ile Thr Ala Asp Thr Phe Arg Lys Leu Phe
580 585 590

Arg Val Tyr Ser Asn Phe Leu Arg Gly Lys Leu Lys Leu Tyr Thr Gly
595 600 605

Glu Ala Cys Arg Thr Gly Asp Arg
610 615

<210> SEQ ID NO 258
<211> LENGTH: 1931
<212> TYPE: DNA
<213> ORGANISM: Artificial Sequence
<220> FEATURE:
<223> OTHER INFORMATION: Nucleotide sequence encoding the amino acid sequence of fusion protein of heavy chain of anti-hTfR antibody No. 3 (humanized 2) and hEPO, synthetic sequence

<400> SEQUENCE: 258
acgcgtgccg ccaccatggg ctggagctgg attctgctgt tcctcctgag cgtgacagca 60
ggagtgcaca gcgaggtgca actagtgcag tctggagcag aggtgaaaaa gcccggggag 120
tctctgaaga tttcctgtaa gggttctgga tacagcttta ccaactactg gctgggatgg 180
gtgcgccaga tgcccgggaa aggcctggag tggatggggg acatctaccc cggcggagac 240
taccctacat acagcgagaa gttcaaggtc caggtcacca tctcagccga caagtccatc 300
agcaccgcct acctgcagtg gagcagcctg aaggcctcgg acaccgccat gtattactgt 360
gcgagatcag gcaattacga cgaagtggcc tactggggcc aaggaaccct ggtcaccgtc 420
tcctcagcta gcaccaaggg cccatcggtc ttccccctgg caccctcctc caagagcacc 480
tctgggggca cagcggccct gggctgcctg gtcaaggact acttccccga accggtgacg 540
gtgtcgtgga actcaggcgc cctgaccagc ggcgtgcaca ccttcccggc tgtcctacag 600
tcctcaggac tctactccct cagcagcgtg gtgaccgtgc cctccagcag cttgggcacc 660
cagacctaca tctgcaacgt gaatcacaag cccagcaaca ccaaggtgga caagaaagtt 720
gagcccaaat cttgtgacaa aactcacacg tgcccaccgt gcccagcacc tgaactcctg 780
ggaggtccgt cagtcttcct cttcccccca aaacccaagg acaccctcat gatctcccgg 840
acccctgagg tcacatgcgt ggtggtggac gtgagccacg aagaccctga ggtcaagttc 900
aactggtacg tggacggcgt ggaggtgcat aatgccaaga caaagccgcg ggaggagcag 960
tacaacagca cgtaccgggt ggtcagcgtc ctcaccgtcc tgcaccagga ctggctgaat 1020
ggcaaggagt acaagtgcaa ggtctccaac aaagccctcc cagcccccat cgagaaaacc 1080
atctccaaag ccaaagggca gccccgagaa ccacaggtgt acaccctgcc cccatcccgg 1140
gatgagctga ccaagaacca ggtcagcctg acctgcctgg tcaaaggctt ctatcccagc 1200
gacatcgccg tggagtggga gagcaatggg cagccggaga acaactacaa gaccacgcct 1260
cccgtgctgg actccgacgg ctccttcttc ctctacagca agctcaccgt ggacaagagc 1320
aggtggcagc aggggaacgt cttctcatgc tccgtgatgc atgaggctct gcacaaccac 1380
tacacgcaga agagcctctc cctgtctccg ggtaaaggat ctgcccccac acgcctcatc 1440
tgtgacagcc gagtcctgga gaggtacctc ttggaggcca aggaggccga gaatatcacg 1500
acgggctgtg ctgaacactg cagcttgaat gagaatatca ctgtcccaga caccaaagtt 1560
aatttctatg cctggaagag gatggaggtc gggcagcagg ccgtagaagt ctggcagggc 1620
ctggccctgc tgtcggaagc tgtcctgcgg ggccaggccc tgttggtcaa ctcttcccag 1680
ccgtgggagc ccctgcagct gcatgtggat aaagccgtca gtggccttcg cagcctcacc 1740

```
actctgcttc gggctctggg agcccagaag gaagccatct cccctccaga tgcggcctca   1800

gctgctccac tccgaacaat cactgctgac actttccgca aactcttccg agtctactcc   1860

aatttcctcc ggggaaagct gaagctgtac acaggggagg cctgcaggac aggggacaga   1920

taagcggccg c                                                        1931


<210> SEQ ID NO 259
<211> LENGTH: 489
<212> TYPE: PRT
<213> ORGANISM: Homo sapiens

<400> SEQUENCE: 259

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
        35                  40                  45

Ser Leu Cys Thr Pro Ser Arg Ala Ala Leu Leu Thr Gly Arg Leu Pro
    50                  55                  60

Val Arg Met Gly Met Tyr Pro Gly Val Leu Val Pro Ser Ser Arg Gly
65                  70                  75                  80

Gly Leu Pro Leu Glu Glu Val Thr Val Ala Glu Val Leu Ala Ala Arg
                85                  90                  95

Gly Tyr Leu Thr Gly Met Ala Gly Lys Trp His Leu Gly Val Gly Pro
            100                 105                 110

Glu Gly Ala Phe Leu Pro Pro His Gln Gly Phe His Arg Phe Leu Gly
        115                 120                 125

Ile Pro Tyr Ser His Asp Gln Gly Pro Cys Gln Asn Leu Thr Cys Phe
    130                 135                 140

Pro Pro Ala Thr Pro Cys Asp Gly Gly Cys Asp Gln Gly Leu Val Pro
145                 150                 155                 160

Ile Pro Leu Leu Ala Asn Leu Ser Val Glu Ala Gln Pro Pro Trp Leu
                165                 170                 175

Pro Gly Leu Glu Ala Arg Tyr Met Ala Phe Ala His Asp Leu Met Ala
            180                 185                 190

Asp Ala Gln Arg Gln Asp Arg Pro Phe Phe Leu Tyr Tyr Ala Ser His
        195                 200                 205

His Thr His Tyr Pro Gln Phe Ser Gly Gln Ser Phe Ala Glu Arg Ser
    210                 215                 220

Gly Arg Gly Pro Phe Gly Asp Ser Leu Met Glu Leu Asp Ala Ala Val
225                 230                 235                 240

Gly Thr Leu Met Thr Ala Ile Gly Asp Leu Gly Leu Leu Glu Glu Thr
                245                 250                 255

Leu Val Ile Phe Thr Ala Asp Asn Gly Pro Glu Thr Met Arg Met Ser
            260                 265                 270

Arg Gly Gly Cys Ser Gly Leu Leu Arg Cys Gly Lys Gly Thr Thr Tyr
        275                 280                 285

Glu Gly Gly Val Arg Glu Pro Ala Leu Ala Phe Trp Pro Gly His Ile
    290                 295                 300

Ala Pro Gly Val Thr His Glu Leu Ala Ser Ser Leu Asp Leu Leu Pro
305                 310                 315                 320

Thr Leu Ala Ala Leu Ala Gly Ala Pro Leu Pro Asn Val Thr Leu Asp
                325                 330                 335
```

```
Gly Phe Asp Leu Ser Pro Leu Leu Leu Gly Thr Gly Lys Ser Pro Arg
            340                 345                 350

Gln Ser Leu Phe Phe Tyr Pro Ser Tyr Pro Asp Glu Val Arg Gly Val
        355                 360                 365

Phe Ala Val Arg Thr Gly Lys Tyr Lys Ala His Phe Phe Thr Gln Gly
    370                 375                 380

Ser Ala His Ser Asp Thr Thr Ala Asp Pro Ala Cys His Ala Ser Ser
385                 390                 395                 400

Ser Leu Thr Ala His Glu Pro Pro Leu Leu Tyr Asp Leu Ser Lys Asp
                405                 410                 415

Pro Gly Glu Asn Tyr Asn Leu Leu Gly Gly Val Ala Gly Ala Thr Pro
            420                 425                 430

Glu Val Leu Gln Ala Leu Lys Gln Leu Gln Leu Leu Lys Ala Gln Leu
        435                 440                 445

Asp Ala Ala Val Thr Phe Gly Pro Ser Gln Val Ala Arg Gly Glu Asp
    450                 455                 460

Pro Ala Leu Gln Ile Cys Cys His Pro Gly Cys Thr Pro Arg Pro Ala
465                 470                 475                 480

Cys Cys His Cys Pro Asp Pro His Ala
                485


<210> SEQ ID NO 260
<211> LENGTH: 939
<212> TYPE: PRT
<213> ORGANISM: Artificial Sequence
<220> FEATURE:
<223> OTHER INFORMATION: Amino acid sequence of the fusion protein of
      heavy chain of anti-hTfR antibody No.3 (humanized 2) and hARSA

<400> SEQUENCE: 260

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

-continued

```
Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser Arg Pro Pro Asn Ile Val Leu Ile Phe Ala Asp Asp Leu Gly
    450                 455                 460

Tyr Gly Asp Leu Gly Cys Tyr Gly His Pro Ser Ser Thr Thr Pro Asn
465                 470                 475                 480

Leu Asp Gln Leu Ala Ala Gly Gly Leu Arg Phe Thr Asp Phe Tyr Val
                485                 490                 495

Pro Val Ser Leu Cys Thr Pro Ser Arg Ala Ala Leu Leu Thr Gly Arg
            500                 505                 510

Leu Pro Val Arg Met Gly Met Tyr Pro Gly Val Leu Val Pro Ser Ser
        515                 520                 525

Arg Gly Gly Leu Pro Leu Glu Glu Val Thr Val Ala Glu Val Leu Ala
    530                 535                 540

Ala Arg Gly Tyr Leu Thr Gly Met Ala Gly Lys Trp His Leu Gly Val
545                 550                 555                 560

Gly Pro Glu Gly Ala Phe Leu Pro Pro His Gln Gly Phe His Arg Phe
                565                 570                 575

Leu Gly Ile Pro Tyr Ser His Asp Gln Gly Pro Cys Gln Asn Leu Thr
            580                 585                 590

Cys Phe Pro Pro Ala Thr Pro Cys Asp Gly Gly Cys Asp Gln Gly Leu
        595                 600                 605

Val Pro Ile Pro Leu Leu Ala Asn Leu Ser Val Glu Ala Gln Pro Pro
    610                 615                 620
```

Trp Leu Pro Gly Leu Glu Ala Arg Tyr Met Ala Phe Ala His Asp Leu
625 630 635 640

Met Ala Asp Ala Gln Arg Gln Asp Arg Pro Phe Phe Leu Tyr Tyr Ala
645 650 655

Ser His His Thr His Tyr Pro Gln Phe Ser Gly Gln Ser Phe Ala Glu
660 665 670

Arg Ser Gly Arg Gly Pro Phe Gly Asp Ser Leu Met Glu Leu Asp Ala
675 680 685

Ala Val Gly Thr Leu Met Thr Ala Ile Gly Asp Leu Gly Leu Leu Glu
690 695 700

Glu Thr Leu Val Ile Phe Thr Ala Asp Asn Gly Pro Glu Thr Met Arg
705 710 715 720

Met Ser Arg Gly Gly Cys Ser Gly Leu Leu Arg Cys Gly Lys Gly Thr
725 730 735

Thr Tyr Glu Gly Gly Val Arg Glu Pro Ala Leu Ala Phe Trp Pro Gly
740 745 750

His Ile Ala Pro Gly Val Thr His Glu Leu Ala Ser Ser Leu Asp Leu
755 760 765

Leu Pro Thr Leu Ala Ala Leu Ala Gly Ala Pro Leu Pro Asn Val Thr
770 775 780

Leu Asp Gly Phe Asp Leu Ser Pro Leu Leu Leu Gly Thr Gly Lys Ser
785 790 795 800

Pro Arg Gln Ser Leu Phe Phe Tyr Pro Ser Tyr Pro Asp Glu Val Arg
805 810 815

Gly Val Phe Ala Val Arg Thr Gly Lys Tyr Lys Ala His Phe Phe Thr
820 825 830

Gln Gly Ser Ala His Ser Asp Thr Thr Ala Asp Pro Ala Cys His Ala
835 840 845

Ser Ser Ser Leu Thr Ala His Glu Pro Pro Leu Leu Tyr Asp Leu Ser
850 855 860

Lys Asp Pro Gly Glu Asn Tyr Asn Leu Leu Gly Gly Val Ala Gly Ala
865 870 875 880

Thr Pro Glu Val Leu Gln Ala Leu Lys Gln Leu Gln Leu Leu Lys Ala
885 890 895

Gln Leu Asp Ala Ala Val Thr Phe Gly Pro Ser Gln Val Ala Arg Gly
900 905 910

Glu Asp Pro Ala Leu Gln Ile Cys Cys His Pro Gly Cys Thr Pro Arg
915 920 925

Pro Ala Cys Cys His Cys Pro Asp Pro His Ala
930 935

<210> SEQ ID NO 261
<211> LENGTH: 2900
<212> TYPE: DNA
<213> ORGANISM: Artificial Sequence
<220> FEATURE:
<223> OTHER INFORMATION: Nucleotide sequence encoding the amino acid sequence of fusion protein of heavy chain of anti-hTfR antibody No.3 (humanized 2) and hARSA, synthetic sequence

<400> SEQUENCE: 261
acgcgtgccg ccaccatggg ctggagctgg attctgctgt tcctcctgag cgtgacagca 60
ggagtgcaca gcgaggtgca actagtgcag tctggagcag aggtgaaaaa gcccggggag 120
tctctgaaga tttcctgtaa gggttctgga tacagcttta ccaactactg gctgggatgg 180
gtgcgccaga tgcccgggaa aggcctggag tggatggggg acatctaccc cggcggagac 240

```
taccctacat acagcgagaa gttcaaggtc caggtcacca tctcagccga caagtccatc    300
agcaccgcct acctgcagtg gagcagcctg aaggcctcgg acaccgccat gtattactgt    360
gcgagatcag gcaattacga cgaagtggcc tactggggcc aaggaaccct ggtcaccgtc    420
tcctcagcta gcaccaaggg cccatcggtc ttccccctgg caccctcctc caagagcacc    480
tctgggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacacg tgcccaccgt gcccagcacc tgaactcctg    780
ggaggtccgt cagtcttcct cttcccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaaggat ctcgtccgcc caacatcgtg   1440
ctgatctttg ccgacgacct cggctatggg gacctgggct gctatgggca ccccagctct   1500
accactccca acctggacca gctggcggcg ggagggctgc ggttcacaga cttctacgtg   1560
cctgtgtctc tgtgcacacc ctctagggcc gccctcctga ccggccggct cccggttcgg   1620
atgggcatgt accctggcgt cctggtgccc agctcccggg ggggcctgcc cctggaggag   1680
gtgaccgtgg ccgaagtcct ggctgcccga ggctacctca caggaatggc cggcaagtgg   1740
caccttgggg tggggcctga gggggccttc ctgccccccc atcagggctt ccatcgattt   1800
ctaggcatcc cgtactccca cgaccagggc ccctgccaga acctgacctg cttcccgccg   1860
gccactcctt gcgacggtgg ctgtgaccag ggcctggtcc ccatcccact gttggccaac   1920
ctgtccgtgg aggcgcagcc cccctggctg cccggactag aggcccgcta catggctttc   1980
gcccatgacc tcatggccga cgcccagcgc caggatcgcc ccttcttcct gtactatgcc   2040
tctcaccaca cccactaccc tcagttcagt gggcagagct ttgcagagcg ttcaggccgc   2100
gggccatttg gggactccct gatggagctg gatgcagctg tggggaccct gatgacagcc   2160
ataggggacc tggggctgct tgaagagacg ctggtcatct tcactgcaga caatggacct   2220
gagaccatgc gtatgtcccg aggcggctgc tccggtctct tgcggtgtgg aaagggaacg   2280
acctacgagg gcggtgtccg agagcctgcc ttggccttct ggccaggtca tatcgctccc   2340
ggcgtgaccc acgagctggc cagctccctg gacctgctgc ctaccctggc agccctggct   2400
ggggccccac tgcccaatgt caccttggat ggctttgacc tcagccccct gctgctgggc   2460
acaggcaaga gccctcggca gtctctcttc ttctacccgt cctacccaga cgaggtccgt   2520
ggggtttttg ctgtgcggac tggaaagtac aaggctcact tcttcaccca gggctctgcc   2580
```

```
cacagtgata ccactgcaga ccctgcctgc cacgcctcca gctctctgac tgctcatgag   2640

cccccgctgc tctatgacct gtccaaggac cctggtgaga actacaacct gctgggggt    2700

gtggccgggg ccaccccaga ggtgctgcaa gccctgaaac agcttcagct gctcaaggcc   2760

cagttagacg cagctgtgac cttcggcccc agccaggtgg cccggggcga ggaccccgcc   2820

ctgcaaatct gctgtcatcc tggctgcacc ccccgcccag cttgctgcca ttgcccagat   2880

ccccatgcct aagcggccgc                                               2900
```

<210> SEQ ID NO 262
<211> LENGTH: 279
<212> TYPE: PRT
<213> ORGANISM: Homo sapiens

<400> SEQUENCE: 262

```
Asp Pro Pro Ala Pro Leu Pro Leu Val Ile Trp His Gly Met Gly Asp
1               5                   10                  15

Ser Cys Cys Asn Pro Leu Ser Met Gly Ala Ile Lys Lys Met Val Glu
            20                  25                  30

Lys Lys Ile Pro Gly Ile Tyr Val Leu Ser Leu Glu Ile Gly Lys Thr
        35                  40                  45

Leu Met Glu Asp Val Glu Asn Ser Phe Phe Leu Asn Val Asn Ser Gln
    50                  55                  60

Val Thr Thr Val Cys Gln Ala Leu Ala Lys Asp Pro Lys Leu Gln Gln
65                  70                  75                  80

Gly Tyr Asn Ala Met Gly Phe Ser Gln Gly Gly Gln Phe Leu Arg Ala
                85                  90                  95

Val Ala Gln Arg Cys Pro Ser Pro Pro Met Ile Asn Leu Ile Ser Val
            100                 105                 110

Gly Gly Gln His Gln Gly Val Phe Gly Leu Pro Arg Cys Pro Gly Glu
        115                 120                 125

Ser Ser His Ile Cys Asp Phe Ile Arg Lys Thr Leu Asn Ala Gly Ala
    130                 135                 140

Tyr Ser Lys Val Val Gln Glu Arg Leu Val Gln Ala Glu Tyr Trp His
145                 150                 155                 160

Asp Pro Ile Lys Glu Asp Val Tyr Arg Asn His Ser Ile Phe Leu Ala
                165                 170                 175

Asp Ile Asn Gln Glu Arg Gly Ile Asn Glu Ser Tyr Lys Lys Asn Leu
            180                 185                 190

Met Ala Leu Lys Lys Phe Val Met Val Lys Phe Leu Asn Asp Ser Ile
        195                 200                 205

Val Asp Pro Val Asp Ser Glu Trp Phe Gly Phe Tyr Arg Ser Gly Gln
    210                 215                 220

Ala Lys Glu Thr Ile Pro Leu Gln Glu Thr Ser Leu Tyr Thr Gln Asp
225                 230                 235                 240

Arg Leu Gly Leu Lys Glu Met Asp Asn Ala Gly Gln Leu Val Phe Leu
                245                 250                 255

Ala Thr Glu Gly Asp His Leu Gln Leu Ser Glu Glu Trp Phe Tyr Ala
            260                 265                 270

His Ile Ile Pro Phe Leu Gly
        275
```

<210> SEQ ID NO 263
<211> LENGTH: 729
<212> TYPE: PRT
<213> ORGANISM: Artificial Sequence
<220> FEATURE:
<223> OTHER INFORMATION: Amino acid sequence of the fusion protein of heavy chain of anti-hTfR antibody No.3 (humanized 2) and hPPT-1

<400> SEQUENCE: 263

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser Asp Pro Pro Ala Pro Leu Pro Leu Val Ile Trp His Gly Met
    450                 455                 460

Gly Asp Ser Cys Cys Asn Pro Leu Ser Met Gly Ala Ile Lys Lys Met
465                 470                 475                 480

Val Glu Lys Lys Ile Pro Gly Ile Tyr Val Leu Ser Leu Glu Ile Gly
                485                 490                 495

Lys Thr Leu Met Glu Asp Val Glu Asn Ser Phe Phe Leu Asn Val Asn
            500                 505                 510

Ser Gln Val Thr Thr Val Cys Gln Ala Leu Ala Lys Asp Pro Lys Leu
        515                 520                 525

Gln Gln Gly Tyr Asn Ala Met Gly Phe Ser Gln Gly Gly Gln Phe Leu
    530                 535                 540

Arg Ala Val Ala Gln Arg Cys Pro Ser Pro Pro Met Ile Asn Leu Ile
545                 550                 555                 560

Ser Val Gly Gly Gln His Gln Gly Val Phe Gly Leu Pro Arg Cys Pro
                565                 570                 575

Gly Glu Ser Ser His Ile Cys Asp Phe Ile Arg Lys Thr Leu Asn Ala
            580                 585                 590

Gly Ala Tyr Ser Lys Val Val Gln Glu Arg Leu Val Gln Ala Glu Tyr
        595                 600                 605

Trp His Asp Pro Ile Lys Glu Asp Val Tyr Arg Asn His Ser Ile Phe
    610                 615                 620

Leu Ala Asp Ile Asn Gln Glu Arg Gly Ile Asn Glu Ser Tyr Lys Lys
625                 630                 635                 640

Asn Leu Met Ala Leu Lys Lys Phe Val Met Val Lys Phe Leu Asn Asp
                645                 650                 655

Ser Ile Val Asp Pro Val Asp Ser Glu Trp Phe Gly Phe Tyr Arg Ser
            660                 665                 670

Gly Gln Ala Lys Glu Thr Ile Pro Leu Gln Glu Thr Ser Leu Tyr Thr
        675                 680                 685

Gln Asp Arg Leu Gly Leu Lys Glu Met Asp Asn Ala Gly Gln Leu Val
    690                 695                 700

Phe Leu Ala Thr Glu Gly Asp His Leu Gln Leu Ser Glu Glu Trp Phe
705                 710                 715                 720

Tyr Ala His Ile Ile Pro Phe Leu Gly
                725
```

<210> SEQ ID NO 264
<211> LENGTH: 2270
<212> TYPE: DNA
<213> ORGANISM: Artificial Sequence
<220> FEATURE:
<223> OTHER INFORMATION: Nucleotide sequence encoding the amino acid sequence of fusion protein of heavy chain of anti-hTfR antibody No.3 (humanized 2) and hPPT-1, synthetic sequence

<400> SEQUENCE: 264

```
acgcgtgccg ccaccatggg ctggagctgg attctgctgt tcctcctgag cgtgacagca     60
```

```
ggagtgcaca gcgaggtgca actagtgcag tctggagcag aggtgaaaaa gcccggggag    120
tctctgaaga tttcctgtaa gggttctgga tacagcttta ccaactactg gctgggatgg    180
gtgcgccaga tgcccgggaa aggcctggag tggatggggg acatctaccc cggcggagac    240
taccctacat acagcgagaa gttcaaggtc caggtcacca tctcagccga caagtccatc    300
agcaccgcct acctgcagtg gagcagcctg aaggcctcgg acaccgccat gtattactgt    360
gcgagatcag gcaattacga cgaagtggcc tactggggcc aaggaaccct ggtcaccgtc    420
tcctcagcta gcaccaaggg cccatcggtc ttccccctgg caccctcctc caagagcacc    480
tctgggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacacg tgcccaccgt gcccagcacc tgaactcctg    780
ggaggtccgt cagtcttcct cttcccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaaggat ctgacccgcc ggcgccgctg   1440
ccgttggtga tctggcatgg gatgggagac agctgttgca atcccttaag catgggtgct   1500
attaaaaaaa tggtggagaa gaaaatacct ggaatttacg tcttatcttt agagattggg   1560
aagaccctga tggaggacgt ggagaacagc ttcttcttga atgtcaattc ccaagtaaca   1620
acagtgtgtc aggcacttgc taaagatcct aaattgcagc aaggctacaa tgctatggga   1680
ttctcccagg gaggccaatt tctgagggca gtggctcaga gatgcccttc acctcccatg   1740
atcaatctga tctcggttgg gggacaacat caaggtgttt ttggactccc tcgatgccca   1800
ggagagagct ctcacatctg tgacttcatc cgaaaaacac tgaatgctgg ggcgtactcc   1860
aaagttgttc aggaacgcct cgtgcaagcc gaatactggc atgaccccat aaaggaggat   1920
gtgtatcgca accacagcat cttcttggca gatataaatc aggagcgggg tatcaatgag   1980
tcctacaaga aaaacctgat ggccctgaag aagtttgtga tggtgaaatt cctcaatgat   2040
tccattgtgg accctgtaga ttcggagtgg tttggatttt acagaagtgg ccaagccaag   2100
gaaaccattc ccttacagga gacctccctg tacacacagg accgcctggg gctaaaggaa   2160
atggacaatg caggacagct agtgtttctg gctacagaag ggggaccatct tcagttgtct   2220
gaagaatggt tttatgccca catcatacca ttccttggat aagcggccgc              2270
```

<210> SEQ ID NO 265
<211> LENGTH: 544
<212> TYPE: PRT
<213> ORGANISM: Homo sapiens

<400> SEQUENCE: 265

Ser Tyr Ser Pro Glu Pro Asp Gln Arg Arg Thr Leu Pro Pro Gly Trp
1 5 10 15

Val Ser Leu Gly Arg Ala Asp Pro Glu Glu Glu Leu Ser Leu Thr Phe
20 25 30

Ala Leu Arg Gln Gln Asn Val Glu Arg Leu Ser Glu Leu Val Gln Ala
35 40 45

Val Ser Asp Pro Ser Ser Pro Gln Tyr Gly Lys Tyr Leu Thr Leu Glu
50 55 60

Asn Val Ala Asp Leu Val Arg Pro Ser Pro Leu Thr Leu His Thr Val
65 70 75 80

Gln Lys Trp Leu Leu Ala Ala Gly Ala Gln Lys Cys His Ser Val Ile
85 90 95

Thr Gln Asp Phe Leu Thr Cys Trp Leu Ser Ile Arg Gln Ala Glu Leu
100 105 110

Leu Leu Pro Gly Ala Glu Phe His His Tyr Val Gly Gly Pro Thr Glu
115 120 125

Thr His Val Val Arg Ser Pro His Pro Tyr Gln Leu Pro Gln Ala Leu
130 135 140

Ala Pro His Val Asp Phe Val Gly Gly Leu His His Phe Pro Pro Thr
145 150 155 160

Ser Ser Leu Arg Gln Arg Pro Glu Pro Gln Val Thr Gly Thr Val Gly
165 170 175

Leu His Leu Gly Val Thr Pro Ser Val Ile Arg Lys Arg Tyr Asn Leu
180 185 190

Thr Ser Gln Asp Val Gly Ser Gly Thr Ser Asn Asn Ser Gln Ala Cys
195 200 205

Ala Gln Phe Leu Glu Gln Tyr Phe His Asp Ser Asp Leu Ala Gln Phe
210 215 220

Met Arg Leu Phe Gly Gly Asn Phe Ala His Gln Ala Ser Val Ala Arg
225 230 235 240

Val Val Gly Gln Gln Gly Arg Gly Arg Ala Gly Ile Glu Ala Ser Leu
245 250 255

Asp Val Gln Tyr Leu Met Ser Ala Gly Ala Asn Ile Ser Thr Trp Val
260 265 270

Tyr Ser Ser Pro Gly Arg His Glu Gly Gln Glu Pro Phe Leu Gln Trp
275 280 285

Leu Met Leu Leu Ser Asn Glu Ser Ala Leu Pro His Val His Thr Val
290 295 300

Ser Tyr Gly Asp Asp Glu Asp Ser Leu Ser Ser Ala Tyr Ile Gln Arg
305 310 315 320

Val Asn Thr Glu Leu Met Lys Ala Ala Ala Arg Gly Leu Thr Leu Leu
325 330 335

Phe Ala Ser Gly Asp Ser Gly Ala Gly Cys Trp Ser Val Ser Gly Arg
340 345 350

His Gln Phe Arg Pro Thr Phe Pro Ala Ser Ser Pro Tyr Val Thr Thr
355 360 365

Val Gly Gly Thr Ser Phe Gln Glu Pro Phe Leu Ile Thr Asn Glu Ile
370 375 380

Val Asp Tyr Ile Ser Gly Gly Gly Phe Ser Asn Val Phe Pro Arg Pro
385 390 395 400

Ser Tyr Gln Glu Glu Ala Val Thr Lys Phe Leu Ser Ser Ser Pro His 405 410 415

Leu Pro Pro Ser Ser Tyr Phe Asn Ala Ser Gly Arg Ala Tyr Pro Asp
420 425 430

Val Ala Ala Leu Ser Asp Gly Tyr Trp Val Val Ser Asn Arg Val Pro
435 440 445

Ile Pro Trp Val Ser Gly Thr Ser Ala Ser Thr Pro Val Phe Gly Gly
450 455 460

Ile Leu Ser Leu Ile Asn Glu His Arg Ile Leu Ser Gly Arg Pro Pro
465 470 475 480

Leu Gly Phe Leu Asn Pro Arg Leu Tyr Gln Gln His Gly Ala Gly Leu
485 490 495

Phe Asp Val Thr Arg Gly Cys His Glu Ser Cys Leu Asp Glu Glu Val
500 505 510

Glu Gly Gln Gly Phe Cys Ser Gly Pro Gly Trp Asp Pro Val Thr Gly
515 520 525

Trp Gly Thr Pro Asn Phe Pro Ala Leu Leu Lys Thr Leu Leu Asn Pro
530 535 540

<210> SEQ ID NO 266
<211> LENGTH: 994
<212> TYPE: PRT
<213> ORGANISM: Artificial Sequence
<220> FEATURE:
<223> OTHER INFORMATION: Amino acid sequence of the fusion protein of heavy chain of anti-hTfR antibody No.3 (humanized 2) and hTPP-1

<400> SEQUENCE: 266

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asn Tyr
20 25 30

Trp Leu Gly Trp Val Arg Gln Met Pro Gly Lys Gly Leu Glu Trp Met
35 40 45

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

-continued

```
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser Ser Tyr Ser Pro Glu Pro Asp Gln Arg Arg Thr Leu Pro Pro
    450                 455                 460

Gly Trp Val Ser Leu Gly Arg Ala Asp Pro Glu Glu Glu Leu Ser Leu
465                 470                 475                 480

Thr Phe Ala Leu Arg Gln Gln Asn Val Glu Arg Leu Ser Glu Leu Val
                485                 490                 495

Gln Ala Val Ser Asp Pro Ser Ser Pro Gln Tyr Gly Lys Tyr Leu Thr
            500                 505                 510

Leu Glu Asn Val Ala Asp Leu Val Arg Pro Ser Pro Leu Thr Leu His
        515                 520                 525

Thr Val Gln Lys Trp Leu Leu Ala Ala Gly Ala Gln Lys Cys His Ser
    530                 535                 540

Val Ile Thr Gln Asp Phe Leu Thr Cys Trp Leu Ser Ile Arg Gln Ala
545                 550                 555                 560

Glu Leu Leu Leu Pro Gly Ala Glu Phe His His Tyr Val Gly Gly Pro
                565                 570                 575

Thr Glu Thr His Val Val Arg Ser Pro His Pro Tyr Gln Leu Pro Gln
            580                 585                 590

Ala Leu Ala Pro His Val Asp Phe Val Gly Gly Leu His His Phe Pro
        595                 600                 605

Pro Thr Ser Ser Leu Arg Gln Arg Pro Glu Pro Gln Val Thr Gly Thr
    610                 615                 620

Val Gly Leu His Leu Gly Val Thr Pro Ser Val Ile Arg Lys Arg Tyr
625                 630                 635                 640

Asn Leu Thr Ser Gln Asp Val Gly Ser Gly Thr Ser Asn Asn Ser Gln
```

```
                645                 650                 655

Ala Cys Ala Gln Phe Leu Glu Gln Tyr Phe His Asp Ser Asp Leu Ala
            660                 665                 670

Gln Phe Met Arg Leu Phe Gly Gly Asn Phe Ala His Gln Ala Ser Val
        675                 680                 685

Ala Arg Val Val Gly Gln Gln Gly Arg Gly Arg Ala Gly Ile Glu Ala
    690                 695                 700

Ser Leu Asp Val Gln Tyr Leu Met Ser Ala Gly Ala Asn Ile Ser Thr
705                 710                 715                 720

Trp Val Tyr Ser Ser Pro Gly Arg His Glu Gly Gln Glu Pro Phe Leu
                725                 730                 735

Gln Trp Leu Met Leu Leu Ser Asn Glu Ser Ala Leu Pro His Val His
            740                 745                 750

Thr Val Ser Tyr Gly Asp Asp Glu Asp Ser Leu Ser Ser Ala Tyr Ile
        755                 760                 765

Gln Arg Val Asn Thr Glu Leu Met Lys Ala Ala Ala Arg Gly Leu Thr
    770                 775                 780

Leu Leu Phe Ala Ser Gly Asp Ser Gly Ala Gly Cys Trp Ser Val Ser
785                 790                 795                 800

Gly Arg His Gln Phe Arg Pro Thr Phe Pro Ala Ser Ser Pro Tyr Val
                805                 810                 815

Thr Thr Val Gly Gly Thr Ser Phe Gln Glu Pro Phe Leu Ile Thr Asn
            820                 825                 830

Glu Ile Val Asp Tyr Ile Ser Gly Gly Gly Phe Ser Asn Val Phe Pro
        835                 840                 845

Arg Pro Ser Tyr Gln Glu Glu Ala Val Thr Lys Phe Leu Ser Ser Ser
    850                 855                 860

Pro His Leu Pro Pro Ser Ser Tyr Phe Asn Ala Ser Gly Arg Ala Tyr
865                 870                 875                 880

Pro Asp Val Ala Ala Leu Ser Asp Gly Tyr Trp Val Val Ser Asn Arg
                885                 890                 895

Val Pro Ile Pro Trp Val Ser Gly Thr Ser Ala Ser Thr Pro Val Phe
            900                 905                 910

Gly Gly Ile Leu Ser Leu Ile Asn Glu His Arg Ile Leu Ser Gly Arg
        915                 920                 925

Pro Pro Leu Gly Phe Leu Asn Pro Arg Leu Tyr Gln Gln His Gly Ala
    930                 935                 940

Gly Leu Phe Asp Val Thr Arg Gly Cys His Glu Ser Cys Leu Asp Glu
945                 950                 955                 960

Glu Val Glu Gly Gln Gly Phe Cys Ser Gly Pro Gly Trp Asp Pro Val
                965                 970                 975

Thr Gly Trp Gly Thr Pro Asn Phe Pro Ala Leu Leu Lys Thr Leu Leu
            980                 985                 990

Asn Pro
```

<210> SEQ ID NO 267
<211> LENGTH: 3065
<212> TYPE: DNA
<213> ORGANISM: Artificial Sequence
<220> FEATURE:
<223> OTHER INFORMATION: Nucleotide sequence encoding the amino acid sequence of fusion protein of heavy chain of anti-hTfR antibody No.3 (humanized 2) and hTPP-1, synthetic sequence

<400> SEQUENCE: 267

-continued

```
acgcgtgccg ccaccatggg ctggagctgg attctgctgt tcctcctgag cgtgacagca     60
ggagtgcaca gcgaggtgca actagtgcag tctggagcag aggtgaaaaa gcccggggag    120
tctctgaaga tttcctgtaa gggttctgga tacagcttta ccaactactg gctgggatgg    180
gtgcgccaga tgcccgggaa aggcctggag tggatggggg acatctaccc cggcggagac    240
taccctacat acagcgagaa gttcaaggtc caggtcacca tctcagccga caagtccatc    300
agcaccgcct acctgcagtg gagcagcctg aaggcctcgg acaccgccat gtattactgt    360
gcgagatcag gcaattacga cgaagtggcc tactggggcc aaggaaccct ggtcaccgtc    420
tcctcagcta gcaccaaggg cccatcggtc ttccccctgg caccctcctc caagagcacc    480
tctgggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacacg tgcccaccgt gcccagcacc tgaactcctg    780
ggaggtccgt cagtcttcct cttcccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaaggat ctagttacag cccggagccc   1440
gaccagcgga ggacgctgcc cccaggctgg gtgtccctgg gccgtgcgga ccctgaggaa   1500
gagctgagtc tcacctttgc cctgagacag cagaatgtgg aaagactctc ggagctggtg   1560
caggctgtgt cagatcccag ctctcctcaa tacggaaaat acctgaccct agagaatgtg   1620
gctgatctgg tgaggccatc cccactgacc ctccacacgg tgcaaaaatg gctcttggca   1680
gccggagccc agaagtgcca ttctgtgatc acacaggact ttctgacttg ctggctgagc   1740
atccgacaag cagagctgct gctccctggg gctgagtttc atcactatgt gggaggacct   1800
acggaaaccc atgttgtaag gtccccacat ccctaccagc ttccacaggc cttggccccc   1860
catgtggact ttgtgggggg actgcaccat tttcccccaa catcatccct gaggcaacgt   1920
cctgagccgc aggtgacagg gactgtaggc ctgcatctgg gggtaacccc ctctgtgatc   1980
cgtaagcgat acaacttgac ctcacaagac gtgggctctg gcaccagcaa taacagccaa   2040
gcctgtgccc agttcctgga gcagtatttc catgactcag acctggctca gttcatgcgc   2100
ctcttcggtg gcaactttgc acatcaggca tcagtagccc gtgtggttgg acaacagggc   2160
cggggccggg ccgggattga ggccagtcta gatgtgcagt acctgatgag tgctggtgcc   2220
aacatctcca cctgggtcta cagtagccct ggccggcatg agggacagga gcccttcctg   2280
cagtggctca tgctgctcag taatgagtca gccctgccac atgtgcatac tgtgagctat   2340
ggagatgatg aggactccct cagcagcgcc tacatccagc gggtcaacac tgagctcatg   2400
```

```
aaggctgctg ctcggggtct caccctgctc ttcgcctcag gtgacagtgg ggccgggtgt   2460

tggtctgtct ctggaagaca ccagttccgc cctaccttcc ctgcctccag cccctatgtc   2520

accacagtgg gaggcacatc cttccaggaa cctttcctca tcacaaatga aattgttgac   2580

tatatcagtg gtggtggctt cagcaatgtg ttcccacggc cttcatacca ggaggaagct   2640

gtaacgaagt tcctgagctc tagcccccac ctgccaccat ccagttactt caatgccagt   2700

ggccgtgcct acccagatgt ggctgcactt tctgatggct actgggtggt cagcaacaga   2760

gtgcccattc catgggtgtc cggaacctcg gcctctactc cagtgtttgg gggtatccta   2820

tccttgatca atgagcacag aatccttagt ggccgccccc ctcttggctt tctcaaccca   2880

aggctctacc agcagcatgg ggcaggactc tttgatgtaa cccgtggctg ccatgagtcc   2940

tgtctggatg aagaggtaga gggccagggt ttctgctctg gtcctggctg ggaccctgta   3000

acaggctggg gaacacccaa cttcccagct ttgctgaaga ctctactcaa cccctaagcg   3060

gccgc                                                               3065


<210> SEQ ID NO 268
<211> LENGTH: 628
<212> TYPE: PRT
<213> ORGANISM: Homo sapiens

<400> SEQUENCE: 268

Ala Glu Ala Pro His Leu Val His Val Asp Ala Ala Arg Ala Leu Trp
1               5                   10                  15

Pro Leu Arg Arg Phe Trp Arg Ser Thr Gly Phe Cys Pro Pro Leu Pro
            20                  25                  30

His Ser Gln Ala Asp Gln Tyr Val Leu Ser Trp Asp Gln Gln Leu Asn
        35                  40                  45

Leu Ala Tyr Val Gly Ala Val Pro His Arg Gly Ile Lys Gln Val Arg
    50                  55                  60

Thr His Trp Leu Leu Glu Leu Val Thr Thr Arg Gly Ser Thr Gly Arg
65                  70                  75                  80

Gly Leu Ser Tyr Asn Phe Thr His Leu Asp Gly Tyr Leu Asp Leu Leu
                85                  90                  95

Arg Glu Asn Gln Leu Leu Pro Gly Phe Glu Leu Met Gly Ser Ala Ser
            100                 105                 110

Gly His Phe Thr Asp Phe Glu Asp Lys Gln Gln Val Phe Glu Trp Lys
        115                 120                 125

Asp Leu Val Ser Ser Leu Ala Arg Arg Tyr Ile Gly Arg Tyr Gly Leu
    130                 135                 140

Ala His Val Ser Lys Trp Asn Phe Glu Thr Trp Asn Glu Pro Asp His
145                 150                 155                 160

His Asp Phe Asp Asn Val Ser Met Thr Met Gln Gly Phe Leu Asn Tyr
                165                 170                 175

Tyr Asp Ala Cys Ser Glu Gly Leu Arg Ala Ala Ser Pro Ala Leu Arg
            180                 185                 190

Leu Gly Gly Pro Gly Asp Ser Phe His Thr Pro Pro Arg Ser Pro Leu
        195                 200                 205

Ser Trp Gly Leu Leu Arg His Cys His Asp Gly Thr Asn Phe Phe Thr
    210                 215                 220

Gly Glu Ala Gly Val Arg Leu Asp Tyr Ile Ser Leu His Arg Lys Gly
225                 230                 235                 240

Ala Arg Ser Ser Ile Ser Ile Leu Glu Gln Glu Lys Val Val Ala Gln
```

```
                245                 250                 255

Gln Ile Arg Gln Leu Phe Pro Lys Phe Ala Asp Thr Pro Ile Tyr Asn
            260                 265                 270

Asp Glu Ala Asp Pro Leu Val Gly Trp Ser Leu Pro Gln Pro Trp Arg
        275                 280                 285

Ala Asp Val Thr Tyr Ala Ala Met Val Val Lys Val Ile Ala Gln His
    290                 295                 300

Gln Asn Leu Leu Leu Ala Asn Thr Thr Ser Ala Phe Pro Tyr Ala Leu
305                 310                 315                 320

Leu Ser Asn Asp Asn Ala Phe Leu Ser Tyr His Pro His Pro Phe Ala
                325                 330                 335

Gln Arg Thr Leu Thr Ala Arg Phe Gln Val Asn Asn Thr Arg Pro Pro
            340                 345                 350

His Val Gln Leu Leu Arg Lys Pro Val Leu Thr Ala Met Gly Leu Leu
        355                 360                 365

Ala Leu Leu Asp Glu Glu Gln Leu Trp Ala Glu Val Ser Gln Ala Gly
    370                 375                 380

Thr Val Leu Asp Ser Asn His Thr Val Gly Val Leu Ala Ser Ala His
385                 390                 395                 400

Arg Pro Gln Gly Pro Ala Asp Ala Trp Arg Ala Ala Val Leu Ile Tyr
                405                 410                 415

Ala Ser Asp Asp Thr Arg Ala His Pro Asn Arg Ser Val Ala Val Thr
            420                 425                 430

Leu Arg Leu Arg Gly Val Pro Pro Gly Pro Gly Leu Val Tyr Val Thr
        435                 440                 445

Arg Tyr Leu Asp Asn Gly Leu Cys Ser Pro Asp Gly Glu Trp Arg Arg
    450                 455                 460

Leu Gly Arg Pro Val Phe Pro Thr Ala Glu Gln Phe Arg Arg Met Arg
465                 470                 475                 480

Ala Ala Glu Asp Pro Val Ala Ala Ala Pro Arg Pro Leu Pro Ala Gly
                485                 490                 495

Gly Arg Leu Thr Leu Arg Pro Ala Leu Arg Leu Pro Ser Leu Leu Leu
            500                 505                 510

Val His Val Cys Ala Arg Pro Glu Lys Pro Pro Gly Gln Val Thr Arg
        515                 520                 525

Leu Arg Ala Leu Pro Leu Thr Gln Gly Gln Leu Val Leu Val Trp Ser
    530                 535                 540

Asp Glu His Val Gly Ser Lys Cys Leu Trp Thr Tyr Glu Ile Gln Phe
545                 550                 555                 560

Ser Gln Asp Gly Lys Ala Tyr Thr Pro Val Ser Arg Lys Pro Ser Thr
                565                 570                 575

Phe Asn Leu Phe Val Phe Ser Pro Asp Thr Gly Ala Val Ser Gly Ser
            580                 585                 590

Tyr Arg Val Arg Ala Leu Asp Tyr Trp Ala Arg Pro Gly Pro Phe Ser
        595                 600                 605

Asp Pro Val Pro Tyr Leu Glu Val Pro Val Pro Arg Gly Pro Pro Ser
    610                 615                 620

Pro Gly Asn Pro
625
```

<210> SEQ ID NO 269
<211> LENGTH: 1078
<212> TYPE: PRT
<213> ORGANISM: Artificial Sequence
<220> FEATURE:
<223> OTHER INFORMATION: Amino acid sequence of the fusion protein of
heavy chain of anti-hTfR antibody No.3 (humanized 2) and hIDUA

<400> SEQUENCE: 269

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Asn Tyr
20 25 30

Trp Leu Gly Trp Val Arg Gln Met Pro Gly Lys Gly Leu Glu Trp Met
35 40 45

Gly Asp Ile Tyr Pro Gly Gly Asp Tyr Pro Thr Tyr Ser Glu Lys Phe
50 55 60

Lys Val Gln Val Thr Ile Ser Ala Asp Lys Ser Ile Ser Thr Ala Tyr
65 70 75 80

Leu Gln Trp Ser Ser Leu Lys Ala Ser Asp Thr Ala Met Tyr Tyr Cys
85 90 95

Ala Arg Ser Gly Asn Tyr Asp Glu Val Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp

-continued 385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

Gly Ser Ala Glu Ala Pro His Leu Val His Val Asp Ala Ala Arg Ala
450 455 460

Leu Trp Pro Leu Arg Arg Phe Trp Arg Ser Thr Gly Phe Cys Pro Pro
465 470 475 480

Leu Pro His Ser Gln Ala Asp Gln Tyr Val Leu Ser Trp Asp Gln Gln
485 490 495

Leu Asn Leu Ala Tyr Val Gly Ala Val Pro His Arg Gly Ile Lys Gln
500 505 510

Val Arg Thr His Trp Leu Leu Glu Leu Val Thr Thr Arg Gly Ser Thr
515 520 525

Gly Arg Gly Leu Ser Tyr Asn Phe Thr His Leu Asp Gly Tyr Leu Asp
530 535 540

Leu Leu Arg Glu Asn Gln Leu Leu Pro Gly Phe Glu Leu Met Gly Ser
545 550 555 560

Ala Ser Gly His Phe Thr Asp Phe Glu Asp Lys Gln Gln Val Phe Glu
565 570 575

Trp Lys Asp Leu Val Ser Ser Leu Ala Arg Arg Tyr Ile Gly Arg Tyr
580 585 590

Gly Leu Ala His Val Ser Lys Trp Asn Phe Glu Thr Trp Asn Glu Pro
595 600 605

Asp His His Asp Phe Asp Asn Val Ser Met Thr Met Gln Gly Phe Leu
610 615 620

Asn Tyr Tyr Asp Ala Cys Ser Glu Gly Leu Arg Ala Ala Ser Pro Ala
625 630 635 640

Leu Arg Leu Gly Gly Pro Gly Asp Ser Phe His Thr Pro Pro Arg Ser
645 650 655

Pro Leu Ser Trp Gly Leu Leu Arg His Cys His Asp Gly Thr Asn Phe
660 665 670

Phe Thr Gly Glu Ala Gly Val Arg Leu Asp Tyr Ile Ser Leu His Arg
675 680 685

Lys Gly Ala Arg Ser Ser Ile Ser Ile Leu Glu Gln Glu Lys Val Val
690 695 700

Ala Gln Gln Ile Arg Gln Leu Phe Pro Lys Phe Ala Asp Thr Pro Ile
705 710 715 720

Tyr Asn Asp Glu Ala Asp Pro Leu Val Gly Trp Ser Leu Pro Gln Pro
725 730 735

Trp Arg Ala Asp Val Thr Tyr Ala Ala Met Val Val Lys Val Ile Ala
740 745 750

Gln His Gln Asn Leu Leu Leu Ala Asn Thr Thr Ser Ala Phe Pro Tyr
755 760 765

Ala Leu Leu Ser Asn Asp Asn Ala Phe Leu Ser Tyr His Pro His Pro
770 775 780

Phe Ala Gln Arg Thr Leu Thr Ala Arg Phe Gln Val Asn Asn Thr Arg
785 790 795 800

Pro Pro His Val Gln Leu Leu Arg Lys Pro Val Leu Thr Ala Met Gly
805 810 815

```
Leu Leu Ala Leu Leu Asp Glu Glu Gln Leu Trp Ala Glu Val Ser Gln
            820                 825                 830

Ala Gly Thr Val Leu Asp Ser Asn His Thr Val Gly Val Leu Ala Ser
        835                 840                 845

Ala His Arg Pro Gln Gly Pro Ala Asp Ala Trp Arg Ala Ala Val Leu
    850                 855                 860

Ile Tyr Ala Ser Asp Asp Thr Arg Ala His Pro Asn Arg Ser Val Ala
865                 870                 875                 880

Val Thr Leu Arg Leu Arg Gly Val Pro Pro Gly Pro Gly Leu Val Tyr
                885                 890                 895

Val Thr Arg Tyr Leu Asp Asn Gly Leu Cys Ser Pro Asp Gly Glu Trp
            900                 905                 910

Arg Arg Leu Gly Arg Pro Val Phe Pro Thr Ala Glu Gln Phe Arg Arg
        915                 920                 925

Met Arg Ala Ala Glu Asp Pro Val Ala Ala Ala Pro Arg Pro Leu Pro
    930                 935                 940

Ala Gly Gly Arg Leu Thr Leu Arg Pro Ala Leu Arg Leu Pro Ser Leu
945                 950                 955                 960

Leu Leu Val His Val Cys Ala Arg Pro Glu Lys Pro Pro Gly Gln Val
                965                 970                 975

Thr Arg Leu Arg Ala Leu Pro Leu Thr Gln Gly Gln Leu Val Leu Val
            980                 985                 990

Trp Ser Asp Glu His Val Gly Ser  Lys Cys Leu Trp Thr  Tyr Glu Ile
        995                 1000                1005

Gln Phe  Ser Gln Asp Gly Lys  Ala Tyr Thr Pro Val  Ser Arg Lys
    1010                 1015                 1020

Pro Ser  Thr Phe Asn Leu Phe  Val Phe Ser Pro Asp  Thr Gly Ala
    1025                 1030                 1035

Val Ser  Gly Ser Tyr Arg Val  Arg Ala Leu Asp Tyr  Trp Ala Arg
    1040                 1045                 1050

Pro Gly  Pro Phe Ser Asp Pro  Val Pro Tyr Leu Glu  Val Pro Val
    1055                 1060                 1065

Pro Arg  Gly Pro Pro Ser Pro  Gly Asn Pro
    1070                 1075
```

<210> SEQ ID NO 270
<211> LENGTH: 3317
<212> TYPE: DNA
<213> ORGANISM: Artificial Sequence
<220> FEATURE:
<223> OTHER INFORMATION: Nucleotide sequence encoding the amino acid sequence of fusion protein of heavy chain of anti-hTfR antibody No.3 (humanized 2) and hIDUA, synthetic sequence

<400> SEQUENCE: 270

```
acgcgtgccg ccaccatggg ctggagctgg attctgctgt tcctcctgag cgtgacagca     60

ggagtgcaca gcgaggtgca actagtgcag tctggagcag aggtgaaaaa gcccggggag    120

tctctgaaga tttcctgtaa gggttctgga tacagcttta ccaactactg gctgggatgg    180

gtgcgccaga tgcccgggaa aggcctggag tggatggggg acatctaccc cggcggagac    240

taccctacat acagcgagaa gttcaaggtc caggtcacca tctcagccga caagtccatc    300

agcaccgcct acctgcagtg gagcagcctg aaggcctcgg acaccgccat gtattactgt    360

gcgagatcag gcaattacga cgaagtggcc tactggggcc aaggaaccct ggtcaccgtc    420

tcctcagcta gcaccaaggg cccatcggtc ttccccctgg caccctcctc caagagcacc    480
```

```
tctgggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacacg tgcccaccgt gcccagcacc tgaactcctg    780
ggaggtccgt cagtcttcct cttcccccca aaacccaagg acaccctcat gatctcccgg    840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga acaactacaa gaccacgcct   1260
cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaaggat ctgccgaggc cccgcacctg   1440
gtgcacgtgg acgcggcccg cgcgctgtgg cccctgcggc gcttctggag gagcacaggc   1500
ttctgccccc cgctgccaca cagccaggct gaccagtacg tcctcagctg ggaccagcag   1560
ctcaacctcg cctatgtggg cgccgtccct caccgcggca tcaagcaggt ccggacccac   1620
tggctgctgg agcttgtcac caccaggggg tccactggac ggggcctgag ctacaacttc   1680
acccacctgg acgggtactt ggaccttctc agggagaacc agctcctccc agggtttgag   1740
ctgatgggca gcgcctcggg ccacttcact gactttgagg acaagcagca ggtgtttgag   1800
tggaaggact tggtctccag cctggccagg agatacatcg gtaggtacgg actggcgcat   1860
gtttccaagt ggaacttcga gacgtggaat gagccagacc accacgactt tgacaacgtc   1920
tccatgacca tgcaaggctt cctgaactac tacgatgcct gctcggaggg tctgcgcgcc   1980
gccagccccg ccctgcggct gggaggcccc ggcgactcct tccacacccc accgcgatcc   2040
ccgctgagct ggggcctcct gcgccactgc cacgacggta ccaacttctt cactggggag   2100
gcgggcgtgc ggctggacta catctccctc cacaggaagg gtgcgcgcag ctccatctcc   2160
atcctggagc aggagaaggt cgtcgcgcag cagatccggc agctcttccc caagttcgcg   2220
gacaccccca tttacaacga cgaggcggac ccgctggtgg gctggtccct gccacagccg   2280
tggagggcgg acgtgaccta cgcggccatg gtggtgaagg tcatcgcgca gcatcagaac   2340
ctgctactgg ccaacaccac ctccgccttc ccctacgcgc tcctgagcaa cgacaatgcc   2400
ttcctgagct accacccgca ccccttcgcg cagcgcacgc tcaccgcgcg cttccaggtc   2460
aacaacaccc gcccgccgca cgtgcagctg ttgcgcaagc cggtgctcac ggccatgggg   2520
ctgctggcgc tgctggatga ggagcagctc tgggccgaag tgtcgcaggc cgggaccgtc   2580
ctggacagca accacacggt gggcgtcctg gccagcgccc accgccccca gggcccggcc   2640
gacgcctggc gcgccgcggt gctgatctac gcgagcgacg acacccgcgc ccaccccaac   2700
cgcagcgtcg cggtgaccct gcggctgcgc ggggtgcccc ccggcccggg cctggtctac   2760
gtcacgcgct acctggacaa cgggctctgc agccccgacg gcgagtggcg gcgcctgggc   2820
```

cggcccgtct tccccacggc agagcagttc cggcgcatgc gcgcggctga ggacccggtg 2880
gccgcggcgc cccgcccctt acccgccggt ggccgcctga ccctgcgccc cgcgctgcgg 2940
ctgccgtcgc ttttgctggt gcacgtgtgt gcgcgccccg agaagccgcc cgggcaggtc 3000
acgcggctcc gcgccctgcc cctgacccaa gggcagctgg ttctggtctg gtcggatgaa 3060
cacgtgggct ccaagtgcct gtggacatac gagatccagt tctctcagga cggtaaggcg 3120
tacaccccgg tcagcaggaa gccatcgacc ttcaacctct ttgtgttcag cccagacaca 3180
ggtgctgtct ctggctccta ccgagttcga gccctggact actgggcccg accaggcccc 3240
ttctcggacc ctgtgccgta cctggaggtc cctgtgccaa gagggccccc atccccgggc 3300
aatccataag cggccgc 3317

<210> SEQ ID NO 271
<211> LENGTH: 235
<212> TYPE: PRT
<213> ORGANISM: Homo sapiens

<400> SEQUENCE: 271

Leu Pro Ala Gln Val Ala Phe Thr Pro Tyr Ala Pro Glu Pro Gly Ser
1 5 10 15

Thr Cys Arg Leu Arg Glu Tyr Tyr Asp Gln Thr Ala Gln Met Cys Cys
20 25 30

Ser Lys Cys Ser Pro Gly Gln His Ala Lys Val Phe Cys Thr Lys Thr
35 40 45

Ser Asp Thr Val Cys Asp Ser Cys Glu Asp Ser Thr Tyr Thr Gln Leu
50 55 60

Trp Asn Trp Val Pro Glu Cys Leu Ser Cys Gly Ser Arg Cys Ser Ser
65 70 75 80

Asp Gln Val Glu Thr Gln Ala Cys Thr Arg Glu Gln Asn Arg Ile Cys
85 90 95

Thr Cys Arg Pro Gly Trp Tyr Cys Ala Leu Ser Lys Gln Glu Gly Cys
100 105 110

Arg Leu Cys Ala Pro Leu Arg Lys Cys Arg Pro Gly Phe Gly Val Ala
115 120 125

Arg Pro Gly Thr Glu Thr Ser Asp Val Val Cys Lys Pro Cys Ala Pro
130 135 140

Gly Thr Phe Ser Asn Thr Thr Ser Ser Thr Asp Ile Cys Arg Pro His
145 150 155 160

Gln Ile Cys Asn Val Val Ala Ile Pro Gly Asn Ala Ser Met Asp Ala
165 170 175

Val Cys Thr Ser Thr Ser Pro Thr Arg Ser Met Ala Pro Gly Ala Val
180 185 190

His Leu Pro Gln Pro Val Ser Thr Arg Ser Gln His Thr Gln Pro Thr
195 200 205

Pro Glu Pro Ser Thr Ala Pro Ser Thr Ser Phe Leu Leu Pro Met Gly
210 215 220

Pro Ser Pro Pro Ala Glu Gly Ser Thr Gly Asp
225 230 235

<210> SEQ ID NO 272
<211> LENGTH: 685
<212> TYPE: PRT
<213> ORGANISM: Artificial Sequence
<220> FEATURE:
<223> OTHER INFORMATION: Amino acid sequence of the fusion protein of
heavy chain of anti-hTfR antibody No.3 (humanized 2) and -continued hTNF-alpha receptor

<400> SEQUENCE: 272

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser Leu Pro Ala Gln Val Ala Phe Thr Pro Tyr Ala Pro Glu Pro
    450                 455                 460

Gly Ser Thr Cys Arg Leu Arg Glu Tyr Tyr Asp Gln Thr Ala Gln Met
465                 470                 475                 480

Cys Cys Ser Lys Cys Ser Pro Gly Gln His Ala Lys Val Phe Cys Thr
                485                 490                 495

Lys Thr Ser Asp Thr Val Cys Asp Ser Cys Glu Asp Ser Thr Tyr Thr
            500                 505                 510

Gln Leu Trp Asn Trp Val Pro Glu Cys Leu Ser Cys Gly Ser Arg Cys
        515                 520                 525

Ser Ser Asp Gln Val Glu Thr Gln Ala Cys Thr Arg Glu Gln Asn Arg
    530                 535                 540

Ile Cys Thr Cys Arg Pro Gly Trp Tyr Cys Ala Leu Ser Lys Gln Glu
545                 550                 555                 560

Gly Cys Arg Leu Cys Ala Pro Leu Arg Lys Cys Arg Pro Gly Phe Gly
                565                 570                 575

Val Ala Arg Pro Gly Thr Glu Thr Ser Asp Val Val Cys Lys Pro Cys
            580                 585                 590

Ala Pro Gly Thr Phe Ser Asn Thr Thr Ser Ser Thr Asp Ile Cys Arg
        595                 600                 605

Pro His Gln Ile Cys Asn Val Val Ala Ile Pro Gly Asn Ala Ser Met
    610                 615                 620

Asp Ala Val Cys Thr Ser Thr Ser Pro Thr Arg Ser Met Ala Pro Gly
625                 630                 635                 640

Ala Val His Leu Pro Gln Pro Val Ser Thr Arg Ser Gln His Thr Gln
                645                 650                 655

Pro Thr Pro Glu Pro Ser Thr Ala Pro Ser Thr Ser Phe Leu Leu Pro
            660                 665                 670

Met Gly Pro Ser Pro Pro Ala Glu Gly Ser Thr Gly Asp
        675                 680                 685
```

<210> SEQ ID NO 273
<211> LENGTH: 2138
<212> TYPE: DNA
<213> ORGANISM: Artificial Sequence
<220> FEATURE:
<223> OTHER INFORMATION: Nucleotide sequence encoding the amino acid sequence of fusion protein of heavy chain of anti-hTfR antibody No.3 (humanized 2) and hTNF-alpha receptor, synthetic sequence

<400> SEQUENCE: 273

```
acgcgtgccg ccaccatggg ctggagctgg attctgctgt tcctcctgag cgtgacagca      60

ggagtgcaca gcgaggtgca actagtgcag tctggagcag aggtgaaaaa gcccggggag     120

tctctgaaga tttcctgtaa gggttctgga tacagcttta ccaactactg gctgggatgg     180

gtgcgccaga tgcccgggaa aggcctggag tggatggggg acatctaccc cggcggagac     240

taccctacat acagcgagaa gttcaaggtc caggtcacca tctcagccga caagtccatc     300

agcaccgcct acctgcagtg gagcagcctg aaggcctcgg acaccgccat gtattactgt     360

gcgagatcag gcaattacga cgaagtggcc tactggggcc aaggaaccct ggtcaccgtc     420
```

```
tcctcagcta gcaccaaggg cccatcggtc ttccccctgg caccctcctc caagagcacc    480

tctgggggca cagcggccct gggctgcctg gtcaaggact acttccccga accggtgacg    540

gtgtcgtgga actcaggcgc cctgaccagc ggcgtgcaca ccttcccggc tgtcctacag    600

tcctcaggac tctactccct cagcagcgtg gtgaccgtgc cctccagcag cttgggcacc    660

cagacctaca tctgcaacgt gaatcacaag cccagcaaca ccaaggtgga caagaaagtt    720

gagcccaaat cttgtgacaa aactcacacg tgcccaccgt gcccagcacc tgaactcctg    780

ggaggtccgt cagtcttcct cttcccccca aaacccaagg acaccctcat gatctcccgg    840

acccctgagg tcacatgcgt ggtggtggac gtgagccacg aagaccctga ggtcaagttc    900

aactggtacg tggacggcgt ggaggtgcat aatgccaaga caaagccgcg ggaggagcag    960

tacaacagca cgtaccgggt ggtcagcgtc ctcaccgtcc tgcaccagga ctggctgaat   1020

ggcaaggagt acaagtgcaa ggtctccaac aaagccctcc cagcccccat cgagaaaacc   1080

atctccaaag ccaaagggca gccccgagaa ccacaggtgt acaccctgcc cccatcccgg   1140

gatgagctga ccaagaacca ggtcagcctg acctgcctgg tcaaaggctt ctatcccagc   1200

gacatcgccg tggagtggga gagcaatggg cagccggaga acaactacaa gaccacgcct   1260

cccgtgctgg actccgacgg ctccttcttc ctctacagca agctcaccgt ggacaagagc   1320

aggtggcagc aggggaacgt cttctcatgc tccgtgatgc atgaggctct gcacaaccac   1380

tacacgcaga agagcctctc cctgtctccg ggtaaaggat ctttgcccgc ccaggtggca   1440

tttacaccct acgccccgga gcccgggagc acatgccggc tcagagaata ctatgaccag   1500

acagctcaga tgtgctgcag caagtgctcg ccgggccaac atgcaaaagt cttctgtacc   1560

aagacctcgg acaccgtgtg tgactcctgt gaggacagca catacaccca gctctggaac   1620

tgggttcccg agtgcttgag ctgtggctcc cgctgtagct ctgaccaggt ggaaactcaa   1680

gcctgcactc gggaacagaa ccgcatctgc acctgcaggc ccggctggta ctgcgcgctg   1740

agcaagcagg aggggtgccg gctgtgcgcg ccgctgcgca agtgccgccc gggcttcggc   1800

gtggccagac caggaactga aacatcagac gtggtgtgca agccctgtgc cccggggacg   1860

ttctccaaca cgacttcatc cacggatatt tgcaggcccc accaaatctg taacgtggtg   1920

gccatccctg ggaatgcaag catggatgca gtctgcacgt ccacgtcccc cacccggagt   1980

atggccccag gggcagtaca cttaccccag ccagtgtcca cacgatccca acacacgcag   2040

ccaactccag aacccagcac tgctccaagc acctccttcc tgctcccaat gggccccagc   2100

cccccagctg aagggagcac tggcgactaa gcggccgc                           2138
```

<210> SEQ ID NO 274
<211> LENGTH: 482
<212> TYPE: PRT
<213> ORGANISM: Homo sapiens

<400> SEQUENCE: 274

```
Arg Pro Arg Asn Ala Leu Leu Leu Leu Ala Asp Asp Gly Gly Phe Glu
1               5                   10                  15

Ser Gly Ala Tyr Asn Asn Ser Ala Ile Ala Thr Pro His Leu Asp Ala
            20                  25                  30

Leu Ala Arg Arg Ser Leu Leu Phe Arg Asn Ala Phe Thr Ser Val Ser
        35                  40                  45

Ser Cys Ser Pro Ser Arg Ala Ser Leu Leu Thr Gly Leu Pro Gln His
    50                  55                  60
```

-continued

```
Gln Asn Gly Met Tyr Gly Leu His Gln Asp Val His His Phe Asn Ser
65                  70                  75                  80

Phe Asp Lys Val Arg Ser Leu Pro Leu Leu Leu Ser Gln Ala Gly Val
                85                  90                  95

Arg Thr Gly Ile Ile Gly Lys Lys His Val Gly Pro Glu Thr Val Tyr
            100                 105                 110

Pro Phe Asp Phe Ala Tyr Thr Glu Glu Asn Gly Ser Val Leu Gln Val
        115                 120                 125

Gly Arg Asn Ile Thr Arg Ile Lys Leu Leu Val Arg Lys Phe Leu Gln
    130                 135                 140

Thr Gln Asp Asp Arg Pro Phe Phe Leu Tyr Val Ala Phe His Asp Pro
145                 150                 155                 160

His Arg Cys Gly His Ser Gln Pro Gln Tyr Gly Thr Phe Cys Glu Lys
                165                 170                 175

Phe Gly Asn Gly Glu Ser Gly Met Gly Arg Ile Pro Asp Trp Thr Pro
            180                 185                 190

Gln Ala Tyr Asp Pro Leu Asp Val Leu Val Pro Tyr Phe Val Pro Asn
        195                 200                 205

Thr Pro Ala Ala Arg Ala Asp Leu Ala Ala Gln Tyr Thr Thr Val Gly
    210                 215                 220

Arg Met Asp Gln Gly Val Gly Leu Val Leu Gln Glu Leu Arg Asp Ala
225                 230                 235                 240

Gly Val Leu Asn Asp Thr Leu Val Ile Phe Thr Ser Asp Asn Gly Ile
                245                 250                 255

Pro Phe Pro Ser Gly Arg Thr Asn Leu Tyr Trp Pro Gly Thr Ala Glu
            260                 265                 270

Pro Leu Leu Val Ser Ser Pro Glu His Pro Lys Arg Trp Gly Gln Val
        275                 280                 285

Ser Glu Ala Tyr Val Ser Leu Leu Asp Leu Thr Pro Thr Ile Leu Asp
    290                 295                 300

Trp Phe Ser Ile Pro Tyr Pro Ser Tyr Ala Ile Phe Gly Ser Lys Thr
305                 310                 315                 320

Ile His Leu Thr Gly Arg Ser Leu Leu Pro Ala Leu Glu Ala Glu Pro
                325                 330                 335

Leu Trp Ala Thr Val Phe Gly Ser Gln Ser His His Glu Val Thr Met
            340                 345                 350

Ser Tyr Pro Met Arg Ser Val Gln His Arg His Phe Arg Leu Val His
        355                 360                 365

Asn Leu Asn Phe Lys Met Pro Phe Pro Ile Asp Gln Asp Phe Tyr Val
    370                 375                 380

Ser Pro Thr Phe Gln Asp Leu Leu Asn Arg Thr Thr Ala Gly Gln Pro
385                 390                 395                 400

Thr Gly Trp Tyr Lys Asp Leu Arg His Tyr Tyr Tyr Arg Ala Arg Trp
                405                 410                 415

Glu Leu Tyr Asp Arg Ser Arg Asp Pro His Glu Thr Gln Asn Leu Ala
            420                 425                 430

Thr Asp Pro Arg Phe Ala Gln Leu Leu Glu Met Leu Arg Asp Gln Leu
        435                 440                 445

Ala Lys Trp Gln Trp Glu Thr His Asp Pro Trp Val Cys Ala Pro Asp
    450                 455                 460

Gly Val Leu Glu Glu Lys Leu Ser Pro Gln Cys Gln Pro Leu His Asn
465                 470                 475                 480

Glu Leu
```

<210> SEQ ID NO 275
<211> LENGTH: 932
<212> TYPE: PRT
<213> ORGANISM: Artificial Sequence
<220> FEATURE:
<223> OTHER INFORMATION: Amino acid sequence of the fusion protein of heavy chain of anti-hTfR antibody No.3 (humanized 2) and hSGSH

<400> SEQUENCE: 275

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
```

```
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Gly Ser Arg Pro Arg Asn Ala Leu Leu Leu Leu Ala Asp Asp Gly Gly
    450                 455                 460

Phe Glu Ser Gly Ala Tyr Asn Asn Ser Ala Ile Ala Thr Pro His Leu
465                 470                 475                 480

Asp Ala Leu Ala Arg Arg Ser Leu Leu Phe Arg Asn Ala Phe Thr Ser
                485                 490                 495

Val Ser Ser Cys Ser Pro Ser Arg Ala Ser Leu Leu Thr Gly Leu Pro
            500                 505                 510

Gln His Gln Asn Gly Met Tyr Gly Leu His Gln Asp Val His His Phe
        515                 520                 525

Asn Ser Phe Asp Lys Val Arg Ser Leu Pro Leu Leu Leu Ser Gln Ala
    530                 535                 540

Gly Val Arg Thr Gly Ile Ile Gly Lys Lys His Val Gly Pro Glu Thr
545                 550                 555                 560

Val Tyr Pro Phe Asp Phe Ala Tyr Thr Glu Glu Asn Gly Ser Val Leu
                565                 570                 575

Gln Val Gly Arg Asn Ile Thr Arg Ile Lys Leu Leu Val Arg Lys Phe
            580                 585                 590

Leu Gln Thr Gln Asp Asp Arg Pro Phe Phe Leu Tyr Val Ala Phe His
        595                 600                 605

Asp Pro His Arg Cys Gly His Ser Gln Pro Gln Tyr Gly Thr Phe Cys
    610                 615                 620

Glu Lys Phe Gly Asn Gly Glu Ser Gly Met Gly Arg Ile Pro Asp Trp
625                 630                 635                 640

Thr Pro Gln Ala Tyr Asp Pro Leu Asp Val Leu Val Pro Tyr Phe Val
                645                 650                 655

Pro Asn Thr Pro Ala Ala Arg Ala Asp Leu Ala Ala Gln Tyr Thr Thr
            660                 665                 670

Val Gly Arg Met Asp Gln Gly Val Gly Leu Val Leu Gln Glu Leu Arg
        675                 680                 685

Asp Ala Gly Val Leu Asn Asp Thr Leu Val Ile Phe Thr Ser Asp Asn
    690                 695                 700

Gly Ile Pro Phe Pro Ser Gly Arg Thr Asn Leu Tyr Trp Pro Gly Thr
705                 710                 715                 720

Ala Glu Pro Leu Leu Val Ser Ser Pro Glu His Pro Lys Arg Trp Gly
                725                 730                 735

Gln Val Ser Glu Ala Tyr Val Ser Leu Leu Asp Leu Thr Pro Thr Ile
            740                 745                 750

Leu Asp Trp Phe Ser Ile Pro Tyr Pro Ser Tyr Ala Ile Phe Gly Ser
        755                 760                 765

Lys Thr Ile His Leu Thr Gly Arg Ser Leu Leu Pro Ala Leu Glu Ala
    770                 775                 780
```

Glu Pro Leu Trp Ala Thr Val Phe Gly Ser Gln Ser His His Glu Val
785 790 795 800

Thr Met Ser Tyr Pro Met Arg Ser Val Gln His Arg His Phe Arg Leu
805 810 815

Val His Asn Leu Asn Phe Lys Met Pro Phe Pro Ile Asp Gln Asp Phe
820 825 830

Tyr Val Ser Pro Thr Phe Gln Asp Leu Leu Asn Arg Thr Thr Ala Gly
835 840 845

Gln Pro Thr Gly Trp Tyr Lys Asp Leu Arg His Tyr Tyr Tyr Arg Ala
850 855 860

Arg Trp Glu Leu Tyr Asp Arg Ser Arg Asp Pro His Glu Thr Gln Asn
865 870 875 880

Leu Ala Thr Asp Pro Arg Phe Ala Gln Leu Leu Glu Met Leu Arg Asp
885 890 895

Gln Leu Ala Lys Trp Gln Trp Glu Thr His Asp Pro Trp Val Cys Ala
900 905 910

Pro Asp Gly Val Leu Glu Glu Lys Leu Ser Pro Gln Cys Gln Pro Leu
915 920 925

His Asn Glu Leu
930

<210> SEQ ID NO 276
<211> LENGTH: 2879
<212> TYPE: DNA
<213> ORGANISM: Artificial Sequence
<220> FEATURE:
<223> OTHER INFORMATION: Nucleotide sequence encoding the amino acid sequence of fusion protein of heavy chain of anti-hTfR antibody No.3 (humanized 2) and hSGSH, synthetic sequence

<400> SEQUENCE: 276
acgcgtgccg ccaccatggg ctggagctgg attctgctgt tcctcctgag cgtgacagca 60
ggagtgcaca gcgaggtgca actagtgcag tctggagcag aggtgaaaaa gcccggggag 120
tctctgaaga tttcctgtaa gggttctgga tacagcttta ccaactactg gctgggatgg 180
gtgcgccaga tgcccgggaa aggcctggag tggatggggg acatctaccc cggcggagac 240
taccctacat acagcgagaa gttcaaggtc caggtcacca tctcagccga caagtccatc 300
agcaccgcct acctgcagtg gagcagcctg aaggcctcgg acaccgccat gtattactgt 360
gcgagatcag gcaattacga cgaagtggcc tactggggcc aaggaaccct ggtcaccgtc 420
tcctcagcta gcaccaaggg cccatcggtc ttccccctgg caccctcctc caagagcacc 480
tctgggggca cagcggccct gggctgcctg gtcaaggact acttccccga accggtgacg 540
gtgtcgtgga actcaggcgc cctgaccagc ggcgtgcaca ccttcccggc tgtcctacag 600
tcctcaggac tctactccct cagcagcgtg gtgaccgtgc cctccagcag cttgggcacc 660
cagacctaca tctgcaacgt gaatcacaag cccagcaaca ccaaggtgga caagaaagtt 720
gagcccaaat cttgtgacaa aactcacacg tgcccaccgt gcccagcacc tgaactcctg 780
ggaggtccgt cagtcttcct cttcccccca aaacccaagg acaccctcat gatctcccgg 840
acccctgagg tcacatgcgt ggtggtggac gtgagccacg aagaccctga ggtcaagttc 900
aactggtacg tggacggcgt ggaggtgcat aatgccaaga caaagccgcg ggaggagcag 960
tacaacagca cgtaccgggt ggtcagcgtc ctcaccgtcc tgcaccagga ctggctgaat 1020
ggcaaggagt acaagtgcaa ggtctccaac aaagccctcc cagcccccat cgagaaaacc 1080

```
atctccaaag ccaaagggca gccccgagaa ccacaggtgt acaccctgcc cccatcccgg   1140

gatgagctga ccaagaacca ggtcagcctg acctgcctgg tcaaaggctt ctatcccagc   1200

gacatcgccg tggagtggga gagcaatggg cagccggaga acaactacaa gaccacgcct   1260

cccgtgctgg actccgacgg ctccttcttc ctctacagca agctcaccgt ggacaagagc   1320

aggtggcagc aggggaacgt cttctcatgc tccgtgatgc atgaggctct gcacaaccac   1380

tacacgcaga agagcctctc cctgtctccg ggtaaaggat ctcgtccccg gaacgcactg   1440

ctgctcctcg cggatgacgg aggctttgag agtggcgcgt acaacaacag cgccatcgcc   1500

accccgcacc tggacgcctt ggcccgccgc agcctcctct ttcgcaatgc cttcacctcg   1560

gtcagcagct gctctcccag ccgcgccagc ctcctcactg gcctgcccca gcatcagaat   1620

gggatgtacg ggctgcacca ggacgtgcac cacttcaact ccttcgacaa ggtgcggagc   1680

ctgccgctgc tgctcagcca agctggtgtg cgcacaggca tcatcgggaa gaagcacgtg   1740

gggccggaga ccgtgtaccc gtttgacttt gcgtacacgg aggagaatgg ctccgtcctc   1800

caggtggggc ggaacatcac tagaattaag ctgctcgtcc ggaaattcct gcagactcag   1860

gatgaccggc ctttcttcct ctacgtcgcc ttccacgacc cccaccgctg tgggcactcc   1920

cagccccagt acggaacctt ctgtgagaag tttggcaacg gagagagcgg catgggtcgt   1980

atcccagact ggaccccccca ggcctacgac ccactggacg tgctggtgcc ttacttcgtc   2040

cccaacaccc cggcagcccg agccgacctg gccgctcagt acaccaccgt cggccgcatg   2100

gaccaaggag ttggactggt gctccaggag ctgcgtgacg ccggtgtcct gaacgacaca   2160

ctggtgatct tcacgtccga caacggtatc cccttcccca gcggcaggac caacctgtac   2220

tggccgggca ctgctgaacc cttactggtg tcatccccgg agcacccaaa acgctggggc   2280

caagtcagcg aggcctacgt gagcctccta gacctcacgc ccaccatctt ggattggttc   2340

tcgatcccgt accccagcta cgccatcttt ggctcgaaga ccatccacct cactggccgg   2400

tccctcctgc cggcgctgga ggccgagccc ctctgggcca ccgtctttgg cagccagagc   2460

caccacgagg tcaccatgtc ctaccccatg cgctccgtgc agcaccggca cttccgcctc   2520

gtgcacaacc tcaacttcaa gatgcccttt cccatcgacc aggacttcta cgtctcaccc   2580

accttccagg acctcctgaa ccgcaccaca gctggtcagc ccacgggctg gtacaaggac   2640

ctccgtcatt actactaccg ggcgcgctgg gagctctacg accggagccg ggaccccccac   2700

gagacccaga acctggccac cgacccgcgc tttgctcagc ttctggagat gcttcgggac   2760

cagctggcca agtggcagtg ggagacccac gacccctggg tgtgcgcccc cgacggcgtc   2820

ctggaggaga agctctctcc ccagtgccag cccctccaca atgagctgta agcggccgc    2879
```

```
<210> SEQ ID NO 277
<211> LENGTH: 245
<212> TYPE: PRT
<213> ORGANISM: Artificial Sequence
<220> FEATURE:
<223> OTHER INFORMATION: Amino acid sequence of anti-hTfR single-chain
      antibody

<400> SEQUENCE: 277

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45
```

-continued

```
Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Thr Pro Leu Ser Leu
    130                 135                 140

Ser Val Thr Pro Gly Gln Pro Ala Ser Ile Ser Cys Arg Ser Ser Gln
145                 150                 155                 160

Ser Leu Val His Ser Asn Gly Asn Thr Tyr Leu His Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Ser Gln Ser Thr His Val Pro Trp Thr Phe Gly Gln Gly Thr
225                 230                 235                 240

Lys Val Glu Ile Lys
                245


<210> SEQ ID NO 278
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No. 6

<400> SEQUENCE: 278

Ile Ile Trp Gly Asp Gly Ser Thr Asn Tyr His Ser Ala Leu Ile Ser
1               5                   10                  15


<210> SEQ ID NO 279
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No. 8

<400> SEQUENCE: 279

Ile Ile Trp Gly Asp Gly Ser Thr Asn Tyr Arg Ser Ala Leu Ile Ser
1               5                   10                  15
```

ANTI-HUMAN TRANSFERRIN RECEPTOR ANTIBODY PERMEATING BLOOD-BRAIN BARRIER

SEQUENCE LISTING SUBMISSION VIA EFS-WEB

A computer readable text file, entitled "SequenceListing.txt," created on or about Dec. 21, 2017 with a file size of about 333 kb contains the sequence listing for this application and is hereby incorporated by reference in its entirety.

TECHNICAL FIELD

The present invention relates to an anti-human transferrin receptor antibody to be utilized for conjugation with a compound that needs to exhibit its function in the central nervous system when administered parenterally (a protein or a low-molecular-weight compound and the like) in order to make that compound able to pass through the blood-brain barrier after parenterally administered, and also a method for production thereof, as well as a method of use thereof.

BACKGROUND ART

Unlike the capillaries in other tissues such as muscles, the capillaries that supply the blood to most of the brain tissues except some areas including the circumventricular organs (pineal gland, pituitary body, area postrema, etc.) differ in that the endothelial cells forming their endothelium are mutually connected by tight intercellular junctions. Passive transfer of substances from the capillaries to the brain is thereby restricted, and although there are some exceptions, substances are unlikely to move into the brain from the blood except such compounds as are lipid-soluble or of low-molecular-weight (not greater than 200 to 500 Dalton) and electrically neutral around the physiological pH. This system, which restricts exchange of substances between the blood and the tissue fluid of the brain through the endothelium of capillaries in the brain, is called the blood-brain barrier or BBB. The blood-brain barrier not only restricts exchange of substances between the blood and the brain but also between the tissue fluid of the central nervous system, including the brain and the spinal chord, and the blood.

Owing to the blood-brain barrier, most of the cells of the central nervous system escape the effects of fluctuating concentrations of substances like hormones and lymphokines in the blood, and their biochemical homeostasis is thus maintained.

The blood-brain barrier, however, imposes a problem when it comes to develop pharmaceutical agents. For mucopolysaccharidosis type I (Hurler syndrome), an inherited metabolic disease caused by α-L-iduronidase deficiency, for example, although an enzyme replacement therapy is carried out by intravenous supplementation with a recombinant α-L-iduronidase as a therapy, the therapy is not effective for the notable abnormality observed in the central nervous system (CNS) in Hurler syndrome because the enzyme cannot pass through the blood-brain barrier.

Development of various methods has been attempted to make those macromolecular substances as proteins or the like, which need to be brought into function in the central nervous system, pass through the blood-brain barrier. In the case of nerve growth factor, for example, while attempts have been made for a method to cause the factor to pass through the blood-brain barrier by allowing liposomes encapsulating the factor to fuse with the cell membrane of endothelial cells in brain capillaries, they have not been reached practical application (Non Patent Literature 1). In the case of α-L-iduronidase, an attempt has been made to enhance the passive transfer of the enzyme through the blood-brain barrier by raising its blood concentration through an increased single dose of the enzyme, and it thus has been demonstrated, using a Hurler syndrome animal model, that the abnormality in the central nervous system (CNS) is ameliorated by that method (Non Patent Literature 2).

Furthermore, circumventing the blood-brain barrier, an attempt has also been made to administer a macromolecular substance directly into the medullary cavity or into the brain. For example, reports have been made about a method in which human α-L-iduronidase was intrathecally administered to a patient with a Hurler syndrome (mucopolysaccharidosis type I) (Patent Literature 1), a method in which human acid sphingomyelinase was administered into the brain ventricles of a patient with Niemann-Pick disease (Patent Literature 2), and a method in which iduronate 2-sulfatase (I2S) was administered into the brain ventricles of Hunter syndrome model animals (Patent Literature 3). While it seems possible by one of such methods to definitely let a pharmaceutical agent act in the central nervous system, they have a problem as being highly invasive.

There have been reported various methods to let a macromolecular substance get into the brain through the blood-brain barrier, in which the macromolecular substance is modified to give it an affinity to membrane proteins existing on the endothelial cells of the brain capillaries. Examples of those membrane proteins which exist on the endothelial cells of the brain capillaries include receptors for compounds such as insulin, transferrin, insulin-like growth factor (IGF-I, IGF-II), LDL, and leptin.

For example, a technique has been reported in which nerve growth factor (NGF) was synthesized in the form of a fusion protein with insulin, and this fusion protein was allowed to pass through the blood-brain barrier via its binding to the insulin receptor (Patent Literatures 4-6). Further, a technique has been reported in which nerve growth factor (NGF) was synthesized in the form of a fusion protein with anti-insulin receptor antibody, and this fusion protein was allowed to pass through the blood-brain barrier via its binding to the insulin receptor (Patent Literatures 4 and 7). Further, a technique has been reported in which nerve growth factor (NGF) was synthesized in the form of a fusion protein with transferrin, and this fusion protein was allowed to pass through the blood-brain barrier via its binding to the transferrin receptor (TfR) (Patent Literature 8). Further, a technique has been reported in which nerve growth factor (NGF) was synthesized in the form of a fusion protein with anti-transferrin receptor antibody (anti-TfR antibody), and this fusion protein is allowed to pass through the blood-brain barrier via its binding to TfR (Patent Literatures 4 and 9).

Looking further into the techniques that utilize an anti-transferrin receptor antibody, there has been reported that in the field of the technique to make a pharmaceutical agent pass through the blood-brain barrier by binding it to an anti-TfR antibody, a single-chain antibody could be used (Non Patent Literature 3). Further, it has been reported that anti-hTfR antibodies exhibiting relatively high dissociation constants with hTfR (low-affinity anti-hTfR antibody) could be favorably used in the technique to make pharmaceutical agents pass through the blood-brain barrier (Patent Literatures 10 and 11, and Non Patent Literature 4). Still further, it has also been reported that an anti-TfR antibodies whose affinity to hTfR varies depending on pH could be employed as a carrier for making pharmaceutical agents pass through the blood-brain barrier (Patent Literature 12, and Non Patent Literature 5).

CITATION LIST

Patent Literature

Patent Literature 1: JP2007-504166 A1
Patent Literature 2: JP2009-525963 A1
Patent Literature 3: JP2012-62312 A1
Patent Literature 4: U.S. Pat. No. 5,154,924 B1
Patent Literature 5: JP2011-144178 A1
Patent Literature 6: US2004/0101904 A1
Patent Literature 7: JP2006-511516 A1
Patent Literature 8: JPH06-228199 A1
Patent Literature 9: U.S. Pat. No. 5,977,307 B1
Patent Literature 10: WO 2012/075037
Patent Literature 11: WO 2013/177062
Patent Literature 12: WO 2012/143379

Non Patent Literature

Non Patent Literature 1: Xie Y. et al., J Control Release. 105. 106-19 (2005)
Non Patent Literature 2: Ou L. et al., Mol Genet Metab. 111. 116-22 (2014)
Non Patent Literature 3: Li JY Protein Engineering. 12. 787-96 (1999)
Non Patent Literature 4: Bien-Ly N. et al., J Exp Med. 211. 233-44 (2014)
Non Patent Literature 5: Sada H. PLoS ONE. 9. E96340 (2014)

SUMMARY OF INVENTION

Problems to be Solved by the Invention

Against the above background, it is an objective of the present invention to provide an anti-TfR antibody that can be utilized for conjugation with a compound that needs to exhibit its function in the central nervous system when administered parenterally (a protein or a low-molecular-weight compound and the like) in order to make that compound able to pass through the blood-brain barrier, and also a method for production thereof, as well as a method of use thereof.

Means for Solving the Problems

As a result of intense studies aimed at the above objective, the present inventors have found that anti-human transferrin receptor antibodies (anti-hTfR antibodies) that recognize the extracellular region of hTfR which are obtained by the method for antibody production described in detail in the specification, efficiently passes through the blood-brain barrier when administered to the body, and have completed the present invention thereupon. Thus the present invention provides what follows:

1. An anti-human transferrin receptor antibody, wherein the amino acid sequence of the light chain variable region of the antibody is selected from the group consisting of (1) to (14) below:

(1) an amino acid sequence comprising the amino acid sequence set forth as SEQ ID NO:6 or SEQ ID NO:7 in CDR1, the amino acid sequence set forth as SEQ ID NO:8 or SEQ ID NO:9 or the amino acid sequence Trp-Thr-Ser in CDR2, and the amino acid sequence set forth as SEQ ID NO:10 in CDR3;

(2) an amino acid sequence comprising the amino acid sequence set forth as SEQ ID NO:11 or SEQ ID NO:12 in CDR1, the amino acid sequence set forth as SEQ ID NO:13 or SEQ ID NO:14 or the amino acid sequence Tyr-Ala-Ser in CDR2, and the amino acid sequence set forth as SEQ ID NO:15 in CDR3;

(3) an amino acid sequence comprising the amino acid sequence set forth as SEQ ID NO:16 or SEQ ID NO:17 in CDR1, the amino acid sequence set forth as SEQ ID NO:18 or SEQ ID NO:19 or the amino acid sequence Lys-Val-Ser in CDR2, and the amino acid sequence set forth as SEQ ID NO:20 in CDR3;

(4) an amino acid sequence comprising the amino acid sequence set forth as SEQ ID NO:21 or SEQ ID NO:22 in CDR1, the amino acid sequence set forth as SEQ ID NO:23 or SEQ ID NO:24 or the amino acid sequence Asp-Thr-Ser in CDR2, and the amino acid sequence set forth as SEQ ID NO:25 in CDR3;

(5) an amino acid sequence comprising the amino acid sequence set forth as SEQ ID NO:26 or SEQ ID NO:27 in CDR1, the amino acid sequence set forth as SEQ ID NO:28 or SEQ ID NO:29 or the amino acid sequence Asp-Thr-Ser in CDR2, and the amino acid sequence set forth as SEQ ID NO:30 in CDR3;

(6) an amino acid sequence comprising the amino acid sequence set forth as SEQ ID NO:31 or SEQ ID NO:32 in CDR1, the amino acid sequence set forth as SEQ ID NO:33 or SEQ ID NO:34 or the amino acid sequence Ala-Ala-Ser in CDR2, and the amino acid sequence set forth as SEQ ID NO:35 in CDR3;

(7) an amino acid sequence comprising the amino acid sequence set forth as SEQ ID NO:36 or SEQ ID NO:37 in CDR1, the amino acid sequence set forth as SEQ ID NO:38 or SEQ ID NO:39 or the amino acid sequence Gln-Thr-Ser in CDR2, and the amino acid sequence set forth as SEQ ID NO:40 in CDR3;

(8) an amino acid sequence comprising the amino acid sequence set forth as SEQ ID NO:41 or SEQ ID NO:42 in CDR1, the amino acid sequence set forth as SEQ ID NO:43 or SEQ ID NO:44 or the amino acid sequence Gly-Thr-Ser in CDR2, and the amino acid sequence set forth as SEQ ID NO:45 in CDR3;

(9) an amino acid sequence comprising the amino acid sequence set forth as SEQ ID NO:46 or SEQ ID NO:47 in CDR1, the amino acid sequence set forth as SEQ ID NO:48 or SEQ ID NO:49 or the amino acid sequence Phe-Thr-Ser in CDR2, and the amino acid sequence set forth as SEQ ID NO:50 in CDR3;

(10) an amino acid sequence comprising the amino acid sequence set forth as SEQ ID NO:51 or SEQ ID NO:52 in CDR1, the amino acid sequence set forth as SEQ ID NO:53 or SEQ ID NO:54 or the amino acid sequence Ala-Ala-Ser in CDR2, and the amino acid sequence set forth as SEQ ID NO:55 in CDR3;

(11) an amino acid sequence comprising the amino acid sequence set forth as SEQ ID NO:56 or SEQ ID NO:57 in CDR1, the amino acid sequence set forth as SEQ ID NO:58 or SEQ ID NO:59 or the amino acid sequence Tyr-Ala-Ser in CDR2, and the amino acid sequence set forth as SEQ ID NO:60 in CDR3;

(12) an amino acid sequence comprising the amino acid sequence set forth as SEQ ID NO:61 or SEQ ID NO:62 in CDR1, the amino acid sequence set forth as SEQ ID NO:63 or SEQ ID NO:64 or the amino acid sequence Trp-Ser-Ser in CDR2, and the amino acid sequence set forth as SEQ ID NO:65 in CDR3;

(13) an amino acid sequence comprising the amino acid sequence set forth as SEQ ID NO:66 or SEQ ID NO:67 in CDR1, the amino acid sequence set forth as SEQ ID NO:68 or SEQ ID NO:69 or the amino acid sequence Tyr-Ala-Ser in CDR2, and the amino acid sequence set forth as SEQ ID NO:70 in CDR3; and

(14) an amino acid sequence comprising the amino acid sequence set forth as SEQ ID NO:71 or SEQ ID NO:72 in CDR1, the amino acid sequence set forth as SEQ ID NO:73 or SEQ ID NO:74 or the amino acid sequence Asp-Thr-Ser in CDR2, and the amino acid sequence set forth as SEQ ID NO:75 in CDR3.

2. The anti-human transferrin receptor antibody according to 1 above, wherein the amino acid sequence of the light chain variable region of the antibody is selected from the group consisting of (1) to (14) below:

(1) an amino acid sequence comprising the amino acid sequence set forth as SEQ ID NO:6 in CDR1, the amino acid sequence set forth as SEQ ID NO:8 in CDR2, and the amino acid sequence set forth as SEQ ID NO:10 in CDR3;

(2) an amino acid sequence comprising the amino acid sequence set forth as SEQ ID NO:11 in CDR1, the amino acid sequence set forth as SEQ ID NO:13 in CDR2, and the amino acid sequence set forth as SEQ ID NO:15 in CDR3;

(3) an amino acid sequence comprising the amino acid sequence set forth as SEQ ID NO:16 in CDR1, the amino acid sequence set forth as SEQ ID NO:18 in CDR2, and the amino acid sequence set forth as SEQ ID NO:20 in CDR3;

(4) an amino acid sequence comprising the amino acid sequence set forth as SEQ ID NO:21 in CDR1, the amino acid sequence set forth as SEQ ID NO:23 in CDR2, and the amino acid sequence set forth as SEQ ID NO:25 in CDR3;

(5) an amino acid sequence comprising the amino acid sequence set forth as SEQ ID NO:26 in CDR1, the amino acid sequence set forth as SEQ ID NO:28 in CDR2, and the amino acid sequence set forth as SEQ ID NO:30 in CDR3;

(6) an amino acid sequence comprising the amino acid sequence set forth as SEQ ID NO:31 in CDR1, the amino acid sequence set forth as SEQ ID NO:33 in CDR2, and the amino acid sequence set forth as SEQ ID NO:35 in CDR3;

(7) an amino acid sequence comprising the amino acid sequence set forth as SEQ ID NO:36 in CDR1, the amino acid sequence set forth as SEQ ID NO:38 in CDR2, and the amino acid sequence set forth as SEQ ID NO:40 in CDR3;

(8) an amino acid sequence comprising the amino acid sequence set forth as SEQ ID NO:41 in CDR1, the amino acid sequence set forth as SEQ ID NO:43 in CDR2, and the amino acid sequence set forth as SEQ ID NO:45 in CDR3;

(9) an amino acid sequence comprising the amino acid sequence set forth as SEQ ID NO:46 in CDR1, the amino acid sequence set forth as SEQ ID NO:48 in CDR2, and the amino acid sequence set forth as SEQ ID NO:50 in CDR3;

(10) an amino acid sequence comprising the amino acid sequence set forth as SEQ ID NO:51 in CDR1, the amino acid sequence set forth as SEQ ID NO:53 in CDR2, and the amino acid sequence set forth as SEQ ID NO:55 in CDR3;

(11) an amino acid sequence comprising the amino acid sequence set forth as SEQ ID NO:56 in CDR1, the amino acid sequence set forth as SEQ ID NO:58 in CDR2, and the amino acid sequence set forth as SEQ ID NO:60 in CDR3;

(12) an amino acid sequence comprising the amino acid sequence set forth as SEQ ID NO:61 in CDR1, the amino acid sequence set forth as SEQ ID NO:63 in CDR2, and the amino acid sequence set forth as SEQ ID NO:65 in CDR3;

(13) an amino acid sequence comprising the amino acid sequence set forth as SEQ ID NO:66 in CDR1, the amino acid sequence set forth as SEQ ID NO:68 in CDR2, and the amino acid sequence set forth as SEQ ID NO:70 in CDR3; and

(14) an amino acid sequence comprising the amino acid sequence set forth as SEQ ID NO:71 in CDR1, the amino acid sequence set forth as SEQ ID NO:73 in CDR2, and the amino acid sequence set forth as SEQ ID NO:75 in CDR3.

3. An anti-human transferrin receptor antibody, wherein the amino acid sequences of CDR1, CDR2 and CDR3 in the light chain variable region thereof have a homology not lower than 80% to the amino acid sequences of CDR1, CDR2 and CDR3, respectively, in the light chain according to 1 or 2 above.

4. An anti-human transferrin receptor antibody, wherein the amino acid sequences of CDR1, CDR2 and CDR3 in the light chain variable region thereof have a homology not lower than 90% to the amino acid sequences of CDR1, CDR2 and CDR3, respectively, in the light chain according to 1 or 2 above.

5. An anti-human transferrin receptor antibody, wherein 1 to 5 amino acids are substituted, deleted or added relative to the amino acid sequence that forms at least one of the CDRs in the light chain according to 1 or 2 above.

6. An anti-human transferrin receptor antibody, wherein 1 to 3 amino acids are substituted, deleted or added relative to the amino acid sequence that forms at least one of the CDRs in the light chain according to 1 or 2 above.

7. An anti-human transferrin receptor antibody, wherein the amino acid sequence of the heavy chain variable region of the antibody is selected from the group consisting of (1) to (14) below:

(1) an amino acid sequence comprising the amino acid sequence set forth as SEQ ID NO:76 or SEQ ID NO:77 in CDR1, the amino acid sequence set forth as SEQ ID NO:78 or SEQ ID NO:79 in CDR2, and the amino acid sequence set forth as SEQ ID NO:80 or SEQ ID NO:81 in CDR3;

(2) an amino acid sequence comprising the amino acid sequence set forth as SEQ ID NO:82 or SEQ ID NO:83 in CDR1, the amino acid sequence set forth as SEQ ID NO:84 or SEQ ID NO:85 in CDR2, and the amino acid sequence set forth as SEQ ID NO:86 or SEQ ID NO:87 in CDR3;

(3) an amino acid sequence comprising the amino acid sequence set forth as SEQ ID NO:88 or SEQ ID NO:89 in CDR1, the amino acid sequence set forth as SEQ ID NO:90 or SEQ ID NO:91 in CDR2, and the amino acid sequence set forth as SEQ ID NO:92 or SEQ ID NO:93 in CDR3;

(4) an amino acid sequence comprising the amino acid sequence set forth as SEQ ID NO:94 or SEQ ID NO:95 in CDR1, the amino acid sequence set forth as SEQ ID NO:96 or SEQ ID NO:97 in CDR2, and the amino acid sequence set forth as SEQ ID NO:98 or SEQ ID NO:99 in CDR3;

(5) an amino acid sequence comprising the amino acid sequence set forth as SEQ ID NO:100 or SEQ ID NO:101 in CDR1, the amino acid sequence set forth as SEQ ID NO:102 or SEQ ID NO:103 in CDR2, and the amino acid sequence set forth as SEQ ID NO:104 or SEQ ID NO:105 in CDR3;

(6) an amino acid sequence comprising the amino acid sequence set forth as SEQ ID NO:106 or SEQ ID NO:107 in CDR1, the amino acid sequence set forth as SEQ ID NO:108 or SEQ ID NO:278 in CDR2, and the amino acid sequence set forth as SEQ ID NO:109 or SEQ ID NO:110 in CDR3;

(7) an amino acid sequence comprising the amino acid sequence set forth as SEQ ID NO:111 or SEQ ID NO:112 in CDR1, the amino acid sequence set forth as SEQ ID NO:113 or SEQ ID NO:114 in CDR2, and the amino acid sequence set forth as SEQ ID NO:115 or SEQ ID NO:116 in CDR3;

(8) an amino acid sequence comprising the amino acid sequence set forth as SEQ ID NO:117 or SEQ ID NO:118 in CDR1, the amino acid sequence set forth as SEQ ID NO:119 or SEQ ID NO:279 in CDR2, and the amino acid sequence set forth as SEQ ID NO:120 or SEQ ID NO:121 in CDR3;

(9) an amino acid sequence comprising the amino acid sequence set forth as SEQ ID NO:122 or SEQ ID NO:123 in CDR1, the amino acid sequence set forth as SEQ ID NO:124 or SEQ ID NO:125 in CDR2, and the amino acid sequence set forth as SEQ ID NO:126 or SEQ ID NO:127 in CDR3;

(10) an amino acid sequence comprising the amino acid sequence set forth as SEQ ID NO:128 or SEQ ID NO:129 or CDR1, the amino acid sequence set forth as SEQ ID NO:130 or SEQ ID NO:131 in CDR2, and the amino acid sequence set forth as SEQ ID NO:132 or SEQ ID NO:133 in CDR3;

(11) an amino acid sequence comprising the amino acid sequence set forth as SEQ ID NO:134 or SEQ ID NO:135 in CDR1, the amino acid sequence set forth as SEQ ID NO:136 or SEQ ID NO:137 in CDR2, and the amino acid sequence set forth as SEQ ID NO:138 or SEQ ID NO:139 in CDR3;

(12) an amino acid sequence comprising the amino acid sequence set forth as SEQ ID NO:140 or SEQ ID NO:141 in CDR1, the amino acid sequence set forth as SEQ ID NO:142 or SEQ ID NO:143 in CDR2, and the amino acid sequence set forth as SEQ ID NO:144 or SEQ ID NO:145 in CDR3;

(13) an amino acid sequence comprising the amino acid sequence set forth as SEQ ID NO:146 or SEQ ID NO:147 in CDR1, the amino acid sequence set forth as SEQ ID NO:148 or SEQ ID NO:149 in CDR2, and the amino acid sequence set forth as SEQ ID NO:150 or SEQ ID NO:151 in CDR3; and

(14) an amino acid sequence comprising the amino acid sequence set forth as SEQ ID NO:152 or SEQ ID NO:153 in CDR1, the amino acid sequence set forth as SEQ ID NO:154 or SEQ ID NO:155 in CDR2, and the amino acid sequence set forth as SEQ ID NO:156 or SEQ ID NO:157 in CDR3.

8. The anti-human transferrin receptor antibody according to 7 above, wherein the amino acid sequence of the heavy chain variable region of the antibody is selected from the group consisting of (1) to (14) below:

(1) an amino acid sequence comprising the amino acid sequence set forth as SEQ ID NO:76 in CDR1, the amino acid sequence set forth as SEQ ID NO:78 in CDR2, and the amino acid sequence set forth as SEQ ID NO:80 in CDR3;

(2) an amino acid sequence comprising the amino acid sequence set forth as SEQ ID NO:82 in CDR1, the amino acid sequence set forth as SEQ ID NO:84 in CDR2, and the amino acid sequence set forth as SEQ ID NO:86 in CDR3;

(3) an amino acid sequence comprising the amino acid sequence set forth as SEQ ID NO:88 in CDR1, the amino acid sequence set forth as SEQ ID NO:90 in CDR2, and the amino acid sequence set forth as SEQ ID NO:92 in CDR3;

(4) an amino acid sequence comprising the amino acid sequence set forth as SEQ ID NO:94 in CDR1, the amino acid sequence set forth as SEQ ID NO:96 in CDR2, and the amino acid sequence set forth as SEQ ID NO:98 in CDR3;

(5) an amino acid sequence comprising the amino acid sequence set forth as SEQ ID NO:100 in CDR1, the amino acid sequence set forth as SEQ ID NO:102 in CDR2, and the amino acid sequence set forth as SEQ ID NO:104 in CDR3;

(6) an amino acid sequence comprising the amino acid sequence set forth as SEQ ID NO:106 in CDR1, the amino acid sequence set forth as SEQ ID NO:108 in CDR2, and the amino acid sequence set forth as SEQ ID NO:109 in CDR3;

(7) an amino acid sequence comprising the amino acid sequence set forth as SEQ ID NO:111 in CDR1, the amino acid sequence set forth as SEQ ID NO:113 in CDR2, and the amino acid sequence set forth as SEQ ID NO:115 as CDR3;

(8) an amino acid sequence comprising the amino acid sequence set forth as SEQ ID NO:117 in CDR1, the amino acid sequence set forth as SEQ ID NO:119 in CDR2, and the amino acid sequence set forth as SEQ ID NO:120 in CDR3;

(9) an amino acid sequence comprising the amino acid sequence set forth as SEQ ID NO:122 in CDR1, the amino acid sequence set forth as SEQ ID NO:124 in CDR2, and the amino acid sequence set forth as SEQ ID NO:126 in CDR3;

(10) an amino acid sequence comprising the amino acid sequence set forth as SEQ ID NO:128 in CDR1, the amino acid sequence set forth as SEQ ID NO:130 in CDR2, and the amino acid sequence set forth as SEQ ID NO:132 in CDR3;

(11) an amino acid sequence comprising the amino acid sequence set forth as SEQ ID NO:134 in CDR1, the amino acid sequence set forth as SEQ ID NO:136 in CDR2, and the amino acid sequence set forth as SEQ ID NO:138 in CDR3;

(12) an amino acid sequence comprising the amino acid sequence set forth as SEQ ID NO:140 in CDR1, the amino acid sequence set forth as SEQ ID NO:142 in CDR2, and the amino acid sequence set forth as SEQ ID NO:144 in CDR3;

(13) an amino acid sequence comprising the amino acid sequence set forth as SEQ ID NO:146 in CDR1, the amino acid sequence set forth as SEQ ID NO:148 in CDR2, and the amino acid sequence set forth as SEQ ID NO:150 in CDR3; and

(14) an amino acid sequence comprising the amino acid sequence set forth as SEQ ID NO:152 in CDR1, the amino acid sequence set forth as SEQ ID NO:154 in CDR2, and the amino acid sequence set forth as SEQ ID NO:156 in CDR3.

9. An anti-human transferrin receptor antibody, wherein the amino acid sequence of CDR1, CDR2 and CDR3 in the heavy chain variable region thereof have a homology not lower than 80% to the amino acid sequences of CDR1, CDR2 and CDR3, respectively, in the heavy chain according to 7 or 8 above.

10. An anti-human transferrin receptor antibody, wherein the amino acid sequence of CDR1, CDR2 and CDR3 in the heavy chain variable region thereof have a homology not lower than 90% to the amino acid sequences of CDR1, CDR2 and CDR3, respectively, in the heavy chain according to 7 or 8 above.

11. An anti-human transferrin receptor antibody, wherein 1 to 5 amino acids are substituted, deleted or added relative to the amino acid sequence that forms at least one of the CDRs in the heavy chain according to 7 or 8 above.

12. An anti-human transferrin receptor antibody, wherein 1 to 3 amino acids are substituted, deleted or added relative to the amino acid sequence that forms at least one of the CDRs in the heavy chain according to 7 or 8 above.

13. An anti-human transferrin receptor antibody, wherein the light chain variable region and the heavy chain variable region thereof are selected from the group consisting of (1) to (14) below:

(1) the light chain variable region comprising the amino acid sequence set forth as SEQ ID NO:6 or SEQ ID NO:7 as CDR1, the amino acid sequence set forth as SEQ ID NO:8 or SEQ ID NO:9 or the amino acid sequence Trp-Thr-Ser as CDR2, and the amino acid sequence set forth as SEQ ID NO:10 as CDR3; and the heavy chain variable region comprising the amino acid sequence set forth as SEQ ID NO:76 or SEQ ID NO:77 as CDR1, the amino acid sequence set forth as SEQ ID NO:78 or SEQ ID NO:79 as CDR2, and the amino acid sequence set forth as SEQ ID NO:80 or SEQ ID NO:81 as CDR3;

(2) the light chain variable region comprising the amino acid sequence set forth as SEQ ID NO:11 or SEQ ID NO:12 as CDR1, the amino acid sequence set forth as SEQ ID NO:13 or SEQ ID NO:14 or the amino acid sequence Tyr-Ala-Ser as CDR2, and the amino acid sequence set forth as SEQ ID NO:15 as CDR3; and the heavy chain variable region comprising the amino acid sequence set forth as SEQ ID NO:82 or SEQ ID NO:83 as CDR1, the amino acid sequence set forth as SEQ ID NO:84 or SEQ ID NO:85 as CDR2, and the amino acid sequence set forth as SEQ ID NO:86 or SEQ ID NO:87 as CDR3;

(3) the light chain variable region comprising the amino acid sequence set forth as SEQ ID NO:16 or SEQ ID NO:17 as CDR1, the amino acid sequence set forth as SEQ ID NO:18 or SEQ ID NO:19 or the amino acid sequence Lys-Val-Ser as CDR2, and the amino acid sequence set forth as SEQ ID NO:20 as CDR3; and the heavy chain variable region comprising the amino acid sequence set forth as SEQ ID NO:88 or SEQ ID NO:89 as CDR1, the amino acid sequence set forth as SEQ ID NO:90 or SEQ ID NO:91 as CDR2, and the amino acid sequence set forth as SEQ ID NO:92 or SEQ ID NO:93 as CDR3;

(4) the light chain variable region comprising the amino acid sequence set forth as SEQ ID NO:21 or SEQ ID NO:22 as CDR1, the amino acid sequence set forth as SEQ ID NO:23 or SEQ ID NO:24 or the amino acid sequence Asp-Thr-Ser as CDR2, and the amino acid sequence set forth as SEQ ID NO:25 as CDR3; and the heavy chain variable region comprising the amino acid sequence set forth as SEQ ID NO:94 or SEQ ID NO:95 as CDR1, the amino acid sequence set forth as SEQ ID NO:96 or SEQ ID NO:97 as CDR2, and the amino acid sequence set forth as SEQ ID NO:98 or SEQ ID NO:99 as CDR3;

(5) the light chain variable region comprising the amino acid sequence set forth as SEQ ID NO:26 or SEQ ID NO:27 as CDR1, the amino acid sequence set forth as SEQ ID NO:28 or SEQ ID NO:29 or the amino acid sequence Asp-Thr-Ser as CDR2, and the amino acid sequence set forth as SEQ ID NO:30 as CDR3; and the heavy chain variable region comprising the amino acid sequence set forth as SEQ ID NO:100 or SEQ ID NO:101 as CDR1, the amino acid sequence set forth as SEQ ID NO:102 or SEQ ID NO:103 as CDR2, and the amino acid sequence set forth as SEQ ID NO:104 or SEQ ID NO:105 as CDR3;

(6) the light chain variable region comprising the amino acid sequence set forth as SEQ ID NO:31 or SEQ ID NO:32 as CDR1, the amino acid sequence set forth as SEQ ID NO:33 or SEQ ID NO:34 or the amino acid sequence Ala-Ala-Ser as CDR2, and the amino acid sequence set forth as SEQ ID NO:35 as CDR3; and the heavy chain variable region comprising the amino acid sequence set forth as SEQ ID NO:106 or SEQ ID NO:107 as CDR1, the amino acid sequence set forth as SEQ ID NO:108 or SEQ ID NO:278, as CDR2, and the amino acid sequence set forth as SEQ ID NO:109 or SEQ ID NO:110 as CDR3;

(7) the light chain variable region comprising the amino acid sequence set forth as SEQ ID NO:36 or SEQ ID NO:37 as CDR1, the amino acid sequence set forth as SEQ ID NO:38 or SEQ ID NO:39 or the amino acid sequence Gln-Thr-Ser as CDR2, and the amino acid sequence set forth as SEQ ID NO:40 as CDR3; and the heavy chain variable region comprising the amino acid sequence set forth as SEQ ID NO:111 or SEQ ID NO:112 as CDR1, the amino acid sequence set forth as SEQ ID NO:113 or SEQ ID NO:114 as CDR2, and the amino acid sequence set forth as SEQ ID NO:115 or SEQ ID NO:116 as CDR3;

(8) the light chain variable region comprising the amino acid sequence set forth as SEQ ID NO:41 or SEQ ID NO:42 as CDR1, the amino acid sequence set forth as SEQ ID NO:43 or SEQ ID NO:44 or the amino acid sequence Gly-Thr-Ser as CDR2, and the amino acid sequence set forth as SEQ ID NO:45 as CDR3; and the heavy chain variable region comprising the amino acid sequence set forth as SEQ ID NO:117 or SEQ ID NO:118 as CDR1, the amino acid sequence set forth as SEQ ID NO:119 or SEQ ID NO:279 as CDR2, and the amino acid sequence set forth as SEQ ID NO:120 or SEQ ID NO:121 as CDR3;

(9) the light chain variable region comprising the amino acid sequence set forth as SEQ ID NO:46 or SEQ ID NO:47 as CDR1, the amino acid sequence set forth as SEQ ID NO:48 or SEQ ID NO:49 or the amino acid sequence Phe-Thr-Ser as CDR2, and the amino acid sequence set forth as SEQ ID NO:50 as CDR3; and the heavy chain variable region comprising the amino acid sequence set forth as SEQ ID NO:122 or SEQ ID NO:123 as CDR1, the amino acid sequence set forth as SEQ ID NO:124 or SEQ ID NO:125 as CDR2, and the amino acid sequence set forth as SEQ ID NO:126 or SEQ ID NO:127 as CDR3;

(10) the light chain variable region comprising the amino acid sequence set forth as SEQ ID NO:51 or SEQ ID NO:52 as CDR1, the amino acid sequence set forth as SEQ ID NO:53 or SEQ ID NO:54 or the amino acid sequence Ala-Ala-Ser as CDR2, and the amino acid sequence set forth as SEQ ID NO:55 as CDR3; and the heavy chain variable region comprising the amino acid sequence set forth as SEQ ID NO:128 or SEQ ID NO:129 as CDR1, the amino acid sequence set forth as SEQ ID NO:130 or SEQ ID NO:131 as CDR2, and the amino acid sequence set forth as SEQ ID NO:132 or SEQ ID NO:133 as CDR 3;

(11) the light chain variable region comprising the amino acid sequence set forth as SEQ ID NO:56 or SEQ ID NO:57 as CDR1, the amino acid sequence set forth as SEQ ID NO:58 or SEQ ID NO:59 or the amino acid sequence Tyr-Ala-Ser as CDR2, and the amino acid sequence set forth as SEQ ID NO:60 as CDR3; and the heavy chain variable region comprising the amino acid sequence set forth as SEQ ID NO:134 or SEQ ID NO:135 as CDR1, the amino acid sequence set forth as SEQ ID NO:136 or SEQ ID NO:137 as CDR2, and the amino acid sequence set forth as SEQ ID NO:138 or SEQ ID NO:139 as CDR3;

(12) the light chain variable region comprising the amino acid sequence set forth as SEQ ID NO:61 or SEQ ID NO:62 as CDR1, the amino acid sequence set forth as SEQ ID NO:63 or SEQ ID NO:64 or the amino acid sequence Trp-Ser-Ser as CDR2, and the amino acid sequence set forth as SEQ ID NO:65 as CDR3; and the heavy chain variable region comprising the amino acid sequence set forth as SEQ ID NO:140 or SEQ ID NO:141 as CDR1, the amino acid sequence set forth as SEQ ID NO:142 or SEQ ID NO:143 as CDR2, and the amino acid sequence set forth as SEQ ID NO:144 or SEQ ID NO:145 as CDR3;

(13) the light chain variable region comprising the amino acid sequence set forth as SEQ ID NO:66 or SEQ ID NO:67 as CDR1, the amino acid sequence set forth as SEQ ID NO:68 or SEQ ID NO:69 or the amino acid sequence Tyr-Ala-Ser as CDR2, and the amino acid sequence set forth as SEQ ID NO:70 as CDR3; and the heavy chain variable region comprising the amino acid sequence set forth as SEQ ID NO:146 or SEQ ID NO:147 as CDR1, the amino acid sequence set forth as SEQ ID NO:148 or SEQ ID NO:149 as CDR2, and the amino acid sequence set forth as SEQ ID NO:150 or SEQ ID NO:151 as CDR3; and

(14) the light chain variable region comprising the amino acid sequence set forth as SEQ ID NO:71 or SEQ ID NO:72 as CDR1, the amino acid sequence set forth as SEQ ID NO:73 or SEQ ID NO:74 or the amino acid sequence Asp-Thr-Ser as CDR2, and the amino acid sequence set forth as SEQ ID NO:75 as CDR3; and the heavy chain variable region comprising the amino acid sequence set forth as SEQ ID NO:152 or SEQ ID NO:153 as CDR1, the amino acid sequence set forth as SEQ ID NO:154 or SEQ ID NO:155 as CDR2, and the amino acid sequence set forth as SEQ ID NO:156 or SEQ ID NO:157 as CDR3.

14. The anti-human transferrin receptor antibody according to 13 above, wherein the light chain variable region and the heavy chain variable region thereof are selected from the group consisting of (1) to (14) below:

(1) the light chain variable region comprising the amino acid sequence set forth as SEQ ID NO:6 as CDR1, the amino acid sequence set forth as SEQ ID NO:8 as CDR2, and the amino acid sequence set forth as SEQ ID NO:10 as CDR3; and the heavy chain variable region comprising the amino acid sequence set forth as SEQ ID NO:76 as CDR1, the amino acid sequence set forth as SEQ ID NO:78 as CDR2, and the amino acid sequence set forth as SEQ ID NO:80 as CDR3;

(2) the light chain variable region comprising the amino acid sequence set forth as SEQ ID NO:11 as CDR1, the amino acid sequence set forth as SEQ ID NO:13 as CDR2, and the amino acid sequence set forth as SEQ ID NO:15 as CDR3; and the heavy chain variable region comprising the amino acid sequence set forth as SEQ ID NO:82 as CDR1, the amino acid sequence set forth as SEQ ID NO:84 as CDR2, and the amino acid sequence set forth as SEQ ID NO:86 as CDR3;

(3) the light chain variable region comprising the amino acid sequence set forth as SEQ ID NO:16 as CDR1, the amino acid sequence set forth SEQ ID NO:18 as CDR2, and the amino acid sequence set forth as SEQ ID NO:20 as CDR3; and the heavy chain variable region comprising the amino acid sequence set forth as SEQ ID NO:88 as CDR1, the amino acid sequence set forth as SEQ ID NO:90 as CDR2, and the amino acid sequence set forth as SEQ ID NO:92 as CDR3;

(4) the light chain variable region comprising the amino acid sequence set forth as SEQ ID NO:21 as CDR1, the amino acid sequence set forth as SEQ ID NO:23 as CDR2, and the amino acid sequence set forth as SEQ ID NO:25 as CDR3; and the heavy chain variable region comprising the amino acid sequence set forth as SEQ ID NO:94 as CDR1, the amino acid sequence set forth as SEQ ID NO:96 as CDR2, and the amino acid sequence set forth as SEQ ID NO:98 as CDR3;

(5) the light chain variable region comprising the amino acid sequence set forth as SEQ ID NO:26 as CDR1, the amino acid sequence set forth as SEQ ID NO:28 as CDR2, and the amino acid sequence set forth as SEQ ID NO:30 as CDR3; and the heavy chain variable region comprising the amino acid sequence set forth as SEQ ID NO:100 as CDR1, the amino acid sequence set forth as SEQ ID NO:102 as CDR2, and the amino acid sequence set forth as SEQ ID NO:104 as CDR3;

(6) the light chain variable region comprising the amino acid sequence set forth as SEQ ID NO:31 as CDR1, the amino acid sequence set forth as SEQ ID NO:33 as CDR2, and the amino acid sequence set forth as SEQ ID NO:35 as CDR3; and the heavy chain variable region comprising the amino acid sequence set forth as SEQ ID NO:106 as CDR1, the amino acid sequence set forth as SEQ ID NO:108 as CDR2, and the amino acid sequence set forth as SEQ ID NO:109 as CDR3;

(7) the light chain variable region comprising the amino acid sequence set forth as SEQ ID NO:36 as CDR1, the amino acid sequence set forth as SEQ ID NO:38 as CDR2, and the amino acid sequence set forth as SEQ ID NO:40 as CDR3; and the heavy chain variable region comprising the amino acid sequence set forth as SEQ ID NO:111 as CDR1, the amino acid sequence set forth as SEQ ID NO:113 as CDR2, and the amino acid sequence set forth as SEQ ID NO:115 as CDR3;

(8) the light chain variable region comprising the amino acid sequence set forth as SEQ ID NO:41 as CDR1, the amino acid sequence set forth as SEQ ID NO:43 as CDR2, and the amino acid sequence set forth as SEQ ID NO:45 as CDR3; and the heavy chain variable region comprising the amino acid sequence set forth as SEQ ID NO:117 as CDR1, the amino acid sequence set forth as SEQ ID NO:119 as CDR2, and the amino acid sequence set forth as SEQ ID NO:120 as CDR 3;

(9) the light chain variable region comprising the amino acid sequence set forth as SEQ ID NO:46 as CDR1, the amino acid sequence set forth as SEQ ID NO:48 as CDR2, and the amino acid sequence set forth as SEQ ID NO:50 as CDR3; and the heavy chain variable region comprising the amino acid sequence set forth as SEQ ID NO:122 as CDR1, the amino acid sequence set forth as SEQ ID NO:124 as CDR2, and the amino acid sequence set forth as SEQ ID NO:126 as CDR3;

(10) the light chain variable region comprising the amino acid sequence set forth as SEQ ID NO:51 as CDR1, the amino acid sequence set forth as SEQ ID NO:53 as CDR2, and the amino acid sequence set forth as SEQ ID NO:55 as CDR3; and the heavy chain variable region comprising the amino acid sequence set forth as SEQ ID NO:128 as CDR1, the amino acid sequence set forth as SEQ ID NO:130 as CDR2, and the amino acid sequence set forth as SEQ ID NO:132 as CDR3;

(11) the light chain variable region comprising the amino acid sequence set forth as SEQ ID NO:56 as CDR1, the amino acid sequence set forth as SEQ ID NO:58 as CDR2, and the amino acid sequence set forth as SEQ ID NO:60 as CDR3; and the heavy chain variable region comprising the amino acid sequence set forth as SEQ ID NO:134 as CDR1, the amino acid sequence set forth as SEQ ID NO:136 as CDR2, and the amino acid sequence set forth as SEQ ID NO:138 as CDR3;

(12) the light chain variable region comprising the amino acid sequence set forth as SEQ ID NO:61 as CDR1, the amino acid sequence set forth as SEQ ID NO:63 as CDR2, and the amino acid sequence set forth as SEQ ID NO:65 as CDR3; and the heavy chain variable region comprising the amino acid sequence set forth as SEQ ID NO:140 as CDR1, the amino acid sequence set forth as SEQ ID NO:142 as CDR2, and the amino acid sequence set forth as SEQ ID NO:144 as CDR3;

(13) the light chain variable region comprising the amino acid sequence set forth as SEQ ID NO:66 as CDR1, the amino acid sequence set forth as SEQ ID NO:68 as CDR2, and the amino acid sequence set forth as SEQ ID NO:70 as CDR3; and the heavy chain variable region comprising the amino acid sequence set forth as SEQ ID NO:146 as CDR1, the amino acid sequence set forth as SEQ ID NO:148 as CDR2, and the amino acid sequence set forth as SEQ ID NO:150 as CDR3; and

(14) the light chain variable region comprising the amino acid sequence set forth as SEQ ID NO:71 as CDR1, the amino acid sequence set forth as SEQ ID NO:73 as CDR2, and the amino acid sequence set forth as SEQ ID NO:75 as CDR3; and the heavy chain variable region comprising the amino acid sequence set forth as SEQ ID NO:152 as CDR1, the amino acid sequence set forth as SEQ ID NO:154 as CDR2, and the amino acid sequence set forth as SEQ ID NO:156 as CDR3.

15. An anti-human transferrin receptor antibody, wherein the amino acid sequence of each of CDR1, CDR2 and CDR3 in the light chain and the heavy chain thereof has a homology not lower than 80% to the amino acid sequence of the CDR1, CDR2 and CDR3, of one of the combinations of the light chain and the heavy chain according to 13 or 14 above.

16. An anti-human transferrin receptor antibody, wherein the amino acid sequence of each of CDR1, CDR2 and CDR3 in the light chain and the heavy chain thereof has a homology not lower than 90% to the amino acid sequence of the CDR1, CDR2 and CDR3, of one of the combinations of the light chain and the heavy chain according to 13 or 14 above.

17. An anti-human transferrin receptor antibody, wherein 1 to 5 amino acids are substituted, deleted or added relative to the amino acid sequence that forms at least one CDR in each of the light chain and the heavy chain of one of the combinations of the light chain and the heavy chain according to 13 or 14 above.

18. An anti-human transferrin receptor antibody, wherein 1 to 3 amino acids are substituted, deleted or added relative to the amino acid sequence that forms at least one CDR in each of the light chain and the heavy chain of one of the combinations of the light chain and the heavy chain according to 13 or 14 above.

19. An anti-human transferrin receptor antibody, wherein the light chain variable region of the antibody comprises an amino acid sequence selected from the group consisting of the amino acid sequences set forth as SEQ ID NO:158, SEQ ID NO:159, SEQ ID NO:160, SEQ ID NO:161, SEQ ID NO:162, and SEQ ID NO:163; and wherein the heavy chain variable region of the antibody comprises an amino acid sequence selected from the group consisting of the amino acid sequences set forth as SEQ ID NO:166, SEQ ID NO:167, SEQ ID NO:168, SEQ ID NO:169, SEQ ID NO:170, and SEQ ID NO:171.

20. An anti-human transferrin receptor antibody, wherein the light chain variable region of the antibody comprises an amino acid sequence selected from the group consisting of the amino acid sequences set forth as SEQ ID NO:174, SEQ ID NO:175, SEQ ID NO:176, SEQ ID NO:177, SEQ ID NO:178, and SEQ ID NO:179; and wherein the heavy chain variable region of the antibody comprises an amino acid sequence selected from the group consisting of the amino acid sequences set forth as SEQ ID NO:182, SEQ ID NO:183, SEQ ID NO:184, SEQ ID NO:185, SEQ ID NO:186, and SEQ ID NO:187.

21. An anti-human transferrin receptor antibody, wherein the light chain variable region of the antibody comprises an amino acid sequence selected from the group consisting of the amino acid sequences set forth as SEQ ID NO:190, SEQ ID NO:191, SEQ ID NO:192, SEQ ID NO:193, SEQ ID NO:194, and SEQ ID NO:195, and wherein the heavy chain variable region of the antibody comprises an amino acid sequence selected from the group consisting of the amino acid sequences set forth as SEQ ID NO:204, SEQ ID NO:205, SEQ ID NO:206, SEQ ID NO:207, SEQ ID NO:208, and SEQ ID NO:209.

22. An anti-human transferrin receptor antibody selected from the group consisting of (1) to (6) below:

(1) an antibody, wherein the light chain variable region thereof comprises the amino acid sequence set forth as SEQ ID NO:163; and wherein the heavy chain variable region thereof comprises the amino acid sequence set forth as SEQ ID NO:171, (2) an antibody, wherein the light chain variable region thereof comprises the amino acid sequence set forth as SEQ ID NO:179; and wherein the heavy chain variable region thereof comprises the amino acid sequence set forth as SEQ ID NO:187, (3) an antibody, wherein the light chain variable region thereof comprises the amino acid sequence set forth as SEQ ID NO:191; and wherein the heavy chain variable region thereof comprises the amino acid sequence set forth as SEQ ID NO:205, (4) an antibody, wherein the light chain variable region thereof comprises the amino acid sequence set forth as SEQ ID NO:193; and wherein the heavy chain variable region thereof comprises the amino acid sequence set forth as SEQ ID NO:205, (5) an antibody, wherein the light chain variable region thereof comprises the amino acid sequence set forth as SEQ ID NO:194; and wherein the heavy chain variable region thereof comprises the amino acid sequence set forth as SEQ ID NO:205, and (6) an antibody, wherein the light chain variable region thereof comprises the amino acid sequence set forth as SEQ ID NO:195; and wherein the heavy chain variable region thereof comprises the amino acid sequence set forth as SEQ ID NO:205.

23. An anti-human transferrin receptor antibody selected from the group consisting of (1) to (10) below:

(1) an antibody, wherein the light chain thereof comprises the amino acid sequence set forth as SEQ ID NO:164; and wherein the heavy chain thereof comprises the amino acid sequence set forth as SEQ ID NO:172, (2) an antibody, wherein the light chain thereof comprises the amino acid sequence set forth as SEQ ID NO:180; and wherein the heavy chain thereof comprises the amino acid sequence set forth as SEQ ID NO:188, (3) an antibody, wherein the light chain thereof comprises the amino acid sequence set forth as SEQ ID NO:196; and wherein the heavy chain thereof comprises the amino acid sequence set forth as SEQ ID NO:210, (4) an antibody, wherein the light chain thereof comprises the amino acid sequence set forth as SEQ ID NO:198; and wherein the heavy chain thereof comprises the amino acid sequence set forth as SEQ ID NO:210, (5) an antibody, wherein the light chain thereof comprises the amino acid sequence set forth as SEQ ID NO:200; and wherein the heavy chain thereof comprises the amino acid sequence set forth as SEQ ID NO:210, (6) an antibody, wherein the light chain thereof comprises the amino acid sequence set forth as SEQ ID NO:202; and wherein the heavy chain thereof comprises the amino acid sequence set forth as SEQ ID NO:210, (7) an antibody, wherein the light chain thereof comprises the amino acid sequence set forth as SEQ ID NO:196; and wherein the heavy chain thereof comprises the amino acid sequence set forth as SEQ ID NO:212, (8) an antibody, wherein the light chain thereof comprises the amino acid sequence set forth as SEQ ID NO:198; and wherein the heavy chain thereof comprises the amino acid sequence set forth as SEQ ID NO:212, (9) an antibody, wherein the light chain thereof comprises the amino acid sequence set forth as SEQ ID NO:200; and wherein the heavy chain thereof comprises the amino acid sequence set forth as SEQ ID NO:212, and

(10) an antibody, wherein the light chain thereof comprises the amino acid sequence set forth as SEQ ID NO:202; and wherein the heavy chain thereof comprises the amino acid sequence set forth as SEQ ID NO:212.

24. An anti-human transferrin receptor antibody having a homology not lower than 80% to the anti-human transferrin receptor antibody according to any one of 19 to 23 above for the amino acid sequence of the light chain variable region and the amino acid sequence of the heavy chain variable region.

25. An anti-human transferrin receptor antibody having a homology not lower than 90% to the anti-human transferrin receptor antibody according to any one of 19 to 23 above for the amino acid sequence of the light chain variable region and the amino acid sequence of the heavy chain variable region.

26. An anti-human transferrin receptor antibody, wherein 1 to 10 amino acids are substituted, deleted or added relative to the amino acid sequence that forms the light chain variable region of the anti-human transferrin receptor antibody according to any one of 19 to 23 above.

27. An anti-human transferrin receptor antibody, wherein 1 to 3 amino acids are substituted, deleted or added relative to the amino acid sequence that forms the light chain variable region of the anti-human transferrin receptor antibody according to any one of 19 to 23 above.

28. An anti-human transferrin receptor antibody, wherein 1 to 10 amino acids are substituted, deleted or added relative to the amino acid sequence that forms the heavy chain variable region of the anti-human transferrin receptor antibody according to any one of 19 to 23 above.

29. An anti-human transferrin receptor antibody, wherein 1 to 3 amino acids are substituted, deleted or added relative to the amino acid sequence that forms the heavy chain variable region of the anti-human transferrin receptor antibody according to any one of 19 to 23 above.

30. An anti-human transferrin receptor antibody, wherein 1 to 10 amino acids are substituted, deleted or added relative to the respective amino acid sequences that form the light chain variable region and the heavy chain variable region of the anti-human transferrin receptor antibody according to any one of 19 to 23 above.

31. An anti-human transferrin receptor antibody, wherein 1 to 3 amino acids are substituted, deleted or added relative to the respective amino acid sequences that form the light chain variable region and the heavy chain variable region of the anti-human transferrin receptor antibody according to any one of 19 to 23 above.

32. The anti-human transferrin receptor antibody according to any one of 1 to 31 above, wherein the antibody has an affinity to both the extracellular region of human transferrin receptor and the extracellular region of monkey transferrin receptor.

33. The anti-human transferrin receptor antibody according to 32 above, wherein the dissociation constant of its complex with the extracellular region of human transferrin receptor is not greater than $1\times10^{-8}$ M, and the dissociation constant of its complex with the extracellular region of monkey transferrin receptor is not greater than $5\times10^{-8}$M.

34. The anti-human transferrin receptor antibody according to any one of 1 to 33 above, wherein the antibody is Fab antibody, F(ab')2 antibody, or F(ab') antibody.

35. The anti-human transferrin receptor antibody according to any one of 1 to 33 above, wherein the antibody is a single-chain antibody selected from the group consisting of scFab, scF(ab'), scF(ab')2 and scFv.

36. The anti-human transferrin receptor antibody according to 35 above, wherein the light chain and the heavy chain thereof are linked via a linker sequence.

37. The anti-human transferrin receptor antibody according to 35 above, wherein the heavy chain is linked, via a linker sequence, to the light chain on the C-terminal side thereof.

38. The anti-human transferrin receptor antibody according to 35 above, wherein the light chain is linked, via a linker sequence, to the heavy chain on the C-terminal side thereof.

39. The anti-human transferrin receptor antibody according to any one of 36 to 38 above, wherein the linker sequence consists of 8 to 50 amino acid residues.

40. The anti-human transferrin receptor antibody according to 39 above, wherein the linker sequence is selected from the group consisting of the amino acid sequence Gly-Ser, the amino acid sequence Gly-Gly-Ser, the amino acid sequence Gly-Gly-Gly, the amino acid sequences set forth as SEQ ID NO:3, SEQ ID NO:4, and SEQ ID NO:5, and the amino acid sequence consisting of three consecutively linked amino acid sequences each set forth as SEQ ID NO:3.

41. A fusion protein comprising the anti-human transferrin receptor antibody according to any one of 1 to 40 above and the amino acid sequence of a different protein (A) linked to the light chain of the antibody on the C-terminal side or the N-terminal side thereof.

42. A fusion protein comprising an anti-human transferrin receptor antibody and a different protein (A), wherein the anti-human transferrin receptor antibody is the anti-human transferrin receptor antibody according to any one of 1 to 40 above, and wherein the different protein (A) is linked to the light chain of the anti-human transferrin receptor antibody on the C-terminal side or the N-terminal side thereof.

43. The fusion protein according to 41 or 42 above, wherein the different protein (A) is linked, via a linker sequence, to the light chain on the C-terminal side or the N-terminal side thereof.

44. The fusion protein according to 43 above, wherein the linker sequence consists of 1 to 50 amino acid residues.

45. The fusion protein according to 44 above, wherein the linker sequence comprises an amino acid sequence selected from the group consisting of a single glycine, a single serine, the amino acid sequence Gly-Ser, the amino acid sequence Gly-Gly-Ser, the amino acid sequence set forth as SEQ ID NO:3, the amino acid sequence set forth as SEQ ID NO:4, the amino acid sequence set forth as SEQ ID NO:5, and the amino acid sequences consisting of 1 to 10 thereof that are consecutively linked.

46. A fusion protein comprising the anti-human transferrin receptor antibody according to any one of 1 to 40 above and the amino acid sequence of a different protein (A) linked to the heavy chain of the antibody on the C-terminal side or the N-terminal side thereof.

47. A fusion protein of an anti-human transferrin receptor antibody and a different protein (A), wherein the anti-human transferrin receptor antibody is the anti-human transferrin receptor antibody according to any one of 1 to 40 above, and wherein the different protein (A) is linked to the heavy chain of the anti-human transferrin receptor antibody on the C-terminal side or the N-terminal side thereof.

48. The fusion protein according to 46 or 47 above, wherein the different protein (A) is linked, via a linker sequence, to the heavy chain on the C-terminal side or the N-terminal side thereof.

49. The fusion protein according to 48 above, wherein the linker sequence consists of 1 to 50 amino acid residues.

50. The fusion protein according to 48 above, wherein the linker sequence comprises an amino acid sequence selected from the group consisting of a single glycine, a single serine, the amino acid sequence Gly-Ser, the amino acid sequence Gly-Gly-Ser, the amino acid sequence set forth as SEQ ID NO:3, the amino acid sequence set forth as SEQ ID NO:4, the amino acid sequence set forth as SEQ ID NO:5, and the amino acid sequences consisting of 1 to 10 thereof that are consecutively linked.

51. The fusion protein according to any one of 41 to 50 above, wherein the different protein (A) is a protein originating from human.

52. The fusion protein according to any one of 41 to 51 above, wherein the different protein (A) is selected from the group consisting of nerve growth factor (NGF), lysosomal enzymes, ciliary neurotrophic factor (CNTF), glial cell line-derived neurotrophic factor (GDNF), neurotrophin-3, neurotrophin-4/5, neurotrophin-6, neuregulin-1, erythropoietin, darbepoetin, activin, basic fibroblast growth factor (bFGF), fibroblast growth factor 2 (FGF2), epidermal growth factor (EGF), vascular endothelial growth factor (VEGF), interferon α, interferon β, interferon γ, interleukin 6, granulocyte-macrophage colony stimulating factor (GM-CSF), granulocyte colony stimulating factor (G-CSF), macrophage colony stimulating factor (M-CSF), cytokines, tumor necrosis factor α receptor (TNF-α receptor), PD-1 ligands, enzymes having β-amyloid-degrading activity, anti-β-amyloid antibody, anti-BACE antibody, anti-EGFR antibody, anti-PD-1 antibody, anti-PD-L1 antibody, anti-HER2 antibody, anti-TNF-α antibody, and other antibody medicines. 53. The fusion protein according to any one of 41 to 51 above, wherein the different protein (A) is a lysosomal enzyme, and wherein the lysosomal enzyme is selected from the group consisting of α-L-iduronidase, iduronate 2-sulfatase, glucocerebrosidase, β-galactosidase, GM2 activator protein, β-hexosaminidase A, β-hexosaminidase B, N-acetylglucosamine-1-phosphotransferase, α-mannosidase, β-mannosidase, galactosylceramidase, saposin C, arylsulfatase A, α-L-fucosidase, aspartylglucosaminidase, α-N-acetylgalactosaminidase, acidic sphingomyelinase, α-galactosidase A, β-glucuronidase, heparan N-sulfatase, α-N-acetylglucosaminidase, acetyl CoA:α-glucosaminide N-acetyltransferase, N-Acetylglucosamine-6-sulfate sulfatase, acid ceramidase, amylo-1,6-glucosidase, sialidase, palmitoyl protein thioesterase 1, tripeptidyl-peptidase 1, hyaluronidase 1, CLN1 and CLN2.

54. The fusion protein according to any one of 41 to 51 above, wherein the different protein (A) is iduronate 2-sulfatase.

55. The fusion protein according to 50 above, wherein the different protein (A) is human iduronate 2-sulfatase, and wherein the fusion protein is selected from (1) to (3) below:

(1) the fusion protein, wherein the light chain of the humanized anti-hTfR antibody has the amino acid sequence set forth as SEQ ID NO:164, and wherein the heavy chain of the humanized anti-hTfR antibody is linked, on the C-terminal side thereof and via a linker sequence Gly-Ser, to the human iduronate 2-sulfatase, and the whole linked heavy chain has the amino acid sequence set forth as SEQ ID NO:247.

(2) the fusion protein, wherein the light chain of the humanized anti-hTfR antibody has the amino acid sequence set forth as SEQ ID NO:180, and wherein the heavy chain of the humanized anti-hTfR antibody is linked, on the C-terminal side thereof and via a linker sequence Gly-Ser, to the human iduronate 2-sulfatase, and the whole linked heavy chain has the amino acid sequence set forth as SEQ ID NO:249, and (3) the fusion protein, wherein the light chain of the humanized anti-hTfR antibody has the amino acid sequence set forth as SEQ ID NO:196. and wherein the heavy chain of the humanized anti-hTfR antibody is linked, on the C-terminal side thereof and via a linker sequence Gly-Ser, to the human iduronate 2-sulfatase, and the whole linked heavy chain has the amino acid sequence set forth as SEQ ID NO:251.

56. The fusion protein according to 50 above, wherein the different protein (A) is human iduronate 2-sulfatase, and wherein the fusion protein is selected from (1) to (3) below:

(1) the fusion protein comprising: the humanized anti-hTfR antibody light chain having the amino acid sequence set forth as SEQ ID NO:164; and the humanized anti-hTfR antibody heavy chain having the amino acid sequence set forth as SEQ ID NO:172 which is linked, on the C-terminal side thereof and via a linker sequence Gly-Ser, to the human iduronate 2-sulfatase set forth as SEQ ID NO:246;

(2) the fusion protein comprising: the humanized anti-hTfR antibody light chain having the amino acid sequence set forth as SEQ ID NO:180; and the humanized anti-hTfR antibody heavy chain having the amino acid sequence set forth as SEQ ID NO:188 which is linked, on the C-terminal side thereof and via a linker sequence Gly-Ser, to the human iduronate 2-sulfatase set forth as SEQ ID NO:246;

(3) the fusion protein comprising: the humanized anti-hTfR antibody light chain having the amino acid sequence set forth as SEQ ID NO:196; and the humanized anti-hTfR antibody heavy chain having the amino acid sequence set forth as SEQ ID NO:210 which is linked, on the C-terminal side thereof and via a linker sequence Gly-Ser, to the human iduronate 2-sulfatase set forth as SEQ ID NO:246.

57. The fusion protein according to 50 above, wherein the different protein (A) is human iduronate 2-sulfatase, and wherein the fusion protein is selected from (1) to (3) below:

(1) the fusion protein comprising: the human iduronate 2-sulfatase linked via a linker sequence Gly-Ser to the heavy chain on the C-terminal side thereof; and the light chain, wherein the amino acid sequence of the former is set forth as SEQ ID NO:247, and the amino acid sequence of the latter is set forth as SEQ ID NO:164, (2) the fusion protein comprising: the human iduronate 2-sulfatase linked via a linker sequence Gly-Ser to the heavy chain on the C-terminal side thereof; and the light chain, wherein the amino acid sequence of the former is set forth as SEQ ID NO:249, and the amino acid sequence of the latter is set forth as SEQ ID NO:180, and (3) the fusion protein comprising: the human iduronate 2-sulfatase linked via a linker sequence Gly-Ser to the heavy chain on the C-terminal side thereof; and the light chain, wherein the amino acid sequence of the former is set forth as SEQ ID NO:251, and the amino acid sequence of the latter is set forth as SEQ ID NO:196.

58. A DNA fragment encoding the amino acid sequence of the anti-human transferrin receptor antibody according to any one of 1 to 40 above.

59. A DNA fragment encoding the amino acid sequence of the fusion protein according to any one of 41 to 57 above.

60. An expression vector comprising the DNA fragment according to 58 or 59 above that is incorporated therein.

61. A mammalian cell transformed with the expression vector according to 60 above.

62. An anti-human transferrin receptor antibody-pharmacologically active compound complex, wherein the light chain and/or the heavy chain of the anti-human transferrin receptor antibody according to any one of 1 to 40 above is linked to a low-molecular-weight pharmacologically active compound that needs to be allowed to pass through the blood-brain barrier and exhibit the function thereof in the brain.

63. The anti-human transferrin receptor antibody according to 62 above, wherein the pharmacologically active compound is selected from the group consisting of anticancer drug, therapeutic agent for Alzheimer's disease, therapeutic agent for Parkinson's disease, therapeutic agent for Huntington's disease, therapeutic agent for schizophrenia, antidepressant, therapeutic agent for multiple sclerosis, therapeutic agent for amyotrophic lateral sclerosis, therapeutic agent for tumors of central nervous system including brain tumor, therapeutic agent for lysosomal storage disease accompanied by encephalopathy, therapeutic agent for glycogenosis, therapeutic agent for muscular dystrophy, therapeutic agent for cerebral ischemia, therapeutic agent for prion diseases, therapeutic agent for traumatic central nervous system disorders, therapeutic agent for viral and bacterial central nervous system diseases, pharmaceutical agent used for recovery after brain surgery, pharmaceutical agent used for recovery after spinal surgery, siRNA, antisense DNA, and peptide.

64. Use of the anti-human transferrin receptor antibody according to any one of 1 to 40 above for allowing the different protein (A) or a low-molecular-weight pharmacologically active compound to pass through the blood-brain barrier and exhibit the function thereof in the brain.

65. Use of the anti-human transferrin receptor antibody according to any one of 1 to 40 above for the manufacture of a medicament for parenteral administration for the treatment of a disease condition of the central nervous system, by linking thereto the molecule of a physiologically active protein or a pharmacologically active low-molecular-weight compound for the disease condition.

66. A method for treatment of a disorder of the central nervous system comprising parenterally administering to a patient with the disorder a therapeutically effective amount of the physiologically active protein, or pharmacologically active low-molecular-weight compound, for the disorder, in the form of a conjugate with the molecule of the anti-human transferrin receptor antibody according to any one of 1 to 40 above.

67. Use of the anti-human transferrin receptor antibody according to any one of 54 to 57 above for making human iduronate 2-sulfatase pass through the blood-brain barrier and exhibit the function thereof in the brain.

68. Use of the fusion protein according to any one of 54 to 57 for the production of a pharmaceutical agent for parenteral administration for the treatment of a disease condition of the central nervous system accompanying Hunter syndrome.

69. A method for the treatment of a disease of the central nervous system accompanying Hunter syndrome comprising parenterally administering a therapeutically effective amount of the fusion protein according to any one of 54 to 57 above to a patient with the disease.

Effects of the Invention

By the present invention, various compounds, such as proteins and low-molecular-weight compounds that, although physiologically or pharmacologically active, have been unusable by parenteral administration because of their no or little ability to pass through the blood-brain barrier, can be provided in the form that allow them to pass through the blood-brain barrier, thus making them new pharmaceutical agents for parenteral administration for the treatment of a disease condition of the central nervous system.

EMBODIMENTS FOR CARRYING OUT THE INVENTION

Figure 1:
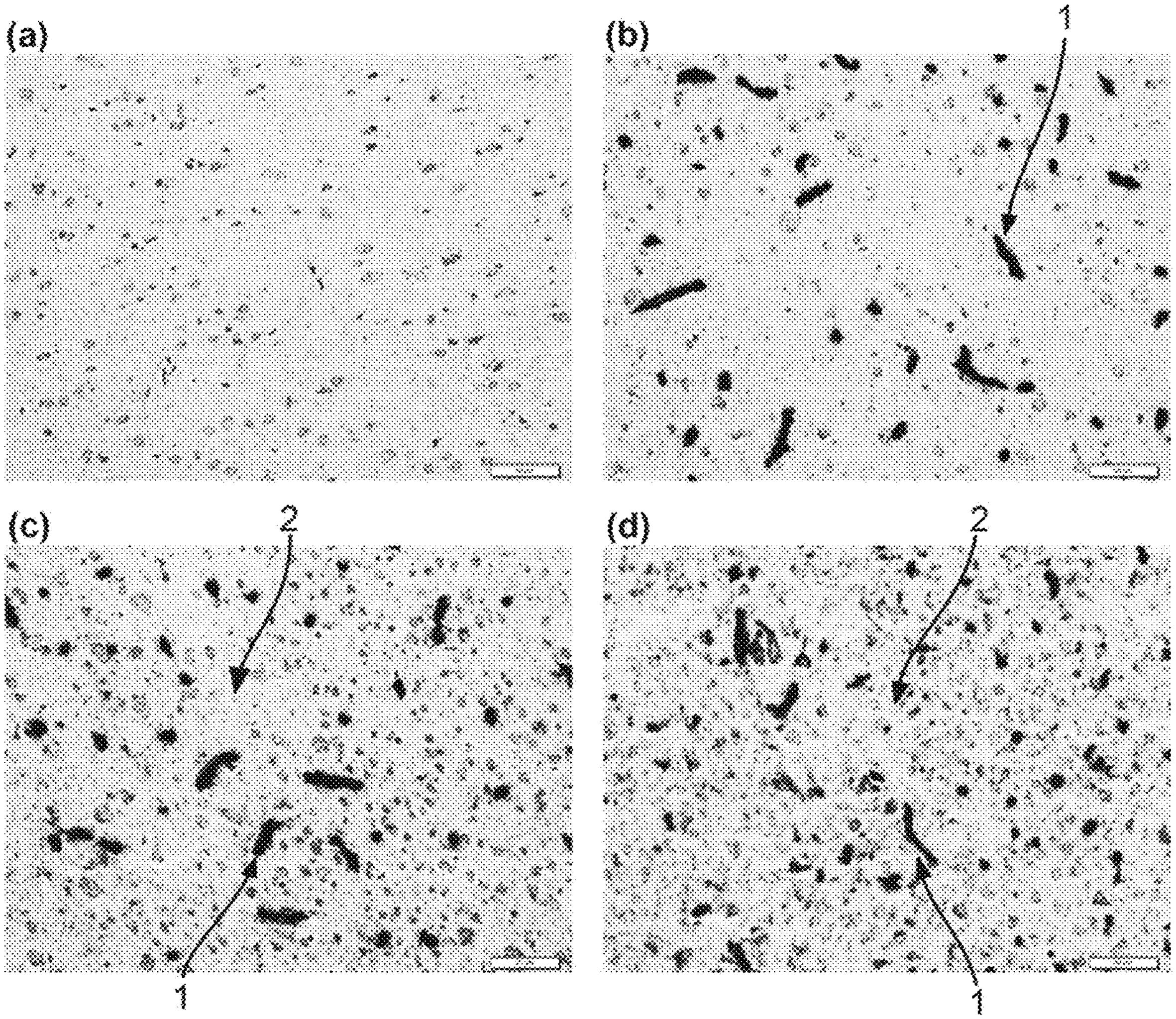
FIG. 1 Substitute photographs for drawings showing the result of the immunohistochemical staining of the anti-hTfR antibody in the cerebral cortex of a cynomolgus monkey after a single intravenous administration of the anti-hTfR antibody. (a) anti-hTfR antibody not administered, (b) anti-hTfR antibody No. 1 administered, (c) anti-hTfR antibody No. 2 administered, (d) anti-hTfR antibody No. 3 administered. The bar at the bottom right in each photograph is a 50-μm gauge.

In the present invention, the term "antibody" refers mainly to a human antibody, mouse antibody, humanized antibody, as well as a chimeric antibody between human antibody and non-human mammalian antibody, and a chimeric antibody between mouse antibody and non-mouse mammalian antibody, but the meaning of the term is not limited to them insofar as a substance of interest has a property to specifically bind to a certain antigen, and there is no specific limitation as to the animal species of the antibody, either.

In the present invention, the term "human antibody" refers to an antibody whose entire protein is encoded by a gene originating from human. The term "human antibody", however, also includes an antibody encoded by a gene obtained by introducing a mutation into an original human gene for a purpose of enhancing expression efficiency of the gene, for example, without modifying the original amino acid sequence. The term "human antibody" also includes an antibody which is obtainable through combining two or more genes encoding human antibodies by replacing a certain part of a human antibody with a part of another human antibody. A human antibody includes three complementarity determining regions (abbr. CDRs) in the light chain of the immunoglobulin and three complementarity determining regions (CDRs) in the heavy chain of the immunoglobulin. The three CDRs in the light chain of the immunoglobulin are called, from the N-terminal side, CDR1, CDR2 and CDR3, respectively. The three CDRs in the heavy chain of the immunoglobulin are also called, from the N-terminal side, CDR1, CDR2 and CDR3, respectively. The term "human antibody" also includes a human antibody produced by replacing a CDR of a human antibody with a CDR of another human antibody to modify such properties as the antigen specificity and the affinity of the original human antibodies, etc.

In the present invention, the term "human antibody" also includes an antibody which is produced through modification of the gene of the original human antibody by introducing a mutation, such as substitution, deletion, addition, to the amino acid sequence of the original antibody. When replacing one or more amino acids of the amino acid sequence of the original antibody with other amino acids, the number of amino acid replaced may preferably be 1 to 20, more preferably 1 to 5, and still more preferably 1 to 3. When deleting one or more amino acids of the amino acid sequence of the original antibody, the number of amino acids deleted may preferably be 1 to 20, more preferably 1 to 5, and still more preferably 1 to 3. An antibody produced by a combined mutation of these substitution and deletion of amino acids is also a "human antibody". In some cases, one or more amino acids, preferably 1 to 20, more preferably 1 to 5, and still more preferably 1 to 3 amino acids may be added inside the amino acid sequence of the original antibody or on its N- or C-terminal side. An antibody produced by a combined mutation of addition, substitution, and deletion of amino acids is also a "human antibody". The amino acid sequence of such a mutated antibody has a homology of preferably not lower than 80%, more preferably not lower than 90%, still more preferably not lower than 95%, and even more preferably not lower than 98%, to the amino acid sequence of the original antibody. Thus, in the present invention, the term "gene originating from human" includes not only the unmutated gene originating from human but also a gene produced by modifying it.

The homology between the amino acid sequence of an unmutated antibody and the amino acid sequence of an antibody produced by introducing a mutation into it may be readily calculated using well-known homology calculator algorithms. As such algorithms, there are, for example, BLAST (Altschul SF. J Mol. Biol. 215. 403-10 (1990)), a similarity search by Pearson and Lipman (Proc. Natl. Acad. Sci. USA. 85. 2444 (1988)), and the local homology algorithm of Smith and Waterman (Adv. Appl. Math. 2. 482-9 (1981)), and the like.

The term "mouse antibody" refers to an antibody whose entire protein consists of an amino acid sequence which is the same as an antibody encoded by a gene originating from a mouse. Therefore, the term "mouse antibody" also includes an antibody that is encoded by a gene produced by introducing a mutation into the original mouse gene without causing a change in its amino acid sequence but in order, for example, to improve the expression efficiency of the gene. Further, the term "mouse antibody" also includes an antibody produced through combining two or more genes encoding mouse antibodies by replacing a part of a mouse antibody with a part of another mouse antibody. A mouse antibody has three complementarity determining regions (CDRs) in the light chain of the immunoglobulin and three complementarity determining regions (CDRs) in the heavy chain of the immunoglobulin. The three CDRs in the light chain of the immunoglobulin are called, from the N-terminal side, CDR1, CDR2 and CDR3, respectively. The three CDRs in the heavy chain of the immunoglobulin are also called, from the N-terminal side, CDR1, CDR2 and CDR3, respectively. The term "mouse antibody" also includes an antibody produced by replacing a CDR of a mouse antibody with a CDR of another mouse antibody to modify the specificity and affinity of the original mouse antibodies.

In the present invention, the term "mouse antibody" also includes an antibody which is produced through modification of the gene of the original mouse antibody by introducing a mutation, such as substitution, deletion, addition, to the amino acid sequence of the original antibody. When replacing one or more amino acids of the amino acid sequence of the original antibody with other amino acids, the number of amino acid replaced may preferably be 1 to 20, more preferably 1 to 5, and still more preferably 1 to 3. When deleting one or more amino acids of the amino acid sequence of the original antibody, the number of amino acids deleted may preferably be 1 to 20, more preferably 1 to 5, and still more preferably 1 to 3. An antibody produced by a combined mutation of these substitution and deletion of amino acids is also a "mouse antibody". When adding one or more amino acids, they may be added inside the amino acid sequence of the original antibody or on its N- or C-terminal side, preferably 1 to 20, more preferably 1 to 5, and still more preferably 1 to 3, in number. An antibody produced by a combined mutation of addition, substitution, and deletion of amino acids is also a "mouse antibody". The amino acid sequence of such a mutated antibody has a homology of preferably not lower than 80%, more preferably not lower than 90%, still more preferably not lower than 95%, and even more preferably not lower than 98%, to the amino acid sequence of the original antibody. Thus, in the present invention, the term "gene originating from mouse" includes not only the unmutated gene originating from mouse but also a gene produced by modifying it.

In the present invention, the term "humanized antibody" refers to an antibody in which part of the amino acid sequence of its variable region (e.g., especially the whole or part of its CDRs) originates from a non-human mammal while the rest originates from human. An example of humanized antibody is an antibody produced by replacing the three complementarity determining regions (CDRs) of the light chain of the immunoglobulin and the three complementarity determining regions (CDRs) of the heavy chain of the immunoglobulin constituting a human antibody, with CDRs from a non-human mammal. As far as it originates from a non-human mammal, there is no particular limitation as to the biological species from which those CDRs originate that are grafted into a proper position of the human antibody, though preferred are mouse, rat, rabbit, horse or non-human primate, more preferred are mouse and rat, and mouse, for example.

In the present invention, the term "chimeric antibody" refers to an antibody produced by connecting fragments of two or more different antibodies originating from two or more different species.

A chimeric antibody between a human antibody and a non-human mammalian antibody is an antibody provided by replacing part of a human antibody with part of a non-human mammalian antibody. As explained below, an antibody is made of an Fc region, a Fab region and a hinge region. A specific example of such chimeric antibodies is a chimeric antibody whose Fc region originates from a human antibody while its Fab region originates from a non-human mammalian antibody. The hinge region either originates from a human antibody or from a non-human mammalian antibody. On the contrary, the term chimeric antibody also includes one whose Fc region originates from a non-human mammalian antibody while its Fab region originates from a human antibody. In such a case also, the hinge region may either originate from a human antibody or from a non-human mammalian antibody. On the contrary, a chimeric antibody is also included as an example whose Fc region originates from a non-human mammalian antibody while its Fab region originates from a human antibody. In this case also, the hinge region may either originate from a human antibody or from a non-human mammalian antibody.

An antibody can be viewed as composed of a variable region and a constant region. Additional examples of chimeric antibodies include an antibody in which the heavy chain constant region ($C_H$) and the light chain constant region ($C_l$) both originate from a human antibody while the heavy chain variable region ($V_H$) and the light chain variable region ($V_L$) both originate from an antibody of a non-human mammal, and conversely, an antibody in which the heavy chain constant region ($C_H$) and the light chain constant region ($C_l$) both originate from an antibody of a non-human mammal, while the heavy chain variable region ($V_H$) and the light chain variable region ($V_L$) both originate from a human antibody. In these, there is no particular limitation as to the biological species of the non-human mammal, as far as it is a non-human mammal, though preferred are mouse, rat, rabbit, horse or non-human primate, and more preferred is mouse.

A chimeric antibody between a mouse antibody and a non-mouse mammalian antibody is an antibody provided by replacing part of a mouse antibody with part of a non-mouse mammalian antibody. Specific examples of such chimeric antibodies include a chimeric antibody whose Fc region originates from a mouse antibody while its Fab region originates from a non-mouse mammalian antibody, and conversely, a chimeric antibody whose Fc region originates from a non-mouse mammal while its Fab region originates from a mouse antibody. In these, there is no particular limitation as to the biological species of the non-mouse mammal, as far as it is a mammal other than mouse, though preferred are rat, rabbit, horse or non-human primate, and more preferred is human.

A chimeric antibody between a human antibody and a mouse antibody is designated in particular "human/mouse chimeric antibody". Examples of human/mouse chimeric antibodies include a chimeric antibody in which the Fc region originates from a human antibody while the Fab region originates from a mouse antibody, and conversely, a chimeric antibody whose Fc region originates from mouse antibody, while its Fab region originates from a human antibody. A hinge region either originate from a human antibody or a mouse antibody.

Additional specific examples of human/mouse chimeric antibodies include those whose heavy chain constant region ($C_H$) and light chain constant region ($C_l$) originate from a human antibody while its heavy chain variable region ($V_H$) and light chain variable region ($V_L$) originate from a mouse antibody, and conversely, those whose heavy chain constant region ($C_H$) and light chain constant region ($C_l$) originate from a mouse antibody while its heavy chain variable region ($V_H$) and light chain variable region ($V_L$) originate from a human antibody.

Originally, an antibody is of the basic structure having four polypeptide chains in total consisting of two immunoglobulin light chains and two immunoglobulin heavy chains. However, in the present invention the term "antibody" refers, besides an antibody having this basic structure, also to:

(1) one consisting of two polypeptide chains: a single immunoglobulin light chain and a single immunoglobulin heavy chain, and also, as explained later, (2) a single-chain antibody consisting of an immunoglobulin light chain which is linked, on the C-terminal side thereof, to a linker sequence which in turn is linked, on the C-terminal side thereof, to an immunoglobulin heavy chain, (3) single-chain antibodies consisting of an immunoglobulin heavy chain which is linked, on the C-terminal side thereof, to a linker sequence which in turn is linked, on the C-terminal side thereof, to an immunoglobulin light chain, and (4) one consisting of a Fab region, i.e., a structure left behind by removal of the Fc region from an antibody having the basic structure, as the original meaning, and one consisting of the Fab region and the whole or part of the hinge region (including Fab, F(ab'), and $F(ab')_2$) also are included in the term "antibody" in the present invention.

The term "Fab" refers to a molecule consisting of a single light chain comprising the variable region and the $C_L$ region (light chain constant region) and a single heavy chain comprising the variable region and the $C_H1$ region (portion 1 of heavy chain constant region) which are combined by a disulfide bond between their respective cysteine residues. While the heavy chain in a Fab can include part of the hinge region in addition to the variable region and the $C_H1$ region (portion 1 of heavy chain constant region), the hinge region in such a case lacks the cysteine residue that otherwise is present in the hinge region and would serve to link two heavy chains of an antibody together. In Fab, the light chain and the heavy chain are connected by a disulfide bond formed between the cysteine residue present in the light chain constant region ($C_L$ region) and the cysteine residue located in the heavy chain constant region ($C_H1$ region) or the hinge region. As it lacks the cysteine residue in the hinge region which serves to bind two heavy chains of an antibody, Fab consists of a single light chain and a single heavy chain. The light chain constituting Fab includes a variable region and a $C_L$ region. The heavy chain as a component of Fab may either consist of a variable region and a $C_H1$ region or also of part of the hinge region in addition to the variable region and the $C_H1$ region. However, in the letter case, the hinge region is so selected as not to include the cysteine residue that could bind two heavy chains, in order to avoid the formation of a disulfide bond between two heavy chains at their hinge regions. In F(ab'), the heavy chain includes, in addition to a variable region and a $C_H1$ region, the whole or part of a hinge region containing a cysteine residue that could bind two heavy chains. F(ab')2 is a molecule consisting of two F(ab')s bound together through a disulfide bond formed between the cysteine residues present in their respective hinge regions. Further, a polymer such as a dimer and a trimer, which consists of two or more antibodies connected with each other, directly or via a linker, is also included in the term "antibody". Moreover, in addition to the aforementioned, any molecule that includes part of an immunoglobulin molecule and has a property to specifically bind to the antigen is also included in the term "antibody" in the present invention. Thus, in the present invention, the term "immunoglobulin light chain" includes a molecule that is derived from an original immunoglobulin light chain and having the amino acid sequence of the whole or part of its variable region. Likewise, the term "immunoglobulin heavy chain" includes a molecule that is derived from an original immunoglobulin heavy chain and having the amino acid sequence of the whole or part of its variable region. Therefore, insofar as having the whole or part of the amino acid sequence of the variable region, a molecule is included in the term "immunoglobulin heavy chain", even if it lacks its Fc region, for example.

In the above, the term "Fc" or "Fc region" refers to a region comprising a fragment consisting of $C_H2$ region (portion 2 of the heavy chain constant region), and $C_H3$ region (portion 3 of the heavy chain constant region) in the antibody molecule.

Furthermore, in the present invention, the term "antibody" also includes:

(5) scFab, scF(ab'), and scF(ab')2, which are single-chain antibodies produced by binding the light chain to the heavy chain that form, respectively, the Fab, F(ab') and F(ab')2 mentioned in (4) above, via a linker sequence. Such scFab, scF(ab') and scF(ab')2 may be a molecule in which either the light chain is linked, on the C-terminal side thereof, to a linker sequence, which in turn is linked, on the C-terminal side thereof, to the heavy chain, or the heavy chain is linked, on the C-terminal side thereof, to a linker sequence, which in turn is linked, on the C-terminal side thereof, to the light chain. Furthermore, a scFv, which is a single-chain antibody provided by binding the light chain variable region to the heavy chain variable region, via a linker sequence between them, is also included in the term "antibody" in the present invention. Such scFv may be a molecule in which either the light chain variable region is linked, on the C-terminal side thereof, to a linker sequence, which in turn is linked, on the C-terminal side thereof, to the heavy chain variable region, or the heavy chain variable region is linked, on the C-terminal side thereof, to a linker sequence, which in turn is linked, on the C-terminal side thereof, to the light chain variable region.

Furthermore, in addition to a full-length antibody and those described in (1) to (5) above, the term "antibody" in the present specification includes, any form of antigen-binding fragment which lacks part of the full-length antibody (antibody fragment), a broader concept which includes (4) and (5) above.

The term "antigen-binding fragment" refers to an antibody fragment that retains at least part of the specific binding activity to its antigen. In addition to those described above in (4) and (5), examples of binding fragments include Fab, Fab', F(ab')2, variable region (Fv); a single-chain antibody (scFv) produced by linking the heavy chain variable region ($V_H$) and the light chain variable region ($V_L$), via a proper linker between them; a diabody, which is a dimer of a polypeptide that comprises a heavy chain variable region ($V_H$) and a light chain variable region ($V_L$); a minibody, which is a dimer of a molecule in which the heavy chain (H chain) of a scFv is linked to part of the constant region ($C_H3$), and other low-molecular-antibodies. However, as far as it has an antigen-binding ability, the term is not limited to these molecules. Such binding fragments include not only those produced by treating a full-length molecule of an antibody protein with a proper enzyme but also those produced by proper host cells using a genetically engineered antibody gene.

In the present invention, the term "single-chain antibody" refers to a protein in which an amino acid sequence comprising the whole or part of an immunoglobulin light chain variable region linked, on the C-terminal side thereof, to a linker sequence, which in turn is linked, on the C-terminal side thereof, to the amino acid sequence of the whole or part of an immunoglobulin heavy chain variable region, and having an ability to specifically bind a certain antigen. For example, those described in (2), (3) and (5) are included in "single-chain antibody". Further, a protein in which an amino acid sequence comprising the whole or part of an immunoglobulin heavy chain variable region is linked, on the C-terminal side thereof, to a linker sequence, which in turn is further linked, on the C-terminal side thereof, to the amino acid sequence of the whole or part of an immunoglobulin light chain variable region, and which has an ability to specifically bind to a certain antigen, is also included in the term "single-chain antibody" in the present invention. In a single-chain antibody in which an immunoglobulin heavy chain is linked, on the C-terminal side thereof and via a linker sequence, to an immunoglobulin light chain, the immunoglobulin heavy chain generally lacks the Fc region. An immunoglobulin light chain variable region has three complementarity determining regions (CDRs) which participate in determining the antigen specificity of an antibody. Likewise, an immunoglobulin heavy chain variable region also has three CDRs. Those CDRs are the primary regions that determine the antigen specificity of an antibody. Therefore, a single-chain antibody preferably contains all the three CDRs of the immunoglobulin heavy chain and all the three CDRs of the immunoglobulin light chain. However, it is also possible to provide a single-chain antibody in which one or more of those CDRs are deleted, insofar as the antigen-specific affinity of the antibody is retained.

In a single-chain antibody, the linker sequence placed between the light chain and the heavy chain of the immunoglobulin is preferably a peptide chain consisting of preferably 2 to 50, more preferably 8 to 50, still more preferably 10 to 30, even more preferably 12 to 18, or 15 to 25, for example 15 or 25 amino acid residues. While there is no particular limitation as to the specific amino acid sequence of such a linker sequence insofar as the anti-hTfR antibody comprising the both chains linked thereby retains the affinity to hTfR, it is preferably made of glycine only, or of glycine and serine: for example the amino acid sequence Gly-Ser, the amino acid sequence Gly-Gly-Ser, the amino acid sequence Gly-Gly-Gly, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence which includes 2 to 10 or 2 to 5 repeats of any of those amino acid sequences. For example, in linking the amino acid sequence of the entire immunoglobulin heavy chain variable region, on the C-terminal side thereof and via a linker sequence, to immunoglobulin light chain variable region, the linker sequence is preferably a linker sequence comprising 15 amino acids corresponding to three of the amino acid sequence Gly-Gly-Gly-Gly-Ser (SEQ ID NO:3) consecutively linked.

In the present invention, the term "human transferrin receptor" or "hTfR" refers to a membrane protein having the amino acid sequence set forth as SEQ ID NO: 1. The anti-hTfR antibody of the present invention is, in one of its embodiments, that which specifically binds to the region from the cysteine residue at the position 89th from the N-terminal side to the phenylalanine at the C-terminus in the amino acid sequence set forth as SEQ ID NO:1 (i.e., the extracellular region of the hTfR), though it is not limited to this embodiment. Further, in the present invention, the term "monkey transferrin receptor" or "monkey TfR" refers in particular to the membrane protein having the amino acid sequence set forth as SEQ ID NO:2, originating from cynomolgus monkey (*Macaca fascicularis*). The anti-hTfR antibody of the present invention is, in one of its embodiments, that which binds also to region from the cysteine residue at the position 89th from the N-terminal side to the phenylalanine at the C-terminus in the amino acid sequence set forth as SEQ ID NO:2 (i.e., the extracellular region of the monkey TfR), though it is not limited to this embodiment.

For preparation of an antibody to hTfR, there is known a general method according to which a recombinant human transferrin receptor (rhTfR) is produced using cells which have an introduced expression vector having an incorporated hTfR gene, and then animals such as mice are immunized with this rhTfR. By collecting those cells which produce antibodies to hTfR from the immunized animals and fusing them with myeloma cells, hybridoma cells can be obtained having an ability to produce the antibody.

Further, cells producing an antibody to hTfR can also be obtained by collecting immunocompetent cells from an animal such as mouse, and immunizing them with rhTfR by in vitro immunization. In conducting in vitro immunization, there is no particular limitation as to the animal species from which the immunocompetent cells are derived, though preferred are mouse, rat, rabbit, guinea pig, dog, cat, horse, and primates including human, and more preferred are mouse, rat and human, and still more preferably mouse and human. As mouse immunocompetent cells, spleen cells prepared from mouse spleen may be used, for example. As human immunocompetent cells, such cells can be used as prepared from human peripheral blood, bone marrow, spleen, and the like. By immunizing human immunocompetent cells according to in vitro immunization, a human antibody to hTfR can be obtained.

After immunizing the immunocompetent cells according to in vitro immunization, the cells can be fused with myeloma cells to prepare hybridoma cells having an ability to produce the antibody. Further, it is also possible to extract mRNAs from the immunized cells, synthesize cDNA, perform PCR reaction using the cDNA as a template to amplify a DNA fragment containing the gene encoding the light chain and the heavy chain of the immunoglobulin, and artificially reconstruct the antibody gene using them.

The hybridoma cells freshly obtained above also include such cells that produce antibodies that recognize other proteins than hTfR. Furthermore, not all the hybridoma cells producing an anti-hTfR antibody necessarily produce an anti-hTfR antibody that exhibits high affinities to hTfR.

Likewise, artificially reconstructed antibody genes include such genes as encode antibodies recognizing other proteins than hTfR as antigens. Moreover, not all the genes encoding anti-hTfR antibodies necessarily have desired properties such as encoding an anti-hTfR antibody exhibiting high affinity to hTfR.

Therefore, a selection step is necessary to select hybridoma cells producing an antibody having desired properties (such as high affinity to hTfR) from the hybridoma cells freshly obtained above. Further, in the case where antibody genes are artificially reconstructed, a selection step is necessary to select from the antibody genes a gene encoding an antibody having desired properties (such as high affinities to hTfR). For selecting hybridoma cells that produce antibodies exhibiting high affinities to hTfR (high affinity antibodies), or for selecting genes encoding high affinity antibodies, following methods explained in detail below are effective. Besides, antibodies exhibiting high affinity to hTfR are those whose dissociation constant ($K_D$) with hTfR as measured by the method described in Example 7 is preferably not greater than $1\times10^{-8}$ M, more preferably not greater than $1\times10^{-9}$ M, still more preferably not greater than $1\times10^{-10}$ M, and even more preferably not greater than $1\times10^{-11}$ M. For example, those having a dissociation constant of $1\times10^{-13}$ M to $1\times10^{-9}$ M, or $1\times10^{-13}$ M to $1\times10^{-10}$ M are preferable.

For example, for selecting hybridoma cells which produce high affinity antibodies to anti-hTfR antibody, a method is employed in which recombinant hTfR is added to a plate and held by it, then the culture supernatant of the hybridoma cells is added, and after removing antibody unbound to the recombinant hTfR from the plate, the amount of the antibody held by the plate is measured. According to this method, the higher the affinity to hTfR of the antibody contained in the culture supernatant of the hybridoma cells added to the plate is, the greater the amount of antibody held by the plate becomes. Therefore, by measuring the amount of the antibody held by the plate, it is possible to select those hybridoma cells corresponding to the plates where the antibody is held in the greater amount as cell lines producing an anti-hTfR antibody having the relatively higher affinity to hTfR. It is also possible to isolate the gene encoding the high-affinity antibody by extracting mRNAs from each cell line selected in this manner, synthesizing cDNAs, and amplifying a DNA fragment containing the gene encoding the anti-hTfR antibody by PCR using the cDNA as a template.

In order to select the gene encoding the high-affinity anti-hTfR antibody from the above artificially reconstructed antibody genes, the artificially reconstructed antibody genes are once incorporated into an expression vector, and the expression vector then is introduced into host cells. Although there is no particular limitation as to the cells to be employed as host cells, even whether they are prokaryotic or eukaryotic, insofar as they can express the antibody gene after introduction of an expression vector having the incorporated artificially reconstructed antibody gene, preferred are cells originating mammals such as human, mouse, Chinese hamster, and the like, and particularly preferred are CHO cells originating from Chinese hamster ovary cells, or NS/0 cells originating from mouse myeloma. Further, there is no particular limitation as to an expression vector to be employed for incorporation of the antibody encoding gene and expression of it, and any expression vector may be used as far as it can express the gene when introduced into mammalian cells. The gene incorporated into an expression vector is located downstream of a DNA sequence that can regulate the frequency of transcription of a gene in mammalian cells (gene expression regulatory site). Examples of gene expression regulatory sites that may be employed in the present invention include cytomegalovirus-derived promoter, SV40 early promoter, human elongation factor-1α (EF-1α) promoter, human ubiquitin C promoter.

Mammalian cells having such an introduced expression vector come to express the artificially reconstructed antibody incorporated in the expression vector. In order to select those cells that produce a high-affinity antibody to anti-hTfR antibody from the above obtained cells expressing the artificially reconstructed antibody, a method is employed in which the recombinant hTfR is added to a plate and held by it, then the recombinant hTfR is contacted by the culture supernatant of the cells, and after the removal of antibody unbound to the recombinant hTfR from the plate, the amount of the antibody held by the plate is measured. According to this method, the higher the affinity to hTfR of the antibody contained in the cells culture supernatant is, the greater the amount of antibody held by the plate becomes. Therefore, by measuring the amount of the antibody held by the plate, one can select those cells corresponding to the plate where the antibody is held in the greater amount, as a cell line producing an anti-hTfR antibody having relatively the high-affinity anti-hTfR antibodyR, and eventually can select a gene encoding an anti-hTfR antibody having a high-affinity anti-hTfR antibody to hTfR. Using cell line selected in this manner, one can perform PCR to amplify a DNA fragment containing the gene encoding the anti-hTfR antibody to isolate the gene encoding the high-affinity antibody.

Selection of the gene encoding a high affinity anti-hTfR antibody from the above artificially reconstructed antibody genes can also be carried out by incorporating the artificially reconstructed antibody genes into an expression vector, introducing the expression vector into *E. coli* cells, culturing the *E. coli* cells, and selecting the *E. coli* cells having the desired gene, in the same manner as in the above selection of hybridoma cells, using the culture supernatant of the *E. coli* cells or an antibody-containing solution prepared by lysing the *E. coli* cells. *E. coli* cells thus selected express the gene encoding an anti-hTfR antibody having a relatively high affinity to hTfR. From this cell line, the gene encoding the anti-hTfR antibody having a relatively the high-affinity anti-hTfR antibody to hTfR can be selected. In order to allow the antibody to be secreted into the *E. coli* culture supernatant, the antibody gene may be incorporated into the expression vector so that a secretion signal sequence is attached on the N-terminal side of the gene.

Another method for selection of the gene encoding a high-affinity anti-hTfR antibody is a method in which the antibody encoded by the above artificially reconstructed antibody gene is expressed and retained on phage particles. For this, the antibody gene is reconstructed as a gene encoding a single-chain antibody. A method for retaining the antibody on the surface of phage particles is disclosed in international publications WO1997/09436 and WO1995/11317, and the like, and thus well known. In order to select phages retaining the high-affinity antibody to anti-hTfR antibody from the phages retaining the antibodies encoded by the artificially reconstructed antibody genes, a method is employed in which a recombinant hTfR is added to a plate and held by it, contacted by the phages, and after removal of the phages unbound to the recombinant hTfR from the plate, the amount of the phages held by the plate is measured. According to this method, the higher the affinity to hTfR of the antibody retained on the phage particles is, the greater the amount of the phage held by the plate becomes. Therefore, by measuring the amount of the phage held by the plate, one can select the phage particles corresponding to the plate where the phages' were held in the greater amount, as the phage particles producing anti-hTfR antibody having a relatively high-affinity anti-hTfR antibody to hTfR, and eventually can select the gene encoding the high-affinity anti-hTfR antibody to hTfR. Using the phage particles thus selected, PCR can be performed to amplify a DNA fragment containing the gene encoding the anti-hTfR antibody and isolate the gene encoding the high-affinity antibody.

It is possible to prepare cDNA or phage DNA from the above cells such as the hybridoma cells producing the high-affinity antibody to anti-hTfR, or from the above phage particles retaining high-affinity antibody to anti-hTfR, and perform PCR or the like using it as a template to amplify and isolate a DNA fragment containing the gene encoding the whole or part of the anti-hTfR antibody light chain, the anti-hTfR antibody heavy chain, or a single-chain antibody. In the same manner, it is also possible to perform PCR or the like to amplify and isolate a DNA fragment containing the gene encoding the whole or part of the light chain variable region of the anti-hTfR antibody, or a DNA fragment containing the gene encoding the whole or part of the heavy chain variable region of the anti-hTfR antibody.

A high-affinity anti-hTfR antibody can be obtained by incorporating the whole or part of the gene encoding the light chain and the heavy chain of this high-affinity anti-hTfR antibody into an expression vector, transforming host cells such as mammalian cells with this expression vector, and culturing the obtained transformant cells. Using the nucleotide sequence of the isolated gene encoding the anti-hTfR antibody, it is also possible to translate the amino acid sequence of the anti-hTfR antibody, and artificially synthesize a DNA fragment encoding the same amino acid sequence. In artificially synthesizing a DNA fragment, the expression level of the anti-hTfR antibody in the host cells can be enhanced by proper selection of the codons.

In order to introduce a mutation such as substitution, deletion, addition and the like into the amino acid sequence of the original anti-hTfR antibody, a mutation may be introduced as desired into the gene encoding the anti-hTfR antibody contained in the isolated DNA fragment. Though the gene encoding the mutated anti-hTfR antibody has a homology preferably not lower than 80%, more preferably not lower than 90%, to the original gene, there is no particular limitation as to the level of homology. By introducing a mutation into the amino acid sequence so as to modify the number or the type of sugar chains bound to the anti-hTfR antibody, it is also possible to enhance the stability of the anti-hTfR antibody in the body.

When introducing a mutation into the gene encoding the whole or part of the light chain variable region of the anti-hTfR antibody, the gene thus mutated has a homology that is preferably not lower than 80%, more preferably not lower than 90%, to the original gene, though there is no particular limitation as to the level of homology. When replacing one or more amino acids of the amino acid sequence of the light chain variable region with other amino acids, the number of amino acids to be replaced is preferably 1 to 10, more preferably 1 to 5, still more preferably 1 to 3, and even more preferably 1 or 2. When deleting one or more amino acids of the amino acid sequence of the light chain variable region, the number of amino acid to be deleted is preferably 1 to 10, more preferably 1 to 5, still more preferably 1 to 3, even more preferably 1 or 2. A combined mutation of these substitution and deletion of amino acids can also be carried out. When adding one or more amino acids to the light chain variable region, they may be added inside, or on the N-terminal side or C-terminal side of, the amino acid sequence of the light chain variable region, and the number of amino acids added is preferably 1 to 10, more preferably 1 to 5, still more preferably 1 to 3, and even more preferably 1 or 2. A combined mutation of these addition, substitution, and deletion of amino acids can also be carried out. The amino acid sequence of the light chain variable region thus mutated has a homology that is preferably not lower than 80%, more preferably not lower than 90%, still more preferably not lower than 95% to the amino acid sequence of the original light chain variable region. In particular, when replacing one or more amino acids of the amino acid sequence of CDR with other amino acids, the number of amino acid replaced is preferably 1 to 5, more preferable 1 to 3, still more preferably 1 or 2. When deleting one or more amino acid of the amino acid sequence of CDR, the number of amino acids to be deleted is preferably 1 to 5, more preferably 1 to 3, still more preferably 1 or 2. A combined mutation of these substitution and deletion of the amino acid can also be carried out. When adding one or more amino acids, they may be added inside, or on the N-terminal side or C-terminal side of, the amino acid sequence, and the number of amino acids added is preferably 1 to 5, more preferably 1 to 3, still more preferably 1 or 2. A combined mutation of these addition, substitution, and deletion of amino acids can also be carried out. The amino acid sequence of respective mutated CDR has a homology that is preferably not lower than 80%, more preferably not lower than 90%, and still more preferably not lower than 95% to the amino acid sequence of the original CDR.

When introducing mutation into the gene encoding the whole or part of the heavy chain variable region of the anti-hTfR antibody, the gene thus mutated has a homology that is preferably not lower than 80%, more preferably not lower than 90%, to the original gene, though there is no particular limitation as to the level of homology. When replacing one or more amino acids of the amino acid sequence of the heavy chain variable region with other amino acids, the number of amino acids to be replaced is preferably 1 to 10, more preferably 1 to 5, still more preferably 1 to 3, and even more preferably 1 or 2. When deleting one or more amino acids of the amino acid sequence of the heavy chain variable region, the number of amino acids to be deleted is preferably 1 to 10, more preferably 1 to 5, still more preferably 1 to 3, even more preferably 1 or 2. A combined mutation of these substitution and deletion of amino acids can also be carried out. When adding one or more amino acid to the heavy chain variable region, they may be added inside, or on the N-terminal side or C-terminal side of, the amino acid sequence of the heavy chain variable region, and the number of amino acids added is preferably 1 to 10, more preferably 1 to 5, still more preferably 1 to 3, and even more preferably 1 or 2. A combined mutation of these addition, substitution, and deletion of amino acids can also be carried out. The amino acid sequence of the heavy chain variable region thus mutated has a homology that is preferably not lower than 80%, more preferably not lower than 90%, still more preferably not lower than 95% to the amino acid sequence of the original heavy chain variable region. In particular, when replacing one or more amino acids of the amino acid sequence of CDR with other amino acids, the number of amino acid replaced is preferably 1 to 5, more preferable 1 to 3, still more preferably 1 or 2. When deleting one or more amino acid of the amino acid sequence of CDR, the number of amino acids to be deleted is preferably 1 to 5, more preferably 1 to 3, still more preferably 1 or 2. A combined mutation of these substitution and deletion of the amino acid can also be carried out. When adding one or more amino acids, they may be added inside, or on the N-terminal side or C-terminal side of, the amino acid sequence, and the number of amino acids added is preferably 1 to 5, more preferably 1 to 3, still more preferably 1 or 2. A combined mutation of these addition, substitution, and deletion of amino acids can also be carried out. The amino acid sequence of respective mutated CDR has a homology that is preferably not lower than 80%, more preferably not lower than 90%, and still more preferably not lower than 95% to the amino acid sequence of the original CDR.

A mutation may be introduced into both the variable regions of the light chain and the heavy chain of the anti-hTfR antibody, by combining the above mutation into the light chain variable region of the anti-hTfR antibody and the above mutation into the heavy chain variable region of the anti-hTfR antibody.

Examples of the above mentioned substitution of one or more amino acids in the amino acid sequence of the light chain and the heavy chain of the anti-hTfR antibody include substitution between acidic amino acids, i.e., aspartic acid and glutamic acid, substitution between amide-type amino acids, i.e., asparagine and glutamine, substitution between basic amino acids, i.e., lysine and arginine, substitution between branched amino acids, i.e., valine, leucine and isoleucine, substitution between aliphatic amino acids, i.e., glycine and alanine, substitution between hydroxyamino acids, i.e., serine and threonine, and substitution between aromatic amino acids, i.e., phenylalanine and tyrosine.

Besides, in the case where a mutation is introduced into the anti-hTfR antibody by adding one or more amino acids to the C-terminus or the N-terminus, if the anti-hTfR antibody and a different protein (A) are fused via the added amino acids, the added amino acids constitutes part of a linker. A detailed explanation will be given later on a linker that is placed between the anti-hTfR antibody and a different protein (A) in the case where the anti-hTfR antibody is fused with the different protein (A).

The anti-hTfR antibody obtained by culturing the cells selected by the above methods and the like to produce an anti-hTfR antibody that has a relatively high-affinity to hTfR, and the anti-hTfR antibody obtained by expression of the gene encoding a high-affinity anti-hTfR antibody, may be modified by introducing a mutation into their amino acid sequences, such as substitution, deletion, addition to give them desired properties. Introduction of a mutation into the amino acid sequence of the anti-hTfR antibody may be performed by introducing a mutation into the gene corresponding to the amino acid sequence.

The affinity of an anti-hTfR antibody to hTfR can be adjusted as desired by introduction of a mutation, such as substitution, deletion, and addition, into the amino acid sequence of a variable region of the antibody. For example, if an antibody has such a high affinity to its antigen that leads to too low a dissociation constant in an aqueous solution, there is a possibility that the antibody could, after administered to the body, fail to dissociate from the antigen, thereby leading to a functional disadvantage. In such a case, a most preferable antibody suitable to a given purpose can be obtained by introducing a mutation into the variable region of the antibody so as to adjust its dissociation constant stepwise to 2 to 5 times, 5 to 10 times, 10 to 100 times, and so on, that of the original antibody. Conversely, the dissociation constant can be adjusted stepwise to 1/2 to 1/5 times, 1/5 to 1/10 times, 1/10 to 1/100 times, and so on, that of the original antibody, by introducing a mutation.

Introduction of a mutation such as substitution, deletion and addition to the amino acid sequence of the anti-hTfR antibody can be performed, for example, either by introducing a mutation into certain positions of the nucleotide sequence of the gene or by random introduction of a mutation, by PCR or the like using the gene encoding the anti-hTfR antibody as a template.

Introduction of a mutation into the amino acid sequence of the anti-hTfR antibody for adjusting the affinity of the antibody to hTfR can be carried out by, for example, incorporating a gene encoding the anti-hTfR antibody as a single-chain antibody into a phagemid, preparing with this phagemid a phage with expressed single-chain antibody on the surface of its capsid, letting the phage multiply while introducing a mutation into the gene encoding the single-chain antibody by application of a mutagen or the like, and selecting, from the multiplied phage, a phage expressing a single-chain antibody having a desired dissociation constant either by the method described above or by purification using an antigen column under a certain condition.

The antibodies having a relatively high-affinity to hTfR obtained by the above-mentioned method of selecting the cells producing a high affinity antibody, are those whose dissociation constant ($K_D$) with hTfR as measured by the method described in Example 7 is preferably not greater than $1\times10^{-8}$ M, more preferably not greater than $1\times10^{-9}$ M, still more preferably not greater than $1\times10^{-10}$ M, and even more preferably not greater than $1\times10^{-11}$ M. For example, those having a dissociation constant of $1\times10^{-13}$ M to $1\times10^{-9}$ M, or $1\times10^{-13}$ M to $1\times10^{-10}$ M are preferable. The same also applies if the antibodies are single-chain antibodies. Once an antibody is obtained, it can be modified as desired by, e.g., introducing a mutation to give it a desired property.

Antibody having affinity both to human and monkey TfRs can be obtained by selection of antibodies having affinity to monkey TfR from the antibodies having a relatively high-affinity that have been obtained by the above described method involving selection of the cells producing high affinity antibody. Selection of antibodies having affinity to monkey TfR can be carried out by, for example, ELISA using a recombinant monkey TfR which is prepared utilizing recombinant DNA technologies. In such an ELISA, a recombinant monkey TfR is added to a plate and held by it, and contacted by the anti-hTfR antibody, and, after removal of antibody unbound to the recombinant monkey TfR from the plate, the amount of the antibody held by the plate is measured. The higher the affinity of it to the recombinant monkey hTfR is, the greater the amount of the antibody held by the plate becomes. Consequently, the antibody corresponding to the plate which held the greater amount of antibody can be selected as the antibody having affinity to monkey TfR. Here, the term "monkey" is preferably classified as simians except human, more preferably as Cercopithecidae, still more preferably as macaques, and for example cynomolgus monkey or Rhesus monkey, among which cynomolgus monkey is convenient for use in examination.

An antibody having affinity both to human and monkey hTfRs offers an advantage that it allows pharmacokinetic observation of the antibody administered to the body using a monkey. For example, if a medical drug is being developed utilizing such an anti-hTfR antibody of the present invention, the progress of its development can be remarkably accelerated, for its pharmacokinetic study can be performed using a monkey.

An antibody having a relatively high-affinity to hTfR and having affinity both to human and monkey TfRs, simultaneously, exhibits a dissociation constant with monkey TfR, as measured by the method described in Example 7, that is preferably not greater than $5\times10^{-8}$ M, more preferably not greater than $2\times10^{-8}$ M, and still more preferably not greater than $1\times10^{-8}$M. For example, one which exhibits a dissociation constant of $1\times10^{-13}$M to $2\times10^{-8}$M, or $1\times10^{-13}$M to $2\times10^{-8}$ M is preferred. The same also applies if the antibody is a single-chain antibody.

If an antibody having a relatively high-affinity to hTfR and obtained by the above method in which those cells producing a high affinity antibody were selected, is an antibody of a non-human animal, it may be converted to a humanized antibody. A humanized antibody is an antibody produced by replacing a proper region of a human antibody with an amino acid sequence of part of the variable region (e.g., the whole or part of the CDRs) of a non-human animal antibody (implant of the sequence into the proper region of a human antibody), while maintaining the specificity to the antigen. Examples of humanized antibodies include an antibody produced by replacing the three complementarity determining regions (CDRs) in the immunoglobulin light chain and the three complementarity determining regions (CDRs) in the immunoglobulin heavy chain, both constituting a human antibody, with CDRs of a non-human mammal Though there is no particular limitation as to the biological species from which the CDRs to be incorporated into the human antibody are derived so long as it is a non-human mammal, it preferably is a mouse, rat, rabbit, horse, and non-human primate, more preferably a mouse and rat, and still more preferably a mouse.

Methods for preparation of humanized antibody are well known in the art and the most common is a method in which the amino acid sequence of the complementarity determining regions (CDRs) in the variable region of a human antibody is replaced with the CDRs of an antibody of non-human mammal, as devised by Winter et al. (Verhoeyen M. Science. 239, 1534-1536 (1988)). It is also well known that in some cases, corresponding part of an acceptor human antibody needs to be replaced not only with the CDRs of the non-human mammalian antibody but also amino acid sequences occurring in regions outside the CDRs that play a role either in maintaining the structure of the CDRs or in binding to the antigen, in order to reproduce the activity that the donor antibody originally possesses (Queen C. Proc. Natl. Acad. Sci. USA. 86. 10029-10033 (1989)). Here, the regions outside the CDRs are called framework (FR) regions.

Thus, preparation of humanized antibody involves processes of implanting the CDRs (and their neighboring FRs, as the case may be) of non-human mammalian antibody in place of the CDRs (and their neighboring FRs, as the case may be) in the variable region of a human antibody. In such processes, the starting framework region of the variable region of a human antibody can be obtained from a public DNA database and the like which includes germ line antibody genes. For example, germ line DNA sequences, as well as amino acid sequences, of human heavy chain and light chain variable regions can be selected from "VBase" human germline database (available in the Internet, at www.mrc-cpe.cam.ac.uk/vbase). Besides, they can be selected from DNA sequences and amino acid sequences described in published literatures, such as "Kabat EA. Sequences of Proteins of Immunological Interest, 5th Ed., U.S. Department of Health and Human Services, NIH Publication No. 91-3242 (1991)"; "Tomlinson IM. J. fol. Biol. 227. 776-98 (1992)"; and "Cox JPL. Eur. J Immunol 24:827-836 (1994)".

As aforementioned, in a humanized antibody, the regions of a non-human mammal antibody to be implanted into the variable regions of the original human antibody generally include CDRs themselves, or CDRs and their neighboring part of FRs. However, such FRs implanted together with CDRs also play a role either in maintaining the structure of the CDRs or in binding to the antigen, thus having a substantial function in determining the complementarity of an antibody, and the term "CDR" in the present invention, therefore, refers to such regions that are, or could be, taken from a non-human mammal antibody and grafted into a humanized antibody, in preparing a humanized antibody. Thus, a region generally considered to be in a FR region is included in a CDR in the present invention as far as it takes part either in maintaining the structure of the CDR or in binding to the antigen, and is thus considered to have a substantial function in determining the complementarity of the antigen.

The anti-hTfR antibody of the present invention, when administered to the body, e.g., by intravenous injection, efficiently binds to hTfR existing on the endothelial cells of the capillaries in the brain. The antibody bound to the hTfR is taken into the brain across the blood-brain barrier by such mechanisms as endocytosis, and transcytosis. Therefore, by binding to the anti-hTfR antibody of the present invention, proteins, low-molecular-weight compounds and the like that need to be brought into function in the brain, can be efficiently delivered into the brain across the blood-brain barrier. Further, the anti-hTfR antibody of the present invention can, after passing through the blood-brain barrier, can reach the cerebral parenchyma, and neuron-like cells in the hippocampus; Purkinje cells and the like of the cerebellum or at least one of them. And it is also expected that it reaches to the neuron-like cells in the striatum of the cerebrum; and the neuron-like cells in the substantia nigra of the mesencephalon. Therefore, it is possible to make one of those proteins, low-molecular-weight compounds and the like, which could act on such tissues or cells, reach the tissues or cells, by binding it to the anti-hTfR antibody of the present invention.

The anti-hTfR antibody of the present invention can be an effective means to make those compounds (proteins, low-molecular-weight compounds and the like) transfer from the blood into the brain and function there, which compounds otherwise cannot pass through the blood-brain barrier when intravenously administered and therefore cannot or can hardly exhibit their physiological or pharmacological functions in the brain. In particular, the anti-hTfR antibody of the present invention can, after passing through the blood-brain barrier, reach the cerebral parenchyma, and neuron-like cells in the hippocampus; Purkinje cells and the like of the cerebellum or at least one of them. And it is also expected that it reaches to the neuron-like cells in the striatum of the cerebrum; as well as to the neuron-like cells in the substantia nigra of the mesencephalon. Therefore, it is possible to make those compounds function or augment their function, in those tissues or cells in the brain by administering those compounds in a combined form with the anti-hTfR antibody molecule, parenterally, e.g., intravenously.

For binding an anti-hTfR antibody to such compounds (proteins, low-molecular-weight compounds and the like), a method is available to bind them together via a non-peptide linker or a peptide linker. As non-peptide linkers, there can be used polyethylene glycol, polypropylene glycol, copolymer of ethylene glycol and propylene glycol, polyoxyethylated polyol, polyvinyl alcohol, polysaccharides, dextran, polyvinyl ether, biodegradable polymer, polymerized lipid, chitins, and hyaluronic acid, or derivatives thereof, or combinations thereof. A peptide linker is a peptide chain consisting of 1 to 50 amino acids linked by peptide bonds or a derivative thereof, whose N-terminus and C-terminus are to be covalently bonded either to an anti-hTfR antibody or a compound such as a protein, a low-molecular-weight compound and the like, respectively, to bind the anti-hTfR antibody to such a compound like a protein or a low-molecular-weight compound.

In particular, a conjugate which is formed by binding the anti-hTfR antibody of the present invention to a desired different protein (A) via PEG as a non-peptide linker, is designated "anti-hTfR antibody-PEG-protein". An anti-hTfR antibody-PEG-protein can be prepared by first binding the anti-hTfR antibody to PEG to form anti-hTfR antibody-PEG, and then binding the anti-hTfR antibody-PEG to the different protein (A). Alternatively, an anti-hTfR antibody-PEG-protein can be prepared by first binding the different protein (A) to PEG to form "protein-PEG", and then binding the "protein-PEG" to the anti-hTfR antibody. In order to bind PEG to the anti-hTfR antibody and the different protein (A), a PEG is employed which is modified with such functional groups as carbonate, carbonylimidazole, active ester of carboxylic acid, azlactone, cyclic imide thione, isocyanate, isothiocyanate, imidate, aldehyde or the like. Such functional groups introduced to PEG react mainly with amino groups in the anti-hTfR antibody and a different protein (A) to covalently bind PEG to the hTfR antibody and a different protein (A). Though there is no particular limitation as to the molecular weight and the configuration of PEG employed here, its mean molecular weight (MW) is as follows: preferably MW=500 to 60000, more preferably MW=500 to 20000. For example, such PEG whose mean molecular weight is about 300, about 500, about 1000, about 2000, about 4000, about 10000, about 20000, and the like. PEG is preferably used as a non-peptide linker. The anti-hTfR antibody can be bound to a desired low-molecular-weight compound in the same manner as above.

For example, "anti-hTfR antibody-PEG" can be prepared by mixing the anti-hTfR antibody with a polyethylene glycol having aldehyde groups as functional groups (ALD-PEG-ALD) so that the molar ratio of ALD-PEG-ALD to the antibody is 11, 12.5, 15, 110, 120 and the like, and then adding to the mixture a reducing agent such as $NaCNBH_3$ to let a reaction take place. Then, by reacting "anti-hTfR antibody-PEG" with a different protein (A) in the presence of a reducing agent such as $NaCNBH_3$, "anti-hTfR antibody-PEG-protein" is obtained. On the contrary, it is also possible to obtain "anti-hTfR antibody-PEG-protein" by first binding a different protein (A) to ALD-PEG-ALD to prepare "protein-PEG", and then binding the "protein-PEG" to the anti-hTfR antibody.

The anti-hTfR antibody and a different protein (A) can also be bound together through peptide bonds by linking the anti-hTfR antibody heavy chain or light chain, on the C-terminal side or the N-terminal side thereof, either via a linker sequence or directly, to the N-terminus or the C-terminus of the different protein (A), respectively. Thus the fusion protein between the anti-hTfR antibody and a different protein (A) can be obtained by incorporating into a mammalian expression vector a DNA fragment in which a cDNA encoding the different protein (A) is placed in-frame directly, or via a DNA fragment encoding a linker sequence, on the 3'-end or 5'-end side of a cDNA encoding the heavy chain or light chain of the anti-hTfR antibody, and culturing mammalian cells into which the above expression vector has been introduced. Where the DNA fragment encoding a different protein (A) is linked to the heavy chain, a mammalian expression vector in which a cDNA fragment encoding the anti-hTfR antibody light chain is also introduced into the same host cells, whereas if DNA fragment encoding a different protein (A) is linked to the light chain, a mammalian expression vector in which a cDNA fragment encoding the anti-hTfR antibody heavy chain is also incorporated into the same host cells. In the case where the anti-hTfR antibody is a single-chain antibody, the fusion protein comprising the anti-hTfR antibody and a different protein (A) combined can be obtained by incorporating, into an expression vector (for eukaryotic cells such as mammalian and yeast, or for prokaryotic cells such as *E. coli*), a DNA fragment which is formed by linking the cDNA encoding a different protein (A), on the 5'-end side or on the 3'-end side thereof, directly or via a DNA fragment encoding a linker sequence, to the cDNA encoding the single-chain anti-hTfR antibody, and allowing the fusion protein be expressed in those cells into which the expression vector has been introduced.

In a fusion protein of the type in which a different protein (A) is linked to the anti-hTfR antibody light chain on the C-terminal side thereof, the anti-human transferrin receptor antibody comprises an amino acid sequence including the whole or part of the light chain variable region and an amino acid sequence including the whole or part of the heavy chain variable region, and the different protein (A) is linked to the light chain of this anti-human transferrin receptor antibody on the C-terminal side thereof. Here, the anti-hTfR antibody light chain and a different protein (A) may be linked together, directly or via a linker.

In a fusion protein of the type in which a different protein (A) is linked to the anti-hTfR antibody heavy chain on the C-terminal side thereof, the anti-human transferrin receptor antibody comprises an amino acid sequence including the whole or part of the light chain variable region and an amino acid sequence including the whole or part of the heavy chain variable region, and the different protein (A) is linked to the heavy chain of this anti-human transferrin receptor antibody on the C-terminal side thereof. Here, the anti-hTfR antibody heavy chain and a different protein (A) may be linked together, directly or via a linker.

In a fusion protein of the type in which a different protein (A) is linked to the anti-hTfR antibody light chain on the N-terminal side thereof, the anti-human transferrin receptor antibody comprises an amino acid sequence including the whole or part of the light chain variable region and an amino acid sequence including the whole or part of the heavy chain variable region, and the different protein (A) is linked to the light chain of this anti-human transferrin receptor antibody on the N-terminal side thereof. Here, the anti-hTfR antibody light chain and a different protein (A) may be linked together, directly or via a linker.

In a fusion protein of the type in which a different protein (A) is linked to the anti-hTfR antibody heavy chain on the N-terminal side thereof, the anti-human transferrin receptor antibody comprises an amino acid sequence including the whole or part of the light chain variable region and an amino acid sequence including the whole or part of the heavy chain variable region, and the different protein (A) is linked to the heavy chain of this anti-human transferrin receptor antibody on the N-terminal side thereof. Here, the anti-hTfR antibody heavy chain and a different protein (A) may be linked together, directly or via a linker.

In the above, the linker sequence placed between the anti-hTfR antibody and a different protein (A) may be a peptide chain consisting preferably of 1 to 50, more preferably of 1 to 17, still more preferably of 1 to 10, even more preferably of 1 to 5 amino acids, and in accordance with the different protein (A) to be linked to the anti-hTfR antibody, the number of amino acids of the linker sequence may be adjusted to 1, 2, 3, 1 to 17, 1 to 10, 10 to 40, 20 to 34, 23 to 31, 25 to 29, 27, etc., as desired. Though there is no particular limitation as to amino acid sequence of the linker sequence insofar as the anti-hTfR antibody linked by it retains the affinity to hTfR and a different protein (A) linked by the linker sequence also exhibits the protein's own physiological activity under a physiological condition, the linker may preferably be composed of glycine and serine. Examples of such linkers include one consisting of a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence which includes 1 to 10 or 2 to 5 of any of those amino acid sequences consecutively linked. They have sequences consisting of 1 to 50, 2 to 17, 2 to 10, 10 to 40, 20 to 34, 23 to 31, 25 to 29, or 27 amino acids. For example, those comprising the amino acid sequence Gly-Ser may preferably be used as linker sequences. Further, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

In a fusion protein of the anti-hTfR antibody and a different protein (A), where the anti-hTfR antibody is a single-chain antibody, the amino acid sequence including the whole or part of the immunoglobulin light chain variable region and the amino acid sequence including the whole or part of the immunoglobulin heavy chain variable region are linked, generally via a linker sequence. Insofar as the affinity of the anti-hTfR antibody to hTfR is retained, the amino acid sequence derived from the light chain may be linked, on the C-terminal side thereof, to a linker sequence which in turn being linked, on the C-terminal side thereof, to the amino acid sequence derived from the heavy chain or, conversely, the amino acid sequence derived from the heavy chain may be linked, on the C-terminal side thereof, to a linker sequence which in turn being linked, on the C-terminal side thereof, to the amino acid sequence derived from the light chain.

The linker sequence placed between the light chain and the heavy chain of the immunoglobulin is a peptide chain consisting preferably of 2 to 50, more preferably 8 to 50, still more preferably 10 to 30, even more preferably 12 to 18 or 15 to 25, and for example 15 or 25 amino acids. Though there is no specific limitation as to the linker sequence insofar as the anti-hTfR antibody made of the both chains which are linked via the linker retains the affinity to hTfR and a different protein (A) linked to the antibody also exhibits the protein's own physiological activity under a physiological condition, the linker is preferably composed of glycine, or glycine and serine. Examples of such linkers include the amino acid sequence Gly-Ser, the amino acid sequence Gly-Gly-Ser, the amino acid sequence Gly-Gly-Gly, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly) (SEQ ID NO:5), or a sequence which includes 2 to 10 or 2 to 5 of any of these amino acid sequences consecutively linked. A preferred embodiment of such a linker sequence comprises 15 amino acids consisting of consecutively linked three copies of the amino acid sequence Gly-Gly-Gly-Gly-Ser (SEQ ID NO:3).

In the case where the anti-hTfR antibody is a single-chain antibody, an example of specific embodiments of the fusion protein between the humanized anti-hTfR antibody of the present invention and a different protein (A) is a fusion protein consisting of the different protein (A) which is linked, on the C-terminal side thereof and via a first linker sequence consisting of 27 amino acids composed of the amino acid sequence Gly-Ser followed by consecutively linked five copies of the amino acid sequence Gly-Gly-Gly-Gly-Ser (SEQ ID NO:3), to the single-chain antibody. An example of a preferred embodiment of single-chain antibodies employed here is an antibody having the amino acid sequence set forth as SEQ ID NO:277, which is composed of the amino acid sequence of the anti-hTfR antibody heavy chain variable region set forth as SEQ ID NO:205 that is linked, at the C-terminus thereof and via a first linker sequence consisting of 15 amino acids consisting of consecutively linked three copies of the amino acid sequence Gly-Gly-Gly-Gly-Ser (SEQ ID NO:3), to the anti-hTfR antibody light chain variable region having the amino acid sequence set forth as SEQ ID NO:191.

Where the anti-hTfR antibody is a single-chain antibody, such a fusion protein can be produced by, for example, transforming host cells such as mammalian cells with an expression vector having an incorporated DNA fragment containing a nucleotide sequence encoding the fusion protein, and then culturing the host cells.

Besides, in the present invention, when a peptide chain includes a plurality of linker sequences, each of those linker sequences is designated, from the N-terminal side, the first linker sequence, the second linker sequence, and so on, for convenience.

In the case where the anti-hTfR antibody is Fab, an example of specific embodiments of the fusion protein between a humanized anti-hTfR antibody and a different protein (A) of the present invention is a fusion protein which is composed of the different protein (A) that is fused, on the C-terminal side thereof and via a linker sequence consisting of 27 amino acids composed of Gly-Ser followed by consecutively linked five copies of the amino acid sequence Gly-Gly-Gly-Gly-Ser (SEQ ID NO:3), to a region having the anti-hTfR antibody heavy chain variable region and the $C_H1$ region. Though part of the hinge region may be included in addition to the $C_H1$ region here, the hinge region includes no cysteine residue which would form a disulfide bond between heavy chains.

Though there is no particular limitation as to the different protein (A) to be linked to the anti-hTfR antibody, it is a protein that can exhibit its physiological activity in the body, and in particular, such a protein that needs to get inside the brain and exhibit its function there but, due to its inability to pass through the blood-brain barrier as it is, cannot be expected to function in the brain if simply administered intravenously. Examples of such proteins include lysosomal enzymes such as nerve growth factor (NGF), α-L-iduronidase, iduronate 2-sulfatase, glucocerebrosidase, β-galactosidase, GM2 activator protein, β-hexosaminidase A, β-hexosaminidase B, N-acetylglucosamine-1-phosphotransferase, α-mannosidase, β-mannosidase, galactosylceramidase, saposin C, arylsulfatase A, α-L-fucosidase, aspartylglucosaminidase, α-N-acetylgalactosaminidase, acidic sphingomyelinase, α-galactosidase A, β-glucuronidase, heparan N-sulfatase, α-N-acetylglucosaminidase, acetyl CoA:α-glucosaminide N-acetyltransferase, N-Acetylglucosamine-6-sulfate sulfatase, acid ceramidase, amylo-1,6-glucosidase, sialidase, aspartylglucosaminidase (PPT1), tripeptidyl-peptidase 1, hyaluronidase 1, CLN1, and CLN2, and the like.

The nerve growth factor (NGF) linked to the anti-hTfR antibody can be used as a therapeutic agent for dementia in Alzheimer's disease; α-L-iduronidase linked to the anti-hTfR antibody as a therapeutic agent for central nervous system disorders in Hurler syndrome or Hurler-Scheie syndrome; iduronate 2-sulfatase linked to the anti-hTfR antibody as a therapeutic agent for central nervous system disorders in Hunter syndrome; glucocerebrosidase as a therapeutic agent for central nervous system disorders in Gaucher's disease; β-galactosidase as a therapeutic agent for central nervous system disorders in GM1 gangliosidosis Types 1 to 3; GM2 activator protein as a therapeutic agent for central nervous system disorders in GM2-gangliosidosis, AB variant; β-hexosaminidase A as a therapeutic agent for central nervous system disorders in Sandhoffs disease and Tay-Sachs disease; β-hexosaminidase B as a therapeutic agent for central nervous system disorders in Sandhoffs disease; N-acetylglucosamine-1-phosphotransferase as a therapeutic agent for central nervous system disorders in I-cell disease; α-mannosidase as a therapeutic agent for central nervous system disorders in α-mannosidosis; β-mannosidase as a therapeutic agent for central nervous system disorders in β-mannosidosis; galactosylceramidase as a therapeutic agent for central nervous system disorders in Krabbe disease; saposin C as a therapeutic agent for central nervous system disorders in Gaucher's disease-like storage disease; arylsulfatase A as a therapeutic agent for central nervous system disorders in metachromatic white matter degeneration (metachromatic leukodystrophy); α-L-fucosidase as a therapeutic agent for central nervous system disorders in fucosidosis; aspartylglucosaminidase as a therapeutic agent for central nervous system disorders in aspartylglucosaminuria; α-N-acetylgalactosaminidase as a therapeutic agent for central nervous system disorders in Schindler disease and Kawasaki disease; acidic sphingomyelinase as a therapeutic agent for central nervous system disorders in Niemann-Pick disease; α-galactosidase A as a therapeutic agent for central nervous system disorders in Fabry disease; β-glucuronidase as a therapeutic agent for central nervous system disorders in Sly syndrome; heparan N-sulfatase, α-N-acetylglucosaminidase, acetyl CoA: α-glucosaminide N-acetyltransferase and N-Acetylglucosamine-6-sulfate sulfatase as therapeutic agents for central nervous system disorders in Sanfilippo syndrome; acid ceramidase as a therapeutic agent for central nervous system disorders in Farber disease; amylo-1,6-glucosidase as a therapeutic agent for central nervous system disorders in Cori's disease (Forbes-Cori's disease); sialidase as a therapeutic agent for central nervous system disorders in sialidase deficiency; aspartylglucosaminidase as a therapeutic agent for central nervous system disorders in aspartylglucosaminuria; palmitoyl protein thioesterase 1 (PPT-1) as a therapeutic agent for central nervous system disorders in neuronal ceroid lipofuscinosis or Santavuori-Haltia disease; tripeptidyl-peptidase 1 (TPP-1) as a therapeutic agent for central nervous system disorders in neuronal ceroid lipofuscinosis or Jansky-Bielschowsky disease; hyaluronidase 1 as a therapeutic agent for central nervous system disorders in hyaluronidase deficiency; CLN1 and CLN2 as therapeutic agents for central nervous system disorders in Batten disease. In particular, the anti-hTfR antibody of the present invention, after passing through the blood-brain barrier, reaches the brain parenchyma and the hippocampus neuron-like cells of the cerebrum, and Purkinje cells of the cerebellum, and is expected further to reach neuron-like cells of the striatum of the cerebrum and the neuron-like cells of the substantia nigra of the mesencephalon. Therefore, the anti-hTfR antibody can be fused with proteins which need to exhibit their functions in those tissues or cells to strength the pharmacological effects of the proteins. Medical applications of it, however, are not limited thereto.

Further, examples of proteins that can exhibit their pharmacological effects when linked to the anti-hTfR antibody include: lysosomal enzymes, ciliary neurotrophic factor (CNTF), glial cell line derived neurotrophic factor (GDNF), neurotrophin-3, neurotrophin-4/5, neurotrophin-6, neuregulin-1, erythropoietin, darbepoetin, activin, basic fibroblast growth factor (bFGF), fibroblast growth factor 2 (FGF2), epidermal growth factor (EGF), vascular endothelial growth factor (VEGF), interferon α, interferon β, interferon γ, interleukin 6, granulocyte-macrophage colony stimulating factor (GM-CSF), granulocyte colony stimulating factor (G-CSF), macrophage colony stimulating factor (M-CSF), cytokines, tumor necrosis factor α receptor (TNF-α receptor), PD-1 ligands, enzymes having β-amyloid-degrading activity, anti-β-amyloid antibody, anti-BACE antibody, anti-EGFR antibody, anti-PD-1 antibody, anti-PD-L1 antibody, anti-HER2 antibody, anti-TNF-α antibody, and other antibody medicines.

Lysosomal enzymes linked to the anti-hTfR antibody can be used as a therapeutic agent for central nervous system disorders in lysosomal storage diseases; CNTF as a therapeutic agent for amyotrophic lateral sclerosis; GDNF, neurotrophin-3 and neurotrophin-4/5 as therapeutic agents for cerebral ischemia; GDNF as a therapeutic agent for Parkinson's disease; neuregulin-1 as a therapeutic agent for schizophrenia; erythropoietin and darbepoetin as therapeutic agents for cerebral ischemia; bFGF and FGF2 as therapeutic agents for traumatic central nervous system disorders; for recovery after brain surgery and spinal surgery; enzymes having β-amyloid-degrading activity, anti-β-amyloid antibody and anti-BACE antibody as therapeutic agents for Alzheimer's disease; anti-EGFR antibody, anti-PD-1 antibody, anti-PD-L 1 antibody, and anti-HER2 antibody as therapeutic agents for tumors of central nervous system including brain tumor; and TNFαR-anti-hTfR antibody as therapeutic agents for a cerebral ischemia and encephalitis.

Possible candidates for a "different protein (A)" to be fused to the anti-hTfR antibody generally include those therapeutic agents for diseases such as neurodegenerative diseases such as Alzheimer's disease, Parkinson's disease, and Huntington's disease; mental disorders such as schizophrenia and depression; multiple sclerosis; amyotrophic lateral sclerosis; tumors of the central nervous system including brain tumor; lysosomal storage diseases accompanied by encephalopathy; glycogenosis; muscular dystrophy; cerebral ischemia; encephalitis; prion diseases; traumatic central nervous system disorders. In addition, therapeutic agent for viral and bacterial central nervous system diseases can also be candidates for a different protein (A) to be fused to the anti-hTfR antibody, in general. Further, pharmaceutical agents that can be used for recovery after brain surgery or spinal surgery can also be candidates for a "different protein (A)" to be fused to the anti-hTfR antibody, in general.

In addition to the above mentioned natural-type (wild-type) proteins, a different protein (A) to be linked to the anti-hTfR antibody may also be one of their analogues in which one or more amino acids of those natural-type (wild-type) proteins are modified, e.g., replaced with other amino acids or deleted, insofar as they fully or partly have the functions of their respective original proteins. When replacing one or more amino acids with other amino acids, the number of amino acids to be replaced is preferably 1 to 10, more preferably 1 to 5, still more preferably 1 to 3. When deleting one or more amino acids, the number of amino acids to be deleted is preferably 1 to 10, more preferably 1 to 5, still more preferably 1 to 3. A combination of such substitution and deletion of amino acids can also be carried out to prepare desired analogues. Further, amino acid sequences produced by adding one or more amino acids inside, or on the N-terminal side or on the C-terminal side of, the amino acid sequence of natural-type (wild-type) proteins or their analogues, are also included in the proteins mentioned above insofar as they fully or partly have the functions of their respective original proteins. The number of amino acids to be added here is preferably 1 to 10, more preferably 1 to 5, still more preferably 1 to 3. It is also possible to prepare desired analogues to the original proteins by combining addition, substitution, and deletion of amino acids.

Besides, in the case where a mutation is introduced into a different protein (A) by adding one or more amino acids on its C-terminus or the N-terminus, if the added amino acids are positioned between the protein and the anti-hTfR antibody when they are fused, the added amino acids constitute part of a linker.

The natural-type human I2S (hI2S) is a lysosomal enzyme composed of 525 amino acids set forth as SEQ ID NO:246. A specific example of fusion proteins of the present invention between the anti-hTfR antibody and a different protein (A) is a type in which the anti-hTfR antibody heavy chain is fused, on the C-terminus thereof and via the amino acid sequence Gly-Ser as a linker sequence, to the natural-type human I2S. Examples of such a type of fusion proteins include:

(1) one whose light chain consists of the amino acid sequence set forth as SEQ ID NO:164, and whose heavy chain linked by peptide pond, on the C-terminal side thereof and via the linker sequence Gly-Ser, to human I2S forms the amino acid sequence set forth as SEQ ID NO:247, (2) one whose light chain consists of the amino acid sequence set forth as SEQ ID NO:180, and whose heavy chain linked by peptide pond, on the C-terminal side thereof and via the linker sequence Gly-Ser, to human 12S forms the amino acid sequence set forth as SEQ ID NO:249, and (3) one whose light chain consists of the amino acid sequence set forth as SEQ ID NO:196, and whose heavy chain linked by peptide pond, on the C-terminal side thereof and via the linker sequence Gly-Ser, to human 12S forms the amino acid sequence set forth as SEQ ID NO:251.

In the present invention, though the term "human 12S" or "hI2S" refers, in particular, to the hI2S having the same amino acid sequence as the natural-type hI2S, it also includes those amino acid sequences produced by introducing a mutation, such as substitution, deletion, addition and the like, into the amino acid sequence of the natural-type hI2S, insofar as they have the I2S activity. When replacing one or more of the amino acids of the amino acid sequence of hI2S with other amino acids, the number of amino acids to be replaced is preferably 1 to 10, more preferably 1 to 5, still more preferably 1 to 3, even more preferably 1 to 2. When deleting one or more amino acids of the amino acid sequence of hI2S, the number of amino acids to be deleted is 1 to 10, more preferably 1 to 5, still more preferably 1 to 3, and even more preferably 1 or 2. It is also possible to introduce a combined mutation of such substitution and deletion of amino acids. When adding one or more amino acids to hI2S, they may be added, inside, or on the N-terminal side or the C-terminal side of, the amino acid sequence of hI2S, and the number of amino acids to be added is preferably 1 to 10, more preferably 1 to 5, still more preferably 1 to 3, even more preferably 1 or 2. It is also possible to introduce a combined mutation of such addition, substitution, and deletion of the amino acid. The amino acid sequence of the mutated hI2S has a homology of preferably not lower than 80%, more preferably not lower than 90%, still more preferably not lower than 95% to the amino acid sequence of the original hI2S.

The statement that hI2S has the I2S activity herein means that the hI2S fused to anti-hTfR antibody has an activity not lower than 3% of the activity that the natural-type hI2S intrinsically has. However, the activity is preferably not lower than 10%, more preferably not lower than 20%, still more preferably not lower than 50%, even more preferably not lower than 80% of the activity that the natural-type hI2S intrinsically has. The same also applies if the hI2S fused to the anti-hTfR antibody is mutated.

The fusion protein between the anti-hTfR antibody and human I2S can be produced by, for example, transforming host cells, such as mammalian cells, with an expression vector having an incorporated DNA fragment comprising the nucleotide sequence set forth as SEQ ID NO:250 that encodes the amino acid sequence set forth as SEQ ID NO:249 and an expression vector having an incorporated DNA fragment comprising the nucleotide sequence set forth as SEQ ID NO:181 that encodes the anti-hTfR antibody light chain having the amino acid sequence set forth as SEQ ID NO:180, and then culturing the host cells. The fusion protein thus produced can be used as a therapeutic agent for Hunter disease, in particular, a therapeutic agent for central nervous system disorders accompanying Hunter disease.

Besides, in the case where the anti-hTfR antibody or human I2S is mutated by adding one or more amino acids to them on the C-terminus or the N-terminus thereof, if the added amino acids are positioned between the anti-hTfR antibody and human I2S, the added amino acids constitute part of a linker.

Though examples of fusion proteins between the anti-hTfR antibody and human 12S are described above, there is no particular limitation as to the amino acid sequence of the CDRs of the anti-hTfR antibody heavy chain and light chain in preferred embodiments of fusion protein of the anti-hTfR antibody and human I2S insofar as the antibody has a specific affinity to hTfR. However, the anti-hTfR antibody of the present invention exhibits a dissociation constant ($K_D$) with hTfR, as measured by the method described in Example 7, that is preferably not greater than $1\times10^{-8}$M, more preferably not greater than $1\times10^{-9}$ M, still more preferably not greater than $1\times10^{-1}$°. For example, one which exhibits a dissociation constant of $1\times10^{-13}$M to $1\times10^{-9}$M or $1\times10^{-13}$M to $1\times10^{-10}$ M is preferred. The same also applies when the antibody is a single-chain antibody. Further, in the case where the anti-hTfR antibody of the present invention has also an affinity to monkey TfR, the dissociation constant of the anti-hTfR antibody with monkey TfR, as measured by the method described in Example 7, is preferably not greater than $5\times10^{-8}$M, more preferably not greater than $2\times10^{-8}$ M, still more preferably not greater than $1\times10^{-8}$ M. For example, one which exhibits a dissociation constant of $1\times10^{-13}$ M to $2\times10^{-8}$ M is preferred. The same also applies when the antibody is a single-chain antibody.

It is also possible to link a relatively short peptide chain to the anti-hTfR antibody, in the same manner as in linking a different protein (A) to the anti-hTfR antibody. There is no particular limitation as to a peptide chain to be linked to the anti-hTfR antibody, insofar as the peptide chain has a desired physiological activity. For example, there are peptide chains comprising the amino acid sequence of such a region of various proteins that exhibits a physiological activity. Though there is no particular limitation as to the length of the peptide chain, they are composed of preferably 2 to 200 amino acids, for example of 5 to 50 amino acids.

In linking a low-molecular-weight compound to the anti-hTfR antibody, there is no particular limitation as to candidate low-molecular-weight compounds, but they are such low-molecular-weight compound that though needed to get inside the brain and function there, due to their inability to pass through the blood-brain barrier as it is, cannot be expected to function in the brain if simply administered intravenously. Examples of such low-molecular-weight compounds include anticancer drug such as cyclophosphamide, ifosfamide, melphalan, busulfan, thioTEPA, nimustine, ranimustine, dacarbazine, procarbazine, temozolomide, carmustine, streptozocin, bendamustine, cisplatin, carboplatin, oxaliplatin, nedaplatin, 5-fluorouracil, sulfadiazine, sulfamethoxazole, methotrexate, trimethoprim, pyrimethamine, fluorouracil, flucytosine, azathioprine, pentostatin, hydroxyurea, fludarabine, cytarabine, gemcitabine, irinotecan, doxorubicin, etoposide, levofloxacin, ciprofloxacin, vinblastine, vincristine, paclitaxel, docetaxel, Mitomycin C, doxorubicin, epirubicin. Further examples of low-molecular-weight compound to be linked to the anti-hTfR antibody include siRNAs, antisense DNAs, and short peptides.

In linking between the anti-hTfR antibody and a low-molecular-weight compound, either a low-molecular-weight compound may be linked only to either the light chain or the heavy chain, or it may be linked to both the light chain and the heavy chain, respectively. Further, insofar as it has an affinity to hTfR, the anti-hTfR antibody may comprise an amino acid sequence comprising the whole of part of the light chain variable region and/or an amino acid sequence comprising the whole of part of the heavy chain variable region.

Candidates for low-molecular-weight compounds to be fused with the anti-hTfR antibody can generally be those therapeutic agents for diseases such as neurodegenerative diseases such as Alzheimer's disease, Parkinson's disease, Huntington's disease; mental disorders such as schizophrenia, depression; multiple sclerosis; amyotrophic lateral sclerosis; tumor of the central nervous system including brain tumor; lysosomal storage diseases with accompanying encephalopathy; glycogenosis; muscular dystrophy; cerebral ischemia; encephalitis; prion diseases; traumatic disorders of the central nervous system. Further, therapeutic agents for viral and bacterial central nervous system diseases can also be candidates, in general, for low-molecular-weight compounds to be fused with the anti-hTfR antibody. Still further, those pharmaceutical agents which can be used for recovery after brain surgery or spinal surgery can also be candidates, in general, for low-molecular-weight compounds to be fused.

If an anti-hTfR antibody originates from a non-human animal, its administration to human could entail a substantial risk of causing an antigen-antibody interaction, thereby provoking adverse side-effects. By converting them to humanized antibodies, the antigenicity of non-human animal antibodies can be reduced and therefore the provocation of side-effects due to antigen-antibody interaction can be suppressed when administered to a human. Further, it has been reported that according to experiments using monkeys, humanized antibodies are more stable than mouse antibodies in the blood, and it is expected that their therapeutic effect can therefore become longer-lasting accordingly. Provocation of side-effects due to an antigen-antibody interaction can be suppressed also by employing a human antibody as the anti-hTfR antibody.

A detailed explanation will be given below regarding the case where the anti-hTfR antibody is a humanized antibody or human antibody. In human antibody light chain, there are λ and κ chains. The light chain constituting the human antibody may either be λ and κ chain. And in human heavy chain, there are γ, μ, α, σ, and ε chains, which correspond to IgG IgM, IgA, IgD and IgE, respectively. Though the heavy chain constituting the anti-hTfR antibody may be any one of γ, μ, α, σ, and ε chains, preferred is a γ chain. Further, in γ chain of human heavy chain, there are γ1, γ2, γ3 and γ4 chains, which correspond to IgG1, IgG2, IgG3 and IgG4, respectively. Where the heavy chain constituting the anti-hTfR antibody is a γ chain, though the γ chain may be any of γ1, γ2, γ3 and γ4 chains, preferred is a γ1 or γ4 chain. In the case where the anti-hTfR antibody is a humanized antibody or human antibody and IgG, the human antibody light chain may either be λ chain or κ chain, and though the human antibody heavy chain may either be γ1, γ2, γ3 and γ4 chains, preferred is a γ1 or γ4 chain. For example, a preferable embodiment of anti-hTfR antibody includes one whose light chain is a λ chain and heavy chain is a γ1 chain.

In the case where the anti-hTfR antibody is a humanized antibody or a human antibody, the anti-hTfR antibody and a different protein (A) may be bound together by linking the anti-hTfR antibody, at the N-terminus (or the C-terminus) of the heavy chain or light chain, via a linker sequence or directly, to the C-terminus (or the N-terminus), respectively, of the different protein (A), by peptide bonds. When linking the different protein (A) to the anti-hTfR antibody heavy chain on the N-terminal side (or to the C-terminal side) thereof, the C-terminus (or the N-terminus), respectively, of the different protein (A) is linked to the N-terminus (or the C-terminus) of the γ, μ, α, σ or ε chain of anti-hTfR antibody, via a linker sequence or directly, by peptide bonds. When linking the different protein (A) to the anti-hTfR antibody light chain on the N-terminal side (or the C-terminal side) thereof, the C-terminus (or the N-terminus), respectively, of the different protein (A) in linked to the N-terminus (or the C-terminus) of the λ chain and κ chain of anti-hTfR antibody, via a linker sequence or directly, by peptide bonds. However, in the case where the anti-hTfR antibody consists of the Fab region, or of the Fab region and the whole or part of the hinge region (Fab, F(ab')2, and F(ab')), the different protein (A) may be linked at the C-terminus (or the N-terminus) thereof and via a linker sequence or directly, to the N-terminus (or the C-terminus), respectively, of the heavy chain or light chain that constitutes the Fab, F(ab')2 and F(ab'), by peptide bonds.

In a fusion protein produced by linking the different protein (A) to the light chain of the anti-hTfR antibody which is a humanized antibody, or a human antibody, on the C-terminal side thereof, the anti-human transferrin receptor antibody comprises an amino acid sequence comprising the whole or part of the light chain variable region and the amino acid sequence comprising the whole or part of the heavy chain variable region. The anti-hTfR antibody light chain and the different protein (A) here may be linked directly or via a linker.

In a fusion protein produced by linking the different protein (A) to the heavy chain of the anti-hTfR antibody which is a humanized antibody, or human antibody, on the C-terminal side thereof, the anti-human transferrin receptor antibody comprises an amino acid sequence comprising the whole or part of the light chain variable region and the amino acid sequence comprising the whole or part of the heavy chain variable region. The anti-hTfR antibody heavy chain and the different protein (A) here may be linked directly or via a linker.

In a fusion protein produced by linking the different protein (A) to the light chain of the anti-hTfR antibody which is a humanized antibody, or a human antibody, on the N-terminal side thereof, the anti-human transferrin receptor antibody comprises an amino acid sequence comprising the whole or part of the light chain variable region and the amino acid sequence comprising the whole or part of the heavy chain variable region. The anti-hTfR antibody light chain and the different protein (A) here may be linked directly or via a linker.

In a fusion protein produced by linking the different protein (A) to the heavy chain of the anti-hTfR antibody which is a humanized antibody, or human antibody, on the N-terminal side thereof, the anti-human transferrin receptor antibody comprises an amino acid sequence comprising the whole or part of the light chain variable region and the amino acid sequence comprising the whole or part of the heavy chain variable region. The anti-hTfR antibody heavy chain and the different protein (A) here may be linked directly or via a linker.

When placing a linker sequence between the anti-hTfR antibody and a different protein (A), the linker sequence is preferably a peptide chain consisting of 1 to 50 amino acids, though the number of the amino acids constituting such a linker sequence may be adjusted as desired in accordance with the different protein (A) to be linked to the anti-hTfR antibody, like 1 to 17, 1 to 10, 10 to 40, 20 to 34, 23 to 31, 25 to 29, and so on. While there is no particular limitation as to the specific amino acid sequence of such a linker sequence insofar as the anti-hTfR antibody and the different protein (A) linked by the linker sequence retain their respective functions (affinity to hTfR, and activity or function under a physiological condition), it is preferably composed of glycine or serine, for example, one consisting of a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence which includes 1 to 10 or 2 to 5 of any of those amino acid sequences consecutively linked. For example, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

Besides, when stated here that a different protein (A) fused with the anti-hTfR antibody retains its activity or function under a physiological condition, or simply, it "retains the activity", it means that in comparison with the intrinsic activity of the natural-type of the different protein (A), not lower than 3% of the activity or function is retained. However, such an activity or function is preferably not lower than 10%, more preferably not lower than 20%, still more preferably not lower than 50%, and even more preferably not lower than 80%, in comparison with the intrinsic activity of the natural-type of the different protein (A). The same also applies where the different protein (A) fused with the anti-hTfR antibody is a mutated one.

A further example of specific embodiments of the fusion protein between a humanized anti-hTfR antibody and a different protein (A) of the present invention is one produced by fusing the anti-hTfR antibody heavy chain, on the C-terminal side thereof, with a different protein (A), via a linker sequence consisting of 27 amino acids that is composed of the amino acid sequence Gly-Ser followed by consecutively linked five copies of the amino acid sequence Gly-Gly-Gly-Gly-Ser (SEQ ID NO:3).

In the case where the anti-hTfR antibody is Fab, an example of specific embodiments of fusion proteins between a humanized anti-hTfR antibody of the present invention and a different protein (A) is one produced by fusing a different protein (A), on the C-terminal side thereof via a linker sequences, with the region consisting of anti-hTfR antibody heavy chain variable region and its accompanying $C_H1$ region, wherein the linker sequence consists of 27 amino acids that is composed of the amino acid sequence Gly-Ser followed by consecutively linked five copies of the amino acid sequence Gly-Gly-Gly-Gly-Ser (SEQ ID NO:3). Though it is also allowed here that part of the hinge region is also besides the $C_H1$ region, the hinge region does not contain a cysteine residue that would form a disulfide bond between heavy chains.

The specific affinity of the anti-hTfR antibody to hTfR resides mainly in the amino acid sequences of CDRs of the heavy chain and light chain of the anti-hTfR antibody. There is no particular limitation as to the amino acid sequences of those CDRs insofar as the anti-hTfR antibody has a specific affinity to hTfR. However, the anti-hTfR antibody of the present invention is one whose dissociation constant ($K_D$) with hTfR as measured by the method described in Example 7 is preferably not greater than $1\times10^{-8}$M, more preferably not greater than $1\times10^{-9}$ M, still more preferably not greater than $1\times10^{-10}$ M, and even more preferably not greater than $1\times10^{-11}$ M. For example, one having a dissociation constant of $1\times10^{-13}$ M to $1\times10^{-9}$M, or $1\times10^{-13}$ M to $1\times10^{-10}$ M is preferable. The same also applies when the antibody is a single-chain antibody. Further, where the anti-hTfR antibody of the present invention has affinity also to monkey TfR, the dissociation constant of the anti-hTfR antibody with monkey TfR, as measured by the method described in Example 7, is preferably not greater than $5\times10^{-8}$ M, more preferably not greater than $2\times10^{-8}$M, and still more preferably not greater than $1\times10^{-8}$ M. For example, one which exhibits a dissociation constant of $1\times10^{-13}$M to $2\times10^{-8}$M is preferred. The same also applies if the antibody is a single-chain antibody.

Examples of preferable embodiments of the antibody having affinity to hTfR include those whose light chain CDRs have amino acid sequences according to one of (1) to (14) below:

(1) the amino acid sequence set forth as SEQ ID NO:6 or SEQ ID NO:7 as CDR1; the amino acid sequence set forth as SEQ ID NO:8 or SEQ ID NO:9 or the amino acid sequence Trp-Thr-Ser as CDR2; and the amino acid sequence set forth as SEQ ID NO:10 as CDR3;

(2) the amino acid sequence set forth as SEQ ID NO:11 or SEQ ID NO:12 as CDR1; the amino acid sequence set forth as SEQ ID NO:13 or SEQ ID NO:14 or the amino acid sequence Tyr-Ala-Ser as CDR2; and the amino acid sequence set forth as SEQ ID NO:15 as CDR3;

(3) the amino acid sequence set forth as SEQ ID NO:16 or SEQ ID NO:17 as CDR1; the amino acid sequence set forth as SEQ ID NO:18 or SEQ ID NO:19 or the amino acid sequence Lys-Val-Ser as CDR2; and the amino acid sequence set forth as SEQ ID NO:20 as CDR3;

(4) the amino acid sequence set forth as SEQ ID NO:21 or SEQ ID NO:22 as CDR1; the amino acid sequence set forth as SEQ ID NO:23 or SEQ ID NO:24 or the amino acid sequence Asp-Thr-Ser as CDR2; and the amino acid sequence set forth as SEQ ID NO:25 as CDR3;

(5) the amino acid sequence set forth as SEQ ID NO:26 or SEQ ID NO:27 as CDR1; the amino acid sequence set forth as SEQ ID NO:28 or SEQ ID NO:29 or the amino acid sequence Asp-Thr-Ser as CDR2; and the amino acid sequence set forth as SEQ ID NO:30 as CDR3;

(6) the amino acid sequence set forth as SEQ ID NO:31 or SEQ ID NO:32 as CDR1; the amino acid sequence set forth as SEQ ID NO:33 or SEQ ID NO:34 or the amino acid sequence Ala-Ala-Ser as CDR2; and the amino acid sequence set forth as SEQ ID NO:35 as CDR3;

(7) the amino acid sequence set forth as SEQ ID NO:36 or SEQ ID NO:37 as CDR1; the amino acid sequence set forth as SEQ ID NO:38 or SEQ ID NO:39 or the amino acid sequence Gln-Thr-Ser as CDR2; and the amino acid sequence set forth as SEQ ID NO:40 as CDR3;

(8) the amino acid sequence set forth as SEQ ID NO:41 or SEQ ID NO:42 as CDR1; the amino acid sequence set forth as SEQ ID NO:43 or SEQ ID NO:44 or the amino acid sequence Gly-Thr-Ser as CDR2; and the amino acid sequence set forth as SEQ ID NO:45 as CDR3;

(9) the amino acid sequence set forth as SEQ ID NO:46 or SEQ ID NO:47 as CDR1; the amino acid sequence set forth as SEQ ID NO:48 or SEQ ID NO:49 or the amino acid sequence Phe-Thr-Ser as CDR2; and the amino acid sequence set forth as SEQ ID NO:50 as CDR3;

(10) the amino acid sequence set forth as SEQ ID NO:51 or SEQ ID NO:52 as CDR1; the amino acid sequence set forth as SEQ ID NO:53 or SEQ ID NO:54 or the amino acid sequence Ala-Ala-Ser as CDR2; and the amino acid sequence set forth as SEQ ID NO:55 as CDR3;

(11) the amino acid sequence set forth as SEQ ID NO:56 or SEQ ID NO:57 as CDR1; the amino acid sequence set forth as SEQ ID NO:58 or SEQ ID NO:59 or the amino acid sequence Tyr-Ala-Ser as CDR2; and the amino acid sequence set forth as SEQ ID NO:60 as CDR3;

(12) the amino acid sequence set forth as SEQ ID NO:61 or SEQ ID NO:62 as CDR1; the amino acid sequence set forth as SEQ ID NO:63 or SEQ ID NO:64 or the amino acid sequence Trp-Ser-Ser as CDR2; and the amino acid sequence set forth as SEQ ID NO:65 as CDR3;

(13) the amino acid sequence set forth as SEQ ID NO:66 or SEQ ID NO:67 as CDR1; the amino acid sequence set forth as SEQ ID NO:68 or SEQ ID NO:69 or the amino acid sequence Tyr-Ala-Ser as CDR2; and the amino acid sequence set forth as SEQ ID NO:70 as CDR3; and

(14) the amino acid sequence set forth as SEQ ID NO:71 or SEQ ID NO:72 as CDR1; the amino acid sequence set forth as SEQ ID NO:73 or SEQ ID NO:74 or the amino acid sequence Asp-Thr-Ser as CDR2; and the amino acid sequence set forth as SEQ ID NO:75 as CDR3.

Examples of more specific embodiments of the antibody having affinity to hTfR include those whose light chain CDRs have amino acid sequences according to one of (1) to (14) below:

(1) the amino acid sequence set forth as SEQ ID NO:6 as CDR1; SEQ ID NO:8 as CDR2; and SEQ ID NO:10 as CDR3;

(2) the amino acid sequence set forth as SEQ ID NO:11 as CDR1; SEQ ID NO:13 as CDR2; and SEQ ID NO:15 as CDR3;

(3) the amino acid sequence set forth as SEQ ID NO:16 as CDR1; SEQ ID NO:18 as CDR2; and SEQ ID NO:20 as CDR3;

(4) the amino acid sequence set forth as SEQ ID NO:21 as CDR1; SEQ ID NO:23 as CDR2; and SEQ ID NO:25 as CDR3;

(5) the amino acid sequence set forth as SEQ ID NO:26 as CDR1; SEQ ID NO:28 as CDR2; and SEQ ID NO:30 as CDR3;

(6) the amino acid sequence set forth as SEQ ID NO:31 as CDR1; SEQ ID NO:33 as CDR2; and SEQ ID NO:35 as CDR3;

(7) the amino acid sequence set forth as SEQ ID NO:36 as CDR1; SEQ ID NO:38 as CDR2; and SEQ ID NO:40 as CDR3;

(8) the amino acid sequence set forth as SEQ ID NO:41 as CDR1; SEQ ID NO:43 as CDR2; and SEQ ID NO:45 as CDR3;

(9) the amino acid sequence set forth as SEQ ID NO:46 as CDR1; SEQ ID NO:48 as CDR2; and SEQ ID NO:50 as CDR3;

(10) the amino acid sequence set forth as SEQ ID NO:51 as CDR1; SEQ ID NO:53 as CDR2; and SEQ ID NO:55 as CDR3;

(11) the amino acid sequence set forth as SEQ ID NO:56 as CDR1; SEQ ID NO:58 as CDR2; and SEQ ID NO:60 as CDR3;

(12) the amino acid sequence set forth as SEQ ID NO:61 as CDR1; SEQ ID NO:63 as CDR2; and SEQ ID NO:65 as CDR3;

(13) the amino acid sequence set forth as SEQ ID NO:66 as CDR1; SEQ ID NO:68 as CDR2; and SEQ ID NO:70 as CDR3; and

(14) the amino acid sequence set forth as SEQ ID NO:71 as CDR1; SEQ ID NO:73 as CDR2; and SEQ ID NO:75 as CDR3;

Examples of preferable embodiments of the antibody having affinity to hTfR include those whose heavy chain CDRs have amino acid sequences according to one of (1) to (14) below:

(1) the amino acid sequence set forth as SEQ ID NO:76 or SEQ ID NO:77 as CDR1; the amino acid sequence set forth as SEQ ID NO:78 or SEQ ID NO:79 as CDR2; and the amino acid sequence set forth as SEQ ID NO:80 or SEQ ID NO:81 as CDR3;

(2) the amino acid sequence set forth as SEQ ID NO:82 or SEQ ID NO:83 as CDR1; the amino acid sequence set forth as SEQ ID NO:84 or SEQ ID NO:85 as CDR2; and the amino acid sequence set forth as SEQ ID NO:86 or SEQ ID NO:87 as CDR3;

(3) the amino acid sequence set forth as SEQ ID NO:88 or SEQ ID NO:89 as CDR1; the amino acid sequence set forth as SEQ ID NO:90 or SEQ ID NO:91 as CDR2; and the amino acid sequence set forth as SEQ ID NO:92 or SEQ ID NO:93 as CDR3;

(4) the amino acid sequence set forth as SEQ ID NO:94 or SEQ ID NO:95 as CDR1; the amino acid sequence set forth as SEQ ID NO:96 or SEQ ID NO:97 as CDR2; and the amino acid sequence set forth as SEQ ID NO:98 or SEQ ID NO:99 as CDR3;

(5) the amino acid sequence set forth as SEQ ID NO:100 or SEQ ID NO:101 as CDR1; the amino acid sequence set forth as SEQ ID NO:102 or SEQ ID NO:103 as CDR2; and the amino acid sequence set forth as SEQ ID NO:104 or SEQ ID NO:105 as CDR3;

(6) the amino acid sequence set forth as SEQ ID NO:106 or SEQ ID NO:107 as CDR1; the amino acid sequence set forth as SEQ ID NO:108 or SEQ ID NO:278 as CDR2; and the amino acid sequence set forth as SEQ ID NO:109 or SEQ ID NO:110 as CDR3;

(7) the amino acid sequence set forth as SEQ ID NO:111 or SEQ ID NO:112 as CDR1; the amino acid sequence set forth as SEQ ID NO:113 or SEQ ID NO:114 as CDR2; and the amino acid sequence set forth as SEQ ID NO:115 or SEQ ID NO:116 as CDR3;

(8) the amino acid sequence set forth as SEQ ID NO:117 or SEQ ID NO:118 as CDR1; the amino acid sequence set forth as SEQ ID NO:119 or SEQ ID NO:279 as CDR2; and the amino acid sequence set forth as SEQ ID NO:120 or SEQ ID NO:121 as CDR3;

(9) the amino acid sequence set forth as SEQ ID NO:122 or SEQ ID NO:123 as CDR1; the amino acid sequence set forth as SEQ ID NO:124 or SEQ ID NO:125 as CDR2; and the amino acid sequence set forth as SEQ ID NO:126 or SEQ ID NO:127 as CDR3;

(10) the amino acid sequence set forth as SEQ ID NO:128 or SEQ ID NO:129 as CDR1; the amino acid sequence set forth as SEQ ID NO:130 or SEQ ID NO:131 as CDR2; and SEQ ID NO:132 or SEQ ID NO:133 as CDR3;

(11) the amino acid sequence set forth as SEQ ID NO:134 or SEQ ID NO:135 as CDR1; the amino acid sequence set forth as SEQ ID NO:136 or SEQ ID NO:137 as CDR2, and the amino acid sequence set forth as SEQ ID NO:138 or SEQ ID NO:139 as CDR3;

(12) the amino acid sequence set forth as SEQ ID NO:140 or SEQ ID NO:141 as CDR1; the amino acid sequence set forth as SEQ ID NO:142 or SEQ ID NO:143 as CDR2; and the amino acid sequence set forth as SEQ ID NO:144 or SEQ ID NO:145 as CDR3;

(13) the amino acid sequence set forth as SEQ ID NO:146 or SEQ ID NO:147 as CDR1; the amino acid sequence set forth as SEQ ID NO:148 or SEQ ID NO:149 as CDR2; and the amino acid sequence set forth as SEQ ID NO:150 or SEQ ID NO:151 as CDR3; and

(14) the amino acid sequence set forth as SEQ ID NO:152 or SEQ ID NO:153 as CDR1; the amino acid sequence set forth as SEQ ID NO:154 or SEQ ID NO:155 as CDR2; and the amino acid sequence set forth as SEQ ID NO:156 or SEQ ID NO:157 as CDR3.

Examples of more specific embodiments of the antibody having affinity to hTfR include those whose heavy chain CDRs have amino acid sequences according to one of (1) to (14) below:

(1) the amino acid sequence set forth as SEQ ID NO:76 as CDR1; SEQ ID NO:78 as CDR2; and SEQ ID NO:80 as CDR3;

(2) the amino acid sequence set forth as SEQ ID NO:82 as CDR1; SEQ ID NO:84 as CDR2; and SEQ ID NO:86 as CDR3;

(3) the amino acid sequence set forth as SEQ ID NO:88 as CDR1; SEQ ID NO:90 as CDR2; and SEQ ID NO:92 as CDR3;

(4) the amino acid sequence set forth as SEQ ID NO:94 as CDR1; SEQ ID NO:96 as CDR2; and SEQ ID NO:98 as CDR3;

(5) the amino acid sequence set forth as SEQ ID NO:100 as CDR1; SEQ ID NO:102 as CDR2; and SEQ ID NO:104 as CDR3;

(6) the amino acid sequence set forth as SEQ ID NO:106 as CDR1; SEQ ID NO:108 as CDR2; and SEQ ID NO:109 as CDR3;

(7) the amino acid sequence set forth as SEQ ID NO:111 as CDR1; SEQ ID NO:113 as CDR2; and SEQ ID NO:115 as CDR3;

(8) the amino acid sequence set forth as SEQ ID NO:117 as CDR1; SEQ ID NO:119 as CDR2; and SEQ ID NO:120 as CDR3;

(9) the amino acid sequence set forth as SEQ ID NO:122 as CDR1; SEQ ID NO:124 as CDR2; and SEQ ID NO:126 as CDR3;

(10) the amino acid sequence set forth as SEQ ID NO:128 as CDR1; SEQ ID NO:130 as CDR2; and SEQ ID NO:132 as CDR3;

(11) the amino acid sequence set forth as SEQ ID NO:134 as CDR1; SEQ ID NO:136 as CDR2; and SEQ ID NO:138 as CDR3;

(12) the amino acid sequence set forth as SEQ ID NO:140 as CDR1; SEQ ID NO:142 as CDR2; and SEQ ID NO:144 as CDR3;

(13) the amino acid sequence set forth as SEQ ID NO:146 as CDR1; SEQ ID NO:148 as CDR2; and SEQ ID NO:150 as CDR3; and

(14) the amino acid sequence set forth as SEQ ID NO:152 as CDR1; SEQ ID NO:154 as CDR2; and SEQ ID NO:156 as CDR3.

Examples of preferable combinations of the light chain and heavy chain of the antibody having affinity to hTfR include those having the amino acid sequences as CDRs according to (1) to (14) below:

(1) a combination of the light chain having the amino acid sequence set forth as SEQ ID NO:6 or SEQ ID NO:7 as CDR1; the amino acid sequence set forth as SEQ ID NO:8 or SEQ ID NO:9 or the amino acid sequence Trp-Thr-Ser as CDR2; and the amino acid sequence set forth as SEQ ID NO:10 as CDR3; and the heavy chain having the amino acid sequence set forth as SEQ ID NO:76 or SEQ ID NO:77 as CDR1; the amino acid sequence set forth as SEQ ID NO:78 or SEQ ID NO:79 as CDR2; and the amino acid sequence set forth as SEQ ID NO:80 or SEQ ID NO:81 as CDR3;

(2) a combination of the light chain having the amino acid sequence set forth as SEQ ID NO:11 or SEQ ID NO:12 as CDR1; the amino acid sequence set forth as SEQ ID NO:13 or SEQ ID NO:14 or the amino acid sequence Tyr Ala Ser as CDR2; and the amino acid sequence set forth as SEQ ID NO:15 as CDR3; and the heavy chain having the amino acid sequence set forth as SEQ ID NO:82 or SEQ ID NO:83 as CDR1; the amino acid sequence set forth as SEQ ID NO:84 or SEQ ID NO:85 as CDR2; and the amino acid sequence set forth as SEQ ID NO:86 or SEQ ID NO:87 as CDR3;

(3) a combination of the light chain having the amino acid sequence set forth as SEQ ID NO:16 or SEQ ID NO:17 as CDR1; the amino acid sequence set forth as SEQ ID NO:18 or SEQ ID NO:19 or the amino acid sequence Lys-Val-Ser as CDR2; and the amino acid sequence set forth as SEQ ID NO:20 as CDR3; and the heavy chain having the amino acid sequence set forth as SEQ ID NO:88 or SEQ ID NO:89 as CDR1; the amino acid sequence set forth as SEQ ID NO:90 or SEQ ID NO:91 as CDR2; and the amino acid sequence set forth as SEQ ID NO:92 or SEQ ID NO:93 as CDR3;

(4) a combination of the light chain having the amino acid sequence set forth as SEQ ID NO:21 or SEQ ID NO:22 as CDR1; the amino acid sequence set forth as SEQ ID NO:23 or SEQ ID NO:24 or the amino acid sequence Asp-Thr-Ser as CDR2; and the amino acid sequence set forth as SEQ ID NO:25 as CDR3; and the heavy chain having the amino acid sequence set forth as SEQ ID NO:94 or SEQ ID NO:95 as CDR1; the amino acid sequence set forth as SEQ ID NO:96 or SEQ ID NO:97 as CDR2; and the amino acid sequence set forth as SEQ ID NO:98 or SEQ ID NO:99 as CDR3;

(5) a combination of the light chain having the amino acid sequence set forth as SEQ ID NO:26 or SEQ ID NO:27 as CDR1; the amino acid sequence set forth as SEQ ID NO:28 or SEQ ID NO:29 or the amino acid sequence Asp-Thr-Ser as CDR2; and the amino acid sequence set forth as SEQ ID NO:30 as CDR3;

the heavy chain having the amino acid sequence set forth as SEQ ID NO:100 or SEQ ID NO:101 as CDR1; the amino acid sequence set forth as SEQ ID NO:102 or SEQ ID NO:103 as CDR2; and the amino acid sequence set forth as SEQ ID NO:104 or SEQ ID NO:105 as CDR3;

(6) a combination of the light chain having the amino acid sequence set forth as SEQ ID NO:31 or SEQ ID NO:32 as CDR1; the amino acid sequence set forth as SEQ ID NO:33 or SEQ ID NO:34 or the amino acid sequence Ala-Ala-Ser as CDR2; and the amino acid sequence set forth as SEQ ID NO:35 as CDR3; and the heavy chain having the amino acid sequence set forth as SEQ ID NO:106 or SEQ ID NO:107 as CDR1; the amino acid sequence set forth as SEQ ID NO:108 or SEQ ID NO:278 as CDR2; and the amino acid sequence set forth as SEQ ID NO:109 or SEQ ID NO:110 as CDR3;

(7) a combination of the light chain having the amino acid sequence set forth as SEQ ID NO:36 or SEQ ID NO:37 as CDR1; the amino acid sequence set forth as SEQ ID NO:38 or SEQ ID NO:39 or the amino acid sequence Gln-Thr-Ser as CDR2; and the amino acid sequence set forth as SEQ ID NO:40 as CDR3; and the heavy chain having the amino acid sequence set forth as SEQ ID NO:111 or SEQ ID NO:112 as CDR1; the amino acid sequence set forth as SEQ ID NO:113 or SEQ ID NO:114 as CDR2; and the amino acid sequence set forth as SEQ ID NO:115 or SEQ ID NO:116 as CDR3;

(8) a combination of the light chain having the amino acid sequence set forth as SEQ ID NO:41 or SEQ ID NO:42 as CDR1; the amino acid sequence set forth as SEQ ID NO:43 or SEQ ID NO:44 or the amino acid sequence Gly-Thr-Ser as CDR2; and the amino acid sequence set forth as SEQ ID NO:45 as CDR3; and the heavy chain having the amino acid sequence set forth as SEQ ID NO:117 or SEQ ID NO:118 as CDR1; the amino acid sequence set forth as SEQ ID NO:119 or SEQ ID NO:279 as CDR2; and the amino acid sequence set forth as SEQ ID NO:120 or SEQ ID NO:121 as CDR3;

(9) a combination of the light chain having the amino acid sequence set forth as SEQ ID NO:46 or SEQ ID NO:47 as CDR1; the amino acid sequence set forth as SEQ ID NO:48 or SEQ ID NO:49 or the amino acid sequence Phe-Thr-Ser as CDR2; and the amino acid sequence set forth as SEQ ID NO:50 as CDR3; and the heavy chain having the amino acid sequence set forth as SEQ ID NO:122 or SEQ ID NO:123 as CDR1; the amino acid sequence set forth as SEQ ID NO:124 or SEQ ID NO:125 as CDR2; and the amino acid sequence set forth as SEQ ID NO:126 or SEQ ID NO:127 as CDR3;

(10) a combination of the light chain having the amino acid sequence set forth as SEQ ID NO:51 or SEQ ID NO:52 as CDR1; the amino acid sequence set forth as SEQ ID NO:53 or SEQ ID NO:54 or the amino acid sequence Ala-Ala-Ser as CDR2; and the amino acid sequence set forth as SEQ ID NO:55 as CDR3; and the heavy chain having the amino acid sequence set forth as SEQ ID NO:128 or SEQ ID NO:129 as CDR1; the amino acid sequence set forth as SEQ ID NO:130 or SEQ ID NO:131 as CDR2; and the amino acid sequence set forth as SEQ ID NO:132 or SEQ ID NO:133 as CDR3;

(11) a combination of the light chain having the amino acid sequence set forth as SEQ ID NO:56 or SEQ ID NO:57 as CDR1; the amino acid sequence set forth as SEQ ID NO:58 or SEQ ID NO:59 or the amino acid sequence Tyr-Ala-Ser as CDR2; and the amino acid sequence set forth as SEQ ID NO:60 as CDR3; and the heavy chain having the amino acid sequence set forth as SEQ ID NO:134 or SEQ ID NO:135 as CDR1; the amino acid sequence set forth as SEQ ID NO:136 or SEQ ID NO:137 as CDR2; and the amino acid sequence set forth as SEQ ID NO:138 or SEQ ID NO:139 as CDR3;

(12) a combination of the light chain having the amino acid sequence set forth as SEQ ID NO:61 or SEQ ID NO:62 as CDR1; the amino acid sequence set forth as SEQ ID NO:63 or SEQ ID NO:64 or the amino acid sequence Trp-Ser-Ser as CDR2; and the amino acid sequence set forth as SEQ ID NO:65 as CDR3; and the heavy chain having the amino acid sequence set forth as SEQ ID NO:140 or SEQ ID NO:141 as CDR1; the amino acid sequence set forth as SEQ ID NO:142 or SEQ ID NO:143 as CDR2; and the amino acid sequence set forth as SEQ ID NO:144 or SEQ ID NO:145 as CDR3;

(13) a combination of the light chain having the amino acid sequence set forth as SEQ ID NO:66 or SEQ ID NO:67 as CDR1; the amino acid sequence set forth as SEQ ID NO:68 or SEQ ID NO:69 or the amino acid sequence Tyr-Ala-Ser as CDR2; and the amino acid sequence set forth as SEQ ID NO:70 as CDR3; and the heavy chain having the amino acid sequence set forth as SEQ ID NO:146 or SEQ ID NO:147 as CDR1; the amino acid sequence set forth as SEQ ID NO:148 or SEQ ID NO:149 as CDR2; and the amino acid sequence set forth as SEQ ID NO:150 or SEQ ID NO:151 as CDR3;

(14) a combination of the light chain having the amino acid sequence set forth as SEQ ID NO:71 or SEQ ID NO:72 as CDR1; the amino acid sequence set forth as SEQ ID NO:73 or SEQ ID NO:74 or the amino acid sequence Asp-Thr-Ser as CDR2; and the amino acid sequence set forth as SEQ ID NO:75 as CDR3; and the heavy chain having the amino acid sequence set forth as SEQ ID NO:152 or SEQ ID NO:153 as CDR1; the amino acid sequence set forth as SEQ ID NO:154 or SEQ ID NO:155 as CDR2; and he amino acid sequence set forth as SEQ ID NO:156 or SEQ ID NO:157 as CDR3.

Examples of specific embodiments of combinations of the light chain and heavy chain of the antibody having affinity to hTfR include those having the amino acid sequences as CDRs according to one of (1) to (14) below:

(1) a combination of the light chain having the amino acid sequence set forth as SEQ ID NO:6 as CDR1; SEQ ID NO:8 as CDR2; and SEQ ID NO:10 as CDR3; and the heavy chain having the amino acid sequence set forth as SEQ ID NO:76 as CDR1; SEQ ID NO:78 as CDR2; and SEQ ID NO:80 as CDR3;

(2) a combination of the light chain having the amino acid sequence set forth as SEQ ID NO:11 as CDR1; SEQ ID NO:13 as CDR2; and SEQ ID NO:15 as CDR3; and the heavy chain having the amino acid sequence set forth as SEQ ID NO:82 as CDR1; SEQ ID NO:84 as CDR2; and SEQ ID NO:86 as CDR3;

(3) a combination of the light chain having the amino acid sequence set forth as SEQ ID NO:16 as CDR1; SEQ ID NO:18 as CDR2; and SEQ ID NO:20 as CDR3; and the heavy chain having the amino acid sequence set forth as SEQ ID NO:88 as CDR1; SEQ ID NO:90 as CDR2; and SEQ ID NO:92 as CDR3;

(4) a combination of the light chain having the amino acid sequence set forth as SEQ ID NO:21 as CDR1; SEQ ID NO:23 as CDR2; and SEQ ID NO:25 as CDR3; and the heavy chain having the amino acid sequence set forth as SEQ ID NO:94 as CDR1; SEQ ID NO:96 as CDR2; and SEQ ID NO:98 as CDR3;

(5) a combination of the light chain having the amino acid sequence set forth as SEQ ID NO:26 as CDR1; SEQ ID NO:28 as CDR2; and SEQ ID NO:30 as CDR3; and the heavy chain having the amino acid sequence set forth as SEQ ID NO:100 as CDR1; SEQ ID NO:102 as CDR2; and SEQ ID NO:104 as CDR3;

(6) a combination of the light chain having the amino acid sequence set forth as SEQ ID NO:31 as CDR1; SEQ ID NO:33 as CDR2; and SEQ ID NO:35 as CDR3; and the heavy chain having the amino acid sequence set forth as SEQ ID NO:106 as CDR1; SEQ ID NO:108 as CDR2; and SEQ ID NO:109 as CDR3;

(7) a combination of the light chain having the amino acid sequence set forth as SEQ ID NO:36 as CDR1; SEQ ID NO:38 as CDR2; and SEQ ID NO:40 as CDR3; and the heavy chain having the amino acid sequence set forth as SEQ ID NO:111 as CDR1; SEQ ID NO:113 as CDR2; and SEQ ID NO:115 as CDR3;

(8) a combination of the light chain having the amino acid sequence set forth as SEQ ID NO:41 as CDR1; SEQ ID NO:43 as CDR2; and SEQ ID NO:45 as CDR3; and the heavy chain having the amino acid sequence set forth as SEQ ID NO:117 as CDR1; SEQ ID NO:119 as CDR2; and SEQ ID NO:120 as CDR3;

(9) a combination of the light chain having the amino acid sequence set forth as SEQ ID NO:46 as CDR1; SEQ ID NO:48 as CDR2; and SEQ ID NO:50 as CDR3; and the heavy chain having the amino acid sequence set forth as SEQ ID NO:122 as CDR1; SEQ ID NO:124 as CDR2; and SEQ ID NO:126 as CDR3;

(10) a combination of the light chain having the amino acid sequence set forth as SEQ ID NO:51 as CDR1; SEQ ID NO:53 as CDR2; and SEQ ID NO:55 as CDR3; and the heavy chain having the amino acid sequence set forth as SEQ ID NO:128 as CDR1; SEQ ID NO:130 as CDR2; and SEQ ID NO:132 as CDR3;

(11) a combination of the light chain having the amino acid sequence set forth as SEQ ID NO:56 as CDR1; SEQ ID NO:58 as CDR2; and SEQ ID NO:60 as CDR3; and the heavy chain having the amino acid sequence set forth as SEQ ID NO:134 as CDR1; SEQ ID NO:136 as CDR2; and SEQ ID NO:138 as CDR3;

(12) a combination of the light chain having the amino acid sequence set forth as SEQ ID NO:61 as CDR1; SEQ ID NO:63 as CDR2; and SEQ ID NO:65 as CDR3; and the heavy chain having the amino acid sequence set forth as SEQ ID NO:140 as CDR1; SEQ ID NO:142 as CDR2; and SEQ ID NO:144 as CDR3;

(13) a combination of the light chain having the amino acid sequence set forth as SEQ ID NO:66 as CDR1; SEQ ID NO:68 as CDR2; and SEQ ID NO:70 as CDR3; and the heavy chain having the amino acid sequence set forth as SEQ ID NO:146 as CDR1; SEQ ID NO:148 as CDR2; and SEQ ID NO:150 as CDR3; and

(14) a combination of the light chain having the amino acid sequence set forth as SEQ ID NO:71 as CDR1; SEQ ID NO:73 as CDR2; and SEQ ID NO:75 as CDR3; and the heavy chain having the amino acid sequence set forth as SEQ ID NO:152 as CDR1; SEQ ID NO:154 as CDR2; and SEQ ID NO:156 as CDR3.

As preferred embodiments of humanized antibodies having affinity to hTfR, there are humanized antibodies produced using the amino acid sequences of the light chain variable region and the heavy chain variable region of the mouse anti-human TfR antibody set forth as SEQ ID NO:218 to SEQ ID NO:245 as CDRs. The humanized antibodies are produced by replacing proper positions of a human antibody with the amino acid sequences of CDRs of the light chain variable region and the heavy chain variable region of mouse anti-human TfR antibody.

For example, the light chain of a humanized antibody can be made by replacing the amino acid sequences of corresponding to CDRs of the light chain of a human antibody with an amino acid sequence consisting of not less than 3, or not less than 6, consecutive amino acids at the positions 24th to 34th of the amino acid sequence set forth as SEQ ID NO:218 as CDR1; with an amino acid sequence consisting of not less than 3, or not less than 6, consecutive amino acids at the positions 50th to 56th of the amino acid sequence set forth as SEQ ID NO:218 as CDR2; and with an amino acid sequence consisting of not less than 3, or not less than 8, consecutive amino acids at the positions 89th to 97th of the amino acid sequence set forth as SEQ ID NO:218 as CDR3, and the heavy chain of a humanized antibody can be made by replacing the amino acid sequences of corresponding to CDRs of the heavy chain of a human antibody with an amino acid sequence consisting of not less than 3 consecutive amino acids at the positions 26th to 35th of the amino acid sequence set forth as SEQ ID NO:219 as CDR1; with an amino acid sequence consisting of not less than 3, or not less than 8, consecutive amino acids at the positions 50th to 66th of the amino acid sequence set forth as SEQ ID NO:219 as CDR2; with an amino acid sequence consisting of not less than 3, or not less than 7, consecutive amino acids at the positions 97th to 105th of the amino acid sequence set forth as SEQ ID NO:219 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:220 as CDR1; with an amino acid sequence consisting of not less than 3, or not less than 6, consecutive amino acids at the positions 50th to 56th of the amino acid sequence set forth as SEQ ID NO:220 as CDR2; and with an amino acid sequence consisting of not less than 3 or not less than 8, consecutive amino acids at the positions 89th to 97th of the amino acid sequence set forth as SEQ ID NO:220 as CDR3; and the heavy chain of a humanized antibody can be made by replacing the amino acid sequences of corresponding to CDRs of the heavy chain of a human antibody with an amino acid sequence consisting of not less than 3 consecutive amino acids at the positions 26th to 35th of the amino acid sequence set forth as SEQ ID NO:221 as CDR1; with an amino acid sequence consisting of not less than 3, or not less than 8, consecutive amino acids at the positions 50th to 66th of the amino acid sequence set forth as SEQ ID NO:221 as CDR2; and with an amino acid sequence consisting of not less than 3, or not less than 14, consecutive amino acids at the positions 97th to 112nd of the amino acid sequence set forth as SEQ ID NO:221 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 11, consecutive amino acids at the positions 24th to 39th of the amino acid sequence set forth as SEQ ID NO:222 as CDR1; with an amino acid sequence consisting of not less than 3, not less than 6, consecutive amino acids at the positions 55th to 61st of the amino acid sequence set forth as SEQ ID NO:222 as CDR2; and with an amino acid sequence consisting of not less than 3, or not less than 8, consecutive amino acids at the positions 94th to 102nd of the amino acid sequence set forth as SEQ ID NO:222 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:223 as CDR1; with an amino acid sequence consisting of not less than 3, or not less than 8, consecutive amino acids at the positions 50th to 66th of the amino acid sequence set forth as SEQ ID NO:223 as CDR2; and with an amino acid sequence consisting of not less than 3, or not less than 9 consecutive amino acids at the positions 97th to 107th of the amino acid sequence set forth as SEQ ID NO:223 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:224 as CDR1; with an amino acid sequence consisting of not less than 3, or not less than 6, consecutive amino acids at the positions 49th to 55th of the amino acid sequence set forth as SEQ ID NO:224 as CDR2; and with an amino acid sequence consisting of not less than 3, or not less than 8, consecutive amino acids at the positions 88th to 96th of the amino acid sequence set forth as SEQ ID NO:224 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:225 as CDR1; with an amino acid sequence consisting of not less than 3, or not less than 8, consecutive amino acids at the positions 51st to 66th of the amino acid sequence set forth as SEQ ID NO:225 as CDR2; and with an amino acid sequence consisting of not less than 3, or not less than 13, consecutive amino acids at the positions 97th to 111st of the amino acid sequence set forth as SEQ ID NO:225 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:226 as CDR1; with an amino acid sequence consisting of not less than 3, or not less than 6, consecutive amino acids at the positions 49th to 55th of the amino acid sequence set forth as SEQ ID NO:226 as CDR2; and with an amino acid sequence consisting of not less than 3, or not less than 7, consecutive amino acids at the positions 88th to 95th of the amino acid sequence set forth as SEQ ID NO:226 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:227 as CDR1; with an amino acid sequence consisting of not less than 3, or not less than 8, consecutive amino acids at the positions 51st to 66th of the amino acid sequence set forth as SEQ ID NO:227 as CDR2; and with an amino acid sequence consisting of not less than 3, or not less than 9, consecutive amino acids at the positions 97th to 107th of the amino acid sequence set forth as SEQ ID NO:227 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:228 as CDR1; with an amino acid sequence consisting of not less than 3, or not less than 6, consecutive amino acids at the positions 50th to 56th of the amino acid sequence set forth as SEQ ID NO:228 as CDR2; and with an amino acid sequence consisting of not less than 3, or not less than 8, consecutive amino acids at the positions 89th to 97th of the amino acid sequence set forth as SEQ ID NO:228 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:229 as CDR1; with an amino acid sequence consisting of not less than 3, or not less than 7, consecutive amino acids at the positions 50th to 65th of the amino acid sequence set forth as SEQ ID NO:229 as CDR2; and with an amino acid sequence consisting of not less than 3, or not less than 4, consecutive amino acids at the positions 96th to 101st of the amino acid sequence set forth as SEQ ID NO:229 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:230 as CDR1; with an amino acid sequence consisting of not less than 3, or not less than 6, consecutive amino acids at the positions 49th to 55th of the amino acid sequence set forth as SEQ ID NO:230 as CDR2; and with an amino acid sequence consisting of not less than 3, or not less than 8, consecutive amino acids at the positions 88th to 96th of the amino acid sequence set forth as SEQ ID NO:230 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:231 as CDR1; with an amino acid sequence consisting of not less than 3, or not less than 8, consecutive amino acids at the positions 51st to 66th of the amino acid sequence set forth as SEQ ID NO:231 as CDR2; and with an amino acid sequence consisting of not less than 3, or not less than 11, consecutive amino acids at the positions 97th to 109th of the amino acid sequence set forth as SEQ ID NO:231 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:232 as CDR1; with an amino acid sequence consisting of not less than 3, or not less than 6, consecutive amino acids at the positions 49th to 55th of the amino acid sequence set forth as SEQ ID NO:232 as CDR2; and with an amino acid sequence consisting of not less than 3, or not less than 8, consecutive amino acids at the positions 88th to 96th of the amino acid sequence set forth as SEQ ID NO:232 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:233 as CDR1; with an amino acid sequence consisting of not less than 3, or not less than 7, consecutive amino acids at the positions 50th to 65th of the amino acid sequence set forth as SEQ ID NO:233 as CDR2; and with an amino acid sequence consisting of not less than 3, or not less than 4, consecutive amino acids at the positions 96th to 101st of the amino acid sequence set forth as SEQ ID NO:233 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:234 as CDR1; with an amino acid sequence consisting of not less than 3, or not less than 6, consecutive amino acids at the positions 49th to 55th of the amino acid sequence set forth as SEQ ID NO:234 as CDR2; and with an amino acid sequence consisting of not less than 3, or not less than 8, consecutive amino acids at the positions 88th to 96th of the amino acid sequence set forth as SEQ ID NO:234 as CDR3, and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:235 as CDR1; with an amino acid sequence consisting of not less than 3, or not less than 8, consecutive amino acids at the positions 51st to 66th of the amino acid sequence set forth as SEQ ID NO:235 as CDR2, and with an amino acid sequence consisting of not less than 3, or not less than 8, consecutive amino acids at the positions 97th to 106th of the amino acid sequence set forth as SEQ ID NO:235 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:236 as CDR1; with an amino acid sequence consisting of not less than 3, or not less than 6 consecutive amino acids at the positions 50th to 56th of the amino acid sequence set forth as SEQ ID NO:236 as CDR2; and with an amino acid sequence consisting of not less than 3, or not less than 8, consecutive amino acids at the positions 89th to 97th of the amino acid sequence set forth as SEQ ID NO:236 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:237 as CDR1; with an amino acid sequence consisting of not less than 3, or not less than 8, consecutive amino acids at the positions 51st to 66th of the amino acid sequence set forth as SEQ ID NO:237 as CDR2; and with an amino acid sequence consisting of not less than 3, or not less than 11, consecutive amino acids at the positions 97th to 109th of the amino acid sequence set forth as SEQ ID NO:237 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:238 as CDR1; with an amino acid sequence consisting of not less than 3, or not less than 6, consecutive amino acids at the positions 50th to 56th of the amino acid sequence set forth as SEQ ID NO:238 as CDR2; and with an amino acid sequence consisting of not less than 3, or not less than 8, consecutive amino acids at the positions 89th to 97th of the amino acid sequence set forth as SEQ ID NO:238 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:239 as CDR1; with an amino acid sequence consisting of not less than 3 or not less than 8, consecutive amino acids at the positions 51st to 66th of the amino acid sequence set forth as SEQ ID NO:239 as CDR2; and with an amino acid sequence consisting of not less than 3 or not less than 9, consecutive amino acids at the positions 97th to 107th of the amino acid sequence set forth as SEQ ID NO:239 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3 or not less than 6, consecutive amino acids at the positions 24th to 34th of the amino acid sequence set forth as SEQ ID NO:240 as CDR1; with an amino acid sequence consisting of not less than 3 or not less than 6, consecutive amino acids at the positions 50th to 56th of the amino acid sequence set forth as SEQ ID NO:240 as CDR2; and with an amino acid sequence consisting of not less than 3 or not less than 8, consecutive amino acids at the positions 89th to 97th of the amino acid sequence set forth as SEQ ID NO:240 as CDR3, and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:241 as CDR1; with an amino acid sequence consisting of not less than 3 or not less than 8, consecutive amino acids at the positions 51st to 66th of the amino acid sequence set forth as SEQ ID NO:241 as CDR2; and with an amino acid sequence consisting of not less than 3 or not less than 10, consecutive amino acids at the positions 97th to 108th of the amino acid sequence set forth as SEQ ID NO:241 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3 or not less than 6, consecutive amino acids at the positions 24th to 34th of the amino acid sequence set forth as SEQ ID NO:242 as CDR1; with an amino acid sequence consisting of not less than 3 or not less than 6, consecutive amino acids at the positions 50th to 56th of the amino acid sequence set forth as SEQ ID NO:242 as CDR2; and with an amino acid sequence consisting of not less than 3 or not less than 8, consecutive amino acids at the positions 89th to 97th of the amino acid sequence set forth as SEQ ID NO:242 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:243 as CDR1; with an amino acid sequence consisting of not less than 3 or not less than 8, consecutive amino acids at the positions 51st to 66th of the amino acid sequence set forth as SEQ ID NO:243 as CDR2; and with an amino acid sequence consisting of not less than 3 or not less than 9, consecutive amino acids at the positions 97th to 107th of the amino acid sequence set forth as SEQ ID NO:243 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3 or not less than 5, consecutive amino acids at the positions 24th to 33rd of the amino acid sequence set forth as SEQ ID NO:244 as CDR1; with an amino acid sequence consisting of not less than 3 or not less than 6, consecutive amino acids at the positions 49th to 55th of the amino acid sequence set forth as SEQ ID NO:244 as CDR2; and with an amino acid sequence consisting of not less than 3 or not less than 9, consecutive amino acids at the positions 88th to 96th of the amino acid sequence set forth as SEQ ID NO:244 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:245 as CDR1; with an amino acid sequence consisting of not less than 3 or not less than 8, consecutive amino acids at the positions 51st to 66th of the amino acid sequence set forth as SEQ ID NO:245 as CDR2; and with an amino acid sequence consisting of not less than 3, or not less than 9, consecutive amino acids at the positions 97th to 107th of the amino acid sequence set forth as SEQ ID NO:245 as CDR3.

By combining the light chain and the heavy chain of the humanized antibody thus obtained, the humanized antibody can be prepared.

Examples of preferred embodiments of the humanized antibody having affinity to hTfR include those having an amino acid sequence according to one of (1) to (3) below:

(1) An anti-hTfR antibody, wherein the light chain variable region thereof comprises an amino acid sequence selected from the group consisting of the amino acid sequences set forth as SEQ ID NO:158, SEQ ID NO:159, SEQ ID NO:160, SEQ ID NO:161, SEQ ID NO:162, and SEQ ID NO:163, and wherein the heavy chain variable region thereof comprises an amino acid sequence selected from the group consisting of the amino acid sequences set forth as SEQ ID NO:166, SEQ ID NO:167, SEQ ID NO:168, SEQ ID NO:169, SEQ ID NO:170, and SEQ ID NO:171.

(2) an anti-hTfR antibody, wherein the light chain variable region thereof comprises any amino acid sequence of SEQ ID NO:174, SEQ ID NO:175, SEQ ID NO:176, SEQ ID NO:177, SEQ ID NO:178, and SEQ ID NO:179, and wherein the heavy chain variable region thereof comprises any amino acid sequence of SEQ ID NO:182, SEQ ID NO:183, SEQ ID NO:184, SEQ ID NO:185, SEQ ID NO:186, and SEQ ID NO:187.

(3) anti-hTfR antibody, wherein the light chain variable region thereof comprises an amino acid sequence selected from the group consisting of the amino acid sequences set forth as SEQ ID NO:190, SEQ ID NO:191, SEQ ID NO:192, SEQ ID NO:193, SEQ ID NO:194, and SEQ ID NO:195, and wherein the heavy chain variable region thereof comprises an amino acid sequence selected from the group consisting of the amino acid sequences set forth as SEQ ID NO:204, SEQ ID NO:205, SEQ ID NO:206, SEQ ID NO:207, SEQ ID NO:208 and SEQ ID NO:209.

The amino acid sequences of the light chain variable region set forth as SEQ ID NO:158, SEQ ID NO:159, SEQ ID NO:160, SEQ ID NO:161, SEQ ID NO:162 and SEQ ID NO:163 comprise the amino acid sequence set forth as SEQ ID NO:6 or 7 in CDR1; SEQ ID NO:8 or 9 in CDR2; and SEQ ID NO:10 in CDR3. However, the term CDRs as used above in regard to the amino acid sequences of the light chain variable region set forth as SEQ ID NOs:158 to 162 is not limited to those specific sequences but may also include a region containing the amino acid sequences of one of the CDRs or include an amino acid sequence comprising not less than 3 consecutive amino acids of one of the above CDRs.

The amino acid sequences of the heavy chain variable region set forth as SEQ ID NO:166, SEQ ID NO:167, SEQ ID NO:168, SEQ ID NO:169, SEQ ID NO:170, and SEQ ID NO:171 comprise the amino acid sequence set forth as SEQ ID NO:76 or 77 in CDR1; SEQ ID NO:78 or 79 in CDR2; and SEQ ID NO:80 or 81 in CDR3. However, the term CDRs used above in regard to the amino acid sequences of the heavy chain variable region set forth as SEQ ID NOs:166 to 171 is not limited to those specific sequences but may also include a region containing the amino acid sequences of one of the CDRs or include an amino acid sequence comprising not less than 3 consecutive amino acids of one of the above CDRs.

The amino acid sequences of the light chain variable region set forth as SEQ ID NO:174, SEQ ID NO:175, SEQ ID NO:176, SEQ ID NO:177, SEQ ID NO:178, and SEQ ID NO:179 comprise the amino acid sequence set forth as SEQ ID NO:11 or 12 in CDR1; SEQ ID NO:13 or 14 in CDR2; and SEQ ID NO:15 in CDR3. However, the term CDRs as used above in regard to the amino acid sequences of the light chain variable region set forth as SEQ ID NOs:174 to 179 is not limited to those specific sequences but may also include a region containing the amino acid sequences of one of the CDRs or include an amino acid sequence comprising not less than 3 consecutive amino acids of one of the above CDRs.

The amino acid sequences of the heavy chain variable region set forth as SEQ ID NO:182, SEQ ID NO:183, SEQ ID NO:184, SEQ ID NO:185, SEQ ID NO:186, and SEQ ID NO:187 comprise the amino acid sequence set forth as SEQ ID NO:82 or 83 in CDR1; SEQ ID NO:84 or 85 in CDR2; and SEQ ID NO:86 or 87 in CDR3. However, the term CDRs used above in regard to the amino acid sequences of the heavy chain variable region set forth as SEQ ID NOs:182 to 187 is not limited to those specific sequences but may also include a region containing the amino acid sequences of one of the CDRs or include an amino acid sequence comprising not less than 3 consecutive amino acids of one of the above CDRs.

The amino acid sequences of the light chain variable region set forth as SEQ ID NO:190, SEQ ID NO:191, SEQ ID NO:192, SEQ ID NO:193, SEQ ID NO:194, and SEQ ID NO:195 comprise the amino acid sequence set forth as SEQ ID NO:16 or 17 in CDR1, SEQ ID NO:18 or 19 in CDR2, and SEQ ID NO:20 in CDR3. However, the term CDRs as used above in regard to the amino acid sequences of the light chain variable region set forth as SEQ ID NOs:190 to 195 is not limited to those specific sequences but may also include a region containing the amino acid sequences of one of the CDRs or include an amino acid sequence comprising not less than 3 consecutive amino acids of one of the above CDRs.

The amino acid sequences of the heavy chain variable region set forth as SEQ ID NO:204, SEQ ID NO:205, SEQ ID NO:206, SEQ ID NO:207, SEQ ID NO:208 and SEQ ID NO:209 comprise the amino acid sequence set forth as SEQ ID NO:88 or 89 in CDR1; SEQ ID NO:90 or 91 in CDR2, and SEQ ID NO:92 or 93 in CDR3. However, the term CDRs used above in regard to the amino acid sequences of the heavy chain variable region set forth as SEQ ID NOs:204 to 209 is not limited to those specific sequences but may also include a region containing the amino acid sequences of one of the CDRs or include an amino acid sequence comprising not less than 3 consecutive amino acids of one of the above CDRs.

Examples of more specific embodiments of the humanized antibody having affinity to hTfR include:

the one that comprises the amino acid sequence set forth as SEQ ID NO:163 in the light chain variable region and comprises the amino acid sequence set forth as SEQ ID NO:171 in the heavy chain variable region, the one that comprises the amino acid sequence set forth as SEQ ID NO:179 in the light chain variable region and comprises the amino acid sequence set forth as SEQ ID NO:187 in the heavy chain variable region, the one that comprises the amino acid sequence set forth as SEQ ID NO:191 in the light chain variable region and comprises the amino acid sequence set forth as SEQ ID NO:205 in the heavy chain variable region, the one that comprises the amino acid sequence set forth as SEQ ID NO:193 in the light chain variable region and comprises the amino acid sequence set forth as SEQ ID NO:205 in the heavy chain variable region, the one that comprises the amino acid sequence set forth as SEQ ID NO:194 in the light chain variable region and comprises the amino acid sequence set forth as SEQ ID NO:205 in the heavy chain variable region, and the one that comprises the amino acid sequence set forth as SEQ ID NO:195 in the light chain variable region and comprises the amino acid sequence set forth as SEQ ID NO:205 in the heavy chain variable region.

Examples of more specific embodiments of the humanized antibody having affinity to hTfR include:

the one that comprises the amino acid sequence set forth as SEQ ID NO:164 in the light chain and the amino acid sequence set forth as SEQ ID NO:172 in the heavy chain, the one that comprises the amino acid sequence set forth as SEQ ID NO:180 in the light chain and the amino acid sequence set forth as SEQ ID NO:188, in the heavy chain, the one that comprises the amino acid sequence set forth as SEQ ID NO:196 in the light chain and the amino acid sequence set forth as SEQ ID NO:210 in the heavy chain, the one that comprises the amino acid sequence set forth as SEQ ID NO:198 in the light chain and the amino acid sequence set forth as SEQ ID NO:210 in the heavy chain, the one that comprises the amino acid sequence set forth as SEQ ID NO:200 in the light chain and the amino acid sequence set forth as SEQ ID NO:210 in the heavy chain, the one that comprises the amino acid sequence set forth as SEQ ID NO:202 in the light chain and the amino acid sequence set forth as SEQ ID NO:210 in the heavy chain, the one that comprises the amino acid sequence set forth as SEQ ID NO:196 in the light chain and the amino acid sequence set forth as SEQ ID NO:212 in the heavy chain, the one that comprises the amino acid sequence set forth as SEQ ID NO:198 in the light chain and the amino acid sequence set forth as SEQ ID NO:212 in the heavy chain, the one that comprises the amino acid sequence set forth as SEQ ID NO:200 in the light chain and the amino acid sequence set forth as SEQ ID NO:212 in the heavy chain, and the one that comprises the amino acid sequence set forth as SEQ ID NO:202 in the light chain and the amino acid sequence set forth as SEQ ID NO:212 in the heavy chain.

Preferred embodiments of the antibody having affinity to hTfR have been exemplified above. The light chain and heavy chain of those anti-hTfR antibodies may be mutated as desired, by substitution, deletion, addition and the like, in their variable-region amino acid sequences in order to adjust the affinity of the anti-hTfR antibody to hTfR to a suitable level.

When replacing on or more amino acids of the light chain variable-region amino acid sequence with other amino acids, the number of amino acids to be replaced is preferably 1 to 10, more preferably 1 to 5, still more preferably 1 to 3, and even more preferably 1 or 2. When deleting one or more amino acids of the light chain variable-region amino acid sequence, the number of amino acids to be deleted is preferably 1 to 10, more preferably 1 to 5, still more preferably 1 to 3, and even more preferably 1 or 2. Introduction of a combined mutation of such substitution and deletion of amino acids is also allowed.

When adding one or more amino acids to the light chain variable region, they may be added inside, or on the N-terminal side or the C-terminal side of, the light chain variable-region amino acid sequence, and preferably 1 to 10, more preferably 1 to 5, still more preferably 1 to 3, and even more preferably 1 or 2, in number. Introduction of a combined mutation of such addition, substitution, and deletion of amino acids is also allowed. Such a mutated light chain variable-region amino acid sequence has a homology preferably not lower than 80%, more preferably not lower than 90%, still more preferably not lower than 95%, to the amino acid sequence of the original light chain variable-region.

In particular, when replacing one or more amino acids of the amino acid sequence of respective CDRs in the light chain with other amino acids, the number of amino acids to be replaced is preferably 1 to 5, more preferably 1 to 3, still more preferably 1 or 2, and even more preferably 1. When deleting one or more amino acid of the amino acid sequence of the respective CDRs, the number of amino acids to be deleted is preferably 1 to 5, more preferably 1 to 3, still more preferably 1 or 2, and even more preferably 1. Introduction of a combined mutation of such substitution and deletion of amino acids is also allowed.

When adding one or more amino acids to the amino acid sequence of respective CDRs in the light chain, they are added inside, or on the N-terminal side or the C-terminal side of, the amino acid sequence, and preferably 1 to 5, more preferably 1 to 3, still more preferably 1 or 2, in number. Introduction of a combined mutation of such addition, substitution, and deletion of amino acids is also allowed. The amino acid sequence of each of such mutated CDRs has a homology preferably not lower than 80%, more preferably not lower than 90%, and still more preferably not lower than 95%, to the amino acid sequence of the respective original CDRs.

When replacing one or more amino acids of the heavy chain variable-region amino acid sequence with other amino acids, the number of amino acids to be replaced is preferably 1 to 10, more preferably 1 to 5, still more preferably 1 to 3, and even more preferably 1 or 2. When deleting one or more amino acids of the heavy chain variable-region amino acid sequence, the number of amino acids to be deleted is preferably 1 to 10, more preferably 1 to 5, still more preferably 1 to 3, and even more preferably 1 or 2. Introduction of a combined mutation of such substitution and deletion of amino acids is also allowed.

When adding one or more amino acids to the heavy chain variable region, they may be added inside, or on the N-terminal side or the C-terminal side of, the heavy chain variable-region amino acid sequence, and preferably 1 to 10, more preferably 1 to 5, still more preferably 1 to 3, and even more preferably 1 or 2, in number. Introduction of a combined mutation of such addition, substitution, and deletion of amino acids is also allowed. Such a mutated heavy chain variable-region amino acid sequence has a homology preferably not lower than 80%, more preferably not lower than 90%, still more preferably not lower than 95%, to the amino acid sequence of the original heavy chain variable-region.

In particular, when replacing one or more amino acids of the amino acid sequence of respective CDRs in the heavy chain with other amino acids, the number of amino acids to be replaced is preferably 1 to 5, more preferably 1 to 3, still more preferably 1 or 2, and even more preferably 1. When deleting one or more amino acid of the amino acid sequence of the respective CDRs, the number of amino acids to be deleted is preferably 1 to 5, more preferably 1 to 3, still more preferably 1 or 2, and even more preferably 1. Introduction of a combined mutation of such substitution and deletion of amino acids is also allowed.

When adding one or more amino acids to the amino acid sequence of respective CDRs in the heavy chain, they are added inside, or on the N-terminal side or the C-terminal side of, the amino acid sequence, and preferably 1 to 5, more preferably 1 to 3, still more preferably 1 or 2, and even more preferably 1 in number. Introduction of a combined mutation of such addition, substitution, and deletion of amino acids is also allowed. The amino acid sequence of each of such mutated CDRs has a homology preferably not lower than 80%, more preferably not lower than 90%, and still more preferably not lower than 95%, to the amino acid sequence of the respective original CDRs.

In the above, replacement of one or more amino acids of the above anti-hTfR antibody variable-region amino acid sequence with other amino acids is exemplified by interchange between acidic amino acids, i.e., aspartic acid and glutamic acid; interchange between amide-type amino acids, i.e., asparagine and glutamine; interchange between basic amino acids, i.e., lysine and arginine, interchange between branched amino acids, i.e., valine, leucine and isoleucine, interchange between aliphatic amino acids, i.e., glycine and alanine, interchange between hydroxyamino acids, i.e., serine and threonine, and interchange between aromatic amino acids, i.e., phenylalanine and tyrosine.

Besides, in the case where introducing a mutation into the anti-hTfR antibody by adding one or more amino acids on its C-terminus or the N-terminus, if the added amino acids are positioned between the anti-hTfR antibody and a different protein (A) when they are fused, the added amino acids constitute part of a linker.

In the above preferred embodiments of the antibody, including humanized antibody, having affinity to hTfR, there is no particular limitation as to the amino acid sequence of the anti-hTfR antibody heavy chain and light chain CDRs, insofar as the antibody has a specific affinity to hTfR. However, the anti-hTfR antibody of the present invention exhibits a dissociation constant ($K_D$) with hTfR, as measured by the method described in Example 7, which is preferably not greater than $1\times10^{-8}$ M, more preferably not greater than $1\times10^{-9}$ M, still more preferably not greater than $1\times10^{-9}$ M, and even more preferably not greater than $1\times10^{-9}$ M. For example, one which exhibits a dissociation constant of $1\times10^{-13}$ M to $1\times10^{-9}$ M or $1\times10^{-13}$ M to $1\times10^{-10}$ M is preferred. The same applies when the antibody is a single-chain antibody. Further, in the case where the anti-hTfR antibody of the present invention has an affinity also to a monkey TfR, the dissociation constant of the anti-hTfR antibody to the monkey TfR, as measured by the method described in Example 7, is preferably not greater than $5\times10^{-8}$ M, more preferably not greater than $2\times10^{-8}$M, still more preferably not greater than $1\times10^{-8}$M. For example, one which exhibits a dissociation constant of $1\times10^{-13}$M to $2\times10^{-8}$M is preferred. The same applies when the antibody is a single-chain antibody.

Specific embodiments of the above fusion protein between the humanized antibody, which has affinity to hTfR, and a different protein (A) described above include: those in which the different protein (A) is human iduronate 2-sulfatase (hI25), human erythropoietin (hEPO), human arylsulfatase A (hARSA), human PPT-1 (hPPT-1), human TPP-1 (hTPP-1), human α-L-iduronidase (hIDUA), human TNFα receptor (hTNFαR), and human heparan N-sulfatase (hSGSH).

Specific examples of the fusion protein where the different protein (A) is hI2S include;

(1) the one that is composed of: the portion consisting of hTfR heavy chain linked, on the C-terminal side thereof and via a linker sequence Gly-Ser, to hI2S, and the other portion consisting of the hTfR light chain, wherein the amino acid sequence of the former is set forth as SEQ ID NO:247, and the amino acid sequence of the latter is set forth as SEQ ID NO:164, (2) the one that is composed of: the portion consisting of hTfR heavy chain linked, on the C-terminal side thereof and via a linker sequence Gly-Ser, to hI2S, and the other portion consisting of the hTfR light chain wherein the amino acid sequence of the former is set forth as SEQ ID NO:249, and the amino acid sequence of the latter is set forth as SEQ ID NO:180, (3) the one that is composed of: the portion consisting of hTfR heavy chain linked, on the C-terminal side thereof and via a linker sequence Gly-Ser, to hI2S, and the other portion consisting of the hTfR light chain wherein the amino acid sequence of the former is set forth as SEQ ID NO:251, and the amino acid sequence of the latter is set forth as SEQ ID NO:196.

In (1) above, the amino acid sequence of the hTfR heavy chain, which is included in SEQ ID NO:247, is the one set forth as SEQ ID NO:172. Namely, the fusion protein according to (1) above, includes, as a humanized antibody, the amino acid sequence of the light chain set forth as SEQ ID NO:164 and the amino acid sequence of the heavy chain set forth as SEQ ID NO:172.

In (2) above, the amino acid sequence of the hTfR heavy chain, which is included in SEQ ID NO:249, is the one set forth as SEQ ID NO:188. Namely, the fusion protein according to (2) above, includes, as a humanized antibody, the amino acid sequence of the light chain set forth as SEQ ID NO:180 and the amino acid sequence of the heavy chain set forth as SEQ ID NO:188.

In (3) above, the amino acid sequence of the hTfR heavy chain, which is included in SEQ ID NO:251, is the one set forth as SEQ ID NO:210. Namely, the fusion protein according to (3) above, includes, as a humanized antibody, the amino acid sequence of the light chain set forth as SEQ ID NO:196 and the amino acid sequence of the heavy chain set forth as SEQ ID NO:210.

Specific examples of the fusion protein where the different protein (A) is human erythropoietin (hEPO) include;

(1) the one that is composed of: the portion consisting of hTfR heavy chain linked, on the C-terminal side thereof and via a peptide bond, to hEPO, and the other portion consisting of the hTfR light chain, wherein the amino acid sequence of hTfR heavy chain of the former is set forth as SEQ ID NO:172, and the amino acid sequence of the latter is set forth as SEQ ID NO:164, (2) the one that is composed of: the portion consisting of hTfR heavy chain linked, on the C-terminal side thereof and via a peptide bond, to hEPO, and the other portion consisting of the hTfR light chain, wherein the amino acid sequence of hTfR heavy chain of the former is set forth as SEQ ID NO:188, and the amino acid sequence of the latter is set forth as SEQ ID NO:180, and (3) the one that is composed of: the portion consisting of hTfR heavy chain linked, on the C-terminal side thereof and via a peptide bond, to hEPO, and the other portion consisting of the hTfR light chain, wherein the amino acid sequence of hTfR heavy chain of the former is set forth as SEQ ID NO:210, and the amino acid sequence of the latter is set forth as SEQ ID NO:196.

In any of (1) to (3) above, hEPO and the hTfR heavy chain may be linked by peptide bond, either directly or via a linker sequence. Namely, in any of (1) to (3) above, the meaning of the phrase "via a peptide bond" and that of the phrase "directly or via a linker sequence" are the same. The linker sequence employed here consists of 1 to 50 amino acid residues. Though there is no particular limitation as to the amino acid sequence of the linker, it is preferably made of glycine and serine: for example, a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence consisting 1 to 50, or 2 to 17, 2 to 10, 10 to 40, 20 to 34, 23 to 31, 25 to 29, or 27 amino acids which are composed of 1 to 10 or 2 to 5 of any of those amino acid sequences consecutively linked. For example, an amino acid sequence comprising the amino acid sequence Gly-Ser may be preferably used as a linker sequence. Further, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

More specific embodiments of humanized antibody plus hEPO include the one that is composed of the part consisting of hEPO linked, via the linker sequence Gly-Ser, to the C-terminal side of the hTfR heavy chain, and the other part consisting of the hTfR light chain, wherein the amino acid sequence of the former is set forth as SEQ ID NO:257, and the amino acid sequence of the latter is set forth as SEQ ID NO:196.

Besides, in the present invention, though the term "human EPO" or "hEPO" refers, in particular to the hEPO having the same amino acid sequence as the natural-type hEPO set forth as SEQ ID NO:256, it also includes those amino acid sequences produced by introducing a mutation such as substitution, deletion, addition and the like into the amino acid sequence of the natural-type hEPO, insofar as they have the EPO activity. When replacing one or more of the amino acids of the amino acid sequence of hEPO with other amino acids, the number of amino acids to be replaced is preferably 1 to 10, more preferably 1 to 5, still more preferably 1 to 3, even more preferably 1 or 2. When deleting one or more amino acids of the amino acid sequence of hEPO, the number of amino acids to be deleted is preferably 1 to 10, more preferably 1 to 5, still more preferably 1 to 3, and even more preferably 1 or 2. It is also possible to introduce a combined mutation of such substitution and deletion of amino acids. When adding one or more amino acids to hEPO, they may be added, inside, or on the N-terminal side or the C-terminal side of, the amino acid sequence of hEPO, and the number of amino acids to be added is preferably 1 to 10, more preferably 1 to 5, still more preferably 1 to 3, even more preferably 1 or 2. It is also possible to introduce a combined mutation of such addition, substitution, and deletion of the amino acid. The amino acid sequence of each of such mutated hEPO has a homology preferably not lower than 80%, more preferably not lower than 90%, still more preferably not lower than 95%, to the amino acid sequence of the original hEPO. Darbepoetin is an example obtained by mutating natural-type hEPO.

Specific examples of the fusion protein where the different protein (A) is human arylsulfatase A (hARSA) include;

(1) the one that is composed of: the portion consisting of hTfR heavy chain linked, on the C-terminal side thereof and via a peptide bond, to hARSA, and the other portion consisting of the hTfR light chain, wherein the amino acid sequence of hTfR heavy chain of the former is set forth as SEQ ID NO:172, and the amino acid sequence of the latter is set forth as SEQ ID NO:164, (2) the one that is composed of: the portion consisting of hTfR heavy chain linked, on the C-terminal side thereof and via a peptide bond, to hARSA, and the other portion consisting of the hTfR light chain, wherein the amino acid sequence of hTfR heavy chain of the former is set forth as SEQ ID NO:188, and the amino acid sequence of the latter is set forth as SEQ ID NO:180, and (3) the one that is composed of: the portion consisting of hTfR heavy chain linked, on the C-terminal side thereof via a peptide bond, to hARSA, and the other portion consisting of the hTfR light chain, wherein the amino acid sequence of hTfR heavy chain of the former is set forth as SEQ ID NO:210, and the amino acid sequence of the latter is set forth as SEQ ID NO:196.

In any of (1) to (3) above, hARSA and the hTfR heavy chain may be linked by peptide bond, either directly or via a linker sequence. Namely, in any of (1) to (3) above, the meaning of the phrase "via a peptide bond" and that of the phrase "directly or via a linker sequence" are the same. The linker sequence employed here consists of 1 to 50 amino acid residues. Though there is no particular limitation as to the amino acid sequence of the linker, it is preferably made of glycine and serine: for example, a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence consisting 1 to 50, or 2 to 17, 2 to 10, 10 to 40, 20 to 34, 23 to 31, 25 to 29, or 27 amino acids which are composed of 1 to 10 or 2 to 5 of any of those amino acid sequences consecutively linked. For example, an amino acid sequence comprising the amino acid sequence Gly-Ser may be preferably used as a linker sequence. Further, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

More specific embodiments of humanized antibody plus hARSA include the one that is composed of the part consisting of hARSA linked, via the linker sequence Gly-Ser, to the C-terminal side of the hTfR heavy chain, and the other part consisting of the hTfR light chain, wherein the amino acid sequence of the former is set forth as SEQ ID NO:260, and the amino acid sequence of the latter is set forth as SEQ ID NO:196.

Besides, in the present invention, though the term "human ARSA" or "hARSA" refers, in particular to the hARSA having the same amino acid sequence as the natural-type hARSA set forth as SEQ ID NO:259, it also includes those amino acid sequences produced by introducing a mutation such as substitution, deletion, addition and the like into the amino acid sequence of the natural-type hARSA, insofar as they have the ARSA activity. When replacing one or more of the amino acids of the amino acid sequence of hARSA with other amino acids, the number of amino acids to be replaced is preferably 1 to 10, more preferably 1 to 5, still more preferably 1 to 3, even more preferably 1 or 2. When deleting one or more amino acids of the amino acid sequence of hARSA, the number of amino acids to be deleted is preferably 1 to 10, more preferably 1 to 5, still more preferably 1 to 3, and even more preferably 1 or 2. It is also possible to introduce a combined mutation of such substitution and deletion of amino acids. When adding one or more amino acids to hARSA, they may be added, inside, or on the N-terminal side or the C-terminal side of, the amino acid sequence of hARSA, and the number of amino acids to be added is preferably 1 to 10, more preferably 1 to 5, still more preferably 1 to 3, even more preferably 1 or 2. It is also possible to introduce a combined mutation of such addition, substitution, and deletion of the amino acid. The amino acid sequence of each of such mutated hARSA has a homology preferably not lower than 80%, more preferably not lower than 90%, and still more preferably not lower than 95%, to the amino acid sequence of the original hARSA.

Specific examples of the fusion protein where the different protein (A) is human PPT-1 (hPPT-1) include;

(1) the one that is composed of the portion consisting of hTfR heavy chain linked, on the C-terminal side thereof and via a peptide bond, to hPPT-1, and the other portion consisting of the hTfR light chain, wherein the amino acid sequence of hTfR heavy chain of the former is set forth as SEQ ID NO:172, and the amino acid sequence of the latter is set forth as SEQ ID NO:164, (2) the one that is composed of the portion consisting of hTfR heavy chain linked, on the C-terminal side thereof and via a peptide bond, to hPPT-1, and the other portion consisting of the hTfR light chain, wherein the amino acid sequence of hTfR heavy chain of the former is set forth as SEQ ID NO:188, and the amino acid sequence of the latter is set forth as SEQ ID NO:180, and (3) the one that is composed of the portion consisting of hTfR heavy chain linked, on the C-terminal side thereof and via a peptide bond, to hPPT-1, and the other portion consisting of the hTfR light chain, wherein the amino acid sequence of hTfR heavy chain of the former is set forth as SEQ ID NO:210, and the amino acid sequence of the latter is set forth as SEQ ID NO:196.

In any of (1) to (3) above, hPPT-1 and the hTfR heavy chain may be linked by peptide bond, either directly or via a linker sequence. Namely, in any of (1) to (3) above, the meaning of the phrase "via a peptide bond" and that of the phrase "directly or via a linker sequence" are the same. The linker sequence employed here consists of 1 to 50 amino acid residues. Though there is no particular limitation as to the amino acid sequence of the linker, it is preferably made of glycine and serine: for example, a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence consisting 1 to 50, or 2 to 17, 2 to 10, 10 to 40, 20 to 34, 23 to 31, 25 to 29, or 27 amino acids which are composed of 1 to 10 or 2 to 5 of any of those amino acid sequences consecutively linked. For example, an amino acid sequence comprising the amino acid sequence Gly-Ser may be preferably used as a linker sequence. Further, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

More specific embodiments of humanized antibody plus hPPT-1 include the one that is composed of the part consisting of hPPT-1 linked, via the linker sequence Gly-Ser, to the C-terminal side of the hTfR heavy chain, and the other part consisting of the hTfR light chain, wherein the amino acid sequence of the former is set forth as SEQ ID NO:263, and the amino acid sequence of the latter is set forth as SEQ ID NO:196.

Besides, in the present invention, though the term "human PPT-1" or "hPPT-1" refers, in particular to the hPPT-1 having the same amino acid sequence as the natural-type hPPT-1 set forth as SEQ ID NO:262, it also includes those amino acid sequences produced by introducing a mutation such as substitution, deletion, addition and the like into the amino acid sequence of the natural-type hPPT-1, insofar as they have the PPT-1 activity. When replacing one or more of the amino acids of the amino acid sequence of hPPT-1 with other amino acids, the number of amino acids to be replaced is preferably 1 to 10, more preferably 1 to 5, still more preferably 1 to 3, even more preferably 1 or 2. When deleting one or more amino acids of the amino acid sequence of hPPT-1, the number of amino acids to be deleted is preferably 1 to 10, more preferably 1 to 5, still more preferably 1 to 3, and even more preferably 1 or 2. It is also possible to introduce a combined mutation of such substitution and deletion of amino acids. When adding one or more amino acids to hPPT-1, they may be added, inside, or on the N-terminal side or the C-terminal side of, the amino acid sequence of hPPT-1, and the number of amino acids to be added is preferably 1 to 10, more preferably 1 to 5, still more preferably 1 to 3, even more preferably 1 or 2. It is also possible to introduce a combined mutation of such addition, substitution, and deletion of the amino acid. The amino acid sequence of each of such mutated hPPT-1 has a homology preferably not lower than 80%, more preferably not lower than 90%, and still more preferably not lower than 95%, to the amino acid sequence of the original hPPT-1.

Specific examples of the fusion protein where the different protein (A) is human PPT-1 (hPPT-1) include;

(1) the one that is composed of the portion consisting of hTfR heavy chain linked, on the C-terminal side thereof via a peptide bond, to hTPP-1, and the other portion consisting of the hTfR light chain, wherein the amino acid sequence of hTfR heavy chain of the former is set forth as SEQ ID NO:172, and the amino acid sequence of the latter is set forth as SEQ ID NO:164, (2) the one that is composed of the portion consisting of hTfR heavy chain linked, on the C-terminal side thereof via a peptide bond, to hTPP-1, and the other portion consisting of the hTfR light chain, wherein the amino acid sequence of hTfR heavy chain of the former is set forth as SEQ ID NO:188, and the amino acid sequence of the latter is set forth as SEQ ID NO:180, and (3) the one that is composed of the portion consisting of hTfR heavy chain linked, on the C-terminal side thereof via a peptide bond, to hTPP-1, and the other portion consisting of the hTfR light chain, wherein the amino acid sequence of hTfR heavy chain of the former is set forth as SEQ ID NO:210, and the amino acid sequence of the latter is set forth as SEQ ID NO:196.

In any of (1) to (3) above, hTPP-1 and the hTfR heavy chain may be linked by peptide bond, either directly or via a linker sequence. Namely, in any of (1) to (3) above, the meaning of the phrase "via a peptide bond" and that of the phrase "directly or via a linker sequence" are the same. The linker sequence employed here consists of 1 to 50 amino acid residues. Though there is no particular limitation as to the amino acid sequence of the linker, it is preferably made of glycine and serine: for example, a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence consisting 1 to 50, or 2 to 17, 2 to 10, 10 to 40, 20 to 34, 23 to 31, 25 to 29, or 27 amino acids which are composed of 1 to 10 or 2 to 5 of any of those amino acid sequences consecutively linked. For example, an amino acid sequence comprising the amino acid sequence Gly-Ser may be preferably used as a linker sequence. Further, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

More specific embodiments of humanized antibody plus hTPP-1 include the one that is composed of the part consisting of hTPP-1 linked, via the linker sequence Gly-Ser, to the C-terminal side of the hTfR heavy chain, and the other part consisting of the hTfR light chain, wherein the amino acid sequence of the former is set forth as SEQ ID NO:266, and the amino acid sequence of the latter is set forth as SEQ ID NO:196.

Besides, in the present invention, though the term "human TPP-1" or "hTPP-1" refers, in particular to the hTPP-1 having the same amino acid sequence as the natural-type hTPP-1 set forth as SEQ ID NO:265, it also includes those amino acid sequences produced by introducing a mutation such as substitution, deletion, addition and the like into the amino acid sequence of the natural-type hTPP-1, insofar as they have the TPP-1 activity. When replacing one or more of the amino acids of the amino acid sequence of hTPP-1 with other amino acids, the number of amino acids to be replaced is preferably 1 to 10, more preferably 1 to 5, still more preferably 1 to 3, even more preferably 1 or 2. When deleting one or more amino acids of the amino acid sequence of hTPP-1, the number of amino acids to be deleted is preferably 1 to 10, more preferably 1 to 5, still more preferably 1 to 3, and even more preferably 1 or 2. It is also possible to introduce a combined mutation of such substitution and deletion of amino acids. When adding one or more amino acids to hTPP-1, they may be added, inside, or on the N-terminal side or the C-terminal side of, the amino acid sequence of hTPP-1, and the number of amino acids to be added is preferably 1 to 10, more preferably 1 to 5, still more preferably 1 to 3, even more preferably 1 or 2. It is also possible to introduce a combined mutation of such addition, substitution, and deletion of the amino acid. The amino acid sequence of each of such mutated hTPP-1 has a homology preferably not lower than 80%, more preferably not lower than 90%, and still more preferably not lower than 95%, to the amino acid sequence of the original hTPP-1.

Specific examples of the fusion protein where the different protein (A) is humanα-L-iduronidase (hIDUA) include;

(1) the one that is composed of: the portion consisting of hTfR heavy chain linked, on the C-terminal side thereof and via a peptide bond, to hIDUA, and the other portion consisting of the hTfR light chain, wherein the amino acid sequence of hTfR heavy chain of the former is set forth as SEQ ID NO:172, and the amino acid sequence of the latter is set forth as SEQ ID NO:164, (2) the one that is composed of: the portion consisting of hTfR heavy chain linked, on the C-terminal side thereof and via a peptide bond, to hIDUA, and the other portion consisting of the hTfR light chain, wherein the amino acid sequence of hTfR heavy chain of the former is set forth as SEQ ID NO:188, and the amino acid sequence of the latter is set forth as SEQ ID NO:180, and (3) the one that is composed of: the portion consisting of hTfR heavy chain linked, on the C-terminal side thereof and via a peptide bond, to hIDUA, and the other portion consisting of the hTfR light chain, wherein the amino acid sequence of hTfR heavy chain of the former is set forth as SEQ ID NO:210, and the amino acid sequence of the latter is set forth as SEQ ID NO:196.

In any of (1) to (3) above, hIDUA and the hTfR heavy chain may be linked by peptide bond, either directly or via a linker sequence. Namely, in any of (1) to (3) above, the meaning of the phrase "via a peptide bond" and that of the phrase "directly or via a linker sequence" are the same. The linker sequence employed here consists of 1 to 50 amino acid residues. Though there is no particular limitation as to the amino acid sequence of the linker, it is preferably made of glycine and serine: for example, a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence consisting 1 to 50, or 2 to 17, 2 to 10, 10 to 40, 20 to 34, 23 to 31, 25 to 29, or 27 amino acids which are composed of 1 to 10 or 2 to 5 of any of those amino acid sequences consecutively linked. For example, an amino acid sequence comprising the amino acid sequence Gly-Ser may be preferably used as a linker sequence. Further, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

More specific embodiments of humanized antibody plus hIDUA include the one that is composed of the part consisting of hIDUA linked, via the linker sequence Gly-Ser, to the C-terminal side of the hTfR heavy chain, and the other part consisting of the hTfR light chain, wherein the amino acid sequence of the former is set forth as SEQ ID NO:269, and the amino acid sequence of the latter is set forth as SEQ ID NO:196.

In the present invention, though the term "human IDUA" or "hIDUA" refers, in particular, to the hIDUA having the same amino acid sequence as the natural-type hIDUA set forth as SEQ ID NO:268, it also includes those amino acid sequences produced by introducing a mutation such as substitution, deletion, addition and the like into the amino acid sequence of the natural-type hIDUA, insofar as they have the hIDUA activity. When replacing one or more of the amino acids of the amino acid sequence of hIDUA with other amino acids, the number of amino acids to be replaced is preferably 1 to 10, more preferably 1 to 5, still more preferably 1 to 3, even more preferably 1 or 2. When deleting one or more amino acids of the amino acid sequence of hIDUA, the number of amino acids to be deleted is preferably 1 to 10, more preferably 1 to 5, still more preferably 1 to 3, and even more preferably 1 or 2. It is also possible to introduce a combined mutation of such substitution and deletion of amino acids. When adding one or more amino acids to hIDUA, they may be added, inside, or on the N-terminal side or the C-terminal side of, the amino acid sequence of hIDUA, and the number of amino acids to be added is preferably 1 to 10, more preferably 1 to 5, still more preferably 1 to 3, even more preferably 1 or 2. It is also possible to introduce a combined mutation of such addition, substitution, and deletion of the amino acid. The amino acid sequence of the mutated hIDUA has a homology of preferably not lower than 80%, more preferably not lower than 90%, still more preferably not lower than 95% to the amino acid sequence of the original hIDUA.

Specific examples of the fusion protein where the different protein (A) is human TNF-α receptor (hTNFαR) include;

(1) the one that is composed of: the portion consisting of hTfR heavy chain linked, on the C-terminal side thereof and via a peptide bond, to hTNFαR, and the other portion consisting of the hTfR light chain, wherein the amino acid sequence of hTfR heavy chain of the former is set forth as SEQ ID NO:172, and the amino acid sequence of the latter is set forth as SEQ ID NO:164, (2) the one that is composed of: the portion consisting of hTfR heavy chain linked, on the C-terminal side thereof and via a peptide bond, to hTNFαR, and the other portion consisting of the hTfR light chain, wherein the amino acid sequence of hTfR heavy chain of the former is set forth as SEQ ID NO:188, and the amino acid sequence of the latter is set forth as SEQ ID NO:180, and (3) the one that is composed of: the portion consisting of hTfR heavy chain linked, on the C-terminal side thereof and via a peptide bond, to hTNFαR, and the other portion consisting of the hTfR light chain, wherein the amino acid sequence of hTfR heavy chain of the former is set forth as SEQ ID NO:210, and the amino acid sequence of the latter is set forth as SEQ ID NO:196.

In any of (1) to (3) above, hTNFαR and the hTfR heavy chain may be linked by peptide bond, either directly or via a linker sequence. Namely, in any of (1) to (3) above, the meaning of the phrase "via a peptide bond" and that of the phrase "directly or via a linker sequence" are the same. The linker sequence employed here consists of 1 to 50 amino acid residues. Though there is no particular limitation as to the amino acid sequence of the linker, it is preferably made of glycine and serine: for example, a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence consisting 1 to 50, or 2 to 17, 2 to 10, 10 to 40, 20 to 34, 23 to 31, 25 to 29, or 27 amino acids which are composed of 1 to 10 or 2 to 5 of any of those amino acid sequences consecutively linked. For example, an amino acid sequence comprising the amino acid sequence Gly-Ser may be preferably used as a linker sequence.

Further, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

More specific embodiments of humanized antibody plus hTNFαR include the one that is composed of the part consisting of hTNFαR linked, via the linker sequence Gly-Ser, to the C-terminal side of the hTfR heavy chain, and the other part consisting of the hTfR light chain, wherein the amino acid sequence of the former is set forth as SEQ ID NO:272, and the amino acid sequence of the latter is set forth as SEQ ID NO:196.

Besides, in the present invention, though the term "human TNFαR" or "hTNFαR" refers, in particular to the hTNFαR having the same amino acid sequence as the natural-type hTNFαR set forth as SEQ ID NO:271, it also includes those amino acid sequences produced by introducing a mutation such as substitution, deletion, addition and the like into the amino acid sequence of the natural-type hTNFαR, insofar as they have the activity or function as TNFαR. When replacing one or more of the amino acids of the amino acid sequence of hTNFαR with other amino acids, the number of amino acids to be replaced is preferably 1 to 10, more preferably 1 to 5, still more preferably 1 to 3, even more preferably 1 or 2. When deleting one or more amino acids of the amino acid sequence of hTNFαR, the number of amino acids to be deleted is preferably 1 to 10, more preferably 1 to 5, still more preferably 1 to 3, and even more preferably 1 or 2. It is also possible to introduce a combined mutation of such substitution and deletion of amino acids. When adding one or more amino acids to hTNFαR, they may be added, inside, or on the N-terminal side or the C-terminal side of, the amino acid sequence of hTNFαR, and the number of amino acids to be added is preferably 1 to 10, more preferably 1 to 5, still more preferably 1 to 3, even more preferably 1 or 2. It is also possible to introduce a combined mutation of such addition, substitution, and deletion of the amino acid. The amino acid sequence of each of such mutated hTNFαR has a homology preferably not lower than 80%, more preferably not lower than 90%, and still more preferably not lower than 95%, to the amino acid sequence of the original hTNFαR.

Specific examples of the fusion protein where the different protein (A) is human heparan N-sulfatase (hSGSH) include:

(1) the one that is composed of the portion consisting of hTfR heavy chain linked, on the C-terminal side thereof and via a peptide bond, to hSGSH, and the other portion consisting of the hTfR light chain, wherein the amino acid sequence of hTfR heavy chain of the former is set forth as SEQ ID NO:172, and the amino acid sequence of the latter is set forth as SEQ ID NO:164, (2) the one that is composed of the portion consisting of hTfR heavy chain linked, on the C-terminal side thereof and via a peptide bond, to hSGSH, and the other portion consisting of the hTfR light chain, wherein the amino acid sequence of hTfR heavy chain of the former is set forth as SEQ ID NO:188, and the amino acid sequence of the latter is set forth as SEQ ID NO:180, and (3) the one that is composed of: the portion consisting of hTfR heavy chain linked, on the C-terminal side thereof and via a peptide bond, to hSGSH, and the other portion consisting of the hTfR light chain, wherein the amino acid sequence of hTfR heavy chain of the former is set forth as SEQ ID NO:210, and the amino acid sequence of the latter is set forth as SEQ ID NO:196.

In any of (1) to (3) above, hSGSH and the hTfR heavy chain may be linked by peptide bond, either directly or via a linker sequence. Namely, in any of (1) to (3) above, the meaning of the phrase "via a peptide bond" and that of the phrase "directly or via a linker sequence" are the same. The linker sequence employed here consists of 1 to 50 amino acid residues. Though there is no particular limitation as to the amino acid sequence of the linker, it is preferably made of glycine and serine: for example, a single amino acid either glycine or serine, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence consisting 1 to 50, or 2 to 17, 2 to 10, 10 to 40, 20 to 34, 23 to 31, 25 to 29, or 27 amino acids which are composed of 1 to 10 or 2 to 5 of any of those amino acid sequences consecutively linked. For example, an amino acid sequence comprising the amino acid sequence Gly-Ser may be preferably used as a linker sequence. Further, a linker sequence comprising 27 amino acids is preferably used that is composed of the amino acid sequence Gly-Ser followed by consecutively linked five copies of the amino acid sequence Gly-Gly-Gly-Gly-Ser (SEQ ID NO:3).

More specific embodiments of humanized antibody plus hSGSH include the one that is composed of the part consisting of hSGSH linked, via the linker sequence Gly-Ser, to the C-terminal side of the hTfR heavy chain, and the other part consisting of the hTfR light chain, wherein the amino acid sequence of the former is set forth as SEQ ID NO:275, and the amino acid sequence of the latter is set forth as SEQ ID NO:196.

Besides, in the present invention, though the term "human SGSH" or "hSGSH" refers, in particular to the hSGSH having the same amino acid sequence as the natural-type hSGSH set forth as SEQ ID NO:274, it also includes those amino acid sequences produced by introducing a mutation such as substitution, deletion, addition and the like into the amino acid sequence of the natural-type hSGSH, insofar as they have the SGSH activity. When replacing one or more of the amino acids of the amino acid sequence of hSGSH with other amino acids, the number of amino acids to be replaced is preferably 1 to 10, more preferably 1 to 5, still more preferably 1 to 3, even more preferably 1 or 2. When deleting one or more amino acids of the amino acid sequence of hSGSH, the number of amino acids to be deleted is preferably 1 to 10, more preferably 1 to 5, still more preferably 1 to 3, and even more preferably 1 or 2. It is also possible to introduce a combined mutation of such substitution and deletion of amino acids. When adding one or more amino acids to hSGSH, they may be added, inside, or on the N-terminal side or the C-terminal side of, the amino acid sequence of hSGSH, and the number of amino acids to be added is preferably 1 to 10, more preferably 1 to 5, still more preferably 1 to 3, even more preferably 1 or 2. It is also possible to introduce a combined mutation of such addition, substitution, and deletion of the amino acid. The amino acid sequence of each of such mutated hSGSH has a homology preferably not lower than 80%, more preferably not lower than 90%, and still more preferably not lower than 95%, to the amino acid sequence of the original hSGSH.

In the case where the different protein (A) fused with the anti-hTfR antibody is human iduronate 2-sulfatase (hI2S), human erythropoietin (hEPO), human arylsulfatase A (hARSA), human PPT-1 (hPPT-1), human TPP-1 (hTPP-1), human α-L-iduronidase (hIDUA), human TNF-α receptor (hTNFαR), or human heparan N-sulfatase (hSGSH), the expression the different protein (A) fused with the anti-hTfR antibody retains the activity or function that the different protein (A) exhibits under a physiological condition, (or simply, it retains the activity or function), means that the not less than 3% of the activity or function is retained as compared with the activity or function that the corresponding natural-type proteins intrinsically have. However, their activity or function is preferably not less than 10%, more preferably not less than 20%, still more preferably not less than 50%, and even more preferably not less than 80%, as compared with the activity or function that the corresponding natural-type different protein (A) intrinsically have. The same applies where the different protein (A) fused with the anti-hTfR antibody in mutated.

The anti-hTfR antibody according to the present invention can be used for the production of a pharmaceutical agent for parenteral administration for the treatment of a disease condition of the central nervous system by binding it to the molecule of a physiologically active protein or a pharmacologically active low-molecular-weight compound. And the anti-hTfR antibody conjugated with the molecule of a physiologically active protein or a pharmacologically active low-molecular-weight compound, can be used in the method of treatment of a patient with a disease condition of the central nervous system, in which a therapeutically effective amount of a physiologically active protein or pharmacologically active low-molecular-weight compound is administered to the patient with a disease of the central nervous system parenterally (including intravenous injection such as intravenous infusion). The anti-hTfR antibody conjugated with the molecule of a physiologically active protein or a pharmacologically active low-molecular-weight compound, after parenterally administered, can not only get inside the brain but also reach other organs where hTfR is expressed.

In particular, as the anti-hTfR antibody of the present invention can, as a conjugate with human iduronate 2-sulfatase (hI2S), enable hI2S to pass through the blood-brain barrier and function in the brain, the antibody can be used for the production of a pharmaceutical agent for parenteral administration for the treatment of a disease condition of the central nervous system accompanying Hunter syndrome. Further, the anti-hTfR antibody conjugated with hI2S can be used in the method of treatment of a patient with a disease condition of the central nervous system disorder accompanying Hunter syndrome, in which a therapeutically effective amount of the antibody is administered to the patient with Hunter syndrome parenterally (including intravenous injection such as intravenous infusion). The anti-hTfR antibody conjugated with hI2S, after parenterally administered, can not only get inside the brain but also reach other organs where hTfR is expressed.

Further, as the anti-hTfR antibody of the present invention can, as a conjugate with human erythropoietin (hEPO), enable hEPO to pass through the blood-brain barrier and function in the brain, the antibody can be used for the production of a pharmaceutical agent for parenteral administration for the treatment of a disease condition of the central nervous system accompanying cerebral ischemia. Further, the anti-hTfR antibody conjugated with hEPO can be used in the method of treatment of a patient with a disease condition of the central nervous system accompanying cerebral ischemia, in which a therapeutically effective amount of the conjugated antibody is administered to the patient with cerebral ischemia parenterally (including intravenous injection such as intravenous infusion). The anti-hTfR antibody conjugated with hEPO, after parenterally administered, can not only get inside the brain but also reach other organs where hTfR is expressed. The same applies if human erythropoietin is replaced with human darbepoetin.

Further, as the anti-hTfR antibody of the present invention can, as a conjugate with human arylsulfatase A (hARSA), enable hARSA to pass through the blood-brain barrier and function in the brain, the antibody can be used for the production of a pharmaceutical agent for parenteral administration for the treatment of a disease condition of the central nervous system accompanying metachromatic white matter degeneration (metachromatic leukodystrophy). Further, the anti-hTfR antibody conjugated with hARSA can be used in the method of treatment of a patient with a disease condition of the central nervous system accompanying metachromatic white matter degeneration (metachromatic leukodystrophy), in which a therapeutically effective amount of the conjugated antibody is administered to the patient with the disease parenterally (including intravenous injection such as intravenous infusion). The anti-hTfR antibody conjugated with hARSA, after parenterally administered, can not only get inside the brain but also reach other organs where hTfR is expressed.

Further, as the anti-hTfR antibody of the present invention can, as a conjugate with human PPT-1 (hPPT-1), enable hPPT-1 to pass through the blood-brain barrier and function in the brain, the antibody can be used for the production of a pharmaceutical agent for parenteral administration for the treatment of a disease condition of the central nervous system accompanying neuronal ceroid lipofuscinosis or Santavuori-Haltia disease. Further, the anti-hTfR antibody conjugated with hPPT-1 can be used in the method of treatment of a patient with a disease condition of the central nervous system accompanying neuronal ceroid lipofuscinosis or Santavuori-Haltia disease, in which a therapeutically effective amount of the conjugated antibody is administered to the patient with any of these diseases parenterally (including intravenous injection such as intravenous infusion). The anti-hTfR antibody conjugated with hPPT-1, after parenterally administered, can not only get inside the brain but also reach other organs where hTfR is expressed.

Further, as the anti-hTfR antibody of the present invention can, as a conjugate with human TPP-1 (hTPP-1), enable hTPP-1 to pass through the blood-brain barrier and function in the brain, the antibody can be used for the production of a pharmaceutical agent for parenteral administration for the treatment of a disease condition of the central nervous system accompanying neuronal ceroid lipofuscinosis or Jansky-Bielschowsky disease. Further, the anti-hTfR antibody conjugated with hPPT-1 can be used in the method of treatment of a patient with a disease condition of the central nervous system accompanying neuronal ceroid lipofuscinosis or Jansky-Bielschowsky disease, in which a therapeutically effective amount of the conjugated antibody is administered to the patient with any of these diseases parenterally (including intravenous injection such as intravenous infusion). The anti-hTfR antibody conjugated with hTPP-1, after parenterally administered, can not only get inside the brain but also reach other organs where hTfR is expressed.

Further, as the anti-hTfR antibody of the present invention can, as a conjugate with human α-L-iduronidase (hIDUA), enable hIDUA to pass through the blood-brain barrier and function in the brain, the antibody can be used for the production of a pharmaceutical agent for parenteral administration for the treatment of a disease condition of the central nervous system accompanying Hurler syndrome or Hurler-Scheie syndrome. Further, the anti-hTfR antibody conjugated with hIDUA can be used in the method of treatment of a patient with a disease condition of the central nervous system accompanying Hurler syndrome or Hurler-Scheie syndrome, in which a therapeutically effective amount of the conjugated antibody is administered to the patient with any of these diseases parenterally (including intravenous injection such as intravenous infusion). The anti-hTfR antibody conjugated with hIDUA, after parenterally administered, can not only get inside the brain but also reach other organs where hTfR is expressed.

Further, as the anti-hTfR antibody of the present invention can, as a conjugate with human TNF-α receptor (hTNFαR), enable hTNFαR to pass through the blood-brain barrier and function in the brain, the antibody can be used for the production of a pharmaceutical agent for parenteral administration for the treatment of a disease condition of the central nervous system accompanying cerebral ischemia or encephalitis. Further, the anti-hTfR antibody conjugated with hTNFαR can be used in the method of treatment of a patient with a disease condition of the central nervous system accompanying cerebral ischemia or encephalitis, in which a therapeutically effective amount of the conjugated antibody is administered to the patient with any of these diseases parenterally (including intravenous injection such as intravenous infusion). The anti-hTfR antibody conjugated with hTNFαR, after parenterally administered, can not only get inside the brain but also reach other organs where hTfR is expressed.

Further, as the anti-hTfR antibody of the present invention can, as a conjugate with human heparan N-sulfatase (hSGSH), enable hSGSH to pass through the blood-brain barrier and function in the brain, the antibody can be used for the production of a pharmaceutical agent for parenteral administration for the treatment of a disease condition of the central nervous system accompanying Sanfilippo syndrome.

Further, the anti-hTfR antibody conjugated with hSGSH can be used in the method of treatment of a patient with a disease condition of the central nervous system accompanying Sanfilippo syndrome, in which a therapeutically effective amount of the conjugated antibody is administered to the patient with any of these diseases parenterally (including intravenous injection such as intravenous infusion). The anti-hTfR antibody conjugated with hSGSH, after parenterally administered, can not only get inside the brain but also reach other organs where hTfR is expressed.

The proteins, low-molecular-weight compound and the like that are conjugated with the anti-hTfR antibody of the present invention can be used as pharmaceutical agents which are to exhibit their functions in the central nervous system (CNS) after parenterally administered. Such pharmaceutical agents may be administered to patients generally by intravenous injection such as intravenous injection, subcutaneous injection, intramuscular injection and the like, though there is no particular limitation as to the route of their administration.

The proteins, the low-molecular-weight compounds and the like that are conjugated with the anti-hTfR antibody of the present invention can be provided to medical facilities as pharmaceutical agents in such a form as a lyophilized product or an aqueous preparation. In the case of an aqueous preparation, it can be provided in the form of preparations in which one of the pharmaceutical agents is dissolved in a solution containing a stabilizer, buffer, and an isotonizer in advance, and sealed in vials or syringes. A type of preparations sealed in a syringe is generally called a prefilled syringe-type preparation. Taking the form of a prefilled syringe-type preparation facilitates patients' self-administration of the pharmaceutical agent.

Where an aqueous preparation is provided, the concentration of the protein, the low-molecular-weight compound or the like conjugated with the anti-hTfR antibody in the aqueous preparation is, e.g., 1 to 4 mg/mL, though it is to be adjusted as desired in accordance with the dosage. Where there is no particular limitation as to stabilizers to be contained in the aqueous preparation insofar as they are pharmaceutically available, nonionic surfactants may preferably be used. Examples of such nonionic surfactants include polysorbate and poloxamer, either of which may be used alone or in combination. Among polysorbates, polysorbate 20 and polysorbate 80 are preferably used. As poloxamer, poloxamer 188 (polyoxyethylene (160) polyoxypropylene (30) glycol) is particularly preferred. Further, the concentration of nonionic surfactant contained in the aqueous preparation is preferably 0.01 to 1 mg/mL, more preferably, 0.01 to 0.5 mg/mL, and still more preferably 0.1 to 0.5 mg/mL. As stabilizers, amino acids such as histidine, arginine, methionine, and glycine may also be used. Where employed as a stabilizer, the concentration of an amino acid in the aqueous preparation is preferably 0.1 to 40 mg/mL, more preferably 0.2 to 5 mg/mL, and still more preferably 0.5 to 4 mg/mL. While there is no particular limitation as to a buffer to be contained in the aqueous preparation insofar as it is pharmaceutically available, phosphate buffer is preferred, and more preferred is sodium phosphate buffer. Where used as a buffer, the concentration of sodium phosphate is preferably 0.01 to 0.04 M. The pH of the aqueous preparation adjusted with a buffer is preferably 5.5 to 7.2. While there is no particular limitation as to an isotonizer to be contained in the aqueous preparation insofar as it is pharmaceutically available, sodium chloride or mannitol may be preferably used alone or in combination as an isotonizer.

EXAMPLES

Though the present invention is described in further detail below with reference to examples, it is not intended that the present invention be limited to those examples.

[Example 1] Construction of hTfR Expression Vector

Employing human spleen Quick Clone cDNA (Clontech Inc.) as a template and using primer hTfR5' (SEQ ID NO:214) and primer hTfR3' (SEQ ID NO:215), PCR was performed to amplify the gene fragment encoding human transferrin receptor (hTfR). The amplified fragment encoding hTfR was digested with MluI and NotI, and then inserted between MluI and NotI sites of vector pCI-neo (Promega Corp.). The vector thus prepared was designated pCI-neo (hTfR). This vector then was digested with MluI and NotI to cut out the gene fragment encoding hTfR, and this fragment was inserted between MluI and NotI sites of pE-mIRES-GS-puro, an expression vector disclosed in an international publication WO 2012/063799 to construct an hTfR expression vector, pE-mIRES-GS-puro (hTfR).

[Example 2] Preparation of Recombinant hTfR

Into CHO-K1 cells was introduced pE-mIRES-GS-puro (hTfR) by electroporation, and the cells then were subjected to selection culture in a CD OptiCHO™ medium (Invitrogen Inc.) containing methionine sulfoximine (MSX) and puromycin to prepare recombinant hTfR expressing cells. The recombinant hTfR expressing cells were cultured, and recombinant hTfR was prepared.

[Example 3] Immunization of Mouse with Recombinant hTfR

Mice were immunized with recombinant hTfR prepared in Example 2 as antigen. Immunization was carried out by intravenously or intraperitoneally injecting the mice with the antigen.

[Example 4] Preparation of Hybridoma Cells

About one week after the last injection, the spleens of the mice were excised and homogenized to isolate spleen cells. The spleen cells thus obtained were fused with cells of mouse myeloma cell line (P3.X63.Ag8.653) by the polyethylene glycol method. After cell fusion, the cells were suspended in a RPMI 1640 medium containing (1×) HAT supplement (Life Technologies Inc.) and 10% Ultra low IgG fetal bovine serum (Life Technologies Inc.), and the cell suspension was dispensed to twenty 96-well plates, each at 200 μL/well. After the cells were cultured for 10 days in a carbon dioxide gas incubator (37° C., 5% $CO_2$), each well was examined under a microscope, and the wells that contain a single colony were selected.

When the cells in each well reached near confluence, the culture supernatant was collected as a culture supernatant of hybridoma, and subjected to the following screening process.

[Example 5] Screening of High Affinity Antibody Producing Cell Line

The recombinant hTfR solution (Sino Biologics Inc.) was diluted with 50 mM sodium phosphate buffer (pH 9.5 to 9.6) to 5 μg/mL to prepare a solid phase solution. After 50 μL of the solid phase solution was added to each well of a Nunc MaxiSorp' flat-bottom 96-well plate (substrate: polystyrene, mfd. by Nunc Inc.), the plate was left to stand for one hour at room temperature to let the recombinant hTfR adhere to the plate and become immobilized. The solid phase solution was discarded, each well was washed three times with 250 μL of washing solution (PBS containing 0.05% Tween20), 200 μL of a blocking solution (PBS containing 1% BSA) then was added to each well, and the plate was left to stand for one hour at room temperature.

The blocking solution was discarded, and each well was washed three times with 250 μL washing solution (PBS containing 0.05% Tween20). To each well was added 50 μL of the hybridoma culture supernatant, and the plate was left to stand for one hour at room temperature to let the mouse anti-hTfR antibody contained in the culture supernatant bind to the recombinant hTfR. At the same time, to some wells was added 50 μL of culture supernatant of a hybridoma that did not produce mouse anti-hTfR antibody, as a control. In addition, 50 μL of the medium for hybridoma culture was added to the wells, as mock wells, beside the wells to which the culture supernatant was added. Measurement was conducted in an n=2 fashion. Then, the solution was discarded, and each well was washed three times with 250 μL, of washing solution (PBS containing 0.05% Tween20).

To each of the above wells was added 100 μL, of HRP-labelled goat anti-mouse immunoglobulin antibody solution (Promega Inc.), and the plate was left to stand for one minute at room temperature. The solution then was discarded, and each well was washed three times with 250 μL, of washing solution (PBS containing 0.05% Tween20). To each well as added 50 μL, of a chromogenic substrate solution, TMB Stabilized Substrate for Horseradish Peroxidase (Promega Inc.), and the wells were left to stand for 10 to 20 minutes at room temperature. Then, following addition of 100 μL, of a stop solution (2N sulfuric acid), the absorbance of each well was measured on a plate reader at 450 nm. Of the two wells for each of the culture supernatant and control, the mean values were taken, respectively, and from each of the mean values, the respective mean value for the two mock wells placed corresponding to each of the culture supernatant and the control, was subtracted, giving the measurement.

Fourteen types of hybridoma cells corresponding to culture supernatants added to the wells which exhibited the higher measurements were selected as the cell lines (high affinity antibody producing cell line) that produce antibodies exhibiting high affinities to hTfR (high affinity anti-hTfR antibody). These fourteen types of cell lines were designated as Clone 1 line to Clone 14 line. Further, the anti-hTfR antibodies produced by Clone 1 line to Clone 14 line were designated as anti-hTfR antibodies Nos. 1 to 14, respectively.

[Example 6] Analysis of the Variable-Region Amino Acid Sequence of the High Affinity Anti-hTfR Antibodies From each of the Clone 1 line to Clone 14 line selected in Example 5, cDNA were prepared, using which as a template the genes encoding the light chain and the heavy chain of the antibody were amplified. By translating the nucleotide sequence of the amplified genes, the respective amino acid sequences of the light chain and heavy chain variable regions were determined for the anti-hTfR antibodies Nos. 1 to 14 produced by the cell lines.

The anti-hTfR antibody No. 1 was found to include the amino acid sequence set forth as SEQ ID NO:218 as the light chain variable region, and the amino acid sequence set forth as SEQ ID NO:219 as the heavy chain variable region. The light chain variable region was found to include the amino acid sequence set forth as SEQ ID NO:6 or 7 as CDR1; SEQ ID NO:8 or 9 as CDR2, and SEQ ID NO:10 as CDR3; and the heavy chain variable region to include the amino acid sequence set forth as SEQ ID NO:76 or 77 as CDR1, SEQ ID NO:78 or 79 as CDR2, and SEQ ID NO:80 or 81 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 2 was found to include the amino acid sequence set forth as SEQ ID NO:220 as the light chain variable region, and the amino acid sequence set forth as SEQ ID NO:221 as the heavy chain variable region. The light chain variable region was found to include the amino acid sequence set forth as SEQ ID NO:11 or 12 as CDR1; SEQ ID NO:13 or 14 as CDR2, and SEQ ID NO:15 as CDR3; and the heavy chain variable region to include the amino acid sequence set forth as SEQ ID NO:82 or 83 as CDR1, SEQ ID NO:84 or 85 as CDR2, and SEQ ID NO:86 or 87 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 3 was found to include the amino acid sequence set forth as SEQ ID NO:222 as the light chain variable region, and the amino acid sequence set forth as SEQ ID NO:223 as the heavy chain variable region. The light chain variable region was found to include the amino acid sequence set forth as SEQ ID NO:16 or 17 as CDR1; SEQ ID NO:18 or 19 as CDR2, and SEQ ID NO:20 as CDR3; and the heavy chain variable region to include the amino acid sequence set forth as SEQ ID NO:88 or 89 as CDR1, SEQ ID NO:90 or 91 as CDR2, and SEQ ID NO:92 or 93 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 4 was found to include the amino acid sequence set forth as SEQ ID NO:224 as the light chain variable region, and the amino acid sequence set forth as SEQ ID NO:225 as the heavy chain variable region. The light chain variable region was found to include the amino acid sequence set forth as SEQ ID NO:21 or 22 as CDR1; SEQ ID NO:23 or 24 as CDR2, and SEQ ID NO:25 as CDR3; and the heavy chain variable region to include the amino acid sequence set forth as SEQ ID NO:94 or 95 as CDR1, SEQ ID NO:96 or 97 as CDR2, and SEQ ID NO:98 or 99 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 5 was found to include the amino acid sequence set forth as SEQ ID NO:226 as the light chain variable region, and the amino acid sequence set forth as SEQ ID NO:227 as the heavy chain variable region. The light chain variable region was found to include the amino acid sequence set forth as SEQ ID NO:26 or 27 as CDR1; SEQ ID NO:28 or 29 as CDR2, and SEQ ID NO:30 as CDR3; and the heavy chain variable region to include the amino acid sequence set forth as SEQ ID NO:100 or 101 as CDR1, SEQ ID NO:102 or 103 as CDR2, and SEQ ID NO:104 or 105 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 6 was found to include the amino acid sequence set forth as SEQ ID NO:228 as the light chain variable region, and the amino acid sequence set forth as SEQ ID NO:229 as the heavy chain variable region. The light chain variable region was found to include the amino acid sequence set forth as SEQ ID NO:31 or 32 as CDR1; SEQ ID NO:33 or 34 as CDR2, and SEQ ID NO:35 as CDR3; and the heavy chain variable region to include the amino acid sequence set forth as SEQ ID NO:106 or 107 as CDR1, SEQ ID NO:108 or 278 as CDR2, and SEQ ID NO:109 or 110 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 7 was found to include the amino acid sequence set forth as SEQ ID NO:230 as the light chain variable region, and the amino acid sequence set forth as SEQ ID NO:231 as the heavy chain variable region. The light chain variable region was found to include the amino acid sequence set forth as SEQ ID NO:36 or 37 as CDR1; SEQ ID NO:38 or 39 as CDR2, and SEQ ID NO:40 as CDR3; and the heavy chain variable region to include the amino acid sequence set forth as SEQ ID NO:111 or 112 as CDR1, SEQ ID NO:113 or 114 as CDR2, and SEQ ID NO:115 or 116 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 8 was found to include the amino acid sequence set forth as SEQ ID NO:232 as the light chain variable region, and the amino acid sequence set forth as SEQ ID NO:233 as the heavy chain variable region. The light chain variable region was found to include the amino acid sequence set forth as SEQ ID NO:41 or 42 as CDR1; SEQ ID NO:43 or 44 as CDR2, and SEQ ID NO:45 as CDR3; and the heavy chain variable region to include the amino acid sequence set forth as SEQ ID NO:117 or 118 as CDR1, SEQ ID NO:119 or 279 as CDR2, and SEQ ID NO:120 or 121 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 9 was found to include the amino acid sequence set forth as SEQ ID NO:234 as the light chain variable region, and the amino acid sequence set forth as SEQ ID NO:235 as the heavy chain variable region. The light chain variable region was found to include the amino acid sequence set forth as SEQ ID NO:46 or 47 as CDR1; SEQ ID NO:48 or 49 as CDR2, and SEQ ID NO:50 as CDR3; and the heavy chain variable region to include the amino acid sequence set forth as SEQ ID NO:122 or 123 as CDR1, SEQ ID NO:124 or 125 as CDR2, and SEQ ID NO:126 or 127 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 10 was found to include the amino acid sequence set forth as SEQ ID NO:236 as the light chain variable region, and the amino acid sequence set forth as SEQ ID NO:237 as the heavy chain variable region. The light chain variable region was found to include the amino acid sequence set forth as SEQ ID NO:51 or 52 as CDR1; SEQ ID NO:53 or 54 as CDR2, and SEQ ID NO:55 as CDR3; and the heavy chain variable region to include the amino acid sequence set forth as SEQ ID NO:128 or 129 as CDR1, SEQ ID NO:130 or 131 as CDR2, and SEQ ID NO:132 or 133 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 11 was found to include the amino acid sequence set forth as SEQ ID NO:238 as the light chain variable region, and the amino acid sequence set forth as SEQ ID NO:239 as the heavy chain variable region. The light chain variable region was found to include the amino acid sequence set forth as SEQ ID NO:56 or 57 as CDR1; SEQ ID NO:58 or 59 as CDR2, and SEQ ID NO:60 as CDR3; and the heavy chain variable region to include the amino acid sequence set forth as SEQ ID NO:134 or 135 as CDR1, SEQ ID NO:136 or 137, as CDR2, and SEQ ID NO:138 or 139 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 12 was found to include the amino acid sequence set forth as SEQ ID NO:240 as the light chain variable region, and the amino acid sequence set forth as SEQ ID NO:241 as the heavy chain variable region. The light chain variable region was found to include the amino acid sequence set forth as SEQ ID NO:61 or 62 as CDR1; SEQ ID NO:63 or 64 as CDR2, and SEQ ID NO:65 as CDR3; and the heavy chain variable region to include the amino acid sequence set forth as SEQ ID NO:140 or 141 as CDR1, SEQ ID NO:142 or 143 as CDR2, and SEQ ID NO:144 or 145 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 13 was found to include the amino acid sequence set forth as SEQ ID NO:242 as the light chain variable region, and the amino acid sequence set forth as SEQ ID NO:243 as the heavy chain variable region. The light chain variable region was found to include the amino acid sequence set forth as SEQ ID NO:66 or 67 as CDR1; SEQ ID NO:68 or 69 as CDR2, and SEQ ID NO:70 as CDR3; and the heavy chain variable region to include the amino acid sequence set forth as SEQ ID NO:146 or 147 as CDR1, SEQ ID NO:148 or 149 as CDR2, and SEQ ID NO:150 or 151 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 14 was found to include the amino acid sequence set forth as SEQ ID NO:244 as the light chain variable region, and the amino acid sequence set forth as SEQ ID NO:245 as the heavy chain variable region. The light chain variable region was found to include the amino acid sequence set forth as SEQ ID NO:71 or 72 as CDR1; SEQ ID NO:73 or 74 as CDR2, and SEQ ID NO:75 as CDR3; and the heavy chain variable region to include the amino acid sequence set forth as SEQ ID NO:152 or 153 as CDR1, SEQ ID NO:154 or 155 as CDR2, and SEQ ID NO:156 or 157 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

Table 1 shows collectively the SEQ ID NOs of the respective amino acid sequences included in the light chain and the heavy chain variable regions of the anti-hTfR antibody Nos. 1 to 14.

TABLE 1

Sequence numbers of respective amino acid sequences included in the light and the heavy chain variable regions of the anti-hTfR antibodies Nos. 1 to 14

| Antibody No. | light chain variable region | heavy chain variable region |
|---|---|---|
| 1 | 218 | 219 |
| 2 | 220 | 221 |
| 3 | 222 | 223 |
| 4 | 224 | 225 |
| 5 | 226 | 227 |
| 6 | 228 | 229 |
| 7 | 230 | 231 |
| 8 | 232 | 233 |
| 9 | 234 | 235 |
| 10 | 236 | 237 |
| 11 | 238 | 239 |
| 12 | 240 | 241 |
| 13 | 242 | 243 |
| 14 | 244 | 245 |

Table 2 shows collectively the SEQ ID NOs of the respective amino acid sequences contained in CDR1 to CDR3 of the light chain variable region and CDR1 to CDR3 of the heavy chain variable region of anti-hTfR antibodies Nos. 1 to 14. However, Table 2 shows those amino acid sequence only as examples and does not limit the amino acid sequence of each CDR to those in Table 2, but it was considered that CDRs are not limited to those which consist of these amino acid sequences, but they can also either be regions of amino acid sequences that include any of the above sequences, or amino acid sequences consisting of not less than three consecutive amino acids containing part of the above sequences.

TABLE 2

Sequence numbers of respective amino acid sequences contained in CDR1 to CDR3 of the light chain and the heavy chain variable regions of anti-hTfR antibodies Nos. 1 to 14

| Antibody | light chain variable region | | | heavy chain variable region | | |
|---|---|---|---|---|---|---|
| No. | CDR1 | CDR2 | CDR3 | CDR1 | CDR2 | CDR3 |
| 1 | 6, 7 | 8, 9 | 10 | 76, 77 | 78, 79 | 80, 81 |
| 2 | 11, 12 | 13, 14 | 15 | 82, 83 | 84, 85 | 86, 87 |
| 3 | 16, 17 | 18, 19 | 20 | 88, 89 | 90, 91 | 92, 93 |
| 4 | 21, 22 | 23, 24 | 25 | 94, 95 | 96, 97 | 98, 99 |
| 5 | 26, 27 | 28, 29 | 30 | 100, 101 | 102, 103 | 104, 105 |
| 6 | 31, 32 | 33, 34 | 35 | 106, 107 | 108, 278 | 109, 110 |
| 7 | 36, 37 | 38, 29 | 40 | 111, 112 | 113, 114 | 115, 116 |
| 8 | 41, 42 | 43, 44 | 45 | 117, 118 | 119, 279 | 120, 121 |
| 9 | 46, 47 | 48, 49 | 50 | 122, 123 | 124, 125 | 126, 127 |
| 10 | 51, 52 | 53, 54 | 55 | 128, 129 | 130, 131 | 132, 133 |
| 11 | 56, 57 | 58, 59 | 60 | 134, 135 | 136, 137 | 138, 139 |
| 12 | 61, 62 | 63, 64 | 65 | 140, 141 | 142, 143 | 144, 145 |
| 13 | 66, 67 | 68, 69 | 70 | 146, 147 | 148, 149 | 150, 151 |
| 14 | 71, 72 | 73, 74 | 75 | 152, 153 | 154, 155 | 156, 157 |

[Example 7] Measurement of the Affinity of Anti-hTfR Antibody to Human and Monkey TfRs The affinity of the anti-hTfR antibody to human and monkey TfRs were measured on Octet RED96 (ForteBio Inc., a division of Pall Corporation), a system for analysis of interactions between biomolecules utilizing bio-layer interferometry (BLI). The basic principles of bio-layer interferometry are briefly explained below. When a layer of a biomolecule immobilized on the surface of a sensor tip is irradiated with light of a certain wavelength, the light is reflected from two of the surfaces, the one of the biomolecule and the other of inner, reference layer, producing interfering light waves. A molecule in the sample being measured binds to the biomolecule on the surface of the sensor tip and thus increases the thickness of the layers on the sensor tip, which results in a shift between the interfering waves. By measuring the variations of this shift between the interfering waves, determination of the number of the molecules bound to the layer of the biomolecules immobilized to the sensor tip surface and kinetic analysis of it can be performed in real time. The measurement was performed according generally to the operating manual attached to Octet RED96. As a human TfR, a recombinant human TfR (r human TfR: Sino Biological Inc.) was used, which had the amino acid sequence of the hTfR extracellular region, i.e., the cysteine residue at the position 89th from the N-terminal side to the phenylalanine at the C-terminus, of the amino acid sequence set forth as SEQ ID NO:1, with a histidine tag attached to the N-terminus. As a monkey TfR, a recombinant monkey TfR (r monkey TfR: Sino Biological Inc.) was used, which had the amino acid sequence of the cynomolgus monkey TfR extracellular region, i.e., the cysteine residue at the position 89th from the N-terminal side to the phenylalanine at the C-terminus, of the amino acid sequence set forth as SEQ ID NO:2, with a histidine tag attached to the N-terminus.

Clone 1 line to Clone 14 line selected in Example 5 were respectively diluted with a RPMI 1640 medium containing (1×) HAT Supplement (Life Technologies Inc.) and 10% Ultra low IgG fetal bovine serum (Life Technologies Inc.) so as to adjust the cell density to approximately $2\times10^5$ cells/mL. To a 1-L conical flask were added 200 mL of each cell suspension, and the culture was performed for 6 to 7 days in a humid environment at 37° C., 5% $CO_2$ and 95% air, with stirring at a rate of about 70 rpm. The culture supernatant was collected by centrifugation, and filtered through a 0.22 μm filter (Millipore Inc.) to prepare the culture supernatant. The culture supernatant thus collected was loaded onto a Protein G column (column volume: 1 mL, GE Healthcare Inc.) that had been equilibrated in advance with three column volumes of 20 mM Tris buffer (pH 8.0) containing 150 mM NaCl. After the column was washed with 5 column volumes of the same buffer, adsorbed antibody was eluted with 4 column volumes of 50 mM glycine buffer (pH 2.8) containing 150 mM NaCl, and eluted fractions were collected. The eluted fractions were adjusted to pH 7.0 by addition of 1 M Tris buffer (pH 8.0). These were used as purified products of anti-hTfR antibodies Nos. 1 to 14 in the experiments described below.

Each of the antibodies (anti-hTfR antibody Nos. 1 to 14) purified above was subjected to 2-fold dilution steps with HBS-P+ (10 mM HEPES containing 150 mM NaCl, 50 μM EDTA and 0.05% Surfactant P20) to prepare antibody solutions of 7 different concentrations, 0.78125 to 50 nM (0.117 to 7.5 μg/mL). These antibody solutions were used as the sample solutions. The r human and r monkey TfRs were respectively diluted with HBS-P+ to prepare 25 μg/mL solutions, which were used as r human TfR-ECD (Histag) solution and r monkey TfR-ECD (Histag) solution, respectively.

Each of the sample solutions prepared above by 2-fold dilution steps was added, 200 μL/well, to a 96-well plate, black (Greiner Bio-One Inc.). Each of the r human TfR-ECD (Histag) solution and the r monkey TfR-ECD (Histag) solutions prepared above was added, 200 μL/well, to predetermined wells. To respective wells for baseline, dissociation and washing were added HBS-P+, 200 μL/well. To wells for regeneration were added 10 mM Glycine-HCl, pH 1.7, 200 μL/well. To wells for activation was added 0.5 mM $NiCl_2$ solution, 200 μL/well. The plate and biosensor (Biosensor/Ni-NTA: ForteBio Inc., a division of Pall Corporation) were set in the prescribed positions of Octet RED96.

Octet RED96 was run under the conditions shown in Table 3 below to collect data, on which then, using the analyzing software attached to Octet RED96, and fitting the binding reaction curve to 1:1 binding model or 2:1 binding model, the association rate constant ($k_{on}$) and dissociation rate constant ($k_{off}$) of anti-hTfR antibody to r human TfR and r monkey TfR were measured and the dissociation constant ($K_D$) was calculated. The measurement was performed at 25 to 30° C.

TABLE 3

Operating conditions of Octet RED96

| | Step | Contact time (sec) | Rate (rpm) | Threshold |
|---|---|---|---|---|
| 1 | Baseline 1 | 60 | 1000 | — |
| 2 | Load | 600 | 1000 | 1.5-2.0 |
| 3 | Baseline 2 | 60 | 1000 | |
| 4 | Association | 180 | 1000 | |
| 5 | Dissociation | 540 | 1000 | |
| 6 | Regeneration | 5 | 1000 | |
| 7 | Washing | 5 | 1000 | |
| | Steps 6-7 repeated 6 to 7 times | | | |
| 8 | Activation | 60 | 1000 | — |
| | Steps 1-8 repeated until all the samples measured | | | |

Table 4 shows the results of measurement of association rate constant ($k_{on}$), dissociation rate constant ($k_{off}$) of anti-hTfR antibody Nos. 1 to 14 (corresponding to antibody Nos. 1 to 14, respectively, in the table), and dissociation constant ($K_D$) to human TfR.

TABLE 4

Affinity of anti-hTfR antibodies to human TfR

| Antibody No. | kon ($M^{-1}s^{-1}$) | koff ($s^{-1}$) | $K_D$ (M) |
|---|---|---|---|
| 1 | $5.00 \times 10^5$ | $2.55 \times 10^{-6}$ | $5.09 \times 10^{-12}$ |
| 2 | $1.11 \times 10^6$ | $1.23 \times 10^{-5}$ | $1.12 \times 10^{-11}$ |
| 3 | $6.53 \times 10^5$ | $<1.0 \times 10^{-7}$ | $<1.0 \times 10^{-12}$ |
| 4 | $1.91 \times 10^6$ | $2.29 \times 10^{-4}$ | $1.20 \times 10^{-10}$ |
| 5 | $6.71 \times 10^5$ | $2.44 \times 10^{-5}$ | $3.64 \times 10^{-11}$ |
| 6 | $7.54 \times 10^5$ | $7.23 \times 10^{-4}$ | $9.58 \times 10^{-10}$ |
| 7 | $3.69 \times 10^5$ | $3.03 \times 10^{-5}$ | $8.22 \times 10^{-11}$ |
| 8 | $6.96 \times 10^5$ | $<1.0 \times 10^{-7}$ | $<1.0 \times 10^{-12}$ |
| 9 | $7.82 \times 10^5$ | $9.46 \times 10^{-5}$ | $1.21 \times 10^{-10}$ |
| 10 | $6.79 \times 10^5$ | $7.66 \times 10^{-4}$ | $1.13 \times 10^{-9}$ |
| 11 | $2.72 \times 10^5$ | $2.28 \times 10^{-5}$ | $8.37 \times 10^{-11}$ |
| 12 | $7.54 \times 10^5$ | $7.23 \times 10^{-4}$ | $4.32 \times 10^{-10}$ |
| 13 | $8.35 \times 10^5$ | $<1.0 \times 10^{-7}$ | $<1.0 \times 10^{-12}$ |
| 14 | $9.61 \times 10^5$ | $<1.0 \times 10^{-7}$ | $<1.0 \times 10^{-12}$ |

Table 5 shows the results of measurement of association rate constant ($k_{on}$), dissociation rate constant ($k_{off}$) of anti-hTfR antibody Nos. 1 to 14 (corresponding to antibody Nos. 1 to 14, respectively, in the table), and dissociation constant ($K_D$) to monkey TfR.

TABLE 5

Affinity of anti-hTfR antibodies to monkey TfR

| Antibody No. | kon ($M^{-1}s^{-1}$) | koff ($s^{-1}$) | $K_D$ (M) |
|---|---|---|---|
| 1 | $2.80 \times 10^{5}$ | $<1.0 \times 10^{-7}$ | $<1.0 \times 10^{-12}$ |
| 2 | $4.18 \times 10^{5}$ | $1.75 \times 10^{-6}$ | $4.18 \times 10^{-11}$ |
| 3 | $3.89 \times 10^{5}$ | $<1.0 \times 10^{-7}$ | $<1.0 \times 10^{-12}$ |
| 4 | $7.54 \times 10^{5}$ | $1.21 \times 10^{-4}$ | $1.61 \times 10^{-10}$ |
| 5 | $5.19 \times 10^{5}$ | $7.58 \times 10^{-4}$ | $1.46 \times 10^{-9}$ |
| 6 | $4.95 \times 10^{5}$ | $2.36 \times 10^{-4}$ | $1.23 \times 10^{-10}$ |
| 7 | $2.66 \times 10^{5}$ | $4.54 \times 10^{-6}$ | $1.71 \times 10^{-11}$ |
| 8 | $5.52 \times 10^{5}$ | $5.07 \times 10^{-3}$ | $9.18 \times 10^{-9}$ |
| 9 | $6.99 \times 10^{5}$ | $1.47 \times 10^{-4}$ | $2.10 \times 10^{-9}$ |
| 10 | $3.87 \times 10^{5}$ | $1.22 \times 10^{-2}$ | $3.16 \times 10^{-8}$ |
| 11 | $1.24 \times 10^{5}$ | $4.21 \times 10^{-4}$ | $3.38 \times 10^{-9}$ |
| 12 | $5.05 \times 10^{5}$ | $1.26 \times 10^{-4}$ | $2.49 \times 10^{-10}$ |
| 13 | $5.91 \times 10^{5}$ | $7.29 \times 10^{-5}$ | $1.23 \times 10^{-10}$ |
| 14 | $7.00 \times 10^{5}$ | $3.61 \times 10^{-5}$ | $5.16 \times 10^{-11}$ |

As a result of the affinity measurement of those anti-hTfR antibodies to human TfR, the dissociation constant with human TfR was not more than $1\times10^{-8}$ M for all the antibodies; and for 13 antibodies except antibody No. 10, the dissociation constant with human TfR was not more than $1\times10^{-9}$ M; and for antibodies Nos. 3, 8, 13 and 14, in particular, the dissociation constant was not more than $1\times10^{-12}$M (Table 4). The result demonstrates that all of the 14 antibodies are antibodies having a high-affinity antibody to human TfR. Then looking to the result of the measurement of the affinity of the anti-hTfR antibodies to monkey TfR, the dissociation constant with monkey TfR was not more than $5\times10^{-8}$M for all the antibodies, and for antibodies Nos. 1 and 3, in particular, the dissociation constant with monkey TfR was not more than $1\times10^{-12}$ M (Table 5). The result shows that all the 14 antibodies are antibodies having a high-affinity antibody not only to human TfR but also to monkey TfR.

[Example 7-2] Evaluation of Brain Uptake of the Anti-hTfR Antibodies Using Mice Then, for 13 antibodies, anti-hTfR antibodies Nos. 1 to 9 and 11 to 14, evaluation was performed about their transfer into the brain through the BBB, by using hTfR knock-in mice (hTfR-KI mice) in which the gene encoding the extracellular region of mouse transferrin receptor has been replaced with a gene encoding the extracellular region of human transferrin receptor. The hTfR-KI mice were produced by the method described below as a whole. Besides, the purified antibodies of Example 7 were used as the anti-hTfR antibodies.

A DNA fragment having a nucleotide sequence set forth as SEQ ID NO:253 was chemically synthesized, in which a neomycin resistance gene flanked by loxP sequences was placed on the 3'-side of a cDNA encoding a chimeric hTfR whose intracellular region consisted of the amino acid sequence of mouse TfR and the extracellular region consisted of the amino acid sequence of human TfR sequence. This DNA fragment was inserted by a conventional method into a targeting vector having as the 5'-arm sequence a nucleotide sequence set forth as SEQ ID NO:254 and as the 3'-arm sequence a nucleotide sequence set forth as SEQ ID NO:255, and the construct was introduced into mouse ES cells by electroporation. The mouse ES cells to which the gene had been introduced were subjected to selection culture in a medium in the presence of neomycin to select those mouse ES cells in which the targeting vector had been incorporated into the chromosome through homologous recombination. The recombinant mouse ES cells thus obtained were injected into 8-cell stage embryos (host embryos) of ICR mice, and the embryos thus prepared were implanted into pseudo pregnant mice (recipient mice) which had been obtained through mating with mice having undergone vasoligation. The offspring (chimeric mice) obtained were examined by their hair color, and those mice which had the higher proportion of white hairs in their total body hairs were selected, i.e., those mice in which the ES cells had contributed at the higher rates in the development of the individual organisms. Each of these chimeric mice was mated with ICR mice to generate F1 mice. F1 mice with white hair were selected, the DNAs extracted from their tail tissue were analyzed, and those mice whose mouse transferrin receptor gene on their chromosomes had been replaced with chimeric hTfR, were regarded as hTfR-KI mice.

The above 13 anti-hTfR antibodies were fluorescently labeled with fluorescein isothiocyanate (FITC) using Fluorescein Labeling Kit-$NH_2$ (Dojindo Laboratories) according to the attached manual. PBS solutions were prepared each containing one of the FITC fluorescent labeled 13 anti-hTfR antibodies. Each of these PBS antibody solutions was intravenously injected to an hTfR-KI mouse (male, 10 to 12-week old), at the anti-hTfR antibody dosage of 3 mg/kg. As a control, a PBS solution containing mouse IgG1 (Sigma Inc.), fluorescently labeled with FITC in the same manner as above, was intravenously injected to an hTfR-KI mouse (male, 10 to 12-week old), at the dose of 3 mg/kg. About eight hours after the intravenous injection, the whole body was perfused with saline, and the brain (part including the cerebrum and the cerebellum) was obtained. The brain thus excised was weighed (wet weight), and then the brain tissues were homogenized with T-PER (Thermo Fisher Scientific Inc.) containing Protease Inhibitor Cocktail (Sigma Inc.). The homogenate was centrifuged, the supernatant was collected, and the amount of the FITC fluorescent labeled antibody contained in the supernatant was measured in the following manner. First, 10 μL, of anti-FITC Antibody (Bethyl Inc.) was added to each well of a High Bind Plate (Meso Scale Diagnostics Inc.) and left to stand for one hour so as to immobilize it to the plate. Then, the plate was blocked by addition of 150 μL, of SuperBlock Blocking buffer in PBS (Thermo Fisher Scientific Inc.) to each well and shaking of the plate for one hour. Then, 25 μL, of the supernatant of a brain tissue homogenate was added to each well, and the plate was shaken for one hour. Then, 25 μL, of SULFO-TAG Anti-Mouse Antibody (Goat)(Meso Scale Diagnostics Inc.) were added to each well, and shaking was continued for one hour. Then, to each well was added 150 μL, of Read buffer T (Meso Scale Diagnostics Inc.), and the amount of luminescence from each well was read on a Sector™ Imager 6000 reader. The amount of the antibody contained per one gram brain (wet weight) (the concentration of the anti-hTfR antibody in the brain tissues) was calculated, by producing a standard curve based on measurements of standard samples containing known concentrations of fluorescently FITC-labeled anti-hTfR antibody, and then interpolating the measurement of each of the samples with reference to the standard. The results are shown in Table 5-2.

The concentration of any of the antibodies designated anti-hTfR antibodies Nos. 1 to 9 and 11 to 14 in brain tissues was over 25 times greater than that of the control. The concentration of anti-hTfR antibodies Nos. 5 and 6 was both over 100 times greater than that of the control, with anti-hTfR antibody No. 6, in particular, the value reached approximately 160 times as high as that of the control. The results indicate that the antibodies designated anti-hTfR antibody Nos. 1 to 9 and 11 to 14 transfers into the brain, actively passing through the BBB.

TABLE 5-2

Concentration of anti-hTfR antibodies in brain tissues

| Antibody No. | Brain tissues (μg/g wet weight) | Relative value to the control |
|---|---|---|
| Control | 0.003 | 1 |
| 1 | 0.141 | 47.0 |
| 2 | 0.126 | 42.0 |
| 3 | 0.0833 | 27.8 |
| 4 | 0.221 | 73.7 |
| 5 | 0.335 | 112 |
| 6 | 0.492 | 164 |
| 7 | 0.0855 | 28.5 |
| 8 | 0.133 | 44.3 |
| 9 | 0.112 | 37.3 |
| 11 | 0.103 | 34.3 |
| 12 | 0.215 | 71.7 |
| 13 | 0.127 | 42.3 |
| 14 | 0.213 | 71.0 |

[Example 8] Pharmacokinetic Analysis of Anti-hTfR Antibodies in Monkey

Each of anti-hTfR antibodies Nos. 1 to 3 was intravenously administered once to a male cynomolgus monkey at a dosage of 5.0 mg/kg, and 8 hours after the administration, whole body irrigation was carried out with physiological saline. As a negative control, a monkey which had not received anti-hTfR antibody was subjected to whole body irrigation in the same manner After the irrigation, brain tissues including the medulla oblongata were excised. Using the brain tissues, the concentration of the anti-hTfR antibody was measured, and immunohistochemical staining was performed. Besides, the anti-hTfR antibodies employed were purification products of those described in Example 7.

Measurement of the concentration of anti-hTfR antibodies in brain tissues were carried out largely following the procedure described below. Collected brain tissues were divided into the cerebrum, the cerebellum, the hippocampus, and the medulla oblongata, and they were respectively homogenized with RIPA Buffer (Wako Pure Chemical Industries Inc.) containing Protease Inhibitor Cocktail (Sigma-Aldrich Inc.), and centrifuged to collect the supernatant. Affinipure Goat Anti mouse IgG Fcγ pAb (Jackson ImmunoResearch Inc.) was added, 10 μL each, to the wells of a High Bind Plate (Meso Scale Diagnostics Inc.), and the plate was left to stand for one hour to immobilize the antibody. Then, the plate was blocked by addition of 150 μL of SuperBlock Blocking buffer in PBS (Thermo Fisher Scientific Inc.) to each well and shaken for one hour. Then, 25 μL of the supernatant of a brain tissue homogenate was added to each well, and the plate was shaken for one hour. Then, 25 μL of Affinipure Goat Anti mouse IgG Fab-Biotin (Jackson ImmunoResearch Inc.) was added to each well, and shaking was continued for one hour. Then, 25 μL or SULFO-Tag-Streptavidin (Meso Scale Diagnostics Inc.) was added to each well, and shaking was continued for half an hour. To each well was added 150 μL of Read buffer T (Meso Scale Diagnostics Inc.), and the amount of luminescence from each well was read on a Sector™ Imager 6000 reader (Meso Scale Diagnostics). The amount of the antibody contained per one gram of brain (wet weight) (the concentration of the anti-hTfR antibody in brain tissues) was calculated, by producing a standard curve based on measurements of standard samples containing known concentrations of the anti-hTfR antibody, and then interpolating the measurement of each of the samples with reference to the standard.

The result of the measurement of the concentration of the anti-hTfR antibodies in brain tissues is shown in Table 6. Though any of anti-hTfR antibodies Nos. 1 to 3 was observed to accumulate in the cerebrum, the cerebellum, the hippocampus and the medulla oblongata, in their amount there was a relation of anti-hTfR antibody No. 1<anti-hTfR antibody No. 3<anti-hTfR antibody No. 2, showing the lowest with anti-hTfR antibody No. 1 and highest in anti-hTfR antibody No. 2. In comparison with anti-hTfR antibody No. 1, the accumulation of anti-hTfR antibody No. 2 was approximately 4.3 times in the cerebrum, approximately 6.6 times in the cerebellum, approximately 4.6 times in the hippocampus, and approximately 2 times in the medulla oblongata. These results demonstrate that these 3 antibodies had a property to pass through the blood-brain barrier and accumulate in the brain tissues, and show that by binding these antibodies to a pharmaceutical agent which needs to be brought into function in the brain tissues, it is possible to let those pharmaceutical agents efficiently accumulate in the brain tissues.

TABLE 6

Concentration of anti-hTfR antibodies in brain tissues (μg/g wet weight)

| Antibody No. | Cerebrum | Cerebellum | Hippocampus | Medulla oblongata |
|---|---|---|---|---|
| 1 | 0.18 | 0.15 | 0.12 | 0.22 |
| 2 | 0.78 | 0.99 | 0.56 | 0.43 |
| 3 | 0.82 | 0.6 | 0.33 | 0.31 |

Immunohistochemical staining of the anti-hTfR antibodies in these brain tissues was carried out using the following procedures described below basically. The collected tissues were rapidly frozen to −80° C. in a Tissue-Tek Cryo 3DM (Sakura Finetek Inc.) to prepare frozen blocks of tissues. The frozen blocks were sliced into 4-μm sections, and which were affixed to MAS coated glass slides (Matsunami Glass Inc.). The tissue sections were reacted with 4% paraformaldehyde (Wako Pure Chemical Industries Inc.) for 5 minutes at 4° C. and fixed to glass slides. Then, the tissue sections were reacted with methanol solution containing 0.3% hydrogen peroxide (Wako Pure Chemical Industries Inc.) for 30 min to inactivate endogenous peroxidases. Then, the glass slides were blocked by reacting SuperBlock blocking buffer in PBS for 30 min at room temperature. Then, the tissue sections were reacted with Mouse IgG-heavy and light chain Antibody (Bethyl Laboratories Inc.) for one hour at room temperature. The tissue sections were allowed to visualize with DAB substrate (3,3'-diaminobenzidine, Vector Laboratories Inc.), counterstained with Mayer's hematoxylin solution (Merck Inc.), embedded after dehydration and clearing, and observed under an optical microscope.

FIG. 1 shows the result of the immunohistochemical staining of the anti-hTfR antibodies in the cerebral cortex. In the cerebral cortex of monkeys administered anti-hTfR antibodies Nos. 1 to 3, specific staining in the blood vessels were observed (FIG. 1, panels b to d, respectively). In particular, in the cerebral cortex of the monkeys administered anti-hTfR antibodies No. 2 or 3, specific staining was also observed extensively in the brain parenchyma region, outside the blood vessels (FIG. 1, panels c and d, respectively). Besides, no staining was observed in the cerebral cortex of the control monkey non-administered anti-hTfR antibody, indicating that there was almost no background staining (FIG. 1, panel a).

Figure 2:
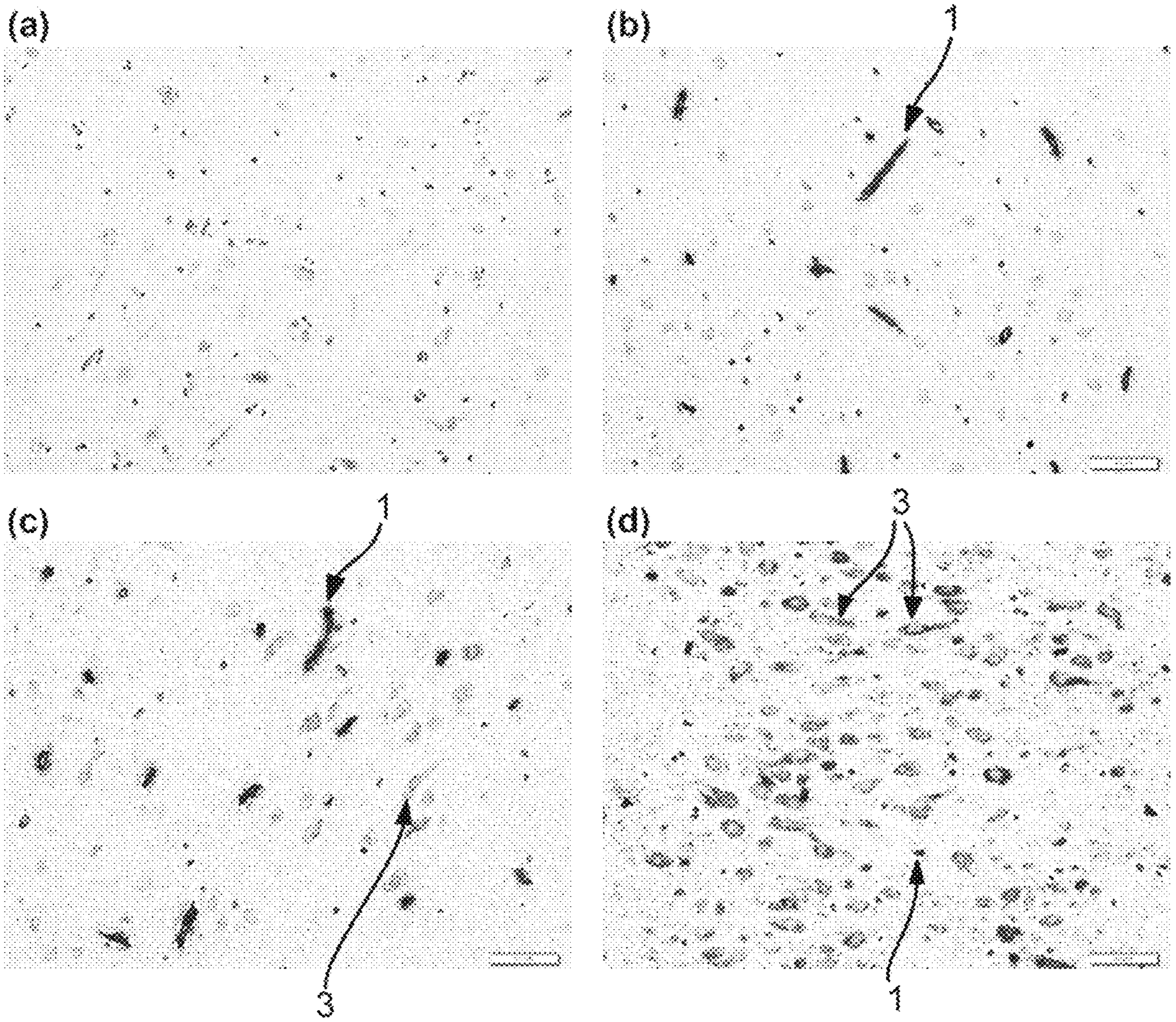
FIG. 2 A figure showing the result of the immunohistochemical staining of the anti-hTfR antibody in the hippocampus of a cynomolgus monkey after a single intravenous administration of the anti-hTfR antibody. (a) anti-hTfR antibody non-administered, (b) anti-hTfR antibody No. 1 administered, (c) anti-hTfR antibody No. 2 administered, (d) anti-hTfR antibody No. 3 administered. The bar at the bottom right in each photograph is a 50-μm gauge.

FIG. 2 shows the result of immunohistochemical staining of anti-hTfR antibodies in the hippocampus. In the cerebrum of monkeys administered anti-hTfR antibodies Nos. 1 to 3, specific staining of blood vessels were observed (FIG. 2, panels b to d, respectively). In particular, in the hippocampus of the monkeys administered anti-hTfR antibodies No. 2 or 3, specific staining of neuron-like cells was also observed (FIG. 2, panels c and d, respectively), and specific and extensive staining of the brain parenchyma region, outside the blood vessels, was also observed. Besides, no staining was observed in the hippocampus of the control monkey non-administered anti-hTfR antibody, indicating that there was almost no background staining (FIG. 2, panel a).

Figure 3:
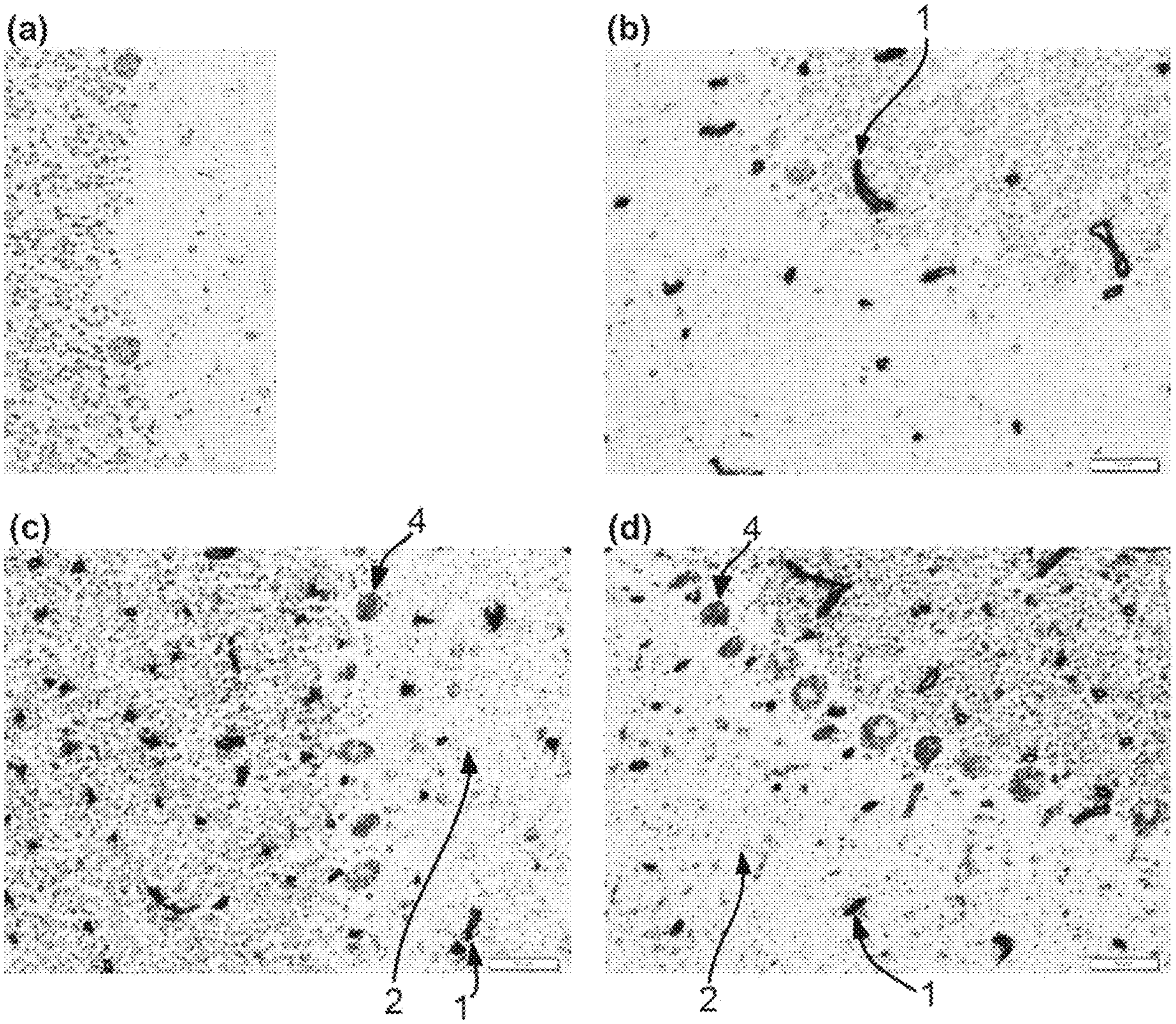
FIG. 3 Substitute photographs for drawings showing the result of the immunohistochemical staining of the anti-hTfR antibody in the cerebellum of a cynomolgus monkey after a single intravenous administration of the anti-hTfR antibody. (a) anti-hTfR antibody not administered, (b) anti-hTfR antibody No. 1 administered, (c) anti-hTfR antibody No. 2 administered, (d) anti-hTfR antibody No. 3 administered. The bar at the bottom right in each photograph is a 50-μm gauge.

FIG. 3 shows the result of immunohistochemical staining of the anti-hTfR antibodies in the cerebellum. In the cerebellum of monkeys administered anti-hTfR antibodies Nos. 1 to 3, specific staining of blood vessels were observed (FIG. 3, panels b to d, respectively). In particular, in the cerebellum of the monkeys administered anti-hTfR antibodies No. 2 or 3, specific staining of Purkinje cells was also observed (FIG. 3, panels c and d, respectively). Besides, no staining was observed in the cerebellum of the control with no anti-hTfR antibody administered, indicating that there was almost no background staining (FIG. 3, panel a).

From the above results of immunohistochemical staining in the cerebrum, the hippocampus, and the cerebellum, it was considered that while anti-hTfR antibody No. 1 can bind to hTfR existing on the endothelium of blood vessels in the brain, relatively small amount of it transfers to the brain parenchyma compared with anti-hTfR antibodies Nos. 2 and 3. On the other hand, it was found that anti-hTfR antibodies Nos. 2 and 3 can bind to hTfR existing on the endothelium of blood vessels of the brain, and after binding to hTfR, they pass through the blood-brain barrier and transfer into the brain parenchyma, and further, are taken up into the brain parenchyma and neuron-like cells in the hippocampus, and are taken up by Purkinje cells in the cerebellum.

[Example 9] Preparation of Humanized Anti-hTfR Antibodies

Humanization was tried of the amino acid sequence included in the light chain and the heavy chain variable regions of anti-hTfR antibodies Nos. 1 to 3 shown in Table 1. From anti-hTfR antibody No. 1 were obtained a humanized light chain variable region having one of the amino acid sequences set forth as SEQ ID NO:158 to SEQ ID NO:163, and a humanized heavy chain variable region having one of the amino acid sequences set forth as SEQ ID NO:166 to SEQ ID NO:171.

From anti-hTfR antibody No. 2 were obtained a humanized light chain variable region having one of the amino acid sequences set forth as SEQ ID NO:174 to SEQ ID NO:179, and a humanized heavy chain variable region having one of the amino acid sequences set forth as SEQ ID NO:182 to SEQ ID NO:187.

From anti-hTfR antibody No. 3 were obtained a humanized light chain variable region having one of the amino acid sequences set forth as SEQ ID NO:190 to SEQ ID NO:195, and a humanized heavy chain variable region having one of the amino acid sequences set forth as SEQ ID NO:204 to SEQ ID NO:209.

[Example 10] Construction of Genes Encoding Humanized Anti-hTfR Antibodies

For each of anti-hTfR antibodies Nos. 1 to 3 above, DNA fragments were artificially synthesized which contained a gene encoding the full length of the light chain, and of the heavy chain, having humanized anti-hTfR antibody light chain and heavy chain variable regions, respectively. In doing this, a MluI sequences and a sequence encoding a leader peptide was added, in this order from the 5' end, on the 5' side of the gene encoding the full length of the light chain, and on the 3' side was added a NotI sequence. And, a MluI sequences and a sequence encoding a leader peptide was added, in this order from the 5' end, on the 5' side of the gene encoding the full length of the heavy chain, and on the 3' side was added a NotI sequence. The leader peptide introduced above is to function as secretion signal when the light chain and heavy chain of the humanized antibody is expressed in mammalian cells as host cells so that the light chain and the heavy chain are secreted out of the cells.

For the light chain of anti-hTfR antibody No. 1, a DNA fragment (SEQ ID NO:165) was synthesized, which included a gene encoding the full length of the light chain (the light chain of humanized anti-hTfR antibody No. 1) consisting of the amino acid sequence set forth as SEQ ID NO:164, which had in the variable region the amino acid sequence set forth as SEQ ID NO:163.

For the heavy chain of anti-hTfR antibody No. 1, a DNA fragment (SEQ ID NO:173) was synthesized, which included a gene encoding the full length of the heavy chain (the heavy chain of humanized anti-hTfR antibody No. 1) consisting of the amino acid sequence set forth as SEQ ID NO:172, which had in the variable region the amino acid sequence set forth as SEQ ID NO:171.

The heavy chain of the humanized anti-hTfR antibody encoded by the DNA fragment set forth as SEQ ID NO:173 is IgG1.

For the light chain of anti-hTfR antibody No. 2, a DNA fragment (SEQ ID NO:181) was synthesized, which included a gene encoding the full length of the light chain (the light chain of humanized anti-hTfR antibody No. 2) consisting of the amino acid sequence set forth as SEQ ID NO:180, which had in the variable region the amino acid sequence set forth as SEQ ID NO:179.

For the heavy chain of anti-hTfR antibody No. 2, a DNA fragment (SEQ ID NO:189) was synthesized, which included a gene encoding the full length of the heavy chain (the heavy chain of humanized anti-hTfR antibody No. 2) consisting of the amino acid sequence set forth as SEQ ID NO:188, which had in the variable region the amino acid sequence set forth as SEQ ID NO:187.

The heavy chain of the humanized anti-hTfR antibody encoded by the DNA fragment set forth as SEQ ID NO:189 is IgG1.

For the light chain of anti-hTfR antibody No. 3, a DNA fragment (SEQ ID NO:197) was synthesized, which included a gene encoding the full length of the light chain (the light chain of humanized anti-hTfR antibody No. 3) consisting of the amino acid sequence set forth as SEQ ID NO:196, which had in the variable region the amino acid sequence set forth as SEQ ID NO:191.

For the heavy chain of anti-hTfR antibody No. 3, a DNA fragment (SEQ ID NO:211) was synthesized, which included a gene encoding the full length of the heavy chain (the heavy chain of humanized anti-hTfR antibody No. 3) consisting of the amino acid sequence set forth as SEQ ID NO:210, which had in the variable region the amino acid sequence set forth as SEQ ID NO:205.

The heavy chain of the humanized anti-hTfR antibody encoded by the DNA fragment set forth as SEQ ID NO:211 is IgG1.

As to the light chain of anti-hTfR antibody No. 3, also synthesized were, a DNA fragment (SEQ ID NO:199) encoding the full length amino acid sequence of the light chain (the light chain of humanized anti-hTfR antibody No. 3-2) consisting of the amino acid sequence set forth as SEQ ID NO:198, which had in the variable region the amino acid sequence set forth as SEQ ID NO:193;

a DNA fragment (SEQ ID NO:201) encoding the full length amino acid sequence of the light chain (the light chain of humanized anti-hTfR antibody No. 3-3) consisting of the amino acid sequence set forth as SEQ ID NO:200, which had in the variable region the amino acid sequence set forth as SEQ ID NO:194;

a DNA fragment (SEQ ID NO:203) encoding the full length amino acid sequence of the light chain (the light chain of humanized anti-hTfR antibody No. 3-4) consisting of the amino acid sequence set forth as SEQ ID NO:202, which had in the variable region the amino acid sequence set forth as SEQ ID NO:195;

Further, for the heavy chain of anti-hTfR antibody No. 3, also synthesized was a DNA fragment (SEQ ID NO:213) encoding the full length amino acid sequence of the heavy chain (the heavy chain IgG4 of humanized anti-hTfR antibody No. 3) consisting of the amino acid sequence set forth as SEQ NO:212, which had in the variable region the amino acid sequence set forth as SEQ ID NO:205;

The heavy chain of the humanized anti-hTfR antibody encoded by the DNA fragment set forth as SEQ ID NO:213 is IgG4.

[Example 11] Construction of Humanized Anti-hTfR Antibody Expression Vector

Vector pEF/myc/nuc (Invitrogen Inc.) was digested with KpnI and NcoI to cut out a region including EF-1α promoter and its first intron, and this was blunt-ended with T4 DNA polymerase. A region including the CMV enhancer/promoter and intron was removed from pCI-neo (Invitrogen Inc.) by digesting it with BglII and EcoRI, and the remaining fragment thus left was blunt-ended with T4 DNA polymerase. To this was inserted the above-mentioned region including EF-1α promoter and its first intron to construct pE-neo vector. This vector, pE-neo, was digested with SfiI and BstXI to remove a region of approximately 1 kb including a neomycin resistance gene. PCR was performed employing pcDNA3.1/Hygro(+)(Invitrogen) as a template and using primer Hyg-Sfi5' (SEQ ID NO:216) and primer Hyg-BstX3' (SEQ ID NO:217) to amplify hygromycin gene. The hygromycin gene thus amplified was digested with SfiI and BstXI and inserted into the above pE-neo vector from which neomycin resistance gene had been removed to construct a vector pE-hygr.

Vectors pE-hygr and pE-neo were both digested with MluI and NotI. The DNA fragment (SEQ ID NO:165) encoding the light chain of humanized anti-hTfR antibody No. 1 and the DNA fragment (SEQ ID NO:173) encoding the heavy chain of the antibody, both synthesized in Example 10, were digested with MluI and NotI, and the fragments thus obtained were inserted into vector pE-hygr and vector pE-neo, respectively, between their MluI and NotI sites. The vectors thus obtained were used as an expression vector for the light chain of humanized anti-hTfR antibody No. 1, pE-hygr(LC1), and as an expression vector for the heavy chain of humanized anti-hTfR antibody No. 1, pE-neo(HC1), in the experiments described below.

In an analogous manner, the DNA fragment (SEQ ID NO:181) encoding the light chain of humanized anti-hTfR antibody No. 2 and the DNA fragment (SEQ ID NO:189) encoding the heavy chain of the antibody, both synthesized in Example 10, were both digested with MluI and NotI, and the fragments thus obtained were inserted into vector pE-hygr and vector pE-neo, respectively, between their MluI and NotI sites. The vectors thus obtained were used as an expression vector for the light chain of humanized anti-hTfR antibody No. 2, pE-hygr(LC2), and as an expression vector for the heavy chain of the antibody of humanized anti-hTfR antibody No. 2, pE-neo(HC2), in the experiments described below.

Further, in the same manner as above, the DNA fragment (SEQ ID NO:197) encoding the light chain of humanized anti-hTfR antibody No. 3 and the DNA fragment (SEQ ID NO:211) encoding the heavy chain of the antibody, both synthesized in Example 10, were both digested with MluI and NotI, and the fragments thus obtained were inserted into vector pE-hygr and vector pE-neo, respectively, between their MluI and NotI sites. The vectors thus obtained were used as an expression vector for the light chain of humanized anti-hTfR antibody No. 3, pE-hygr(LC3), and as an expression vector for the heavy chain of the antibody, pE-neo (HC3), in the experiments described below.

Further, as to the light chain of anti-hTfR antibody No. 3, the following fragments synthesized in Example 10, namely:

the DNA fragment (SEQ ID NO:199) encoding the light chain of humanized anti-hTfR antibody No. 3-2, the DNA fragment (SEQ ID NO:201) encoding the light chain of humanized anti-hTfR antibody No. 3-3, and the DNA fragment (SEQ ID NO:203) encoding the light chain of humanized anti-hTfR antibody No. 3-4, were digested with MluI and NotI, and inserted into the vector pE-hygr between the MluI and NotI sites thereof to construct pE-hygr(LC3-2), an expression vector for the light chain of humanized anti-hTfR antibody No. 3-2, pE-hygr(LC3-3), an expression vector for the light chain of humanized anti-hTfR antibody No. 3-3, and pE-hygr(LC3-4), an expression vector for the light chain of humanized anti-hTfR antibody No. 3-4, respectively.

Further, in the same manner as above, as to the heavy chain of anti-hTfR antibody No. 3, the DNA fragment (SEQ ID NO:213) encoding the heavy chain IgG4 of humanized anti-hTfR antibody No. 3 synthesized in Example 10 was digested with MluI and NotI, and inserted into the vector pE-neo between the MluI and NotI sites thereof to construct pE-neo(HC3-IgG4), an expression vector for the heavy chain IgG4 of humanized anti-hTfR antibody No. 3.

[Example 12] Construction of Cells for Expression of Humanized Anti-hTfR Antibody CHO cells (CHO-K1: obtained from American Type Culture Collection) were transformed with pE-hygr(LC1), the vector for light chain expression, and pE-neo(HC1), the vector for heavy chain expression, both constructed in Example 11, as follows, using GenePulser (Bio-Rad Inc.). Transformation of the cells was performed in the following manner as a whole. $5\times10^5$ of CHO-K1 cells were seeded in a 3.5-cm culture dish containing CD OptiCHO™ medium (Life Technologies Inc.) and cultured overnight at 37° C., 5% $CO_2$. The medium was replaced with Opti-MEM™ I medium (Life Technologies Inc.), and the cells were suspended at the density of $5\times10^6$ cells/mL. 100 μL, of the cell suspension were taken, to which was added 5 μL each of a pE-hygr(LC1) and a pE-neo(HC1) plasmid DNA solution both having been diluted with Opti-MEM™ I medium to 100 μg/mL. These plasmids were introduced into the cells by electroporation using GenePulser (Bio-Rad Inc.). The cells then were cultured overnight under the condition of 37° C., 5% $CO_2$, and subjected to selection culture in CD OptiCHO™ medium supplemented with 0.5 mg/mL of hygromycin and 0.8 mg/mL of G418.

Then, the cells selected above through the selection culture were seeded on 96-well plates so that not more than one cell might be seeded per well by limiting dilution. The cells then were cultured for about 10 days so that monoclonal colonies were formed. Respective culture supernatants of the wells in which monoclonal colony was formed were collected, the amount of the humanized antibody contained in culture supernatants was determined by ELISA, and humanized antibody high-expressing cell lines were selected.

The ELISA above was conducted as follows in general. To each well of 96-well microtiter plates (Nunc Inc.) were added 100 μL, of a goat anti-human IgG polyclonal antibody solution diluted with 0.05 M sodium bicarbonate buffer (pH 9.6) to 4 μg/mL, and the plate was left to stand for at least one hour at room temperature so as to allow the antibody to be adsorbed by the plates. Then, after each well was washed three times with a phosphate-buffered saline (pH 7.4) supplemented with 0.05% Tween20 (PBS-T), 200 μL, of Starting Block (PBS) Blocking Buffer (Thermo Fisher Scientific Inc.) was added to each well, and the plates were left to stand for 30 minutes at room temperature. After each well was washed with PBS-T three times, the culture supernatant or the human IgG reference standard product which had been diluted with a PBS supplemented with 0.5% BSA and 0.05% Tween20 (PBS-BT) to appropriate concentrations, was added to each well, in the amount of 100 μL, and the plates were left to stand for at least one hour at room temperature. After the plates were washed three times with PBS-T, 100 μL, of HRP-labeled anti-human IgG polyclonal antibody solution which had been diluted with PBS-BT, was added to each well, and the plates were left to stand for at least one hour at room temperature. After the wells were washed three times with PBS-T, 0.4 mg/mL o-phenylenediamine in citrate-phosphate buffer (pH 5.0) was added to each well, in the amount of 100 μL, and the wells were left to stand for 8 to 20 minutes at room temperature. Then, 1 mol/L sulfuric acid was added to each well, in the amount of 100 μL, to terminate the reaction, and the absorbance for each well was measured at 490 nm using a 96-well plate reader. The cells corresponding to the wells which exhibited the higher measurements were regarded as a high-expressing cell line for humanized anti-hTfR antibody No. 1. This was designated antibody No. 1 expressing cell line.

In the same manner, CHO cells were transformed with the light chain expression vector pE-hygr(LC2) and the heavy chain expression vector pE-neo(HC2), both constructed in Example 11, and a high-expressing cell line for humanized anti-hTfR antibody No. 2 was obtained. This was designated antibody No. 2 expressing cell line.

Further, in the same manner, CHO cells were transformed with the light chain expression vector pE-hygr(LC3) and the heavy chain expression vector pE-neo(HC3), both constructed in Example 11, and a high-expressing cell line for humanized anti-hTfR antibody No. 3 was obtained. This was designated antibody No. 3 expressing cell line.

Further, in the same manner, CHO cells were transformed with the light chain expression vector pE-hygr(LC3-2) and the heavy chain expression vector pE-neo(HC3), both constructed in Example 11, and a high-expressing cell line for humanized anti-hTfR antibody No. 3-2 was obtained. This was designated antibody No. 3-2 expressing cell line.

Further, in the same manner, CHO cells were transformed with the light chain expression vector pE-hygr(LC3-3) and the heavy chain expression vector pE-neo(HC3), both constructed in Example 11, and a high-expressing cell line for humanized anti-hTfR antibody No. 3-3 was obtained. This was designated antibody No. 3-3 expressing cell line.

Further, in the same manner, CHO cells were transformed with the light chain expression vector pE-hygr(LC3-4) and the heavy chain expression vector pE-neo(HC3) both constructed in Example 11, and a high-expressing cell line for humanized anti-hTfR antibody No. 3-4 was obtained. This was designated antibody No. 3-4 expressing cell line.

Further, in the same manner, CHO cells were transformed with the light chain expression vector pE-hygr(LC3) and the heavy chain expression vector pE-neo(HC3-IgG4) both constructed in Example 11, and a high-expressing cell line for humanized anti-hTfR antibody No. 3(IgG4) was obtained. This was designated antibody No. 3(IgG4) expressing cell line.

Further, in the same manner, CHO cells were transformed with the light chain expression vector pE-hygr(LC3-2) and the heavy chain expression vector pE-neo(HC3-IgG4) both constructed in Example 11, and a high-expressing cell line for humanized anti-hTfR antibody No. 3-2 (IgG4) was obtained. This was designated antibody No. 3-2 (IgG4) expressing cell line.

[Example 13] Purification of Humanized Anti-hTfR Antibodies

Antibody No. 1 expressing cell line, antibody No. 2 expressing cell line, antibody No. 3 expressing cell line, antibody No. 3-2 expressing cell line, antibody No. 3-3 expressing cell line and antibody No. 3-4 expressing cell line obtained in Example 12 were respectively diluted with CD OptiCHO™ medium to the density of approximately $2\times10^5$ cells/mL. The cell suspensions, 200 mL, was added to a 1 L-conical flask, and cultured for 6 to 7 days in a humid environment at 37° C., 5% $CO_2$, 95% air, with stirring at a rate of about 70 rpm. Each culture supernatant was collected by centrifugation, and filtered through a 0.22 μm filter (Millipore Inc.) to prepare the culture supernatant. To each culture supernatant thus obtained was added five volumes of 20 mM Tris buffer (pH 8.0) containing 150 mM NaCl, and loaded onto a Protein A column (column volume: 1 mL, Bio-Rad Inc.) which had been equilibrated in advance with three column volumes of 20 mM Tris buffer (pH 8.0)

containing 150 mM NaCl. Then, the column was washed with five column volumes of the same buffer, and the adsorbed humanized antibody was eluted with four column volumes of 50 mM glycine buffer (pH 2.8) containing 150 mM NaCl, and the eluted fraction was collected. The eluted fractions was added and neutralized with 1 M Tris buffer (pH 8.0) and used as the purified antibody preparation.

In the above, the antibody purified from the culture supernatant of antibody No. 1 expressing cell line was designated humanized anti-hTfR antibody No. 1. The antibody purified from the culture supernatant of antibody No. 2 expressing cell line was designated humanized anti-hTfR antibody No. 2. The antibody purified from the culture supernatant of antibody No. 3 expressing cell line was designated humanized anti-hTfR antibody No. 3. The antibody purified from the culture supernatant of antibody No. 3-2 expressing cell line was designated humanized anti-hTfR antibody No. 3-2. The antibody purified from the culture supernatant of antibody No. 3-3 expressing cell line was designated humanized anti-hTfR antibody No. 3-3. The antibody purified from the culture supernatant of antibody No. 3-4 expressing cell line was designated humanized anti-hTfR antibody No. 3-4.

Further, antibody No. 3(IgG4) expressing cell line and antibody No. 3-2 (IgG4) expressing cell line obtained in Example 12 also were cultured in the same manner as above, and from their culture supernatants were obtained purified humanized anti-hTfR antibody No. 3(IgG4) and humanized anti-hTfR antibody No. 3-2 (IgG4), respectively. These two antibodies were employed in the pharmacokinetic analysis using monkeys described in Example 15.

[Example 14] Measurement of Affinity of Humanized Anti-hTfR Antibodies to Human TfR and Monkey TfR The affinity of the humanized anti-hTfR antibodies obtained in Example 13 to human and monkey TfRs was measured by the method described in Example 7. Table 7 shows the result of the measurement of the association rate constant ($k_{on}$), dissociation rate constant ($k_{off}$), and dissociation constant ($K_D$) of humanized anti-hTfR antibodies Nos. 1 to 3-4 (corresponding to Nos. 1 to 3-4, respectively, in the table) to human TfR.

TABLE 7

Affinity of humanized anti-hTfR antibodies to human TfR

| Antibody No. | kon ($M^{-1}s^{-1}$) | koff ($s^{-1}$) | $K_D$ (M) |
|---|---|---|---|
| 1 | $3.93 \times 10^5$ | $<1.0 \times 10^{-7}$ | $<1.0 \times 10^{-12}$ |
| 2 | $1.97 \times 10^5$ | $<1.0 \times 10^{-7}$ | $<1.0 \times 10^{-12}$ |
| 3 | $1.19 \times 10^6$ | $<1.0 \times 10^{-7}$ | $<1.0 \times 10^{-12}$ |
| 3-2 | $6.06 \times 10^5$ | $1.45 \times 10^{-5}$ | $2.39 \times 10^{-11}$ |
| 3-3 | $6.00 \times 10^5$ | $1.25 \times 10^{-5}$ | $2.09 \times 10^{-11}$ |
| 3-4 | $1.01 \times 10^6$ | $<1.0 \times 10^{-7}$ | $<1.0 \times 10^{-12}$ |

Table 8 shows the result of the measurement of the association rate constant ($k_{on}$), dissociation rate constant ($k_{off}$), and dissociation constant ($K_D$) of humanized anti-hTfR antibodies Nos. 1 to 3-4 (corresponding to Nos. 1 to 3-4, respectively, in the table) to monkey TfR.

TABLE 8

Affinity of humanized anti-hTfR antibodies to monkey TfR

| Antibody No. | kon ($M^{-1}s^{-1}$) | koff ($s^{-1}$) | $K_D$ (M) |
|---|---|---|---|
| 1 | $2.53 \times 10^5$ | $<1.0 \times 10^{-7}$ | $<1.0 \times 10^{-12}$ |
| 2 | $4.87 \times 10^5$ | $3.67 \times 10^{-5}$ | $7.55 \times 10^{-11}$ |
| 3 | $6.03 \times 10^5$ | $6.76 \times 10^{-4}$ | $1.12 \times 10^{-9}$ |
| 3-2 | $4.95 \times 10^5$ | $8.76 \times 10^{-4}$ | $1.77 \times 10^{-9}$ |
| 3-3 | $4.88 \times 10^5$ | $9.32 \times 10^{-4}$ | $1.91 \times 10^{-9}$ |
| 3-4 | $5.19 \times 10^5$ | $1.35 \times 10^{-4}$ | $2.60 \times 10^{-10}$ |

The result of the measurement of the affinity of humanized anti-hTfR antibody Nos. 1 to 3-4 to human TfR showed that the dissociation constant between humanized anti-hTfR antibodies Nos. 1, 2, 3, and 3-4 and human TfR was less than $1\times10^{-12}$M (Table 7). And the dissociation constant between humanized anti-hTfR antibodies Nos. 3-2 and 3-3 and human TfR was $2.39\times10^{-11}$ M and $2.09\times10^{-11}$ M, respectively. At the same time, the dissociation constant between the pre-humanized anti-hTfR antibodies corresponding to those antibodies and human TfR was: $5.09\times10^{-12}$M for antibody No. 1, $1.12\times10^{-11}$M for antibody No. 2, and less than $1\times10^{-12}$M for antibody No. 3 (Table 4). These results demonstrate that the high affinity of those pre-humanized anti-hTfR antibodies to human TfR was maintained after humanization of the antibodies, and indicate that anti-hTfR antibodies Nos. 4 to 14 would also maintain their affinity to human TfR after their humanization.

Then, looking to the result of measurement of the affinity of humanized anti-hTfR antibodies to monkey TfR, it is seen that the dissociation constant of humanized anti-hTfR antibody No. 1 was less than $1\times10^{-12}$ M, indicating that the pre-humanized affinity was maintained after humanization, and also with regard to humanized anti-hTfR antibody No. 2, the dissociation constant was $4.18\times10^{-11}$ M before humanization and $7.55\times10^{-11}$ M after humanization, indicating the affinity was maintained (Table 5, Table 8). On the other hand, regarding to humanized anti-hTfR antibodies Nos. 3 to 3-4, while the dissociation constant of anti-hTfR antibody No. 3, the pre-humanized antibody corresponding to them, to monkey TfR was less than $1\times10^{-12}$ M, their dissociation constant after humanization was $2.60\times10^{-10}$ M to $1.91\times10^{-9}$M, showing a lowering of the affinity to monkey TfR. As to the humanized anti-hTfR antibody No. 3, although a lowering of affinity to monkey TfR was observed, the result indicates that the pre-humanized high affinity of anti-hTfR antibody to monkey TfR was not lost after its humanization but was maintained as a whole. It indicates that as to humanized anti-hTfR antibodies Nos. 4 to 14, too, the pre-humanized affinity to monkey TfR could be maintained after their humanization.

[Example 15] Pharmacokinetic Analysis of Humanized Anti-hTfR Antibody in Monkey Using monkeys, pharmacokinetic analysis was performed with four antibodies: humanized anti-hTfR antibody No. 3, humanized anti-hTfR antibody No. 3-2, humanized anti-hTfR antibody No. 3 (IgG4), and humanized anti-hTfR antibody No. 3-2 (IgG4). Besides, the heavy chain of humanized anti-hTfR antibody No. 3 was IgG1, while in humanized anti-hTfR antibody No. 3 (IgG4), the heavy chain of humanized anti-hTfR antibody No. 3 had been converted into IgG4, with its variable region kept intact. Further, the heavy chain of humanized anti-hTfR antibody No. 3-2 was IgG1, while in humanized anti-hTfR antibody No. 3-2 (IgG4), the heavy chain of humanized anti-hTfR antibody No. 3-2 had been converted into IgG4 with its variable region kept intact. These four antibodies were respectively intravenously administered once to male cynomolgus monkeys, at a dosage of 5.0 mg/kg, and their peripheral blood was sampled before the administration, 2 minutes, 30 minutes, 2 hours, 4 hours and 8 hours after the administration, and then they were subjected to whole body irrigation. As a negative control, trastuzumab (Herceptin™, Chugai Pharmaceutical Co., Ltd.), a humanized antibody to HER2 protein, was intravenously administered once to a single monkey in the same manner, and its peripheral blood was sampled before the administration, 2 minutes, 30 minutes, 2 hours, 4 hours and 8 hours after the administration, and then it was subjected to the whole body irrigation. After the irrigation, the brain and spine tissues including the medulla oblongata and other tissues (liver, heart, spleen and bone marrow) were excised. Using these brain and spinal tissues and other tissues, the concentration of the humanized anti-hTfR antibodies was measured and immunohistochemical staining was carried out.

Measurement of the concentration of humanized anti-hTfR antibodies in tissues and peripheral blood was carried out largely following the procedure described below. Besides, as to the brain, the collected tissues were separated into the cerebral cortex, the cerebellum, the hippocampus and the medulla oblongata, and then the concentration of the humanized anti-hTfR antibodies were measured. The respective tissues thus obtained were homogenized with RIPA Buffer (Wako Pure Chemical Industries Inc.) containing Protease Inhibitor Cocktail (Sigma-Aldrich Inc.), centrifuged, and the supernatant collected. From the above peripheral blood, serum was separated. To each well of High Bind Plate (Meso Scale Diagnostics) was added 10 μL, of Affinipure Goat Anti mouse IgG Fcγ pAb (Jackson ImmunoResearch Inc.), and the plate was left to stand for one hour to provide a solid phase. Then, 150 μL, of SuperBlock blocking buffer in PBS (Thermo Fisher Scientific Inc.) was added to each well, and the plate was blocked by one-hour shaking. Then, 25 μL, of the supernatant of the homogenate or the serum was added to each well, and the wells were shaken for one hour. Then, 25 μL, of Affinipure Goat Anti mouse IgG Fab-Biotin (Jackson ImmunoResearch Inc.) was added to each well, and shaking was continued for one hour. Then, 25 μL, of SULFO-Tag-Streptavidin (Meso Scale Diagnostics Inc.) was added to each well, followed by shaking for half an hour. To each well was added 150 μL, of Read buffer T (Meso Scale Diagnostics Inc.), and the amount of luminescence from each well was read on a Sector™ Imager 6000 reader. The amount of the antibody contained in each tissue and the peripheral blood was calculated by producing a standard curve based on measurements of standard samples containing known concentrations of the anti-hTfR antibody, and then interpolating the measurement of each of the samples with reference to the standard. Measurement of concentration was repeated three times for each sample.

The result of measurement of the concentration of humanized anti-hTfR antibodies in the brain and spinal tissues is shown in Table 9.

TABLE 9

Concentration of humanized anti-hTfR antibodies in brain tissues (μg/g wet weight)

| Antibody No. | Cerebral cortex | Cerebellum | Hippocampus | Medulla oblongata | Spinal cord |
|---|---|---|---|---|---|
| 3 | 0.67 ± 0.12 | 0.61 ± 0.02 | 0.49 ± 0.02 | 0.59 ± 0.10 | 0.46 ± 0.17 |
| 3-2 | 1.05 ± 0.07 | 0.72 ± 0.04 | 0.72 ± 0.07 | 0.69 ± 0.03 | 0.46 ± 0.02 |
| 3 (IgG4) | 0.65 ± 0.05 | 0.59 ± 0.03 | 0.56 ± 0.02 | 0.59 ± 0.02 | 0.46 ± 0.07 |
| 3-2 (IgG4) | 0.76 ± 0.02 | 0.57 ± 0.07 | 0.62 ± 0.05 | 0.73 ± 0.16 | 0.48 ± 0.03 |
| Negative control | 0.0082 ± 0.0032 | 0.0090 ± 0.0067 | 0.0053 ± 0.0009 | 0.011 ± 0.003 | 0.15 ± 0.04 |

All the antibodies, i.e., humanized anti-hTfR antibody No. 3, humanized anti-hTfR antibody No. 3-2, humanized anti-hTfR antibody No. 3 (IgG4) and humanized anti-hTfR antibody No. 3-2 (IgG4), were observed to accumulate in the cerebral cortex, cerebellum, hippocampus, medulla oblongata and spinal cord (Table 9). The respective amount accumulated was as follow:

with humanized anti-hTfR antibody No. 3, approximately 82 times in the cerebral cortex, approximately 68 times in the cerebellum, approximately 92 times in the hippocampus, approximately 54 times in the medulla oblongata, and approximately 3.1 times in the spinal cord, in comparison with the negative control, trastuzumab (Herceptin™), with humanized anti-hTfR antibody No. 3-2, approximately 128 times in the cerebral cortex, approximately 80 times in the cerebellum, approximately 136 times in the hippocampus, approximately 63 times in the medulla oblongata, approximately 3.1 times in the spinal cord, in comparison with the negative control, trastuzumab, with humanized anti-hTfR antibody No. 3 (IgG4), approximately 79 times in the cerebral cortex, approximately 66 times in the cerebellum, approximately 106 times in the hippocampus, approximately 54 times in the medulla oblongata, approximately 3.1 times in the spinal cord, in comparison with the negative control, trastuzumab, and with humanized anti-hTfR antibody No. 3-2 (IgG4), approximately 93 times in the cerebral cortex, approximately 63 times in the cerebellum, approximately 117 times in the hippocampus, approximately 66 times in the medulla oblongata, approximately 3.2 times in the spinal cord, in comparison with the negative control, trastuzumab (Table 10).

These results indicate that these four humanized anti-hTfR antibodies have a property that allows them to pass through the blood-brain barrier and accumulate in the brain tissues, and that it is now possible to let pharmaceutical agents which need to be brought into function in the brain tissues efficiently accumulate there, by binding such pharmaceutical agents to one of these antibodies.

TABLE 10

| Amount of humanized anti-hTfR antibodies accumulated in brain tissues (factors in comparison with negative control) | | | | | |
|---|---|---|---|---|---|
| Antibody No. | Cerebral cortex | Cerebellum | Hip-pocampus | Medulla oblongata | Spinal cord |
| 3 | 82 | 68 | 92 | 54 | 3.1 |
| 3-2 | 128 | 80 | 136 | 63 | 3.1 |
| 3 (IgG4) | 79 | 66 | 106 | 54 | 3.1 |
| 3-2 (IgG4) | 93 | 63 | 117 | 66 | 3.2 |
| Negative control | 1 | 1 | 1 | 1 | 1 |

Figure 4:
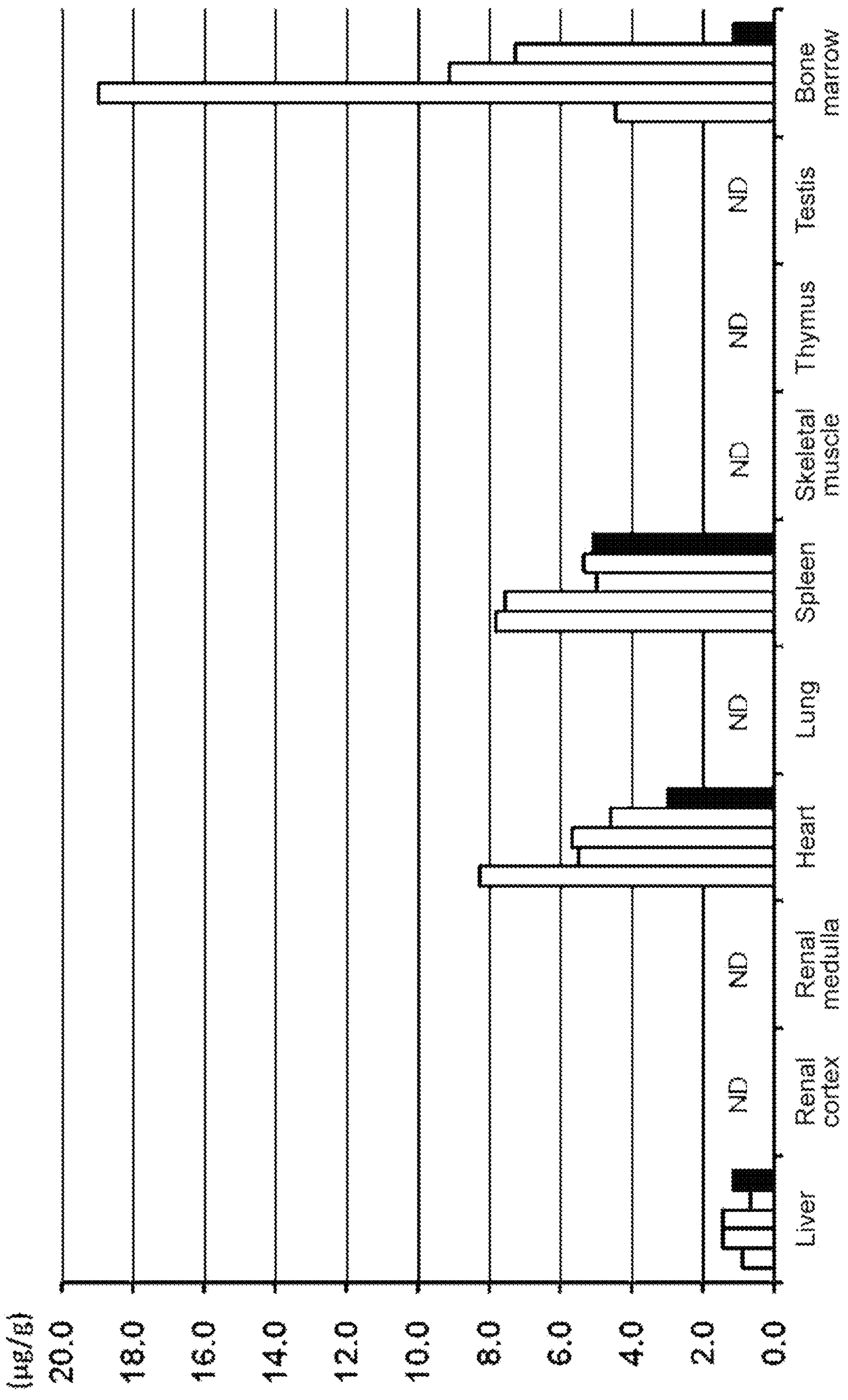
FIG. 4 A figure showing the amount of a humanized anti-hTfR antibody accumulated in various organs other than the brain of a cynomolgus monkey after a single intravenous administration. The vertical axis indicates the amount of the humanized anti-hTfR antibody (μg/g wet weight) per wet weight of each organ. The white bars represent, from the left, the amount accumulated in each organ of the monkey after administration of humanized anti-hTfR antibody No. 3, humanized anti-hTfR antibody No. 3-2, humanized anti-hTfR antibody No. 3 (IgG4), and humanized anti-hTfR antibody No. 3-2 (IgG4), respectively, and the black bars represent the amount accumulated in respective organs of the monkey after administration of trastuzumab (Herceptin™). "ND" denotes "not detected".

Then, FIG. 4 shows the result of measurement of the concentration of the humanized anti-hTfR antibodies in the tissues of the liver, heart, spleen and bone marrow. The four humanized anti-hTfR antibodies, as well as the negative control, trastuzumab, were observed to accumulate in the liver and spleen, and their amount accumulated was equal between the four humanized anti-hTfR antibodies and trastuzumab. In the heart, the humanized anti-hTfR antibodies tended to accumulate more than trastuzumab, the negative control, but the amount was only about 1.5 to 2.8 times that of the negative control. In bone marrow, the humanized anti-hTfR antibodies tended to accumulate markedly more than trastuzumab, the negative control, and the amount was 3.5 to 16 times that of the negative control. The cause of this accumulation of the humanized anti-hTfR antibodies in bone marrow is thought to be that TfR is expressed at high levels in bone marrow, hematopoietic organ, and more humanized anti-hTfR antibodies, therefore, accumulate through binding to TfR, than the negative control. These data indicate that the four humanized anti-hTfR antibodies has a property that allows them to specifically accumulate the cerebrum, cerebellum, hippocampus and medulla oblongata, which constitute the central nervous system, and that it is now possible to let pharmaceutical agents which need to be brought into function in the brain tissues efficiently accumulate there, by binding such pharmaceutical agents to one of these antibodies.

Then, Table 11 shows the result of pharmacokinetic measurement of the humanized anti-hTfR antibodies in the blood. As that of the negative control, trastuzumab, the blood concentration of the four humanized anti-hTfR antibodies was maintained at high levels, higher than 60 μg/mL, even eight hours after administration, indicating that they are stable in the blood.

TABLE 11

| Pharmacokinetics of humanized anti-hTfR antibodies in blood (μg/mL blood( ) | | | | | |
|---|---|---|---|---|---|
| Antibody | Time after administration | | | | |
| No. | 2 min | 30 min | 2 hr | 4 hr | 8 hr |
| 3 | 173 | 147 | 128 | 117 | 97.5 |
| 3-2 | 124 | 99.5 | 78.5 | 76.5 | 61 |
| 3 (IgG4) | 141 | 113 | 99 | 95 | 83 |
| 3-2 (IgG4) | 132 | 111 | 98.5 | 99 | 95.5 |
| Negative control | 124 | 92.5 | 96 | 75.5 | 60.5 |

Immunohistochemical staining of the humanized anti-hTfR antibodies in brain tissues was performed in the following manner. The collected tissues were rapidly frozen to −80° C. in a Tissue-Tek Cryo 3DM (Sakura Finetek Inc.) to prepare frozen blocks of tissues. The frozen blocks were sliced into 4 μm sections, which were affixed to MAS coated glass slides (Matsunami Glass Inc.). The tissue sections were reacted with 4% paraformaldehyde (Wako Pure Chemical Industries Inc.) for 5 minutes at 4° C. and fixed to glass slides. Then, the tissue sections were reacted with methanol solution containing 0.3% hydrogen peroxide (Wako Pure Chemical Industries Inc.) for 30 min to inactivate endogenous peroxidases. Then, the glass slides were blocked by reacting SuperBlock blocking buffer in PBS for 30 min at room temperature. Then, the tissue sections were reacted with Mouse IgG-heavy and light chain Antibody (Bethyl Laboratories) for one hour at room temperature. The tissue sections were allowed to visualize with DAB substrate (3,3'-diaminobenzidine, Vector Laboratories Inc.), counterstained with Mayer's hematoxylin solution (Merck Inc.), embedded after dehydration and cleaning, and observed under a optical microscope.

Figure 5:
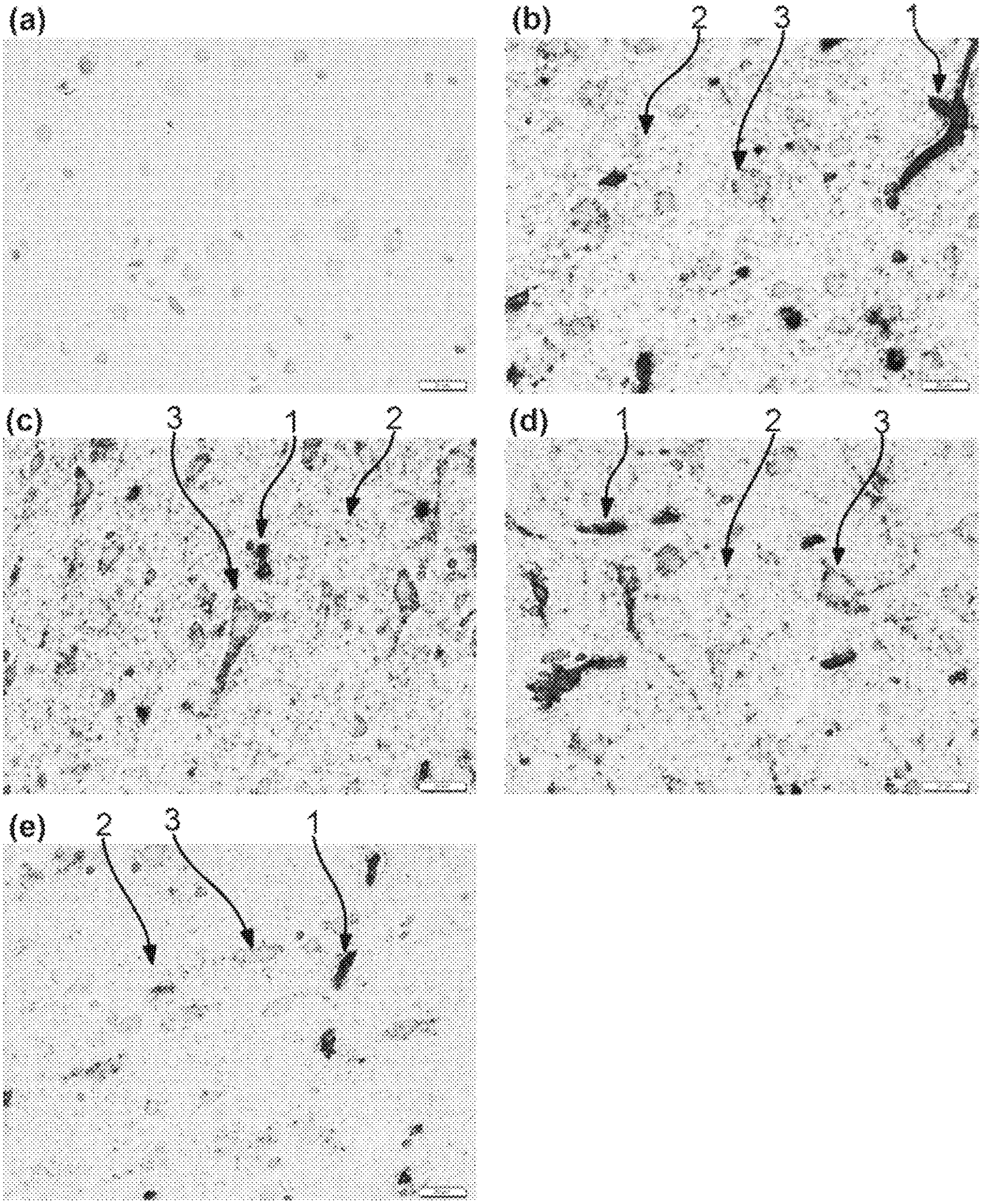
FIG. 5 Substitute photographs for drawings showing the result of immunohistochemical staining of a humanized anti-hTfR antibody in the cerebral cortex of a cynomolgus monkey after a single intravenous administration. (a) Herceptin administered, (b) humanized anti-hTfR antibody No. 3 administered, (c) humanized anti-hTfR antibody No. 3-2 administered, (d) humanized anti-hTfR antibody No. 3 (IgG4) administered, (e) humanized anti-hTfR antibody No. 3-2 (IgG4) administered. The bar at the bottom right in each photograph is a 20-μm gauge.

FIG. 5 shows the result of immunohistochemical staining of the humanized anti-hTfR antibodies in the cerebral cortex. Specific staining of blood vessels and neuron-like cells were observed in the cerebral cortex of the monkeys administered humanized anti-hTfR antibody No. 3, humanized anti-hTfR antibody No. 3-2, humanized anti-hTfR antibody No. 3 (IgG4), and humanized anti-hTfR antibody No. 3-2 (IgG4) (FIG. 5, panels b to e, respectively). In the cerebral cortex of the monkey administered humanized anti-hTfR antibody No. 3-2, in particular, (FIG. 5, panel c), the brain parenchyma region, outside the blood vessels, was also observed specifically stained extensively. Besides, no staining was observed in the cerebral cortex of the monkey administered Herceptin as a control, indicating that the tissue staining observed in FIG. 5, panels b to e was specific for the humanized anti-hTfR antibodies (FIG. 5, panel a).

Figure 6:
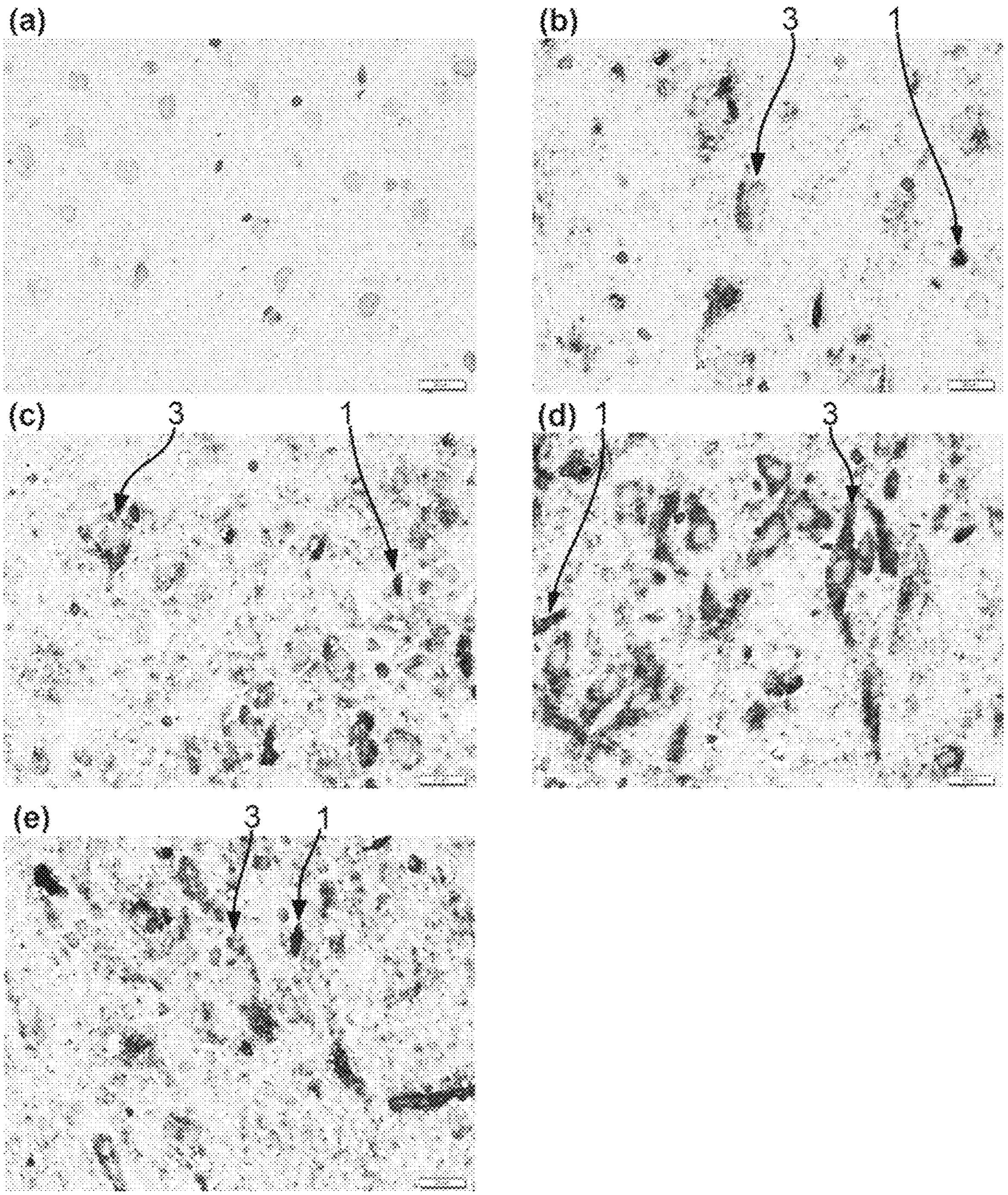
FIG. 6 Substitute photographs for drawing showing the result of immunohistochemical staining of a humanized anti-hTfR antibody in the hippocampus of a cynomolgus monkey after a single intravenous administration. (a) Herceptin administered, (b) humanized anti-hTfR antibody No. 3 administered, (c) humanized anti-hTfR antibody No. 3-2 administered, (d) humanized anti-hTfR antibody No. 3 (IgG4) administered, (e) humanized anti-hTfR antibody No. 3-2 (IgG4) administered. The bar at the bottom right at each photograph is a 20-μm gauge.

FIG. 6 shows the result of immunohistochemical staining of the humanized anti-hTfR antibodies in the hippocampus. Specific staining of blood vessels and neuron-like cells were observed in the hippocampus of the monkeys administered humanized anti-hTfR antibody No. 3, humanized anti-hTfR antibody No. 3-2, humanized anti-hTfR antibody No. 3(IgG4), and humanized anti-hTfR antibody No. 3-2 (IgG4) (FIG. 6, panels b to e, respectively). Besides, no staining was observed in the hippocampus of the monkey administered Herceptin as a control, indicating that the tissue staining observed in FIG. 6, panels b to e was specific for the humanized anti-hTfR antibodies (FIG. 6, panel a).

Figure 7:
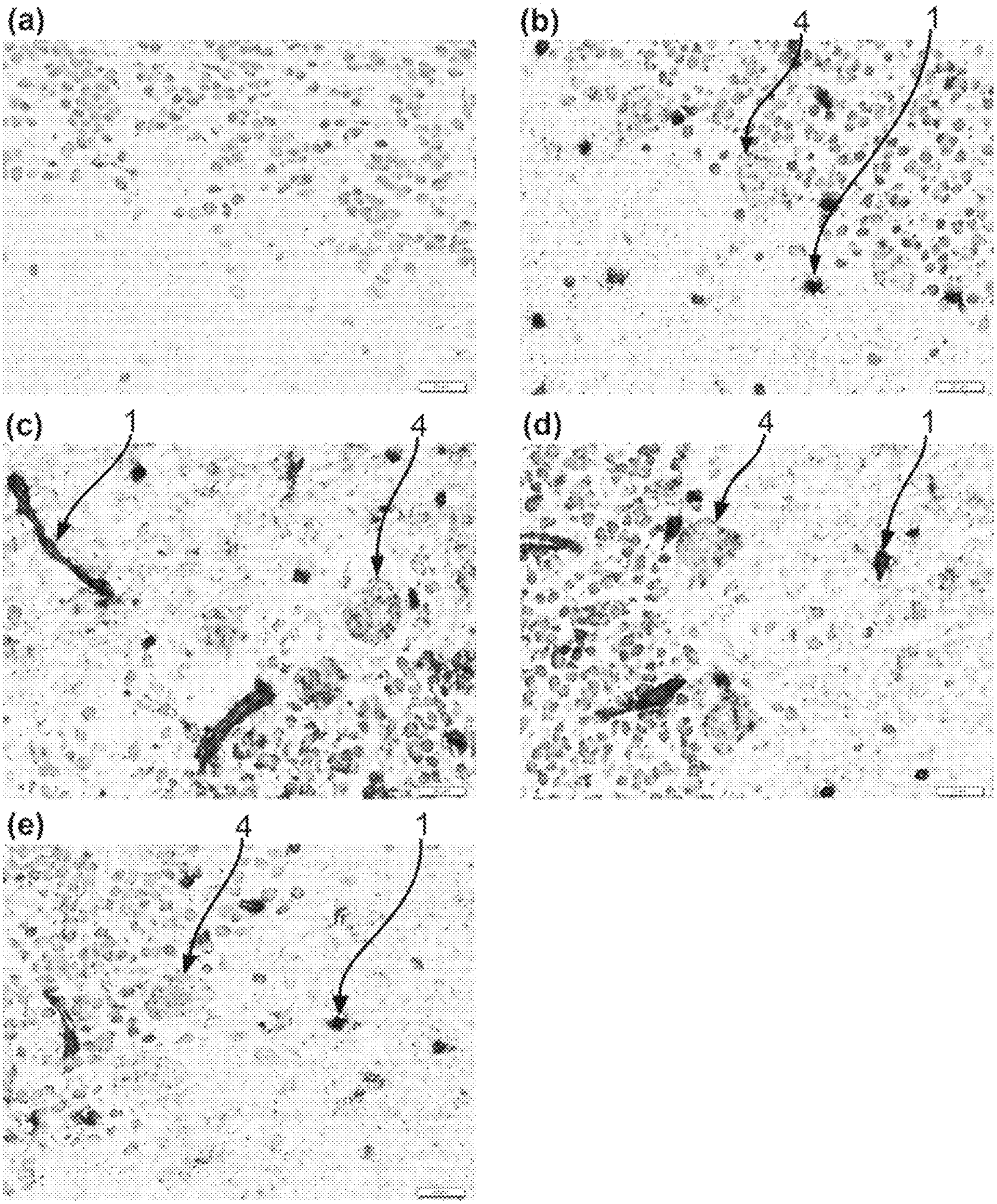
FIG. 7 A figure showing the result of immunohistochemical staining of humanized anti-hTfR antibody in the cerebellum of a cynomolgus monkey after a single intravenous administration. (a) Herceptin administered, (b) humanized anti-hTfR antibody No. 3 administered, (c) humanized anti-hTfR antibody No. 3-2 administered, (d) humanized anti-hTfR antibody No. 3 (IgG4) administered, (e) humanized anti-hTfR antibody No. 3-2 (IgG4) administered. The bar at the bottom right at each photograph is a 20-μm gauge.

FIG. 7 shows the result of immunohistochemical staining of the humanized anti-hTfR antibodies in the cerebellum. Specific staining of blood vessels and Purkinje cells were observed in the cerebellum of the monkeys administered humanized anti-hTfR antibody No. 3, humanized anti-hTfR antibody No. 3-2, humanized anti-hTfR antibody No. 3(IgG4), and humanized anti-hTfR antibody No. 3-2 (IgG4) (FIG. 7, panels b to e, respectively). Besides, no staining was observed in the cerebellum of the monkey administered Herceptin as a control, indicating that the tissue staining observed in FIG. 7, panels b to e was specific for the humanized anti-hTfR antibodies (FIG. 7, panel a).

Figure 8:
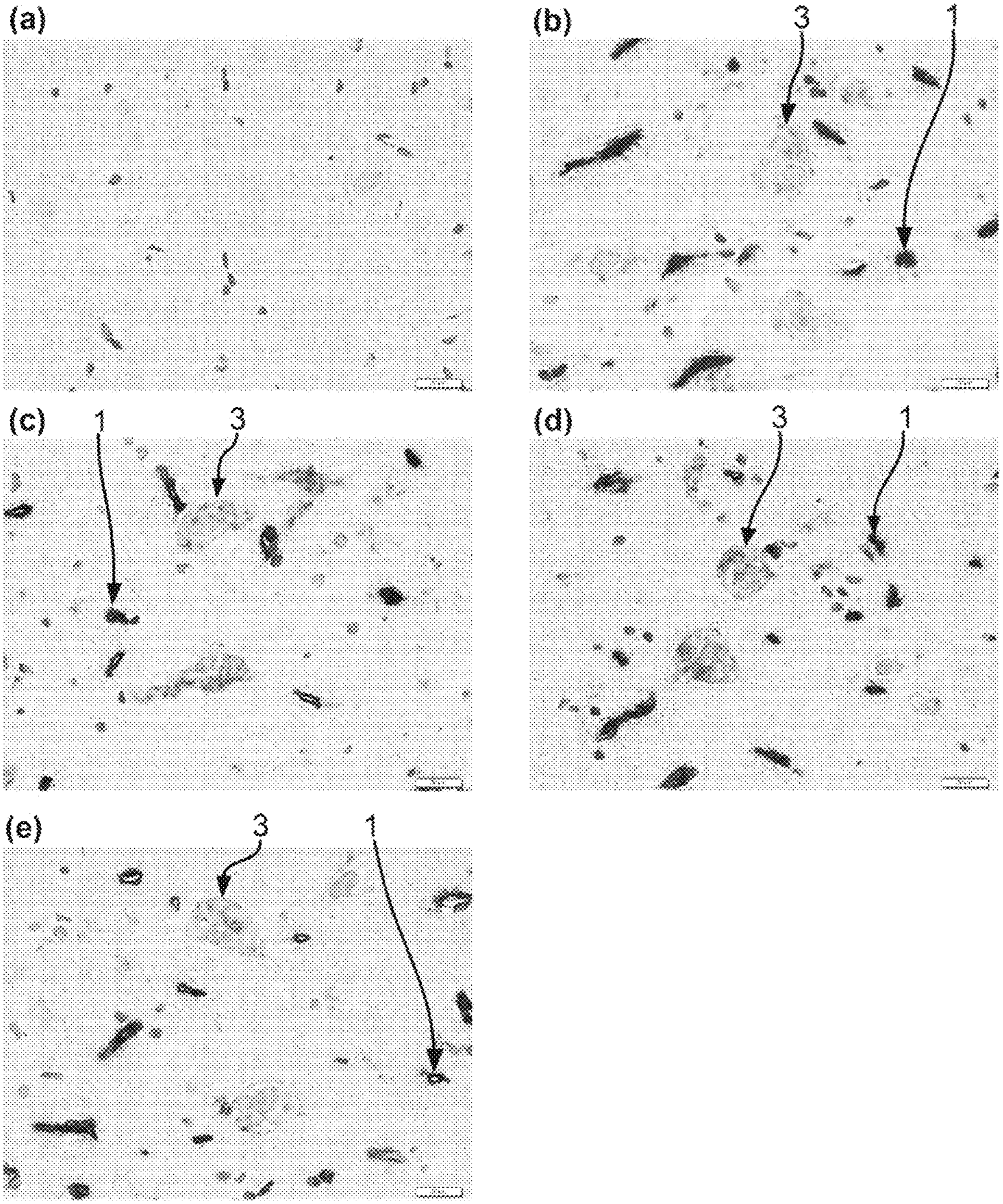
FIG. 8 A figure showing the result of immunohistochemical staining of humanized anti-hTfR antibody in the medulla oblongata of a cynomolgus monkey after a single intravenous administration. (a) Herceptin administered, (b) humanized anti-hTfR antibody No. 3 administered, (c) humanized anti-hTfR antibody No. 3-2 administered, (d) humanized anti-hTfR antibody No. 3 (IgG4) administered, (e) humanized anti-hTfR antibody No. 3-2 (IgG4) administered. The bar at the bottom right at each photograph is a 20-μm gauge.

FIG. 8 shows the result of immunohistochemical staining of the humanized anti-hTfR antibodies in the medulla oblongata. Specific staining of blood vessels and neuron-like cells were observed in the medulla oblongata of the monkeys administered humanized anti-hTfR antibody No. 3, humanized anti-hTfR antibody No. 3-2, humanized anti-hTfR antibody No. 3(IgG4), and humanized anti-hTfR antibody No. 3-2 (IgG4) (FIG. 8, panels b to e, respectively). Besides, no staining was observed in the medulla oblongata of the monkey administered Herceptin as a control, indicating that the tissue staining observed in FIG. 8, panels b to e was specific for the humanized anti-hTfR antibodies (FIG. 8, panel a).

From the result of immunohistochemical staining of the cerebrum and cerebellum in Example 8, it had been anticipated that though the anti-hTfR antibody No. 1, a pre-humanized mouse antibody, can bind to hTfR existing on the endothelium of blood vessel in the brain, the amount transferring to the brain parenchyma would be small. On the other hand, it was shown that anti-hTfR antibodies Nos. 2 and 3, pre-humanized mouse antibodies, can bind to hTfR existing on the endothelium of blood vessel in the brain, and after binding to hTfR, pass through the blood-brain barrier into the brain parenchyma, and further be taken up into the brain parenchyma and neuron-like cells in the hippocampus, and into Purkinje cells in the cerebellum.

From the result of immunohistochemical staining in the cerebrum, hippocampus, cerebellum, and medulla oblongata in Example 15, it was revealed that the tested four humanized anti-hTfR antibodies obtained by humanizing anti-hTfR antibody No. 3 subjected to the experiment can bind to hTfR existing on the endothelium of blood vessels of the brain, and after binding to hTfR, pass through the blood-brain barrier and transfer into the brain parenchyma, and further, be taken up into neuron-like cells in the cerebral cortex; into the brain parenchyma and the neuron-like cells in the hippocampus; into Purkinje cells in the cerebellum; and into neuron-like cells in the medulla oblongata.

[Example 16] Preparation of hI2S-Humanized Anti-hTfR Antibody Fusion Protein Expression Cells By digesting pEF/myc/nucvector (Invitrogen Inc.) with KpnI and NcoI, a region including EF-1α promoter and its first intron was cut out, which then was blunt-ended with T4 DNA polymerase. After digesting pCI-neo (Invitrogen Inc.) with BglII and EcoRI to remove a region including the enhancer/promoter and intron of CMV, the vector was blunt-ended with T4 DNA polymerase, and into which the above mentioned region including EF-1α promoter and its first intron was inserted to construct a vector pE-neo. The vector pE-neo was digested with SfiI and BstXI to cut out a region of approximately 1 kbp including a neomycin resistance gene. Employing pcDNA3.1/Hygro(+) (Invitrogen Inc.) as a template and using primer Hyg-Sfi5' (SEQ ID NO:216) and primer Hyg-BstX3' (SEQ ID NO:217), PCR was performed to amplify the hygromycin gene. The hygromycin gene thus amplified was digested with SfiI and BstXI and inserted into the above vector pE-neo, of which the neomycin resistance gene had been removed, to construct vector pE-hygr.

A DNA fragment was artificially synthesized having the nucleotide sequence set forth as SEQ ID NO:248, which included a gene encoding a protein in which the humanized anti-hTfR antibody heavy chain having the amino acid sequence set forth as SEQ ID NO:172 was linked, on the C-terminal side thereof and via a linker sequence (Gly Ser), to hI2S having the amino acid sequence set forth as SEQ ID NO:246. This DNA fragment encoded a protein in which humanized anti-hTfR antibody heavy chain having the amino acid sequence set forth as SEQ ID NO:247 was linked, via a linker sequence (Gly Ser), to hI2S. This DNA fragment had, on its 5' side, a MluI sequence, and a sequence encoding a leader peptide acting as a secretion signal in this order from the 5' end, and a NotI sequence on its 3' side. The DNA fragment was digested with MluI and NotI, and inserted into the vector pE-neo, between the MluI and NotI thereof, to construct pE-neo(HC-I2S-1).

A DNA fragment was artificially synthesized having the nucleotide sequence set forth as SEQ ID NO:250, which included a gene encoding a protein in which the humanized anti-hTfR antibody heavy chain having the amino acid sequence set forth as SEQ ID NO:188 was linked, on the C-terminal side thereof and via a linker sequence (Gly Ser), to hI2S having the amino acid sequence set forth as SEQ ID NO:246. This DNA fragment encoded a protein in which humanized anti-hTfR antibody heavy chain having the amino acid sequence set forth as SEQ ID NO:249 was linked, via a linker sequence (Gly Ser), to hI2S. This DNA fragment had, on its 5' side, a MluI sequence and a sequence encoding a leader peptide acting as a secretion signal in this order from the 5' end, and a NotI sequence on its 3' side. The DNA fragment was digested with MluI and NotI, and inserted into the vector pE-neo, between the MluI and NotI thereof, to construct pE-neo(HC-I2S-2).

A DNA fragment was artificially synthesized having the nucleotide sequence set forth as SEQ ID NO:252, which included a gene encoding a protein in which the humanized anti-hTfR antibody heavy chain having the amino acid sequence set forth as SEQ ID NO:210 was linked, on the C-terminal side thereof and via a linker sequence (Gly Ser), to hI2S having the amino acid sequence set forth as SEQ ID NO:246. This DNA fragment encoded a protein having the amino acid sequence set forth as SEQ ID NO:251 in which humanized anti-hTfR antibody heavy chain was linked, via a linker sequence (Gly Ser), to hI2S. This DNA fragment had, on its 5' side, a MluI sequence and a sequence encoding a leader peptide acting as a secretion signal in this order from the 5' end, and a NotI sequence on its 3' side. The DNA fragment was digested with MluI and NotI, and inserted into the vector pE-neo, between the MluI and NotI thereof, to construct pE-neo(HC-I2S-3).

CHO cells (CHO-K1: obtained from American Type Culture Collection) were transformed according to the method described in Example 12 with pE-neo(HC-I2S-1) and pE-hygr(LC1) which had been prepared in Example 11, to obtain a cell line expressing a fusion protein between hI2S and a humanized anti-hTfR antibody. This cell line was designated hI2S-anti-hTfR antibody expressing cell line 1. The fusion protein between hI2S and a humanized anti-hTfR antibody expressed by the cell lines was designated I2S-anti-hTfR antibody 1.

In the same manner, CHO cells were transformed with pE-neo(HC-I2S-2) and pE-hygr(LC2) which had been prepared in Example 11, to obtain a cell line expressing a fusion protein between hI2S and a humanized anti-hTfR antibody. This cell line was designated hI2S-anti-hTfR antibody expressing cell line 2. The fusion protein between hI2S and a humanized anti-hTfR antibody expressed by the cell lines was designated I2S-anti-hTfR antibody 2.

Further, in the same manner, CHO cells were transformed with pE-neo(HC-I2S-3) and pE-hygr(LC3) which had been prepared in Example 11, to obtain a cell line expressing a fusion protein between hI2S and a humanized anti-hTfR antibody. This cell line was designated hI2S-anti-hTfR antibody expressing cell line 3. The fusion protein between hI2S and a humanized anti-hTfR antibody expressed by the cell lines was designated I2S-anti-hTfR antibody 3.

[Example 17] Production of I2S-Anti-hTfR Antibodies

I2S-anti-hTfR antibodies were produced by the following method. With CD OptiCHO™ medium, hI2S-anti-hTfR antibody expressing cell lines 1, 2 and 3 obtained in Example 16 were diluted to the density of approximately $2\times10^5$ cells/mL, respectively. The cell suspensions, 200 mL, were added to corresponding 1 L-conical flasks, and cultured for 6 to 7 days in a humid environment at 37° C., 5% $CO_2$, 95% air, with stirring at a rate of about 70 rpm. Each culture supernatant was collected by centrifugation, and filtered through a 0.22 μm filter (Millipore Inc.) to prepare the culture supernatant. To each culture supernatant thus obtained was added five column volumes of 20 mM Tris buffer (pH 8.0) containing 150 mM NaCl, and loaded onto a Protein A column (column volume: 1 mL, Bio-Rad Inc.) which had been equilibrated in advance with three column volumes of 20 mM Tris buffer (pH 8.0) containing 150 mM NaCl. Then, the column was washed with five column volumes of the same buffer, and the adsorbed I2S-anti-hTfR antibody was eluted with four column volumes of 50 mM glycine buffer (pH 2.8) containing 150 mM NaCl. The pH of the eluate containing I2S-anti-hTfR antibody was adjusted to pH 7.0 with 1 M Tris buffer (pH 8.0), and then the buffer was replaced with PBS buffer using Amicon Ultra 30 kDa membrane (Millipore Inc.) to obtain a I2S-anti-hTfR antibody purified product.

The affinity of the I2S-anti-hTfR antibodies thus produced to human and monkey TfRs can be measured by, e.g., the method described in Example 7. Pharmacokinetic analysis of the I2S-anti-hTfR antibodies after their intravenous administration can be conducted by, e.g., the method described in Example 8. The pharmacological effects of the I2S-anti-hTfR antibodies can be evaluated by, e.g., intravenously injecting the I2S-anti-hTfR antibodies to I2S-KO/hTfR KI mice, which can be obtained through mating of iduronate 2-sulfatase gene knockout mice (I2S-KO mice), model mice for Hunter syndrome, with hTfR-KI mice described in Example 7-2, and measuring the reduction of glycosaminoglycans accumulated in the brain.

[Example 18] Evaluation of Transfer of I2S-Anti-hTfR Antibodies into the Brain-1

Each of the purification products of the I2S-anti-hTfR antibody 3 prepared in Example 17 was intravenously injected, at the dose of 1 mg/kg, to hTfR-KI mice generated by the method described in Example 7-2 (I2S-anti-hTfR antibody administered group). As a control, recombinant hI2S (rhI2S) was intravenously injected, at the dose of 1 mg/kg, to hTfR-KI mice (control group). Fifteen hTfR-KI mice were administered in I2S-anti-hTfR antibody administered group, and three in the control group (male, 15 to 18-week old). Besides, the rhI2S used in the above had been prepared in accordance with a conventional method, which was described in an international patent publication (WO 2012/102998). It is also possible to use Elaprase®, a medicinal product available on the market as the rhI2S.

In an I2S-anti-hTfR antibody administered group, three mice were subjected whole body irrigation with physiological saline after 15 min, 1 hr, 4 hr, 8 hr, and 24 hr, respectively, of the administration of I2S-anti-hTfR antibody 3, and the brains (cerebrum and cerebellum) were taken. As for the control group, whole body irrigation with physiological saline was carried out one hour after the rhI2S administration, and the brains (cerebrum and cerebellum) were taken. The weight (wet weight) of the cerebrum and cerebellum excised was weighed, and then the cerebrum and cerebellum were homogenized with T-PER (Thermo Fisher Scientific Inc.) containing Protease Inhibitor Cocktail (Sigma Inc.), and their supernatants were collected after centrifugation. The amount of I2S-anti-hTfR antibody contained in the supernatant of homogenate was measured for I2S-anti-hTfR antibody administered group, and the amount of rhI2S contained in the supernatant of homogenate for the control group by ECL method described in Examples 20 and 21, respectively, and the amount of I2S-anti-hTfR antibody (concentration of I2S-anti-hTfR antibody in brain tissues) as well as the amount of rhI2S (concentration of rhI2S in brain tissues) contained in 1 g of the brain (wet weight) were calculated. The result is shown in Table 12.

The concentration of I2S-anti-hTfR antibody and rhI2S in the brain tissues one hour after administration was 0.368±0.019 μg/g wet weight and 0.00134±0.00232 μg/g wet weight, respectively, showing that the concentration of I2S-anti-hTfR antibody reached approximately 270 times that of rhI2S. The result indicates that rhI2S, which scarcely passes through the blood-brain barrier, in general, and does not transfer to the brain, can be made to pass through the blood-brain barrier and transfer into the brain tissues, by combining it with the anti-hTfR antibody. Further, the concentration of the I2S-anti-hTfR antibody in the brain tissues reached 0.263±0.038 μg/g wet weight in only 15 min after administration, which was approximately 200 times that of rhI2S in the brain tissues one hour after administration. The result also indicates that by combining with the anti-hTfR antibody, it becomes possible to let hI2S rapidly transfer into the brain tissues.

TABLE 12

| Concentration of I2S-anti-hTfR antibody and rhI2S in brain tissues (μg/g wet weight) | | |
|---|---|---|
| Time after administration (hr) | I2S-anti-hTfR antibody | rhI2S |
| 0.25 | 0.263 ± 0.038 | — |
| 1 | 0.368 ± 0.019 | 0.00134 ± 0.00232 |
| 4 | 0.440 ± 0.033 | — |
| 8 | 0.382 ± 0.011 | — |
| 24 | 0.245 ± 0.012 | — |

[Example 19] Evaluation of Transfer of I2S-Anti-hTfR Antibodies into the Brain-2

Figure 9:
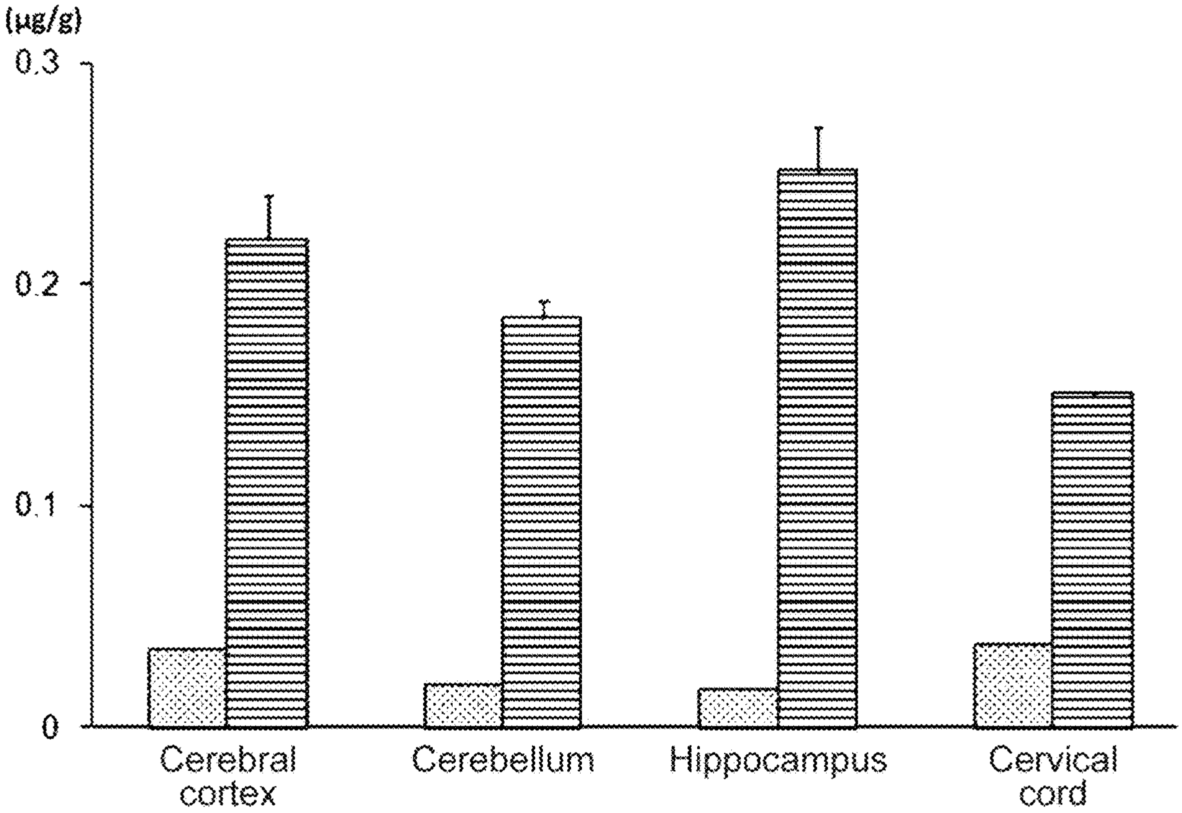
FIG. 9 A figure showing the amount of I2S-anti-hTfR antibody and rhI2S accumulated in brain tissues of a cynomolgus monkey after a single intravenous administration. The vertical axis indicates the amount of I2S-anti-hTfR antibody and rhI2S per wet weight of the brain tissues (μg/g wet weight). The dotted bars represent the amount of rhI2S accumulated in the brain tissues of the cynomolgus monkey. The hatched bars represent the amount of the I2S-anti-hTfR antibody accumulated in the brain tissues of the cynomolgus monkey. Vertical line segment indicates the standard deviation.

The purification product of I2S-anti-hTfR antibody 3 prepared in Example 17 was intravenously administered once to male cynomolgus monkeys, at a dosage of 5 mg/kg (I2S-anti-hTfR antibody administered group). In the same manner, rhI2S was administered once to male cynomolgus monkeys, at a dosage of 5 mg/kg (rhI2S group). The rhI2S employed here had been prepared in accordance with a conventional method, which was described in an international patent publication (WO 2012/102998). It is also possible to use Elaprase®, a medicinal product available on the market as the rhI2S. Two monkeys were administered in each group. Eight hours after administration, whole body irrigation was carried out. After the irrigation, the brain tissues including the cervical cord were excised. The brain tissues thus excised were separated into the cerebral cortex, the cerebellum, the hippocampus and the cervical cord, and each of them was homogenized with T-PER (Thermo Fisher Scientific Inc.)

containing Protease Inhibitor Cocktail (Sigma Inc.), centrifuged, and the supernatant was collected. The amount of the I2S-anti-hTfR antibody contained in the supernatant of homogenate was measured in I2S-anti-hTfR antibody administered group, and the amount of rhI2S contained in the supernatant of homogenate in the control group by ECL method described in Examples 20 and 21, respectively. From the measurement thus obtained, the amount of I2S-anti-hTfR antibody contained in 1 g (g wet weight) of the cerebral cortex, cerebellum, hippocampus, and cervical cord (concentration of I2S-anti-hTfR antibody in those brain tissues), as well as the amount of rhI2S (concentration of rhI2S in those brain tissues), were calculated. The result is shown in FIG. 9.

The concentration of I2S-anti-hTfR antibody in the cerebral cortex was approximately 0.22 μg/g, whereas that of rhI2S was 0.035 μg/g. The concentration of I2S-anti-hTfR antibody in the cerebellum was approximately 0.18 μg/g, whereas that of rhI2S was 0.02 μg/g. The concentration of I2S-anti-hTfR antibody in the hippocampus was approximately 0.25 μg/g, whereas that of rhI2S was 0.017 μg/g. And the concentration of I2S-anti-hTfR antibody in the cervical cord was approximately 0.15 μg/g, whereas that of rhI2S was 0.039 μg/g. Thus, the concentration of I2S-anti-hTfR antibody in the cerebral cortex, cerebellum, hippocampus, and cervical cord was shown to be approximately 6.3 times, approximately 9.0 times, approximately 14.7 times, and approximately 3.8 times that of rhI2S, respectively. The result indicates that by binding hI2S to the anti-hTfR antibody, it becomes possible to let hI2S actively pass through the blood-brain barrier and get into the brain efficiently. In particular, that the concentration of the I2S-anti-hTfR antibody in the hippocampus was approximately as high as approximately 12.5 times that of rhI2S indicates that administration of I2S-anti-hTfR antibody could let I2S exhibit its activity in the hippocampus among others. Encephalopathy in Hunter syndrome patients cannot be ameliorated by enzyme replacement therapy with conventional rhI2S because little rhI2S can pass through the blood-brain barrier. In contrast, as I2S-anti-hTfR antibody can pass through the blood-brain barrier, administration of I2S-anti-hTfR antibody could supplement the activity of I2S in the brain tissues such as the cerebral cortex, hippocampus, and cerebellum. Therefore, the I2S-anti-hTfR antibody (especially I2S-anti-hTfR antibody 3) can be used as therapeutic agents to supplement the I2S activity in the brain of Hunter syndrome patients. Thus, by administering I2S-anti-hTfR antibody (especially I2S-anti-hTfR antibody 3), prophylaxis and treatment of encephalopathy in Hunter syndrome patients are possible, which is difficult by enzyme replacement therapy with conventional rhI2S. It is especially promising as a therapeutic agent for patients with Hunter syndrome accompanied disorders of the hippocampus.

[Example 20] Quantitative Determination of I2S-Anti-hTfR Antibody by ECL Method To each well of a 96-well Streptavidin Gold Plate (Meso Scale Diagnostics Inc.), a streptavidin-coated plate, was added 150 μL, of SuperBlock blocking buffer in PBS (Thermo Fisher Scientific Inc.), and the plate was left to stand for one hour for blocking. Anti-Human Kappa Light chain Goat IgG Biotin (Monkey Absorbed) (IBL Inc.), a biotin-labeled antibody, was diluted with SuperBlock blocking buffer in PBS to 0.5 μg/mL. SULFO-labeled anti-human I2S antibody was diluted with SuperBlock blocking buffer in PBS to 1.0 μg/mL. The diluted solutions of the biotin-labeled antibody and the SULFO-labeled antibody, 25 μL, each, were mixed with 25 μL, of each sample, incubated for one hour to prepare an antibody reaction sample.

Each well of the plate after blocking was washed with 200 μL, of PBS-T (Sigma Inc.), and 25 μL, of the antibody reaction sample was added, and incubated for one hour. After incubation, each well of the plate was washed with 200 μL, of PBS-T, Read buffer T (Meso scale Diagnostics Inc.) was added to each well, and the amount of luminescence from each well was measured on Sector™ Imager 6000 (Meso scale Diagnostics Inc.). A standard curve was produced on measurements of standard samples containing known concentrations of I2S-anti-hTfR antibody, and the amount of I2S-anti-hTfR antibody was determined by interpolating the measurement of each of the samples with reference to the standard.

Besides, the anti-human 12S antibody used in the above was a monoclonal antibody obtained by immunizing mice with rhI2S, as antigen, which had been prepared accordance with a conventional method described in an international patent publication (WO 2012/102998). Multiple monoclonal antibodies had been obtained. As SULFO-labeled anti-human I2S antibody, an anti-human I2S antibody was labelled with SULFO using MSD SULFO-TAG NHS-Ester (Meso scale Diagnostics Inc.) in accordance with the attached manual.

[Example 21] Quantitative Determination of hI2S by ECL Method

To each well of a 96-well Streptavidin Gold Plate (Meso Scale Diagnostics Inc.), a streptavidin-coated plate, was added 150 μL of SuperBlock blocking buffer in PBS (Thermo Fisher Scientific Inc.), and the plate was left to stand for one hour for blocking. Biotin-labeled anti-human I2S antibody was diluted with SuperBlock blocking buffer in PBS to 0.5 μg/mL. SULFO-labeled anti-human I2S antibody was diluted with SuperBlock blocking buffer in PBS to 1.0 μg/mL. The diluted solutions of the biotin-labeled antibody and the SULFO-labeled antibody, 25 μL each, were mixed with 25 μL of each sample, incubated for one hour to prepare an antibody reaction sample.

Each well of the plate after blocking was washed with 200 μL of PBS-T (Sigma Inc.), and 25 μL of the antibody reaction sample was added, and incubated for one hour. After incubation, each well of the plate was washed with 200 μL of PBS-T, Read buffer T (Meso scale Diagnostics Inc.) was added to each well, and the amount of luminescence from each well was measured on Sector™ Imager 6000 (Meso scale Diagnostics Inc.). A standard curve was produced on measurements of standard samples containing known concentrations of hI2S, and the amount of rhI2S was determined by interpolating the measurement of each of the samples with reference to the standard.

Besides, the anti-human I2S antibody used in the above was a monoclonal antibody obtained by immunizing mice with rhI2S, as antigen, which had been prepared accordance with a conventional method described in an international patent publication (WO 2012/102998). As SULFO-labeled anti-human I2S antibody, an anti-human I2S antibody was labelled with SULFO using MSD SULFO-TAG NHS-Ester (Meso scale Diagnostics Inc.) in accordance with the attached manual. Further, as biotin-labeled anti-human I2S antibody, another anti-human I2S antibody, except the one that was employed for labeling with SULFO, was labelled with biotin using Biotin Labelling Kit-$NH_2$ (Dojindo Laboratories Inc.) in accordance with the attached manual.

[Example 22] Assessment of Pharmacological Effect of I2S-Anti-hTfR Antibody

The pharmacological effect of I2S-anti-hTfR antibody was evaluated by measuring the concentration of the glycosaminoglycans (GAG) that was known to accumulate in the organs of Hunter syndrome patients, who genetically lacked hI2S activity. The purification product of I2S-anti-hTfR antibody 3 prepared in Example 17 was intravenously injected to I2S-KO/hTfR-KI mice at a dosage of 0.5 mg/kg, 1.0 mg/kg, and 2.0 mg/kg (0.5 mg/kg-administered group, 1.0 mg/kg-administered group, and 2.0 mg/kg-administered group). Administration was made at a frequency of once a week for four weeks, the mice were euthanized by exsanguination under anesthesia four weeks after the first administration, and the brain, liver, lung, and heart were excised. The excised organs then were lyophilized in a lyophilizer (EYELA Inc.), pulverized, and their dry weight was measured. To 100 mg (dry weight) of each of the dried organ preparations was added 1 mL of 0.5 M Tris buffer (pH 7.5), and heated for 10 min at about 100° C. Then, 50 mg/mL Actinase E solution (Kaken Pharmaceutical Inc.) was added to the dry preparation so that 1 mg of actinase E was added to 50 mg (dry weight) the mixture was incubated for 16 hr at about 60° C. to decompose the protein, and heating was continued for 10 min at about 100° C. After centrifugation for 10 min at 15,000 rpm, the supernatant was collected. The amount of GAG contained in the supernatant was measured using Wieslab™ sGAG quantitative kit (Euro-Diagnostica Inc.), and the amount of GAG contained in 1 g (g dry weight) of each organ was calculated. Besides, as the control group, I2S-KO/hTfR-KI mice non-administered I2S-anti-hTfR antibody was employed. At the same time, the amount of GAG in the organs of wild-type mice was measured. This experiment was conducted with three I2S-KO/hTfR-KI mice (male and female, 19 to 25-week old) in each measurement group. Besides, three wild-type mice, male and female, 19 to 25-week old, were employed.

Figure 10:
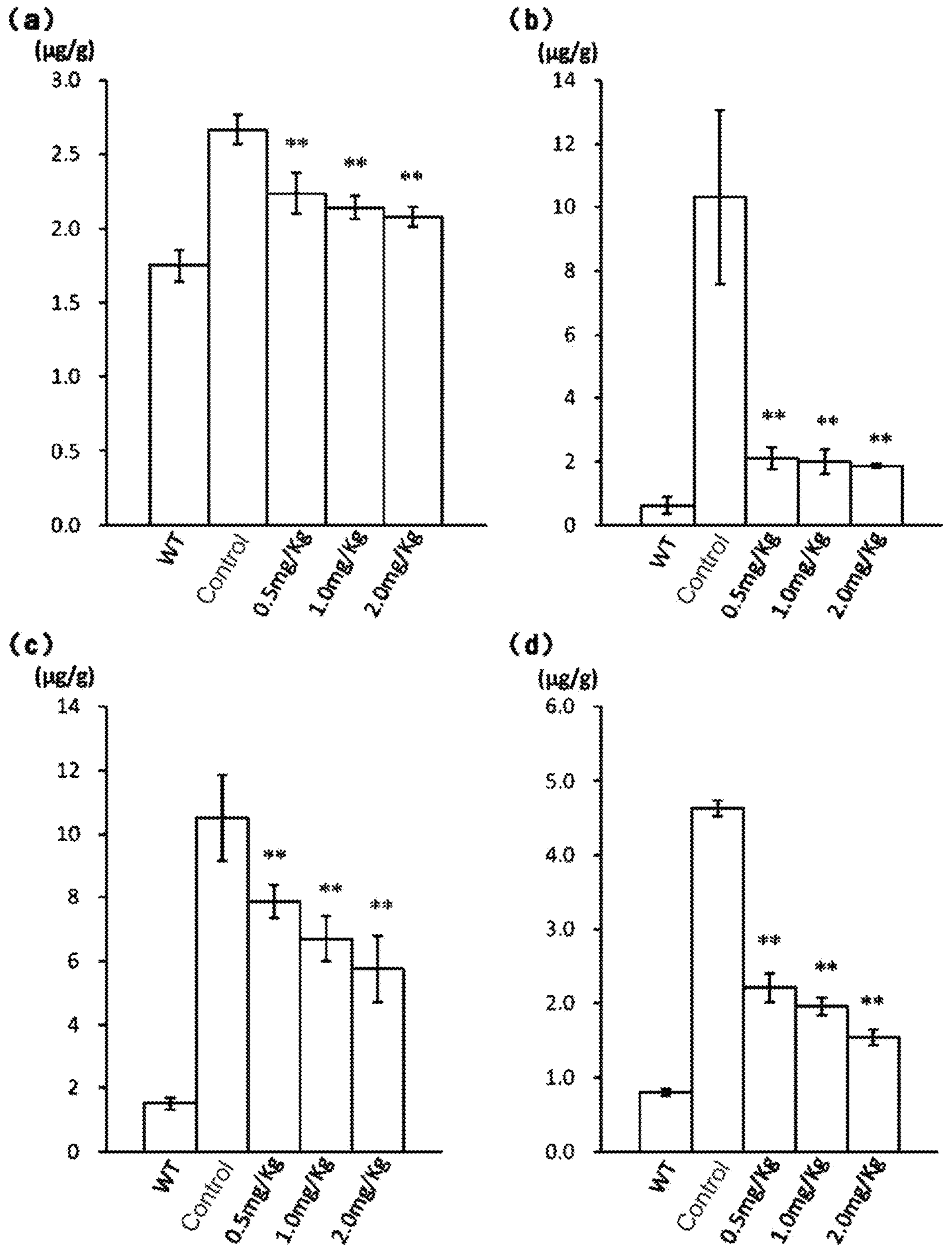
FIG. 10 Graphs showing the amount of the glycosaminoglycan (GAG) in various organs of a I2S gene-knockout mouse (I2S-KO mouse) intravenously injected with a humanized anti-hTfR antibody or rhI2S. (a) brain, (b) liver, (c) lung, (d) heart. For each graph, the bars represent, from the left, wild-type mouse (WT), control group (non-administered group), 0.5 mg/kg administered group, 1.0 mg/kg administered group, and 2.0 mg/kg administered group. The vertical axis indicates the amount of GAG of the dry weight of each organ (μg/g dry weight). Vertical line segments indicates the standard deviation, and "**" indicates $p<0.01$ compared with the control group according to Dunnett's test.

The result is shown in FIG. 10. It was observed that in all the brain, liver, lung and heart, the concentration of GAG significantly decreased dose dependently by 12S-anti-hTfR antibody administration (FIG. 10, panels a to d).

In the brain, the concentration of GAG was approximately 2.66 μg/g in the brain tissues of the control group, whereas the concentration of GAG in the brain tissues of 0.5 mg/kg, 1.0 mg/kg, and 2.0 mg/kg administered groups was approximately 2.23 μg/g, approximately 2.15 μg/g, approximately 2.10 μg/g, respectively, showing a dose dependent decrease (FIG. 10, panel a). Abnormal amount of GAG in the brain tissues of I2S-KO/hTfR-KI mice can be determined as being approximately 0.90 μg/g, i.e., the amount that remains after the concentration of GAG in the brain tissues of the wile-type mice (approximately 1.76 μg/g) is subtracted from the concentration of GAG in the brain tissues of the control group (approximately 2.66 μg/g). Thus, it can be concluded that approximately 48%, approximately 57%, and approximately 62% of GAG abnormally accumulated in the brain tissues of I2S-KO/hTfR-KI mice were decomposed by the I2S-anti-hTfR antibody administered at the doses of 0.5 mg/kg, 1.0 mg/kg, and 2.0 mg/kg, respectively. The result indicates that it is possible to decompose and remove GAG abnormally accumulated in the brain tissues of a Hunter syndrome patient by administering the I2S-anti-hTfR antibody to the patient, and that the I2S-anti-hTfR antibody (I2S-anti-hTfR antibody 3, in particular) could prevent and treat brain lesions caused by accumulation and the like of GAG or its fragments observed in Hunter syndrome patients.

In the liver, the concentration of GAG was approximately 10.3 μg/g in the liver tissue of the control group, whereas the concentration of GAG in the liver tissue of 0.5 mg/kg, 1.0 mg/kg, and 2.0 mg/kg administered groups was approximately 2.2 μg/g, approximately 2.0 μg/g, approximately 1.9 μg/g, respectively, showing a dose dependent decrease (FIG. 10, panel b). Abnormal portion of the amount of GAG in the liver tissue of I2S-KO/hTfR-KI mice can be determined as being approximately 10 μg/g, i.e., the amount that remains after the concentration of GAG in the liver tissue of the wild-type mice (approximately 0.3 μg/g) is subtracted from the concentration of GAG in the liver tissue of the control group (approximately 10.3 μg/g). Thus, it can be concluded that not less than 80% of GAG abnormally accumulated in the liver tissue of I2S-KO/hTfR-KI mice was decomposed by the I2S-anti-hTfR antibody administered at the doses of 0.5 to 2.0 mg/kg.

In the lung, the concentration of GAG was approximately 10.5 μg/g in the lung tissue of the control group, whereas the concentration of GAG in the lung tissue of 0.5 mg/kg, 1.0 mg/kg, and 2.0 mg/kg administered groups was approximately 7.8 μg/g, approximately 6.7 μg/g, approximately 5.7 μg/g, respectively, showing a dose dependent decrease (FIG. 10, panel c). Abnormal portion of the amount of GAG in the lung tissue of I2S-KO/hTfR-KI mice can be determined as being approximately 9.0 μg/g, i.e., the amount that remains after the concentration of GAG in the lung tissue of the wild-type mice (approximately 1.5 μg/g) is subtracted from the concentration of GAG in the lung tissue of the control group (approximately 10.5 μg/g). Thus, it can be concluded that approximately 30%, approximately 42%, and approximately 53% of GAG abnormally accumulated in the lung tissue of I2S-KO/hTfR-KI mice was decomposed by the I2S-anti-hTfR antibody administered at the doses of 0.5 mg/kg, 1.0 mg/kg, and 2.0 mg/kg, respectively.

In the heart, the concentration of GAG was approximately 4.6 μg/g in the heart tissue of the control group, whereas the concentration of GAG in the heart tissue of 0.5 mg/kg, 1.0 mg/kg, and 2.0 mg/kg administered group was approximately 2.2 μg/g, approximately 2.0 μg/g, and approximately 1.5 μg/g, respectively, showing a dose dependent decrease (FIG. 10, panel d). Abnormal portion of the amount of GAG in the heat tissue of I2S-KO/hTfR-KI mice can be determined as being approximately 3.8 μg/g, i.e., the amount that remains after the concentration of GAG in the heart tissue of the wild-type mice (approximately 0.8 μg/g) is subtracted from the concentration of GAG in the heart tissue of the control group (approximately 4.6 μg/g). Thus, it can be concluded that approximately 63%, approximately 70%, and approximately 81% of GAG abnormally accumulated in the heart tissue of I2S-KO/hTfR-KI mice was decomposed by the I2S-anti-hTfR antibody administered at the doses of 0.5 mg/kg, 1.0 mg/kg, and 2.0 mg/kg, respectively.

The above results in the liver, lung and heart demonstrate that the I2S-anti-hTfR antibody decomposes accumulated GAG not only in the brain but also in other organs. This indicates that the I2S-anti-hTfR antibody (especially I2S-anti-hTfR antibody 3), when administered to patients with Hunter syndrome as a pharmaceutical agent in enzyme replacement therapy, could supplement all the patients' organs including the brain with the enzyme. Also indicated is that the I2S-anti-hTfR antibody can supplement the all the patients' organs including the brain with the enzyme through its intravenous administration.

[Example 23] Method for Measurement of GAG

Measurement of GAG was conducted as follows in general, using Wieslab™ sGAG quantitative kit (EURO-DIAGNOSTICA Inc.) in accordance with the attached operating manual. A sample or a standard solution (blank or water), 50

μL each, was added to a 1.5-mL tube. To each tube was added 50 μL of a GuHCl solution, and a reaction was allowed to take place for 15 min at room temperature. A SAT solution, 50 μL, was added to each tube, and a reaction was allowed to proceed for 15 min at room temperature. A mixture solution of water/SAT solution/Alcian Blue stock solution prepared and added to the tubes, 750 μL each, and a reaction was allowed to proceed for 15 min at room temperature. The reaction mixture liquid thus obtained was centrifuged at 12500×g for 15 min to remove the supernatant. To each tube was added 500 μL of DMSO, and following 15-min shaking for mixing at room temperature, the mixture was centrifuged to remove the supernatant. Gu-Prop solution was added to the tubes, 500 μL each, and mixed by shaking for 15 min at room temperature. The mixture solution thus prepared was dispensed, 200 μL each, to the wells of a 96-well plate, and the absorbance of each well was measured at 600 nm using a plate reader. A standard curve was produced on measurements of solutions containing known concentrations of GAG and the GAG concentration was determined by interpolating the measurement of each sample with reference to the standard.

[Example 24] Preparation of Fusion Proteins Between Humanized Anti-hTfR Antibody and Various Physiologically Active Peptides The experiments carried out in Examples 1 to 22 above have shown that human I2S linked to the humanized anti-hTfR antibody passes through the blood-brain barrier, gets into the brain tissues, and exhibits I2S activity in the brain. Then, fusion proteins were prepared between the humanized anti-hTfR antibody and various physiologically active peptides to examine whether those fusion proteins pass through the BBB and get into the brain tissues. Here, human erythropoietin, human arylsulfatase A, human PPT-1, human TPP-1, human α-L-iduronidase, human TNFα receptor, and human N-sulphoglucosamine sulphohydrolase (heparan N-sulfatase) were selected as physiologically active peptides to be fused with the humanized anti-hTfR antibody. The expression vectors used to express fusion proteins between the humanized anti-hTfR antibody and physiologically active peptides, as well as the resulting fusion proteins, were prepared according to Examples 25 to 31 below.

[Example 25] Method for Preparation of Fusion Protein Between Humanized Anti-hTfR Antibody and Human Erythropoietin A DNA fragment was artificially synthesized comprising the nucleotide sequence set forth as SEQ ID NO:258, which included the cDNA encoding a protein consisting of the humanized anti-hTfR antibody having the amino acid sequence set forth as SEQ ID NO:210 and human erythropoietin (hEPO) having the amino acid sequence set forth as SEQ ID NO:256 and linked, via a linker sequence Gly-Ser, on the C-terminal side of the antibody's heavy chain. This DNA fragment encodes a protein having the amino acid sequence set forth as SEQ ID NO:257, which consists of the humanized anti-hTfR antibody and hEPO, which is linked, via a linker sequence Gly-Ser, to the antibody's heavy chain on the C-terminal side thereof. The DNA fragment has in the 5' side a MluI sequence and a sequence encoding a leader peptide acting as a secretion signal, in this order from the 5' end, and a NotI sequence in the 3' side. The DNA fragment was digested with MluI and NotI, and inserted into the vector pE-neo between MluI and NotI sites to construct pE-neo(HC-hEPO).

By the method described in Example 12, CHO cells were transformed with pE-neo(HC-hEPO) and pE-hygr(LC3), which was constructed in Example 11, a cell line was obtained which expresses a fusion protein between hEPO and the humanized anti-hTfR antibody. The cell line was designated hEPO-anti-hTfR antibody expressing cell line. The fusion protein between hEPO and the humanized anti-hTfR antibody, expressed by this cell line, were designated EPO-anti-hTfR antibody.

Cells of hEPO-anti-hTfR antibody expressing cell line were diluted to the density of approximately $2\times10^5$ cells/mL with CD OptiCHO™ medium, and 200 mL of the cell suspension was added to a 1-L conical flask and cultured for 6 to 7 days in a humid environment at 37° C., 5% $CO_2$, 95% air, with stirring at a rate of about 70 rpm. The culture medium was collected by centrifugation and filtered through a 0.22 μm filter (Millipore Inc.) to prepare a culture supernatant. To the culture supernatant thus collected was added five column volumes of 20 mM Tris buffer (pH 8.0) containing 150 mM NaCl, and loaded onto a Protein A column (column volume 1: mL, Bio-Rad Inc.) that had been equilibrated in advance with three column volumes of 20 mM Tris buffer (pH 8.0) containing 150 mM NaCl. Then, five column volumes of the same buffer was supplied to wash the column, the adsorbed EPO-anti-hTfR was eluted with four column volumes of 50 mM glycine buffer (pH 2.8) containing 150 mM NaCl. The eluate containing EPO-anti-hTfR antibody was adjusted to pH 7.0 with 1 M Tris buffer (pH 8.0), and then the buffer exchanged for PBS using Amicon Ultra 30 kDa membrane (Millipore Inc.). The resulting solution was used as the purification product of EPO-anti-hTfR antibody.

[Example 26] Method for Preparation of Fusion Protein Between Humanized Anti-hTfR Antibody and Human Arylsulfatase A A DNA fragment was artificially synthesized comprising the nucleotide sequence set forth as SEQ ID NO:261, which included the cDNA encoding a protein consisting of the humanized anti-hTfR antibody having the amino acid sequence set forth as SEQ ID NO:210 and human arylsulfatase A (hARSA) having the amino acid sequence set forth as SEQ ID NO:259 and linked, via a linker sequence Gly-Ser, to the antibody's heavy chain on the C-terminal side thereof. This DNA fragment encodes a protein having the amino acid sequence set forth as SEQ ID NO:260, which consists of the humanized anti-hTfR antibody and hARSA, which is linked, via a linker sequence Gly-Ser, to the antibody's heavy chain on the C-terminal side thereof. The DNA fragment has in the 5' side a MluI sequence and a sequence encoding a leader peptide acting as a secretion signal, in this order from the 5' end, and a NotI sequence in the 3' side. The DNA fragment was digested with MluI and NotI, and inserted into the vector pE-neo between MluI and NotI sites to construct pE-neo(HC-hARSA).

By the method described in Example 12, CHO cells were transformed with pE-neo(HC-hARSA) and pE-hygr(LC3), which was constructed in Example 11, a cell line was obtained which expresses a fusion protein between hARSA and the humanized anti-hTfR antibody. The cell line was designated hARSA-anti-hTfR antibody expressing cell line. The fusion protein between hARSA and the humanized anti-hTfR antibody, expressed by this cell line, were designated ARSA-anti-hTfR antibody.

Cells of hARSA-anti-hTfR antibody expressing cell line were diluted to the density of approximately $2\times10^5$ cells/mL with CD OptiCHO™ medium, and 200 mL of the cell suspension was added to a 1-L conical flask and cultured for 6 to 7 days in a humid environment at 37° C., 5% $CO_2$, 95% air, with stirring at a rate of about 70 rpm. The culture medium was collected by centrifugation and filtered through a 0.22 μm filter (Millipore Inc.) to prepare a culture supernatant. To the culture supernatant thus collected was added five column volumes of 20 mM Tris buffer (pH 8.0) containing 150 mM NaCl, and loaded onto a Protein A column (column volume: 1 mL, Bio-Rad Inc.) that had been equilibrated in advance with three column volumes of 20 mM Tris buffer (pH 8.0) containing 150 mM NaCl. Then, five column volumes of the same buffer was supplied to wash the column, the adsorbed ARSA-anti-hTfR was eluted with four column volumes of 50 mM glycine buffer (pH 2.8) containing 150 mM NaCl. The eluate containing ARSA-anti-hTfR antibody was adjusted to pH 7.0 with 1 M Tris buffer (pH 8.0), and then the buffer exchanged for PBS using Amicon Ultra 30 kDa membrane (Millipore Inc.). The resulting solution was used as the purification product of ARSA-anti-hTfR antibody.

[Example 27] Method for Preparation of Fusion Protein Between Humanized Anti-hTfR Antibody and Human PPT-1

A DNA fragment was artificially synthesized comprising the nucleotide sequence set forth as SEQ ID NO:264, which included the cDNA encoding a protein consisting of the humanized anti-hTfR antibody having the amino acid sequence set forth as SEQ ID NO:210 and human PPT-1 (hPPT-1) having the amino acid sequence set forth as SEQ ID NO:262 and linked, via a linker sequence Gly-Ser, to the antibody's heavy chain on the C-terminal side thereof. This DNA fragment encodes a protein having the amino acid sequence set forth as SEQ ID NO:263, which consists of the humanized anti-hTfR antibody and hPPT-1, which is linked, via a linker sequence Gly-Ser, to the antibody's heavy chain on the C-terminal side thereof. The DNA fragment has in the 5' side a MluI sequence and a sequence encoding a leader peptide acting as a secretion signal, in this order from the 5' end, and a NotI sequence in the 3' side. The DNA fragment was digested with MluI and NotI, and inserted into the vector pE-neo between MluI and NotI sites to construct pE-neo(HC-hPPT-1).

By the method described in Example 12, CHO cells were transformed with pE-neo(HC-hPPT-1) and pE-hygr(LC3), which was constructed in Example 11, a cell line was obtained which expresses a fusion protein between hPPT-1 and the humanized anti-hTfR antibody. The cell line was designated hPPT-1-anti-hTfR antibody expressing cell line. The fusion protein between hPPT-1 and the humanized anti-hTfR antibody, expressed by this cell line, were designated PPT-1-anti-hTfR antibody.

Cells of hPPT-1-anti-hTfR antibody expressing cell line were diluted to the density of approximately $2\times10^5$ cells/mL with CD OptiCHO™ medium, and 200 mL of the cell suspension was added to a 1-L conical flask and cultured for 6 to 7 days in a humid environment at 37° C., 5% $CO_2$, 95% air, with stirring at a rate of about 70 rpm. The culture medium was collected by centrifugation and filtered through a 0.22 μm filter (Millipore Inc.) to prepare a culture supernatant. To the culture supernatant thus collected was added five column volumes of 20 mM Tris buffer (pH 8.0) containing 150 mM NaCl, and loaded onto a Protein A column (column volume: 1 mL, Bio-Rad Inc.) that had been equilibrated in advance with three column volumes of 20 mM Tris buffer (pH 8.0) containing 150 mM NaCl. Then, five column volumes of the same buffer was supplied to wash the column, the adsorbed PPT-1-anti-hTfR was eluted with four column volumes of 50 mM glycine buffer (pH 2.8) containing 150 mM NaCl. The eluate containing PPT-1-anti-hTfR antibody was adjusted to pH 7.0 with 1 M Tris buffer (pH 8.0), and then the buffer exchanged for PBS using Amicon Ultra 30 kDa membrane (Millipore Inc.). The resulting solution was used as the purification product of PPT-1-anti-hTfR antibody.

[Example 28] Method for Preparation of Fusion Protein Between Humanized Anti-hTfR Antibody and Human TPP-1

A DNA fragment was artificially synthesized comprising the nucleotide sequence set forth as SEQ ID NO:267, which included the cDNA encoding a protein consisting of the humanized anti-hTfR antibody having the amino acid sequence set forth as SEQ ID NO:210 and human TPP-1 (hTPP-1) having the amino acid sequence set forth as SEQ ID NO:265 and linked, via a linker sequence Gly-Ser, to the antibody's heavy chain on the C-terminal side thereof. This DNA fragment encodes a fusion protein having the amino acid sequence set forth as SEQ ID NO:266, which consists of the humanized anti-hTfR antibody and hTPP-1 which is linked, via a linker sequence Gly-Ser, to the antibody's heavy chain on the C-terminal side thereof. The DNA fragment has in the 5' side a MluI sequence and a sequence encoding a leader peptide acting as a secretion signal, in this order from the 5' end, and a NotI sequence in the 3' side. The DNA fragment was digested with MluI and NotI, and inserted into the vector pE-neo between MluI and NotI sites to construct pE-neo(HC-hTPP-1).

By the method described in Example 12, CHO cells were transformed with pE-neo(HC-hTPP-1) and pE-hygr(LC3), which was constructed in Example 11, a cell line was obtained which expresses a fusion protein between hTPP-1 and the humanized anti-hTfR antibody. The cell line was designated hTPP-1-anti-hTfR antibody expressing cell line. The fusion protein between hTPP-1 and the humanized anti-hTfR antibody, expressed by this cell line, were designated TPP-1-anti-hTfR antibody.

Cells of hTPP-1-anti-hTfR antibody expressing cell line were diluted to the density of approximately $2\times10^5$ cells/mL with CD OptiCHO™ medium, and 200 mL of the cell suspension was added to a 1-L conical flask and cultured for 6 to 7 days in a humid environment at 37° C., 5% $CO_2$, 95% air, with stirring at a rate of about 70 rpm. The culture medium was collected by centrifugation and filtered through a 0.22 μm filter (Millipore Inc.) to prepare a culture supernatant. To the culture supernatant thus collected was added five column volumes of 20 mM Tris buffer (pH 8.0) containing 150 mM NaCl, and loaded onto a Protein A column (column volume: 1 mL, Bio-Rad Inc.) that had been equilibrated in advance with three column volumes of 20 mM Tris buffer (pH 8.0) containing 150 mM NaCl. Then, five column volumes of the same buffer was supplied to wash the column, the adsorbed TPP-1-anti-hTfR was eluted with four column volumes of 50 mM glycine buffer (pH 2.8) containing 150 mM NaCl. The eluate containing TPP-1-anti-hTfR antibody was adjusted to pH 7.0 with 1 M Tris buffer (pH 8.0), and then the buffer exchanged for PBS using Amicon Ultra 30 kDa membrane (Millipore Inc.). The resulting solution was used as the purification product of TPP-1-anti-hTfR antibody.

[Example 29] Method for Preparation of Fusion Protein Between Humanized Anti-hTfR Antibody and Human α-L-Iduronidase A DNA fragment was artificially synthesized comprising the nucleotide sequence set forth as SEQ ID NO:270, which included the cDNA encoding a protein consisting of the humanized anti-hTfR antibody having the amino acid sequence set forth as SEQ ID NO:210 and human α-L-iduronidase (hIDUA) having the amino acid sequence set forth as SEQ ID NO:268 and linked, via a linker sequence Gly-Ser, to the antibody's heavy chain on the C-terminal side thereof. This DNA fragment encodes a fusion protein having the amino acid sequence set forth as SEQ ID NO:269, which consists of the humanized anti-hTfR antibody and hIDUA which is linked, via a linker sequence Gly-Ser, to the antibody's heavy chain on the C-terminal side thereof. The DNA fragment has in the 5' side a MluI sequence and a sequence encoding a leader peptide acting as a secretion signal, in this order from the 5' end, and a NotI sequence in the 3' side. The DNA fragment was digested with MluI and NotI, and inserted into the vector pE-neo between MluI and NotI sites to construct pE-neo(HC-hIDUA).

By the method described in Example 12, CHO cells were transformed with pE-neo(HC-hIDUA) and pE-hygr(LC3), which was constructed in Example 11, a cell line was obtained which expresses a fusion protein between hIDUA and the humanized anti-hTfR antibody. The cell line was designated hIDUA-anti-hTfR antibody expressing cell line. The fusion protein between hIDUA and the humanized anti-hTfR antibody, expressed by this cell line, were designated IDUA-anti-hTfR antibody.

Cells of hIDUA-anti-hTfR antibody expressing cell line were diluted to the density of approximately $2\times10^5$ cells/mL with CD OptiCHO™ medium, and 200 mL of the cell suspension was added to a 1-L conical flask and cultured for 6 to 7 days in a humid environment at 37° C., 5% $CO_2$, 95% air, with stirring at a rate of about 70 rpm. The culture medium was collected by centrifugation and filtered through a 0.22 μm filter (Millipore Inc.) to prepare a culture supernatant. To the culture supernatant thus collected was added five column volumes of 20 mM Tris buffer (pH 8.0) containing 150 mM NaCl, and loaded onto a Protein A column (column volume: 1 mL, Bio-Rad Inc.) that had been equilibrated in advance with three column volumes of 20 mM Tris buffer (pH 8.0) containing 150 mM NaCl. Then, five column volumes of the same buffer was supplied to wash the column, the adsorbed IDUA-anti-hTfR was eluted with four column volumes of 50 mM glycine buffer (pH 2.8) containing 150 mM NaCl. The eluate containing IDUA-anti-hTfR antibody was adjusted to pH 7.0 with 1 M Tris buffer (pH 8.0), and then the buffer exchanged for PBS using Amicon Ultra 30 kDa membrane (Millipore Inc.). The resulting solution was used as the purification product of IDUA-anti-hTfR antibody.

[Example 30] Method for Preparation of Fusion Protein Between Humanized Anti-hTfR Antibody and Human TNFα Receptor A DNA fragment was artificially synthesized comprising the nucleotide sequence set forth as SEQ ID NO:273, which included the cDNA encoding a protein consisting of the humanized anti-hTfR antibody having the amino acid sequence set forth as SEQ ID NO:210 and human TNFα receptor (hTNFαR) having the amino acid sequence set forth as SEQ ID NO:271 and linked, via a linker sequence Gly-Ser, to the antibody's heavy chain on the C-terminal side thereof. This DNA fragment encodes a fusion protein having the amino acid sequence set forth as SEQ ID NO:272, which consists of the humanized anti-hTfR antibody and hTNFαR which is linked, via a linker sequence Gly-Ser, to the antibody's heavy chain on the C-terminal side thereof. The DNA fragment has in the 5' side a MluI sequence and a sequence encoding a leader peptide acting as a secretion signal, in this order from the 5' end, and a NotI sequence in the 3' side. The DNA fragment was digested with MluI and NotI, and inserted into the vector pE-neo between MluI and NotI sites to construct pE-neo(HC-hTNFαR).

By the method described in Example 12, CHO cells were transformed with pE-neo(HC-hTNFαR) and pE-hygr(LC3), which was constructed in Example 11, a cell line was obtained which expresses a fusion protein between hTNFαR and the humanized anti-hTfR antibody. The cell line was designated hTNFαR-anti-hTfR antibody expressing cell line. The fusion protein between hTNFαR and the humanized anti-hTfR antibody, expressed by this cell line, were designated TNFαR-anti-hTfR antibody.

Cells of hTNFαR-anti-hTfR antibody expressing cell line were diluted to the density of approximately $2\times10^5$ cells/mL with CD OptiCHO™ medium, and 200 mL of the cell suspension was added to a 1-L conical flask and cultured for 6 to 7 days in a humid environment at 37° C., 5% $CO_2$, 95% air, with stirring at a rate of about 70 rpm. The culture medium was collected by centrifugation and filtered through a 0.22 μm filter (Millipore Inc.) to prepare a culture supernatant. To the culture supernatant thus collected was added five column volumes of 20 mM Tris buffer (pH 8.0) containing 150 mM NaCl, and loaded onto a Protein A column (column volume: 1 mL, Bio-Rad Inc.) that had been equilibrated in advance with three column volumes of 20 mM Tris buffer (pH 8.0) containing 150 mM NaCl. Then, five column volumes of the same buffer was supplied to wash the column, the adsorbed hTNFαR-anti-hTfR was eluted with four column volumes of 50 mM glycine buffer (pH 2.8) containing 150 mM NaCl. The eluate containing TNFαR-anti-hTfR antibody was adjusted to pH 7.0 with 1 M Tris buffer (pH 8.0), and then the buffer exchanged for PBS using Amicon Ultra 30 kDa membrane (Millipore Inc.). The resulting solution was used as the purification product of TNFαR-anti-hTfR antibody.

[Example 31] Method for Preparation of Fusion Protein Between Humanized Anti-hTfR Antibody and Human Heparan N-Sulfatase A DNA fragment was artificially synthesized comprising the nucleotide sequence set forth as SEQ ID NO:276, which included the cDNA encoding a protein consisting of the humanized anti-hTfR antibody having the amino acid sequence set forth as SEQ ID NO:210 and human heparan N-sulfatase (hSGSH) having the amino acid sequence set forth as SEQ ID NO:274 and linked, via a linker sequence Gly-Ser, to the antibody's heavy chain on the C-terminal side thereof. This DNA fragment encodes a fusion protein having the amino acid sequence set forth as SEQ ID NO:275, which consists of the humanized anti-hTfR antibody and hSGSH which is linked, via a linker sequence Gly-Ser, to the antibody's heavy chain on the C-terminal side thereof. The DNA fragment has in the 5' side a MluI sequence and a sequence encoding a leader peptide acting as a secretion signal, in this order from the 5' end, and a NotI sequence in the 3' side. The DNA fragment was digested with MluI and NotI, and inserted into the vector pE-neo between MluI and NotI sites to construct pE-neo(HC-hSGSH).

By the method described in Example 12, CHO cells were transformed with pE-neo(HC-hSGSH) and pE-hygr(LC3), which was constructed in Example 11, a cell line was obtained which expresses a fusion protein between hSGSH and the humanized anti-hTfR antibody. The cell line was designated hSGSH-anti-hTfR antibody expressing cell line. The fusion protein between hSGSH and the humanized anti-hTfR antibody, expressed by this cell line, were designated SGSH-anti-hTfR antibody.

Cells of hSGSH-anti-hTfR antibody expressing cell line were diluted to the density of approximately $2\times10^5$ cells/mL with CD OptiCHO™ medium, and 200 mL of the cell suspension was added to a 1-L conical flask and cultured for 6 to 7 days in a humid environment at 37° C., 5% $CO_2$, 95% air, with stirring at a rate of about 70 rpm. The culture medium was collected by centrifugation and filtered through a 0.22 μm filter (Millipore Inc.) to prepare a culture supernatant. To the culture supernatant thus collected was added five column volumes of 20 mM Tris buffer (pH 8.0) containing 150 mM NaCl, and loaded onto a Protein A column (column volume: 1 mL, Bio-Rad Inc.) that had been equilibrated in advance with three column volumes of 20 mM Tris buffer (pH 8.0) containing 150 mM NaCl. Then, five column volumes of the same buffer was supplied to wash the column, the adsorbed SGSH-anti-hTfR was eluted with four column volumes of 50 mM glycine buffer (pH 2.8) containing 150 mM NaCl. The eluate containing SGSH-anti-hTfR antibody was adjusted to pH 7.0 with 1 M Tris buffer (pH 8.0), and then the buffer exchanged for PBS using Amicon Ultra 30 kDa membrane (Millipore Inc.). The resulting solution was used as the purification product of SGSH-anti-hTfR antibody.

[Example 32] Evaluation of Transfer of Fusion Proteins Between Humanized Anti-hTfR Antibody and Various Physiologically Active Peptides into the Brain Each purification product of EPO-anti-hTfR antibody, ARSA-anti-hTfR antibody, PPT-1-anti-hTfR antibody, TPP-1-anti-hTfR antibody, IDUA-anti-hTfR antibody, TNFαR-anti-hTfR antibody and SGSH-anti-hTfR antibody prepared in Examples 25 to 31, respectively, was intravenously administered once to an hTfR-KI mouse at a dose of 3 mg/kg. As a control, a human immunoglobulin preparation (Benesis: human immunoglobulin for intramuscular injection, Mitsubishi Tanabe Pharma Inc.) was intravenously injected once to an hTfR-KI mouse (17 to 28 week-old) at a dose of 3 mg/kg. A single hTfR-KI mouse (male, 17 to 28 week-old) was used for the administration of each of the fusion proteins and the control.

Eight hours after the intravenous injection, each mouse was subjected to whole body irrigation with physiological saline, and its brain tissues then were excised after the irrigation. The excised brain tissues then were homogenized with T-PER (Thermo Fisher Scientific Inc.) containing Protease Inhibitor Cocktail (Sigma Inc.), and the supernatant was collected after centrifugation. The concentration of the fusion protein contained in the collected supernatant of the homogenate was measured by the following method. Besides the biotin-labeled goat anti-human IgG Fc polyclonal antibody used was prepared by biotin-labeling goat anti-human IgG Fc polyclonal antibody (Bethyl Inc.) with Biotin Labelling Kit-$NH_2$ (Dojindo Laboratories Inc.) in accordance with the attached manual. Further, the SULFO-labeled goat anti-human IgG Fc polyclonal antibody used was prepared by SULFO-labeling goat anti-human IgG Fc polyclonal antibody (Bethyl Inc.) with MSD SULFO-TAG NHS-Ester (Meso scale Diagnostics Inc.) according to the attached manual.

To each well of a Streptavidin Gold Plate 96-well (Meso scale Diagnostics Inc.) was added 150 μL of SuperBlock blocking buffer in PBS (Thermo Fisher Scientific Inc.) and left to stand for one hour at room temperature to block the plate. The biotin-labeled goat anti-human IgG Fc polyclonal antibody was diluted to 0.5 μg/mL with SuperBlock blocking buffer in PBS. The SULFO-labeled goat anti-human IgG Fc polyclonal antibody was diluted to 1.0 μg/mL with SuperBlock blocking buffer in PBS. The diluted solutions of biotin-labeled antibody and SULFO-labeled antibody, 25 μL each, were mixed with 25 μL of each sample, and incubated for one hour to prepare samples for antibody reaction.

After each well of the blocked plate was washed with 200 μL of PBS-T (Sigma Inc.), 25 μL of a sample for antibody reaction was added to the well, and incubated for one hour. Following the incubation, each well of the plate was washed with 200 μL of PBS-T, and Read buffer T (Meso scale Diagnostics Inc.) was added and the amount of luminescence from each well was measured on Sector™ Imager 6000 (Meso scale Diagnostics Inc.). The amount of the fusion protein contained per one gram of brain tissues (g wet weight) (the concentration of the fusion protein in the brain tissues) was calculated by producing a standard curve on measurements of standard samples containing known concentrations of the sample, and then interpolating the measurement of each of the samples with reference to the standard. The result is shown in Table 13.

When the concentration of the human immunoglobulin, the control, in the brain tissues is taken as a unit value, the relative values of concentration of EPO-anti-hTfR antibody, ARSA-anti-hTfR antibody, PPT-1-anti-hTfR antibody, TPP-1-anti-hTfR antibody, IDUA-anti-hTfR antibody, TNFαR-anti-hTfR antibody and SGSH-anti-hTfR antibody in the brain tissues are 4.33, 3.39, 4.87, 6.48, 5.62, 7.44, and 2.24, respectively, demonstrating that these physiologically active peptides linked to the anti-hTfR antibody actively transfer into the brain tissues. The result thus indicates that these physiologically active proteins, which usually do not pass through the blood-brain barrier, can be made to pass through the blood-brain barrier and get into the brain tissues by fusing them to the anti-hTfR antibody.

Thus, the above results indicate that EPO-anti-hTfR antibody can be used as a therapeutic agent for cerebral ischemia, ARSA-anti-hTfR antibody, arylsulfatase A as a therapeutic agent for central nervous system disorders in metachromatic white matter degeneration (metachromatic leukodystrophy), PPT-1-anti-hTfR antibody as a therapeutic agent for central nervous system disorders in neuronal ceroid lipofuscinosis or Santavuori-Haltia disease, TPP-1-anti-hTfR antibody as a therapeutic agent for central nervous system disorders in neuronal ceroid lipofuscinosis or Jansky-Bielschowsky disease, IDUA-anti-hTfR antibody as a therapeutic agent for central nervous system disorders in Hurler syndrome or Hurler-Scheie syndrome, SGSH-anti-hTfR antibody as a therapeutic agent for central nervous system disorders in Sanfilippo syndrome, IDUA-anti-hTfR antibody as a therapeutic agent for central nervous system disorders in Hurler syndrome or Hurler-Scheie syndrome, and TNFαR-anti-hTfR antibody as a therapeutic agent for cerebral ischemia and encephalitis. Besides, the above results also indicate physiologically active proteins of interest which do not usually pass through the blood-brain barrier can be made to pass through the blood-brain barrier and get into the brain tissues, by fusing them with the anti-hTfR antibody.

TABLE 13

Concentration of fusion proteins in brain tissues (μg/g wet weight)

| Fusion protein | Concentration | Relative value to control |
|---|---|---|
| Control | 0.0199 | 1 |
| EPO-anti-hTfR antibody | 0.0862 | 4.33 |
| ARSA-anti-hTfR antibody | 0.0675 | 3.39 |
| PPT-1-anti-hTfR antibody | 0.0970 | 4.87 |
| TPP-1-anti-hTfR antibody | 0.129 | 6.48 |
| IDUA-1-anti-hTfR antibody | 0.112 | 5.62 |
| TNFαR-anti-hTfR antibody | 0.148 | 7.44 |
| SGSH-anti-hTfR antibody | 0.0445 | 2.24 |

INDUSTRIAL APPLICABILITY

The anti-hTfR antibody of the present invention, when fused with physiologically active proteins, low-molecular-weight compounds and the like of interest, can make them able to pass through the blood-brain barrier, and is, therefore, highly useful in providing a means to deliver physiologically active proteins to the brain, low-molecular-weight compounds and the like which are needed to act in the central nervous system.

REFERENCE SIGNS LIST

1 Blood vessel
2 Brain parenchyma
3 Neuron-like cells
4 Purkinje cells Sequence Listing Free Text SEQ ID NO:3: Amino acid sequence of exemplified linker 1

SEQ ID NO:4: Amino acid sequence of exemplified linker 2

SEQ ID NO:5: Amino acid sequence of exemplified linker 3

SEQ ID NO:6: Amino acid sequence 1 of CDR1 in the light chain of mouse anti-hTfR antibody No. 1

SEQ ID NO:7: Amino acid sequence 2 of CDR1 in the light chain of mouse anti-hTfR antibody No. 1

SEQ ID NO:8: Amino acid sequence 1 of CDR2 in the light chain of mouse anti-hTfR antibody No. 1

SEQ ID NO:9: Amino acid sequence 2 of CDR2 in the light chain of mouse anti-hTfR antibody No. 1

SEQ ID NO:10: Amino acid sequence of CDR3 in the light chain of mouse anti-hTfR antibody No. 1

SEQ ID NO:11: Amino acid sequence 1 of CDR1 in the light chain of mouse anti-hTfR antibody No. 2

SEQ ID NO:12: Amino acid sequence 2 of CDR1 in the light chain of mouse anti-hTfR antibody No. 2

SEQ ID NO:13: Amino acid sequence 1 of CDR2 in the light chain of mouse anti-hTfR antibody No. 2

SEQ ID NO:14: Amino acid sequence 2 of CDR2 in the light chain of mouse anti-hTfR antibody No. 2

SEQ ID NO:15: Amino acid sequence of CDR3 in the light chain of mouse anti-hTfR antibody No. 2

SEQ ID NO:16: Amino acid sequence 1 of CDR1 in the light chain of mouse anti-hTfR antibody No. 3

SEQ ID NO:17: Amino acid sequence 2 of CDR1 in the light chain of mouse anti-hTfR antibody No. 3

SEQ ID NO:18: Amino acid sequence 1 of CDR2 in the light chain of mouse anti-hTfR antibody No. 3

SEQ ID NO:19: Amino acid sequence 2 of CDR2 in the light chain of mouse anti-hTfR antibody No. 3

SEQ ID NO:20: Amino acid sequence of CDR3 in the light chain of mouse anti-hTfR antibody No. 3

SEQ ID NO:21: Amino acid sequence 1 of CDR1 in the light chain of mouse anti-hTfR antibody No. 4

SEQ ID NO:22: Amino acid sequence 2 of CDR1 in the light chain of mouse anti-hTfR antibody No. 4

SEQ ID NO:23: Amino acid sequence 1 of CDR2 in the light chain of mouse anti-hTfR antibody No. 4

SEQ ID NO:24: Amino acid sequence 2 of CDR2 in the light chain of mouse anti-hTfR antibody No. 4

SEQ ID NO:25: Amino acid sequence of CDR3 in the light chain of mouse anti-hTfR antibody No. 4

SEQ ID NO:26: Amino acid sequence 1 of CDR1 in the light chain of mouse anti-hTfR antibody No. 5

SEQ ID NO:27: Amino acid sequence 2 of CDR1 in the light chain of mouse anti-hTfR antibody No. 5

SEQ ID NO:28: Amino acid sequence 1 of CDR2 in the light chain of mouse anti-hTfR antibody No. 5

SEQ ID NO:29: Amino acid sequence 2 of CDR2 in the light chain of mouse anti-hTfR antibody No. 5

SEQ ID NO:30: Amino acid sequence of CDR3 in the light chain of mouse anti-hTfR antibody No. 5

SEQ ID NO:31: Amino acid sequence 1 of CDR1 in the light chain of mouse anti-hTfR antibody No. 6

SEQ ID NO:32: Amino acid sequence 2 of CDR1 in the light chain of mouse anti-hTfR antibody No. 6

SEQ ID NO:33: Amino acid sequence 1 of CDR2 in the light chain of mouse anti-hTfR antibody No. 6

SEQ ID NO:34: Amino acid sequence 2 of CDR2 in the light chain of mouse anti-hTfR antibody No. 6

SEQ ID NO:35: Amino acid sequence of CDR3 in the light chain of mouse anti-hTfR antibody No. 6

SEQ ID NO:36: Amino acid sequence 1 of CDR1 in the light chain of mouse anti-hTfR antibody No. 7

SEQ ID NO:37: Amino acid sequence 2 of CDR1 in the light chain of mouse anti-hTfR antibody No. 7

SEQ ID NO:38: Amino acid sequence 1 of CDR2 in the light chain of mouse anti-hTfR antibody No. 7

SEQ ID NO:39: Amino acid sequence 2 of CDR2 in the light chain of mouse anti-hTfR antibody No. 7

SEQ ID NO:40: Amino acid sequence of CDR3 in the light chain of mouse anti-hTfR antibody No. 7

SEQ ID NO:41: Amino acid sequence 1 of CDR1 in the light chain of mouse anti-hTfR antibody No. 8

SEQ ID NO:42: Amino acid sequence 2 of CDR1 in the light chain of mouse anti-hTfR antibody No. 8

SEQ ID NO:43: Amino acid sequence 1 of CDR2 in the light chain of mouse anti-hTfR antibody No. 8

SEQ ID NO:44: Amino acid sequence 2 of CDR2 in the light chain of mouse anti-hTfR antibody No. 8

SEQ ID NO:45: Amino acid sequence of CDR3 in the light chain of mouse anti-hTfR antibody No. 8

SEQ ID NO:46: Amino acid sequence 1 of CDR1 in the light chain of mouse anti-hTfR antibody No. 9

SEQ ID NO:47: Amino acid sequence 2 of CDR1 in the light chain of mouse anti-hTfR antibody No. 9

SEQ ID NO:48: Amino acid sequence 1 of CDR2 in the light chain of mouse anti-hTfR antibody No. 9

SEQ ID NO:49: Amino acid sequence 2 of CDR2 in the light chain of mouse anti-hTfR antibody No. 9

SEQ ID NO:50: Amino acid sequence of CDR3 in the light chain of mouse anti-hTfR antibody No. 9

SEQ ID NO:51: Amino acid sequence 1 of CDR1 in the light chain of mouse anti-hTfR antibody No. 10

SEQ ID NO:52: Amino acid sequence 2 of CDR1 in the light chain of mouse anti-hTfR antibody No. 10

SEQ ID NO:53: Amino acid sequence 1 of CDR2 in the light chain of mouse anti-hTfR antibody No. 10

SEQ ID NO:54: Amino acid sequence 2 of CDR2 in the light chain of mouse anti-hTfR antibody No. 10

SEQ ID NO:55: Amino acid sequence of CDR3 in the light chain of mouse anti-hTfR antibody No. 10

SEQ ID NO:56: Amino acid sequence 1 of CDR1 in the light chain of mouse anti-hTfR antibody No. 11

SEQ ID NO:57: Amino acid sequence 2 of CDR1 in the light chain of mouse anti-hTfR antibody No. 11

SEQ ID NO:58: Amino acid sequence 1 of CDR2 in the light chain of mouse anti-hTfR antibody No. 11

SEQ ID NO:59: Amino acid sequence 2 of CDR2 in the light chain of mouse anti-hTfR antibody No. 11

SEQ ID NO:60: Amino acid sequence of CDR3 in the light chain of mouse anti-hTfR antibody No. 11

SEQ ID NO:61: Amino acid sequence 1 of CDR1 in the light chain of mouse anti-hTfR antibody No. 12

SEQ ID NO:62: Amino acid sequence 2 of CDR1 in the light chain of mouse anti-hTfR antibody No. 12

SEQ ID NO:63: Amino acid sequence 1 of CDR2 in the light chain of mouse anti-hTfR antibody No. 12

SEQ ID NO:64: Amino acid sequence 2 of CDR2 in the light chain of mouse anti-hTfR antibody No. 12

SEQ ID NO:65: Amino acid sequence of CDR3 in the light chain of mouse anti-hTfR antibody No. 12

SEQ ID NO:66: Amino acid sequence 1 of CDR1 in the light chain of mouse anti-hTfR antibody No. 13

SEQ ID NO:67: Amino acid sequence 2 of CDR1 in the light chain of mouse anti-hTfR antibody No. 13

SEQ ID NO:68: Amino acid sequence 1 of CDR2 in the light chain of mouse anti-hTfR antibody No. 13

SEQ ID NO:69: Amino acid sequence 2 of CDR2 in the light chain of mouse anti-hTfR antibody No. 13

SEQ ID NO:70: Amino acid sequence of CDR3 in the light chain of mouse anti-hTfR antibody No. 13

SEQ ID NO:71: Amino acid sequence 1 of CDR1 in the light chain of mouse anti-hTfR antibody No. 14

SEQ ID NO:72: Amino acid sequence 2 of CDR1 in the light chain of mouse anti-hTfR antibody No. 14

SEQ ID NO:73: Amino acid sequence 1 of CDR2 in the light chain of mouse anti-hTfR antibody No. 14

SEQ ID NO:74: Amino acid sequence 2 of CDR2 in the light chain of mouse anti-hTfR antibody No. 14

SEQ ID NO:75: Amino acid sequence of CDR3 in the light chain of mouse anti-hTfR antibody No. 14

SEQ ID NO:76: Amino acid sequence 1 of CDR1 in the heavy chain of mouse anti-hTfR antibody No. 1

SEQ ID NO:77: Amino acid sequence 2 of CDR1 in the heavy chain of mouse anti-hTfR antibody No. 1

SEQ ID NO:78: Amino acid sequence 1 of CDR2 in the heavy chain of mouse anti-hTfR antibody No. 1

SEQ ID NO:79: Amino acid sequence 2 of CDR2 in the heavy chain of mouse anti-hTfR antibody No. 1

SEQ ID NO:80: Amino acid sequence 1 of CDR3 in the heavy chain of mouse anti-hTfR antibody No. 1

SEQ ID NO:81: Amino acid sequence 2 of CDR3 in the heavy chain of mouse anti-hTfR antibody No. 1

SEQ ID NO:82: Amino acid sequence 1 of CDR1 in the heavy chain of mouse anti-hTfR antibody No. 2

SEQ ID NO:83: Amino acid sequence 2 of CDR1 in the heavy chain of mouse anti-hTfR antibody No. 2

SEQ ID NO:84: Amino acid sequence 1 of CDR2 in the heavy chain of mouse anti-hTfR antibody No. 2

SEQ ID NO:85: Amino acid sequence 2 of CDR2 in the heavy chain of mouse anti-hTfR antibody No. 2

SEQ ID NO:86: Amino acid sequence 1 of CDR3 in the heavy chain of mouse anti-hTfR antibody No. 2

SEQ ID NO:87: Amino acid sequence 2 of CDR3 in the heavy chain of mouse anti-hTfR antibody No. 2

SEQ ID NO:88: Amino acid sequence 1 of CDR1 in the heavy chain of mouse anti-hTfR antibody No. 3

SEQ ID NO:89: Amino acid sequence 2 of CDR1 in the heavy chain of mouse anti-hTfR antibody No. 3

SEQ ID NO:90: Amino acid sequence 1 of CDR2 in the heavy chain of mouse anti-hTfR antibody No. 3

SEQ ID NO:91: Amino acid sequence 2 of CDR2 in the heavy chain of mouse anti-hTfR antibody No. 3

SEQ ID NO:92: Amino acid sequence 1 of CDR3 in the heavy chain of mouse anti-hTfR antibody No. 3

SEQ ID NO:93: Amino acid sequence 2 of CDR3 in the heavy chain of mouse anti-hTfR antibody No. 3

SEQ ID NO:94: Amino acid sequence 1 of CDR1 in the heavy chain of mouse anti-hTfR antibody No. 4

SEQ ID NO:95: Amino acid sequence 2 of CDR1 in the heavy chain of mouse anti-hTfR antibody No. 4

SEQ ID NO:96: Amino acid sequence 1 of CDR2 in the heavy chain of mouse anti-hTfR antibody No. 4

SEQ ID NO:97: Amino acid sequence 2 of CDR2 in the heavy chain of mouse anti-hTfR antibody No. 4

SEQ ID NO:98: Amino acid sequence 1 of CDR3 in the heavy chain of mouse anti-hTfR antibody No. 4

SEQ ID NO:99: Amino acid sequence 2 of CDR3 in the heavy chain of mouse anti-hTfR antibody No. 4

SEQ ID NO:100: Amino acid sequence 1 of CDR1 in the heavy chain of mouse anti-hTfR antibody No. 5

SEQ ID NO:101: Amino acid sequence 2 of CDR1 in the heavy chain of mouse anti-hTfR antibody No. 5

SEQ ID NO:102: Amino acid sequence 1 of CDR2 in the heavy chain of mouse anti-hTfR antibody No. 5

SEQ ID NO:103: Amino acid sequence 2 of CDR2 in the heavy chain of mouse anti-hTfR antibody No. 5

SEQ ID NO:104: Amino acid sequence 1 of CDR3 in the heavy chain of mouse anti-hTfR antibody No. 5

SEQ ID NO:105: Amino acid sequence 2 of CDR3 in the heavy chain of mouse anti-hTfR antibody No. 5

SEQ ID NO:106: Amino acid sequence 1 of CDR1 in the heavy chain of mouse anti-hTfR antibody No. 6

SEQ ID NO:107: Amino acid sequence 2 of CDR1 in the heavy chain of mouse anti-hTfR antibody No. 6

SEQ ID NO:108: Amino acid sequence of CDR2 in the heavy chain of mouse anti-hTfR antibody No. 6

SEQ ID NO:109: Amino acid sequence 1 of CDR3 in the heavy chain of mouse anti-hTfR antibody No. 6

SEQ ID NO:110: Amino acid sequence 2 of CDR3 in the heavy chain of mouse anti-hTfR antibody No. 6

SEQ ID NO:111: Amino acid sequence 1 of CDR1 in the heavy chain of mouse anti-hTfR antibody No. 7

SEQ ID NO:112: Amino acid sequence 2 of CDR1 in the heavy chain of mouse anti-hTfR antibody No. 7

SEQ ID NO:113: Amino acid sequence 1 of CDR2 in the heavy chain of mouse anti-hTfR antibody No. 7

SEQ ID NO:114: Amino acid sequence 2 of CDR2 in the heavy chain of mouse anti-hTfR antibody No. 7

SEQ ID NO:115: Amino acid sequence 1 of CDR3 in the heavy chain of mouse anti-hTfR antibody No. 7

SEQ ID NO:116: Amino acid sequence 2 of CDR3 in the heavy chain of mouse anti-hTfR antibody No. 7

SEQ ID NO:117: Amino acid sequence 1 of CDR1 in the heavy chain of mouse anti-hTfR antibody No. 8

SEQ ID NO:118: Amino acid sequence 2 of CDR1 in the heavy chain of mouse anti-hTfR antibody No. 8

SEQ ID NO:119: Amino acid sequence of CDR2 in the heavy chain of mouse anti-hTfR antibody No. 8

SEQ ID NO:120: Amino acid sequence 1 of CDR3 in the heavy chain of mouse anti-hTfR antibody No. 8

SEQ ID NO:121: Amino acid sequence 2 of CDR3 in the heavy chain of mouse anti-hTfR antibody No. 8

SEQ ID NO:122: Amino acid sequence 1 of CDR1 in the heavy chain of mouse anti-hTfR antibody No. 9

SEQ ID NO:123: Amino acid sequence 2 of CDR1 in the heavy chain of mouse anti-hTfR antibody No. 9

SEQ ID NO:124: Amino acid sequence 1 of CDR2 in the heavy chain of mouse anti-hTfR antibody No. 9

SEQ ID NO:125: Amino acid sequence 2 of CDR2 in the heavy chain of mouse anti-hTfR antibody No. 9

SEQ ID NO:126: Amino acid sequence 1 of CDR3 in the heavy chain of mouse anti-hTfR antibody No. 9

SEQ ID NO:127: Amino acid sequence 2 of CDR3 in the heavy chain of mouse anti-hTfR antibody No. 9

SEQ ID NO:128: Amino acid sequence 1 of CDR1 in the heavy chain of mouse anti-hTfR antibody No. 10

SEQ ID NO:129: Amino acid sequence 2 of CDR1 in the heavy chain of mouse anti-hTfR antibody No. 10

SEQ ID NO:130: Amino acid sequence 1 of CDR2 in the heavy chain of mouse anti-hTfR antibody No. 10

SEQ ID NO:131: Amino acid sequence 2 of CDR2 in the heavy chain of mouse anti-hTfR antibody No. 10

SEQ ID NO:132: Amino acid sequence 1 of CDR3 in the heavy chain of mouse anti-hTfR antibody No. 10

SEQ ID NO:133: Amino acid sequence 2 of CDR3 in the heavy chain of mouse anti-hTfR antibody No. 10

SEQ ID NO:134: Amino acid sequence 1 of CDR1 in the heavy chain of mouse anti-hTfR antibody No. 11

SEQ ID NO:135: Amino acid sequence 2 of CDR1 in the heavy chain of mouse anti-hTfR antibody No. 11

SEQ ID NO:136: Amino acid sequence 1 of CDR2 in the heavy chain of mouse anti-hTfR antibody No. 11

SEQ ID NO:137: Amino acid sequence 2 of CDR2 in the heavy chain of mouse anti-hTfR antibody No. 11

SEQ ID NO:138: Amino acid sequence 1 of CDR3 in the heavy chain of mouse anti-hTfR antibody No. 11

SEQ ID NO:139: Amino acid sequence 2 of CDR3 in the heavy chain of mouse anti-hTfR antibody No. 11

SEQ ID NO:140: Amino acid sequence 1 of CDR1 in the heavy chain of mouse anti-hTfR antibody No. 12

SEQ ID NO:141: Amino acid sequence 2 of CDR1 in the heavy chain of mouse anti-hTfR antibody No. 12

SEQ ID NO:142: Amino acid sequence 1 of CDR2 in the heavy chain of mouse anti-hTfR antibody No. 12

SEQ ID NO:143: Amino acid sequence 2 of CDR2 in the heavy chain of mouse anti-hTfR antibody No. 12

SEQ ID NO:144: Amino acid sequence 1 of CDR3 in the heavy chain of mouse anti-hTfR antibody No. 12

SEQ ID NO:145: Amino acid sequence 2 of CDR3 in the heavy chain of mouse anti-hTfR antibody No. 12

SEQ ID NO:146: Amino acid sequence 1 of CDR1 in the heavy chain of mouse anti-hTfR antibody No. 13

SEQ ID NO:147: Amino acid sequence 2 of CDR1 in the heavy chain of mouse anti-hTfR antibody No. 13

SEQ ID NO:148: Amino acid sequence 1 of CDR2 in the heavy chain of mouse anti-hTfR antibody No. 13

SEQ ID NO:149: Amino acid sequence 2 of CDR2 in the heavy chain of mouse anti-hTfR antibody No. 13

SEQ ID NO:150: Amino acid sequence 1 of CDR3 in the heavy chain of mouse anti-hTfR antibody No. 13

SEQ ID NO:151: Amino acid sequence 2 of CDR3 in the heavy chain of mouse anti-hTfR antibody No. 13

SEQ ID NO:152: Amino acid sequence 1 of CDR1 in the heavy chain of mouse anti-hTfR antibody No. 14

SEQ ID NO:153: Amino acid sequence 2 of CDR1 in the heavy chain of mouse anti-hTfR antibody No. 14

SEQ ID NO:154: Amino acid sequence 1 of CDR2 in the heavy chain of mouse anti-hTfR antibody No. 14

SEQ ID NO:155: Amino acid sequence 2 of CDR2 in the heavy chain of mouse anti-hTfR antibody No. 14

SEQ ID NO:156: Amino acid sequence 1 of CDR3 in the heavy chain of mouse anti-hTfR antibody No. 14

SEQ ID NO:157: Amino acid sequence 2 of CDR3 in the heavy chain of mouse anti-hTfR antibody No. 14

SEQ ID NO:158: Amino acid sequence 1 of the light chain variable region of humanized anti-hTfR antibody No. 1

SEQ ID NO:159: Amino acid sequence 2 of the light chain variable region of humanized anti-hTfR antibody No. 1

SEQ ID NO:160: Amino acid sequence 3 of the light chain variable region of humanized anti-hTfR antibody No. 1

SEQ ID NO:161: Amino acid sequence 4 of the light chain variable region of humanized anti-hTfR antibody No. 1

SEQ ID NO:162: Amino acid sequence 5 of the light chain variable region of humanized anti-hTfR antibody No. 1

SEQ ID NO:163: Amino acid sequence 6 of the light chain variable region of humanized anti-hTfR antibody No. 1

SEQ ID NO:164: Amino acid sequence of the light chain of humanized anti-hTfR antibody No. 1 containing amino acid sequence 6 as the variable region, synthetic sequence SEQ ID NO:165: Nucleotide sequence encoding the amino acid sequence of the light chain of humanized anti-hTfR antibody No. 1 containing amino acid sequence 6 as the variable region, synthetic sequence SEQ ID NO:166: Amino acid sequence 1 of the heavy chain variable region of humanized anti-hTfR antibody No. 1

SEQ ID NO:167: Amino acid sequence 2 of the heavy chain variable region of humanized anti-hTfR antibody No. 1

SEQ ID NO:168: Amino acid sequence 3 of the heavy chain variable region of humanized anti-hTfR antibody No. 1

SEQ ID NO:169: Amino acid sequence 4 of the heavy chain variable region of humanized anti-hTfR antibody No. 1

SEQ ID NO:170: Amino acid sequence 5 of the heavy chain variable region of humanized anti-hTfR antibody No. 1

SEQ ID NO:171: Amino acid sequence 6 of the heavy chain variable region of humanized anti-hTfR antibody No. 1

SEQ ID NO:172: Amino acid sequence of the heavy chain of humanized anti-hTfR antibody No. 1 containing amino acid sequence 6 as the variable region SEQ ID NO:173: Nucleotide sequence encoding the amino acid sequence of the heavy chain of humanized anti-hTfR antibody No. 1 containing amino acid sequence 6 as the variable region, synthetic sequence SEQ ID NO:174: Amino acid sequence 1 of the light chain variable region of humanized anti-hTfR antibody No. 2

SEQ ID NO:175: Amino acid sequence 2 of the light chain variable region of humanized anti-hTfR antibody No. 2

SEQ ID NO:176: Amino acid sequence 3 of the light chain variable region of humanized anti-hTfR antibody No. 2

SEQ ID NO:177: Amino acid sequence 4 of the light chain variable region of humanized anti-hTfR antibody No. 2

SEQ ID NO:178: Amino acid sequence 5 of the light chain variable region of humanized anti-hTfR antibody No. 2

SEQ ID NO:179: Amino acid sequence 6 of the light chain variable region of humanized anti-hTfR antibody No. 2

SEQ ID NO:180: Amino acid sequence of the light chain of humanized anti-hTfR antibody No. 2 containing amino acid sequence 6 as the variable region SEQ ID NO:181: Nucleotide sequence comprising a nucleotide sequence encoding the amino acid sequence of the light chain of humanized anti-hTfR antibody No. 2 containing amino acid sequence 6 as the variable region, synthetic sequence SEQ ID NO:182: Amino acid sequence 1 of the heavy chain variable region of humanized anti-hTfR antibody No. 2

SEQ ID NO:183: Amino acid sequence 2 of the heavy chain variable region of humanized anti-hTfR antibody No. 2

SEQ ID NO:184: Amino acid sequence 3 of the heavy chain variable region of humanized anti-hTfR antibody No. 2

SEQ ID NO:185: Amino acid sequence 4 of the heavy chain variable region of humanized anti-hTfR antibody No. 2

SEQ ID NO:186: Amino acid sequence 5 of the heavy chain variable region of humanized anti-hTfR antibody No. 2

SEQ ID NO:187: Amino acid sequence 6 of the heavy chain variable region of humanized anti-hTfR antibody No. 2

SEQ ID NO:188: Amino acid sequence of the heavy chain of humanized anti-hTfR antibody No. 2 containing amino acid sequence 6 as the variable region SEQ ID NO:189: Nucleotide sequence comprising a nucleotide sequence encoding the amino acid sequence of the heavy chain of humanized anti-hTfR antibody No. 2 containing amino acid sequence 6 as the variable region, synthetic sequence SEQ ID NO:190: Amino acid sequence 1 of the light chain variable region of humanized anti-hTfR antibody No. 3

SEQ ID NO:191: Amino acid sequence 2 of the light chain variable region of humanized anti-hTfR antibody No. 3

SEQ ID NO:192: Amino acid sequence 3 of the light chain variable region of humanized anti-hTfR antibody No. 3

SEQ ID NO:193: Amino acid sequence 4 of the light chain variable region of humanized anti-hTfR antibody No. 3

SEQ ID NO:194: Amino acid sequence 5 of the light chain variable region of humanized anti-hTfR antibody No. 3

SEQ ID NO:195: Amino acid sequence 6 of the light chain variable region of humanized anti-hTfR antibody No. 3

SEQ ID NO:196: Amino acid sequence of the light chain of humanized anti-hTfR antibody No. 3 containing amino acid sequence 2 as the variable region SEQ ID NO:197: Nucleotide sequence encoding the amino acid sequence of the light chain of humanized anti-hTfR antibody No. 3 containing amino acid sequence 2 as the variable region, synthetic sequence SEQ ID NO:198: Amino acid sequence of the light chain of humanized anti-hTfR antibody No. 3 containing amino acid sequence 4 as the variable region SEQ ID NO:199: Nucleotide sequence encoding the amino acid sequence of the light chain of humanized anti-hTfR antibody No. 3 containing amino acid sequence 4 as the variable region, synthetic sequence SEQ ID NO:200: Amino acid sequence of the light chain of humanized anti-hTfR antibody No. 3 containing amino acid sequence 5 as the variable region SEQ ID NO:201: Nucleotide sequence encoding the amino acid sequence of the light chain of humanized anti-hTfR antibody No. 3 containing amino acid sequence 5 as the variable region, synthetic sequence SEQ ID NO:202: Humanized anti-hTfR antibody No. 3 containing amino acid sequence 6 as the variable region SEQ ID NO:203: Nucleotide sequence encoding the amino acid sequence of the light chain of humanized anti-hTfR antibody No. 3 containing amino acid sequence 6 as the variable region, synthetic sequence SEQ ID NO:204: Amino acid sequence 1 of the heavy chain variable region of humanized anti-hTfR antibody No. 3

SEQ ID NO:205: Amino acid sequence 2 of the heavy chain variable region of humanized anti-hTfR antibody No. 3

SEQ ID NO:206: Amino acid sequence 3 of the heavy chain variable region of humanized anti-hTfR antibody No. 3

SEQ ID NO:207: Amino acid sequence 4 of the heavy chain variable region of humanized anti-hTfR antibody No. 3

SEQ ID NO:208: Amino acid sequence 5 of the heavy chain variable region of humanized anti-hTfR antibody No. 3

SEQ ID NO:209: Amino acid sequence 6 of the heavy chain variable region of humanized anti-hTfR antibody No. 3

SEQ ID NO:210: Amino acid sequence of the heavy chain of humanized anti-hTfR antibody No. 3 containing amino acid sequence 2 as the variable region SEQ ID NO:211: Nucleotide sequence encoding the amino acid sequence of the heavy chain of humanized anti-hTfR antibody No. 3 containing amino acid sequence 2 as the variable region, synthetic sequence SEQ ID NO:212: Amino acid sequence of the heavy chain (IgG4) of humanized anti-hTfR antibody No. 3 containing amino acid sequence 2 as the variable region SEQ ID NO:213: Nucleotide sequence encoding the amino acid sequence of the heavy chain (IgG4) of humanized anti-hTfR antibody No. 3 containing amino acid sequence 2 as the variable region, synthetic sequence SEQ ID NO:214: Primer hTfR5', synthetic sequence SEQ ID NO:215: Primer hTfR3', synthetic sequence SEQ ID NO:216: Primer Hyg-Sfi5', synthetic sequence SEQ ID NO:217: Primer Hyg-BstX3', synthetic sequence SEQ ID NO:218: Amino acid sequence of the light chain variable region of mouse anti-hTfR antibody No. 1

SEQ ID NO:219: Amino acid sequence of the heavy chain variable region of mouse anti-hTfR antibody No. 1

SEQ ID NO:220: Amino acid sequence of the light chain variable region of mouse anti-hTfR antibody No. 2

SEQ ID NO:221: Amino acid sequence of the heavy chain variable region of mouse anti-hTfR antibody No. 2

SEQ ID NO:222: Amino acid sequence of the light chain variable region of mouse anti-hTfR antibody No. 3

SEQ ID NO:223: Amino acid sequence of the heavy chain variable region of mouse anti-hTfR antibody No. 3

SEQ ID NO:224: Amino acid sequence of the light chain variable region of mouse anti-hTfR antibody No. 4

SEQ ID NO:225: Amino acid sequence of the heavy chain variable region of mouse anti-hTfR antibody No. 4

SEQ ID NO:226: Amino acid sequence of the light chain variable region of mouse anti-hTfR antibody No. 5

SEQ ID NO:227: Amino acid sequence of the heavy chain variable region of mouse anti-hTfR antibody No. 5

SEQ ID NO:228: Amino acid sequence of the light chain variable region of mouse anti-hTfR antibody No. 6

SEQ ID NO:229: Amino acid sequence of the heavy chain variable region of mouse anti-hTfR antibody No. 6

SEQ ID NO:230: Amino acid sequence of the light chain variable region of mouse anti-hTfR antibody No. 7

SEQ ID NO:231: Amino acid sequence of the heavy chain variable region of mouse anti-hTfR antibody No. 7

SEQ ID NO:232: Amino acid sequence of the light chain variable region of mouse anti-hTfR antibody No. 8

SEQ ID NO:233: Amino acid sequence of the heavy chain variable region of mouse anti-hTfR antibody No. 8

SEQ ID NO:234: Amino acid sequence of the light chain variable region of mouse anti-hTfR antibody No. 9

SEQ ID NO:235: Amino acid sequence of the heavy chain variable region of mouse anti-hTfR antibody No. 9

SEQ ID NO:236: Amino acid sequence of the light chain variable region of mouse anti-hTfR antibody No. 10

SEQ ID NO:237: Amino acid sequence of the heavy chain variable region of mouse anti-hTfR antibody No. 10

SEQ ID NO:238: Amino acid sequence of the light chain variable region of mouse anti-hTfR antibody No. 11

SEQ ID NO:239: Amino acid sequence of the heavy chain variable region of mouse anti-hTfR antibody No. 11

SEQ ID NO:240: Amino acid sequence of the light chain variable region of mouse anti-hTfR antibody No. 12

SEQ ID NO:241: Amino acid sequence of the heavy chain variable region of mouse anti-hTfR antibody No. 12

SEQ ID NO:242: Amino acid sequence of the light chain variable region of mouse anti-hTfR antibody No. 13

SEQ ID NO:243: Amino acid sequence of the heavy chain variable region of mouse anti-hTfR antibody No. 13

SEQ ID NO:244: Amino acid sequence of the light chain variable region of mouse anti-hTfR antibody No. 14

SEQ ID NO:245: Amino acid sequence of the heavy chain variable region of mouse anti-hTfR antibody No. 14

SEQ ID NO:247: Amino acid sequence of the fusion protein of heavy chain of anti-hTfR antibody No. 1 (humanized 6) and hI2S SEQ ID NO:248: Nucleotide sequence encoding the amino acid sequence of fusion protein of heavy chain of anti-hTfR antibody No. 1 (humanized 6) and hI2S, synthetic sequence SEQ ID NO:249: Amino acid sequence of the fusion protein of heavy chain of anti-hTfR antibody No. 2 (humanized 6) and hI2S SEQ ID NO:250: Nucleotide sequence encoding the amino acid sequence of fusion protein of heavy chain of anti-hTfR antibody No. 2 (humanized 6) and hI2S, synthetic sequence SEQ ID NO:251: Amino acid sequence of fusion protein of heavy chain of anti-hTfR antibody No. 3 (humanized 2) and hI2S, synthetic sequence SEQ ID NO:252: Nucleotide sequence encoding the amino acid sequence of fusion protein of heavy chain of anti-hTfR antibody No. 3 (humanized 2) and hI2S, synthetic sequence SEQ ID NO:253: Nucleotide sequence of the DNA in which a neomycin resistance gene flanked by loxP sequences was placed on the cDNA's 3' side of a cDNA encoding chimeric hTfR, synthetic sequence SEQ ID NO:254: Nucleotide sequence of the 5'-arm of targeting vector, synthetic sequence SEQ ID NO:255: Nucleotide sequence of the 3'-arm of targeting vector, synthetic sequence SEQ ID NO:257: Amino acid sequence of the fusion protein of heavy chain of anti-hTfR antibody No. 3 (humanized 2) and hEPO SEQ ID NO:258: Nucleotide sequence encoding the amino acid sequence of fusion protein of heavy chain of anti-hTfR antibody No. 3 (humanized 2) and hEPO, synthetic sequence SEQ ID NO:260: Amino acid sequence of the fusion protein of heavy chain of anti-hTfR antibody No. 3 (humanized 2) and hARSA SEQ ID NO:261: Nucleotide sequence encoding the amino acid sequence of fusion protein of heavy chain of anti-hTfR antibody No. 3 (humanized 2) and hARSA, synthetic sequence SEQ ID NO:263: Amino acid sequence of the fusion protein of heavy chain of anti-hTfR antibody No. 3 (humanized 2) and hPPT-1

SEQ ID NO:264: Nucleotide sequence encoding the amino acid sequence of fusion protein of heavy chain of anti-hTfR antibody No. 3 (humanized 2) and hPPT-1, synthetic sequence SEQ ID NO:266: Amino acid sequence of the fusion protein of heavy chain of anti-hTfR antibody No. 3 (humanized 2) and hTPP-1

SEQ ID NO:267: Nucleotide sequence encoding the amino acid sequence of fusion protein of heavy chain of anti-hTfR antibody No. 3 (humanized 2) and hTPP-1, synthetic sequence SEQ ID NO:269: Amino acid sequence of the fusion protein of heavy chain of anti-hTfR antibody No. 3 (humanized 2) and hIDUA SEQ ID NO:270: Nucleotide sequence encoding the amino acid sequence of fusion protein of heavy chain of anti-hTfR antibody No. 3 (humanized 2) and hIDUA, synthetic sequence SEQ ID NO:272: Amino acid sequence of the fusion protein of heavy chain of anti-hTfR antibody No. 3 (humanized 2) and hTNFαR SEQ ID NO:273: Nucleotide sequence encoding the amino acid sequence of fusion protein of heavy chain of anti-hTfRα antibody No. 3 (humanized 2) and hTNFαR, synthetic sequence SEQ ID NO:275: Amino acid sequence of the fusion protein of heavy chain of anti-hTfR antibody No. 3 (humanized 2) and hSGSH SEQ ID NO:276: Nucleotide sequence encoding the amino acid sequence of fusion protein of heavy chain of anti-hTfR antibody No. 3 (humanized 2) and hSGSH, synthetic sequence SEQ ID NO:277: Amino acid sequence of anti-hTfR single-chain antibody SEQ ID NO:278: Amino acid sequence 2 of CDR2 in the heavy chain of mouse anti-hTfR antibody No. 6

SEQ ID NO:279: Amino acid sequence 2 of CDR2 in the heavy chain of mouse anti-hTfR antibody No. 8

The invention claimed is:

1. A fusion protein which penetrates the blood brain barrier following administration to a human comprising a humanized anti-human transferrin receptor (anti-hTfR) antibody amino acid sequence and a human iduronate 2-sulfatase amino acid sequence, wherein the fusion protein is selected from (1) to (3) below:

(1) the fusion protein, wherein the humanized anti-hTfR antibody light chain has the amino acid sequence set forth as SEQ ID NO:164, and wherein the humanized anti-hTfR antibody heavy chain is linked, on the C-terminal side thereof and via a linker sequence Gly-Ser, to the human iduronate 2-sulfatase, and the whole linked heavy chain has the amino acid sequence set forth as SEQ ID NO:247, (2) the fusion protein, wherein the humanized anti-hTfR antibody light chain has the amino acid sequence set forth as SEQ ID NO:180, and wherein the humanized anti-hTfR antibody heavy chain is linked, on the C-terminal side thereof and via a linker sequence Gly-Ser, to the human iduronate 2-sulfatase, and the whole linked heavy chain has the amino acid sequence set forth as SEQ ID NO:249, and (3) the fusion protein, wherein the humanized anti-hTfR antibody light chain has the amino acid sequence set forth as SEQ ID NO:196, and wherein the humanized anti-hTfR antibody heavy chain is linked, on the C-terminal side thereof and via a linker sequence Gly-Ser, to the human iduronate 2-sulfatase, and the whole linked heavy chain has the amino acid sequence set forth as SEQ ID NO:251.

2. A polynucleotide encoding the amino acid sequence of the fusion protein according to claim 1.

3. An expression vector comprising the polynucleotide according to claim 2 that is incorporated therein.

4. A mammalian cell transformed with the expression vector according to claim 3.

5. A method for the treatment of Hunter syndrome comprising parenterally administering a therapeutically effective amount of the fusion protein according to claim 1 to a patient with Hunter syndrome.

6. A pharmaceutical agent comprising the fusion protein according to claim 1.

* * * * *